United States Patent
Furet et al.

(10) Patent No.: US 9,340,537 B2
(45) Date of Patent: May 17, 2016

(54) BENZAMIDE DERIVATIVES FOR INHIBITING THE ACTIVITY OF ABL1, ABL2 AND BCR-ABL1

(71) Applicants: Pascal Furet, Thann (FR); Robert Martin Grotzfeld, Ettingen (CH); Wolfgang Jahnke, Lorrach (DE); Darryl Brynley Jones, Basel (CH); Paul William Manley, Arlesheim (CH); Andreas Marzinzik, Weil (DE); Xavier Francois Andre Pelle, Kembs (FR); Bahaa Salem, Basel (CH); Joseph Schoepfer, Riehen (CH)

(72) Inventors: Pascal Furet, Thann (FR); Robert Martin Grotzfeld, Ettingen (CH); Wolfgang Jahnke, Lorrach (DE); Darryl Brynley Jones, Basel (CH); Paul William Manley, Arlesheim (CH); Andreas Marzinzik, Weil (DE); Xavier Francois Andre Pelle, Kembs (FR); Bahaa Salem, Basel (CH); Joseph Schoepfer, Riehen (CH)

(73) Assignee: NOVATIS AG, Basel (CH)

( * ) Notice: Subject to any disclaimer, the term of this patent is extended or adjusted under 35 U.S.C. 154(b) by 0 days.

(21) Appl. No.: 14/400,992

(22) PCT Filed: May 9, 2013

(86) PCT No.: PCT/IB2013/053771
§ 371 (c)(1),
(2) Date: Nov. 13, 2014

(87) PCT Pub. No.: WO2013/171642
PCT Pub. Date: Nov. 21, 2013

(65) Prior Publication Data
US 2015/0126485 A1    May 7, 2015

Related U.S. Application Data

(60) Provisional application No. 61/789,842, filed on Mar. 15, 2013, provisional application No. 61/647,174, filed on May 15, 2012.

(51) Int. Cl.
| | | |
|---|---|---|
| C07D 417/10 | (2006.01) |
| C07D 417/14 | (2006.01) |
| C07D 401/14 | (2006.01) |
| C07D 405/14 | (2006.01) |
| C07D 413/14 | (2006.01) |
| C07D 401/04 | (2006.01) |
| C07D 403/10 | (2006.01) |
| C07D 409/14 | (2006.01) |
| A61K 31/4025 | (2006.01) |
| A61K 31/427 | (2006.01) |
| A61K 31/4439 | (2006.01) |
| A61K 31/5377 | (2006.01) |
| A61K 45/06 | (2006.01) |

(52) U.S. Cl.
CPC .......... *C07D 417/14* (2013.01); *A61K 31/4025* (2013.01); *A61K 31/427* (2013.01); *A61K 31/4439* (2013.01); *A61K 31/5377* (2013.01); *A61K 45/06* (2013.01); *C07D 401/04* (2013.01); *C07D 401/14* (2013.01); *C07D 403/10* (2013.01); *C07D 405/14* (2013.01); *C07D 409/14* (2013.01); *C07D 413/14* (2013.01); *C07D 417/10* (2013.01)

(58) Field of Classification Search
CPC .................................................... C07D 417/10
USPC ......................................... 548/204; 514/365
See application file for complete search history.

(56) References Cited

U.S. PATENT DOCUMENTS

| | | | |
|---|---|---|---|
| 5,017,211 A | 5/1991 | Wenger et al. |
| 7,642,272 B2 | 1/2010 | Shankar et al. |
| 8,030,336 B2 | 10/2011 | Burns et al. |
| 8,829,195 B2 | 9/2014 | Dodd et al. |
| 2003/0105143 A1 | 6/2003 | Ammendola et al. |
| 2008/0167347 A1 | 7/2008 | Seno et al. |
| 2010/0041657 A1 | 2/2010 | Olesen et al. |
| 2011/0312939 A1 | 12/2011 | Steurer et al. |

(Continued)

FOREIGN PATENT DOCUMENTS

| | | |
|---|---|---|
| EP | 1 746 097 A1 | 1/2007 |
| WO | 89/02891 A1 | 4/1989 |
| WO | 01/55115 A1 | 8/2001 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*

(Continued)

*Primary Examiner* — Patricia L Morris
(74) *Attorney, Agent, or Firm* — Scott W. Reid

(57) ABSTRACT

The present invention relates to compounds of formula (I): in which Y, Y, R, R 2, R 3 and R 4 are defined in the Summary of the Invention; capable of inhibiting the tyrosine kinase enzymatic activity of the Abelson protein (ABL1), the Abelson-related protein (ABL2) and related chimeric proteins, in particular BCR-ABL1. The invention further provides a process for the preparation of compounds of the invention, pharmaceutical preparations comprising such compounds and methods of using such compounds in the treatment of cancers.

(I)

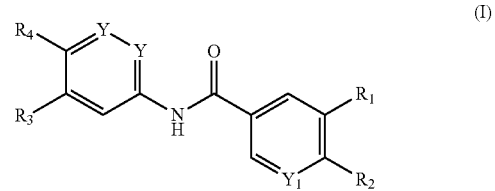

3 Claims, No Drawings

(56) References Cited

U.S. PATENT DOCUMENTS

| | | |
|---|---|---|
| 2012/0149910 A1 | 6/2012 | Mihara et al. |
| 2013/0053370 A1 | 2/2013 | Son et al. |

FOREIGN PATENT DOCUMENTS

| | | |
|---|---|---|
| WO | 03/055477 A1 | 7/2003 |
| WO | 2004/005281 A1 | 1/2004 |
| WO | 2006/039718 A2 | 4/2006 |
| WO | 2008/021725 A2 | 2/2008 |
| WO | 2008/051757 A1 | 5/2008 |
| WO | 2008/112695 A2 | 9/2008 |
| WO | 2008/124393 A1 | 10/2008 |
| WO | 2008/144253 A1 | 11/2008 |
| WO | 2009/016088 A1 | 2/2009 |
| WO | 2009/039127 A1 | 3/2009 |
| WO | 2009/152356 A2 | 12/2009 |
| WO | 2011/008788 A1 | 1/2011 |
| WO | 2011/060295 A1 | 5/2011 |
| WO | 2011/082400 A2 | 7/2011 |
| WO | 2012/129562 A2 | 9/2012 |
| WO | 2012/166951 A1 | 12/2012 |
| WO | 2013/171639 A1 | 11/2013 |
| WO | 2013/171640 A1 | 11/2013 |
| WO | 2013/171641 A1 | 11/2013 |
| WO | 2013/171642 A1 | 11/2013 |

OTHER PUBLICATIONS

Shin-Etsu Chemical Company Brochure for PHARMACOAT, 2005.

Eck et al., The interplay of structural information and functional studies inkinase drug design: insights from BCR-Abl. Current Opinion in Cell Biology, Current Science. London, GB. Apr. 1, 2009;21(2):288-95.

Li et al., Design, Synthesis and Biological Evaluation of 3-(1H-1,2,3-triazol-1-yl)benzamide derivatives as Potent Pan Bcr-Abl Inhibitors Including the Threonine 315—Isoleucine 315 Mutant. Journal of Medicinal Chemistry. Nov. 26, 2012;55(22):10033-46.

* cited by examiner

BENZAMIDE DERIVATIVES FOR INHIBITING THE ACTIVITY OF ABL1, ABL2 AND BCR-ABL1

CROSS-REFERENCED TO RELATED APPLICATIONS

This application is a U.S. National Phase filing of International Application No. PCT/IB2013/053771 filed 9 May 2013, which claims priority to U.S. Application No. 61/789,842 filed 15 Mar. 2013 and U.S. Application No. 61/647,174 filed 15 May 2012, the contents of which are incorporated herein by reference in their entirety.

FIELD OF THE INVENTION

The present invention relates to compounds capable of inhibiting the tyrosine The present invention relates to compounds capable of inhibiting the tyrosine kinase enzymatic activity of the Abelson protein (ABL1), the Abelson-related protein (ABL2) and related chimeric proteins, in particular BCR-ABL1. The invention further provides a process for the preparation of compounds of the invention, pharmaceutical preparations comprising such compounds and methods of using such compounds in the treatment of cancers.

BACKGROUND OF THE INVENTION

The tyrosine kinase activity of the ABL1 protein is normally tightly regulated, with the N-terminal cap region of the SH3 domain playing an important role. One regulatory mechanism involves the N-terminal cap glycine-2 residue being myristoylated and then interacting with a myristate binding site within the SH1 catalytic domain. A hallmark of chronic myeloid leukemia (CML) is the Philadelphia chromosome (Ph), formed by the t(9,22) reciprocal chromosome translocation in a haematopoietic stem cell. This chromosome carries the BCR-ABL1 oncogene which encodes the chimeric BCR-ABL1 protein, that lacks the N-terminal cap and has a constitutively active tyrosine kinase domain.

Although drugs that inhibit the tyrosine kinase activity of BCR-ABL1 via an ATP-competitive mechanism, such as Gleevec®/Glivec® (imatinib), Tasigna® (nilotinib) and Sprycel® (dasatinib), are effective in the treatment of CML, some patients relapse due to the emergence of drug-resistant clones, in which mutations in the SH1 domain compromise inhibitor binding. Although Tasigna® and Sprycel® maintain efficacy towards many Gleevec-resistant mutant forms of BCR-ABL1, the mutation in which the threonine-315 residue is replaced by an isoleucine (T315I) remains insensitive to all three drugs and can result in CML patients developing resistance to therapy. Therefore, inhibiting BCR-ABL1 mutations, such as T315I, remains an unmet medical need. In addition to CML, BCR-ABL1 fusion proteins are causative in a percentage of acute lymphocytic leukemias, and drugs targeting ABL kinase activity also have utility in this indication.

Agents targeting the myristoyl binding site (so-called allosteric inhibitors) have potential for the treatment of BCR-ABL1 disorders (J. Zhang, F. J. Adrian, W. Jahnke, S. W. Cowan-Jacob, A. G. Li, R. E. Iacob4, T. Sim, J. Powers, C. Dierks, F. Sun, G.-R. Guo, Q. Ding, B. Okram, Y. Choi, A. Wojciechowski, X. Deng, G. Liu, G. Fendrich, A. Strauss, N. Vajpai, S. Grzesiek, T. Tuntland, Y. Liu, B. Bursulaya, M. Azam, P. W. Manley, J. R. Engen, G. Q. Daley, M. Warmuth., N. S. Gray. Targeting BCR-ABL by combining allosteric with ATP-binding-site inhibitors. Nature 2010; 463:501-6). To prevent the emergence of drug resistance from ATP inhibitor and/or allosteric inhibitor use, a combination treatment using both types of inhibitor can be developed for the treatment of BCR-ABL1 related disorders. In particular, the need exists for small molecules, or combinations thereof, that inhibit the activity of BCR-ABL1 and BCR-ABL1 mutations via the ATP binding site, the myristoyl binding site or a combination of both sites.

Further, inhibitors of ABL1 kinase activity have the potential to be used as therapies for the treatment of metastatic invasive carcinomas and viral infections such as pox and Ebola viruses.

The compounds from the present invention also have the potential to treat or prevent diseases or disorders associated with abnormally activated kinase activity of wild-type Abl, including non-malignant diseases or disorders, such as CNS diseases in particular neurodegenerative diseases (for example Alzheimer's, Parkinson's diseases), motoneuroneuron diseases (amyotophic lateral sclerosis), muscular dystrophies, autoimmune and inflammatory diseases (diabetes and pulmonary fibrosis), viral infections, prion diseases.

SUMMARY OF THE INVENTION

In one aspect, the present invention provides compounds of formula (I):

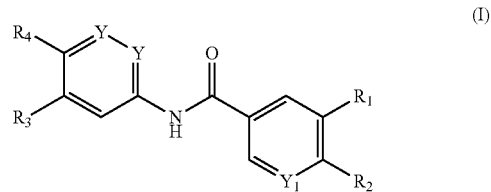

in which:

Y at each occurrence is independently selected from N and CH;

$Y_1$ is selected from N and $CR_5$; wherein $R_5$ is selected from hydrogen, methoxy and imidazolyl; wherein said imidazolyl is unsubstituted or substituted with methyl;

$R_1$ is selected from pyrazolyl, thiazolyl, pyrrolyl, imidazolyl, isoxazolyl, furanyl and thienyl; wherein said thiazolyl, pyrrolyl, imidazolyl, isoxazolyl, furanyl or thienyl of $R_1$ is unsubstituted or substituted with 1 to 3 $R_6$ groups;

$R_2$ is selected from pyrrolidinyl, piperidinyl, azetidinyl, morpholino, piperazinyl, 2-oxa-6-azaspiro[3.4]-octanyl, 3-azabicyclo[3.1.0]hexan-3-yl, pyrrolo[3,4-c]pyrazol-5(1H,4H,6H)-yl, hexahydropyrrolo[3,4-c]pyrrolyl, 6-oxo-2,7-diazaspiro[4.4]-nonanyl, 1H-pyrrolo[3,4-c]pyridinyl, 1,4-oxazepan-4-yl, 2-oxooxazolidinyl, 1,4-diazepanyl, tetrahydro-2H-pyranyl, 3,6-dihydro-2H-pyranyl, 3,8-dioxa-10-azabicyclo[4.3.1]decanyl, —$OR_{5b}$ and —$NR_{5a}R_{5b}$; wherein said piperidinyl, azetidinyl, morpholino, piperazinyl, 1,4-oxazepan-4-yl, pyrrolo[3,4-c]pyrazol-5(1H,4H,6H)-yl, 2-oxa-6-azaspiro[3.4]-octanyl, 3-azabicyclo[3.1.0]hexan-3-yl, hexahydropyrrolo[3,4-c]pyrrolyl, 6-oxo-2,7-diazaspiro[4.4]-nonanyl, 1H-pyrrolo[3,4-c]pyridinyl, 2-oxooxazolidinyl, 1,4-diazepanyl, tetrahydro-2H-pyranyl, 3,6-dihydro-2H-pyranyl, or 3,8-dioxa-10-azabicyclo[4.3.1]decanyl of $R_2$ is unsubstituted or substituted with 1 to 3 $R_7$ groups; wherein said pyrrolidinyl of $R_2$ is unsubstituted or substituted with 2 or 3 $R_7$ groups;

$R_3$ is selected from hydrogen and halo;

$R_4$ is selected from —$SF_5$ and —$Y_2$—$CF_2$—$Y_3$;

$R_{5a}$ is selected from hydrogen and $C_{1-4}$alkyl;

R$_{5b}$ is selected from C$_{1-4}$alkyl and tetrahydro-2H-pyran-4-yl; wherein said alkyl of R$_{5b}$ is unsubstituted or substituted with 1 to 3 groups independently selected from hydroxy and dimethyl-amino;

R$_6$ at each occurrence is independently selected from hydrogen, hydroxy, methyl, hydroxy, methoxy, cyano, trifluoromethyl, hydroxy-methyl, halo, amino, fluoro-ethyl, ethyl, cyclopropyl and dimethyl-amino-carbonyl;

R$_7$ at each occurrence is independently selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyl)oxy, carboxy, methoxy-carbonyl, phosphonooxy, cyano and amino-carbonyl; or two R$_7$ groups combine with the atom to which they are attached to form a ring selected from cyclopropyl, azetidin-3-yl and 3-azabicyclo[3.1.0]hexan-3-yl; with the proviso that when two R$_7$ groups are attached to the same carbon the R$_7$/R$_7$ combination is not: hydroxy/hydroxy; amine/amine; or hydroxy/halo;

Y$_2$ is selected from CF$_2$, O and S(O)$_{0-2}$; and

Y$_3$ is selected from hydrogen, halo, methyl, difluoromethyl and trifluoromethyl.

In a second aspect, the present invention provides a pharmaceutical composition which contains a compound of formula (I) or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of BCR-ABL1 activity can prevent, inhibit or ameliorate the pathology and/or symptomology of the diseases, which method comprises administering to the animal a therapeutically effective amount of a compound of formula (I) or a N-oxide derivative, individual isomers and mixture of isomers thereof, or a pharmaceutically acceptable salt thereof.

In a fourth aspect, the present invention provides the use of a compound of formula (I) in the manufacture of a medicament for treating a disease in an animal in which BCR-ABL1 activity contributes to the pathology and/or symptomology of the disease.

In a fifth aspect, the present invention provides a process for preparing compounds of formula (I) and the N-oxide derivatives, prodrug derivatives, protected derivatives, individual isomers and mixture of isomers thereof, and the pharmaceutically acceptable salts thereof.

DEFINITIONS

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Alkyl" refers to a fully saturated branched or unbranched hydrocarbon moiety having up to 20 carbon atoms. Unless otherwise provided, alkyl refers to hydrocarbon moieties having 1 to 7 carbon atoms (C$_{1-7}$alkyl), or 1 to 4 carbon atoms (C$_{1-4}$alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups. Halo-substituted-alkyl and halo-substituted-alkoxy, can be either straight-chained or branched and includes, methoxy, ethoxy, difluoromethyl, trifluoromethyl, pentafluoroethyl, difluoromethoxy, trifluoromethoxy, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"BCR-ABL1" refers to a fusion protein created from the N-terminal exons of the breakpoint cluster region (BCR) gene and the major C-terminal part (exons 2-11) of the Abelson (ABL1) gene. The most common fusion transcripts encode for a 210-kDa protein (p210 BCR-ABL1), although rarer transcripts encode a 190-kDa protein (p190 BCR-ABL1) and a 230-kDa protein (p230 BCR-ABL1). The ABL1 sequences of these proteins contains an ABL1 tyrosine kinase domain which is tightly regulated in the wild-type protein, but constitutively activated in the BCR-ABL1 fusion proteins. This deregulated tyrosine kinase interacts with multiple cellular signalling pathways leading to transformation and deregulated proliferation of the cells.

"BCR-ABL1 mutants" refers to the numerous single site mutations in BCR-ABL1 including: Glu255→Lysine, Glu255→Valine, Thr315→Isoleucine, Met244→Val, Phe317→Leu, Leu248→Val, Met343→Thr, Gly250→Ala, Met351→Thr, Gly250→Glu, Glu355→Gly, Gln252→His, Phe358→Ala, Gln252→Arg, Phe359→Val, Tyr253→His, Val379→Ile, Tyr253→Phe, Phe382→Leu, Glu255→Lys, Leu387→Met, Glu255→Val, His396→Pro, Phe311→Ile, His396→Arg, Phe311→Leu, Ser417→Tyr, Thr315→Ile, Glu459→Lys and Phe486→Ser.

"Heteroaryl" is as defined for aryl above where one or more of the ring members is a heteroatom. For example C$_{5-10}$heteroaryl is a minimum of 5 members as indicated by the carbon atoms but that these carbon atoms can be replaced by a heteroatom. Consequently, C$_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, C$_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, C$_{1-4}$alkyl or a nitrogen protecting group. For example, C$_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

Compounds of formula (I) may have different isomeric forms. For example, any asymmetric carbon atom may be present in the (R)-, (S)- or (R,S)-configuration, preferably in the (R)- or (S)-configuration. Substituents at a double bond or especially a ring may be present in cis- (═Z—) or trans (═E-) form. The compounds may thus be present as mixtures of isomers or preferably as pure isomers, preferably as pure diastereomers or pure enantiomers. The following compound of the invention, for example, would exist in tautomeric form:

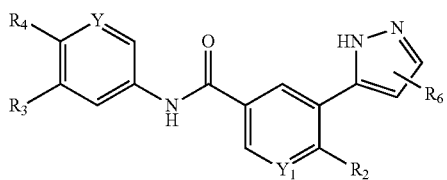

⇌

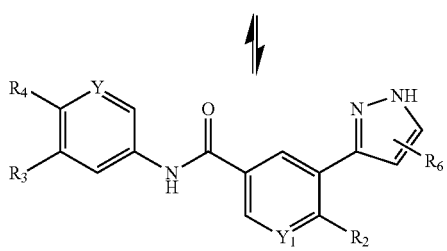

⇌

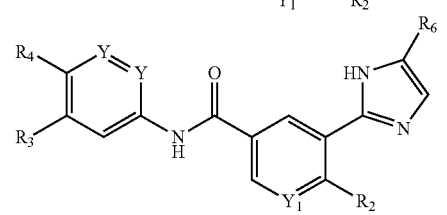

⇌

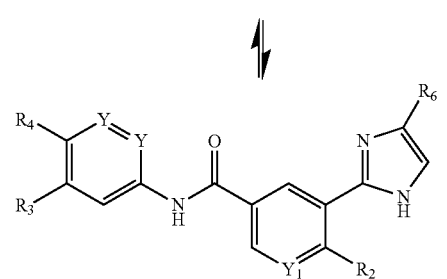

Where the plural form (e.g. compounds, salts) is used, this includes the singular (e.g. a single compound, a single salt). "A compound" does not exclude that (e.g. in a pharmaceutical formulation) more than one compound of the formula (I) (or a salt thereof) is present, the "a" merely representing the indefinite article. "A" can thus preferably be read as "one or more", less preferably alternatively as "one".

Wherever a compound or compounds of the formula (I) are mentioned, this is further also intended to include N-oxides of such compounds and/or tautomers thereof.

The term "and/or an N-oxide thereof, a tautomer thereof and/or a (preferably pharmaceutically acceptable) salt thereof" especially means that a compound of the formula (I) may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula (I) and/or any of these forms or mixtures of two or more of such forms.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include, but are not limited to, isotopes of hydrogen, carbon, nitrogen and oxygen such as $^2$H (D or deuterium), $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

For example, a compound of the invention can incorporate deuterium on the pyrrolidinyl ring as shown:

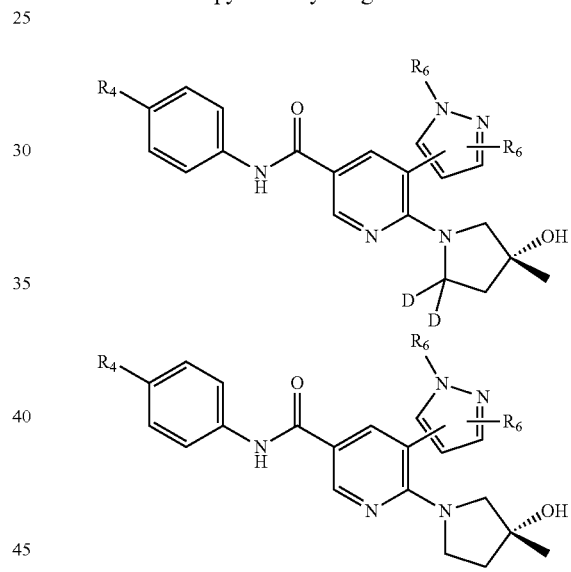

DESCRIPTION OF PREFERRED EMBODIMENTS

The present invention relates to compounds capable of inhibiting the activity of BCR-ABL1 or mutants of BCR-ABL1 through the allosteric, myristoyl binding site.

In one embodiment, with respect to compounds of the invention, are compounds of formula (Ia):

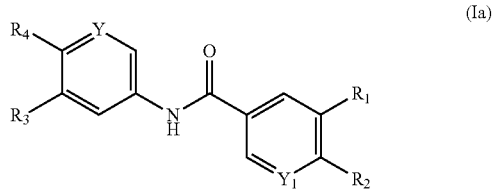

in which: R₁ is selected from pyrazolyl, thiazolyl, pyrrolyl, imidazolyl, isoxazolyl, furanyl and thienyl; wherein said pyrazolyl, thiazolyl, pyrrolyl, imidazolyl, isoxazolyl, furanyl or thienyl of R₁ is unsubstituted or substituted with 1 to 3 R₆ groups;

R₂ is selected from pyrrolidinyl, piperidinyl, azetidinyl, morpholino, piperazinyl, 2-oxa-6-azaspiro[3.4]-octanyl, 3-azabicyclo[3.1.0]hexan-3-yl, pyrrolo[3,4-c]pyrazol-5(1H,4H,6H)-yl, hexahydropyrrolo[3,4-c]pyrrolyl, 6-oxo-2,7-diazaspiro[4.4]-nonanyl, 1H-pyrrolo[3,4-c]pyridinyl, 1,4-oxazepan-4-yl, 2-oxooxazolidinyl, 1,4-diazepanyl, tetrahydro-2H-pyranyl, 3,6-dihydro-2H-pyranyl, 3,8-dioxa-10-azabicyclo[4.3.1]decanyl, —OR₅ᵦ and —NR₅ₐR₅ᵦ; wherein said piperidinyl, azetidinyl, morpholino, piperazinyl, 1,4-oxazepan-4-yl, pyrrolo[3,4-c]pyrazol-5(1H,4H,6H)-yl, 2-oxa-6-azaspiro[3.4]-octanyl, 3-azabicyclo[3.1.0]hexan-3-yl, hexahydropyrrolo[3,4-c]pyrrolyl, 6-oxo-2,7-diazaspiro[4.4]-nonanyl, 1H-pyrrolo[3,4-c]pyridinyl, 2-oxooxazolidinyl, 1,4-diazepanyl, tetrahydro-2H-pyranyl, 3,6-dihydro-2H-pyranyl, or 3,8-dioxa-10-azabicyclo[4.3.1]decanyl or R₂ is unsubstituted or substituted with 1 to 3 R₇ groups; wherein said pyrrolidinyl of R₂ is unsubstituted or substituted with 2 or 3 R₇ groups;

R₃ is selected from hydrogen and halo;

R₄ is selected from —SF₅ and —Y₂—CF₂—Y₃;

R₅ₐ is selected from hydrogen and $C_{1-4}$alkyl;

R₅ᵦ is selected from ethyl, hydroxy-ethyl, hydroxy-propyl, dimethyl-amino-propyl, 2,4-dihydroxybutyl and tetrahydro-2H-pyran-4-yl;

R₆ at each occurrence is independently selected from hydrogen, hydroxy, methyl, methoxy, cyano, trifluoromethyl, hydroxy-methyl, halo, amino, fluoro-ethyl, ethyl, cyclopropyl and dimethyl-amino-carbonyl;

R₇ at each occurrence is independently selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyl)oxy, carboxy, methoxy-carbonyl, phosphonooxy, cyano and amino-carbonyl; or two R₇ groups combine with the atom to which they are attached to form a ring selected from cyclopropyl, azetidin-3-yl and 3-azabicyclo[3.1.0]hexan-3-yl;

Y is selected from CH and N;

Y₁ is selected from N and CR₅; wherein R₅ is selected from hydrogen, methoxy and imidazolyl; wherein said imidazolyl is unsubstituted or substituted with methyl;

Y₂ is selected from CF₂, O and S(O)₀₋₂; and

Y₃ is selected from hydrogen, halo, methyl, difluoromethyl and trifluoromethyl; or the pharmaceutically acceptable salts thereof.

In a further embodiment are compounds of formula (Ic):

(Ic)

R₄ is selected from —SF₅ and —Y₂—CF₂—Y₃;

R₆ at each occurrence is independently selected from hydrogen, hydroxy, methyl, methoxy, cyano, trifluoromethyl, hydroxy-methyl, halo, amino, fluoro-ethyl, ethyl and cyclopropyl;

R₇ at each occurrence is selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, cyano and amino-carbonyl; or two R₇ groups combine with the atom to which they are attached to form a ring selected from cyclopropyl, azetidin-3-yl and 3-azabicyclo[3.1.0]hexan-3-yl;

Y₁ is selected from CH and N;

Y₂ is selected from CF₂, O and S(O)₀₋₂;

Y₃ is selected from hydrogen, fluoro, chloro, methyl, difluoromethyl and trifluoromethyl; or the pharmaceutically acceptable salts thereof.

In a further embodiment are compounds, or pharmaceutically acceptable salts thereof, selected from:

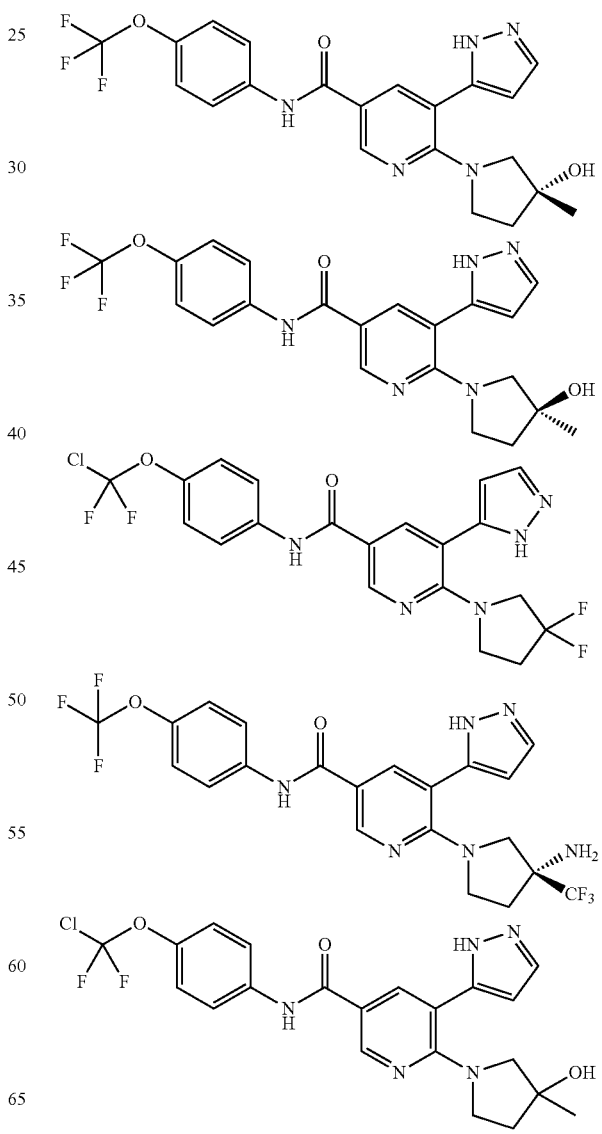

in which: R₃ is selected from hydrogen and halo;

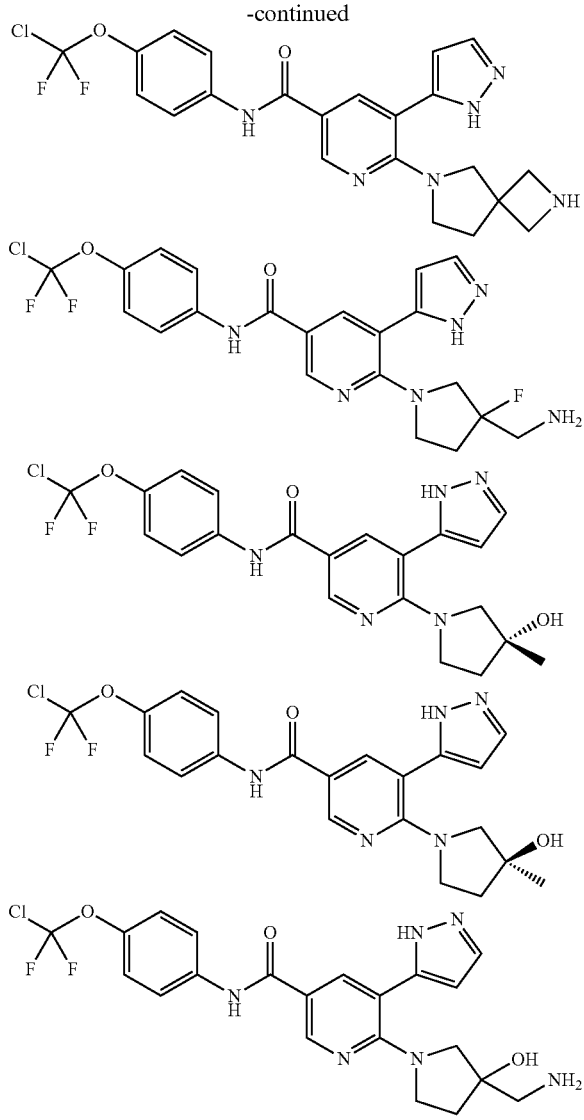

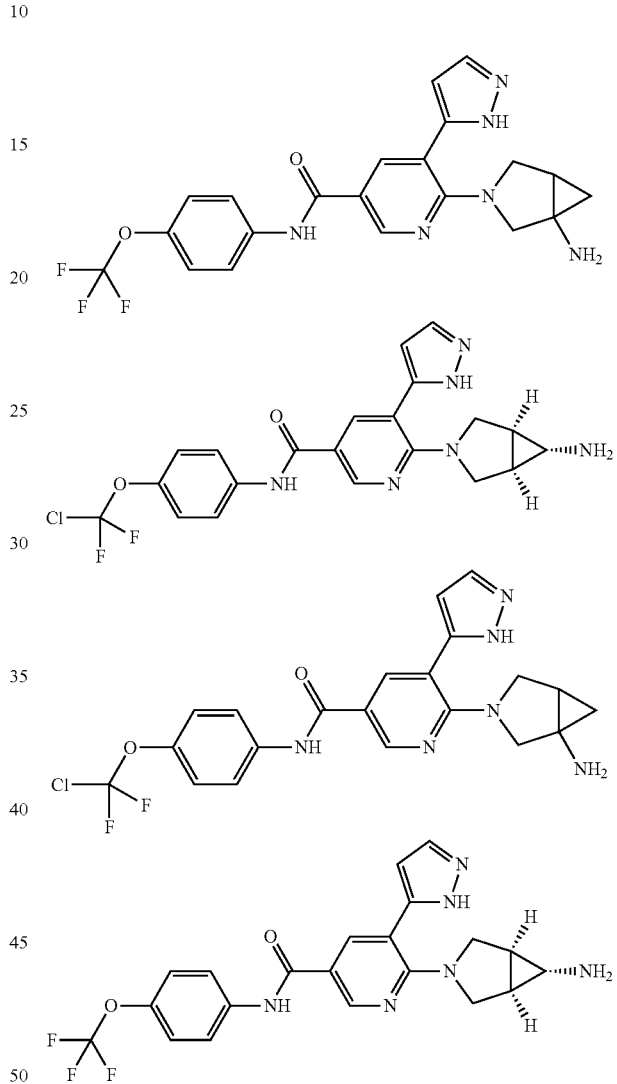

amino, dimethyl-amino, cyano and amino-carbonyl; or two R₇ groups combine with the atom to which they are attached to form a ring selected from cyclopropyl, azetidin-3-yl and 3-azabicyclo[3.1.0]hexan-3-yl; $Y_1$ is selected from CH and N; $Y_2$ is selected from $CF_2$, O and $S(O)_{0-2}$; $Y_3$ is selected from hydrogen, fluoro, chloro, methyl, difluoromethyl and trifluoromethyl; or the pharmaceutically acceptable salts thereof.

In a further embodiment are compounds, or the pharmaceutically acceptable salt thereof, selected from:

In another embodiment are compounds of formula (Id):

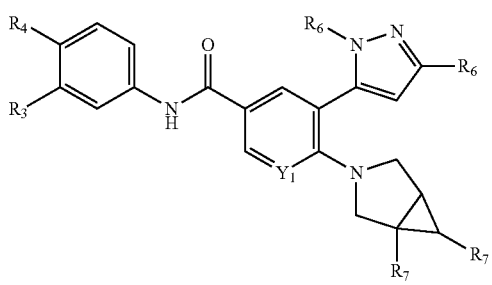

in which: R₃ is selected from hydrogen and halo; R₄ is selected from —SF₅ and —Y₂—CF₂—Y₃; R₆ at each occurrence is independently selected from hydrogen, hydroxy, methyl, methoxy, cyano, trifluoromethyl, hydroxy-methyl, halo, amino, fluoro-ethyl, ethyl and cyclopropyl; R₇ at each occurrence is selected from hydroxy, halo, methyl, methoxy, hydroxy-methyl, amino, methyl-amino, amino-methyl, trifluoromethyl, 2-hydroxypropan-2-yl, methyl-carbonyl- In another embodiment are compounds of formula (Ie):

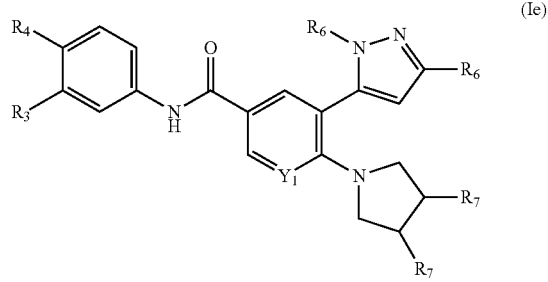

in which: $R_3$ is selected from hydrogen and halo; $R_4$ is selected from —$SF_5$ and —$Y_2$—$CF_2$—$Y_3$; $R_6$ at each occurrence is independently selected from hydrogen, hydroxy, methyl, methoxy, cyano, trifluoromethyl, hydroxy-methyl, halo, amino, fluoro-ethyl, ethyl and cyclopropyl; each $R_7$ is independently selected from fluoro, hydroxy, amino, methoxy and amino-methyl; or both $R_7$ groups are hydrogen (that is, the pyrrolidine ring is unsubstituted); $Y_1$ is selected from CH and N; $Y_2$ is selected from $CF_2$, O and $S(O)_{0-2}$; $Y_3$ is selected from hydrogen, fluoro, chloro, methyl, difluoromethyl and trifluoromethyl; or the pharmaceutically acceptable salts thereof.

In a further embodiment are compounds, or the pharmaceutically acceptable salt thereof, selected from:

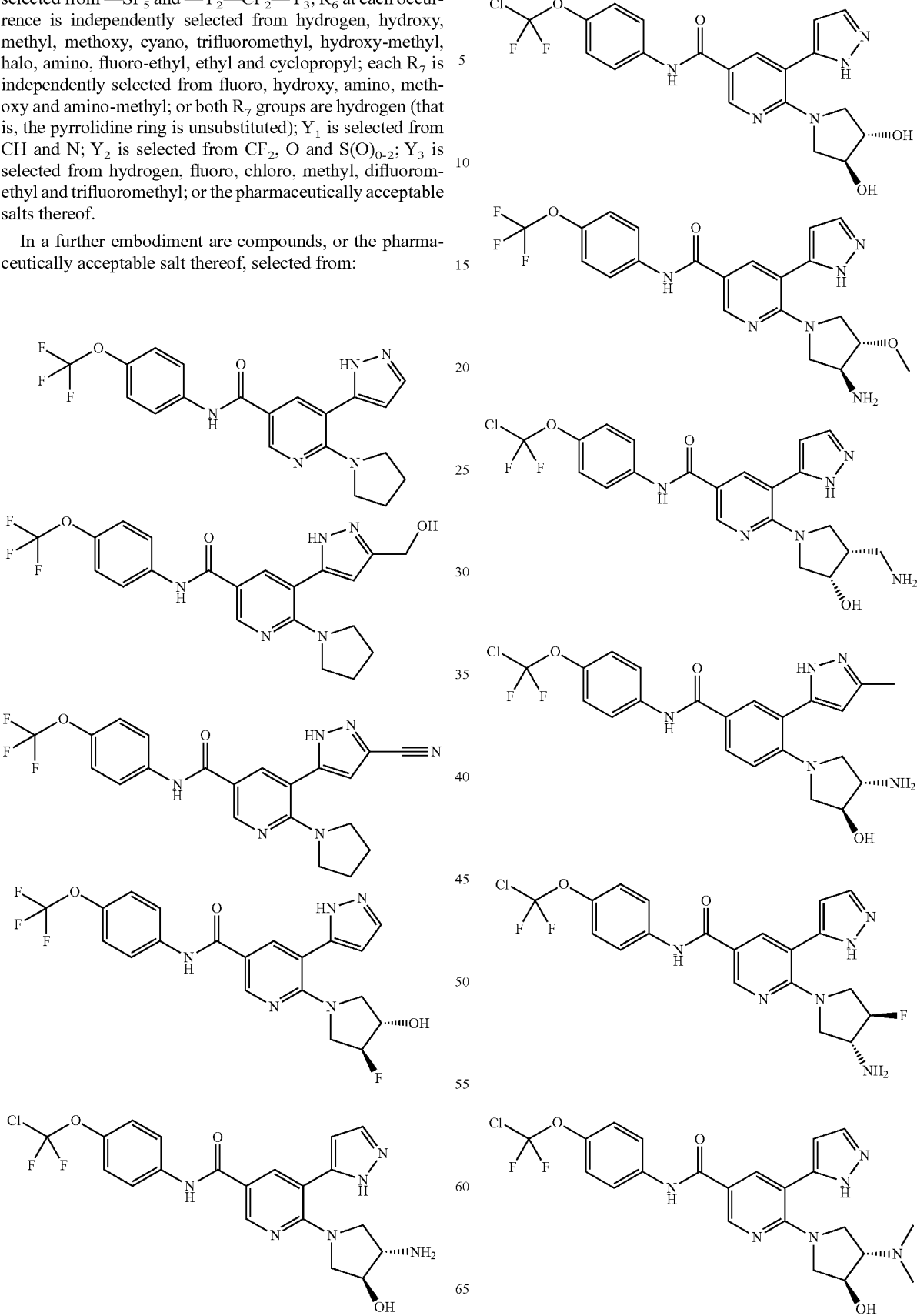

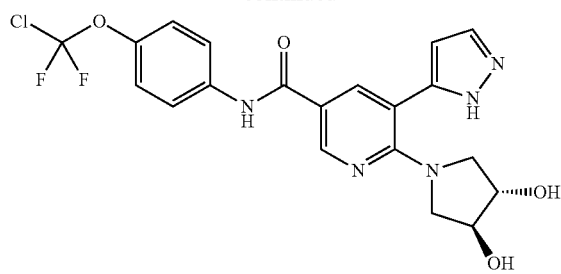

In another embodiment are compounds of formula (If):

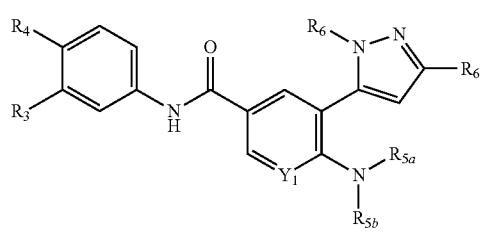

in which: $R_3$ is selected from hydrogen and halo; $R_4$ is selected from —$SF_5$ and —$Y_2$—$CF_2$—$Y_3$; $R_{5a}$ is selected from hydrogen and methyl; $R_{5b}$ is selected from ethyl, hydroxy-ethyl, hydroxy-propyl, dimethyl-amino-propyl, 2,4-dihydroxybutyl, 3,4-dihydroxybutyl and tetrahydro-2H-pyran-4-yl; $R_6$ at each occurrence is independently selected from hydrogen, hydroxy, methyl, methoxy, cyano, trifluoromethyl, hydroxy-methyl, halo, amino, fluoro-ethyl, ethyl and cyclopropyl; $Y_1$ is selected from N and $CR_5$; wherein $R_5$ is selected from hydrogen, methoxy and imidazolyl; wherein said imidazolyl is unsubstituted or substituted with methyl; $Y_2$ is selected from $CF_2$, O and $S(O)_{0-2}$; and $Y_3$ is selected from hydrogen, halo, methyl, difluoromethyl and trifluoromethyl; or the pharmaceutically acceptable salts thereof.

In a further embodiment are compounds, or the pharmaceutically acceptable salt thereof, selected from:

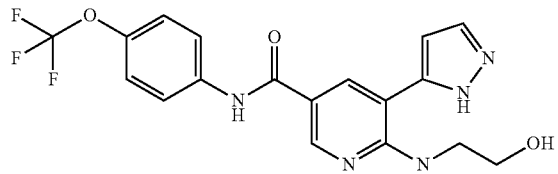

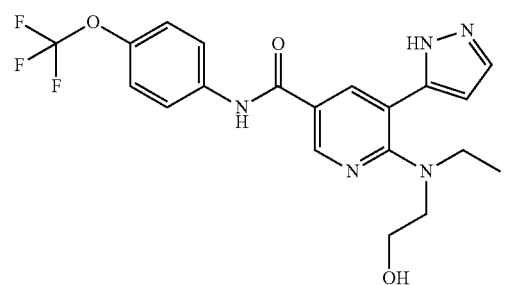

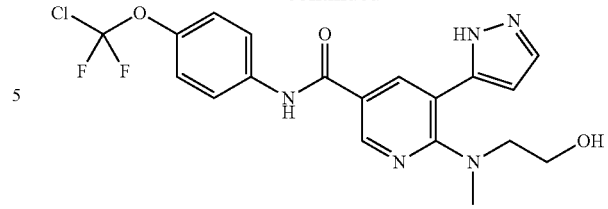

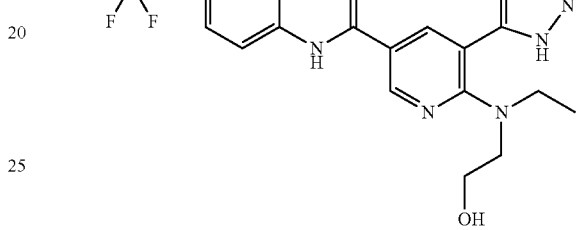

-continued

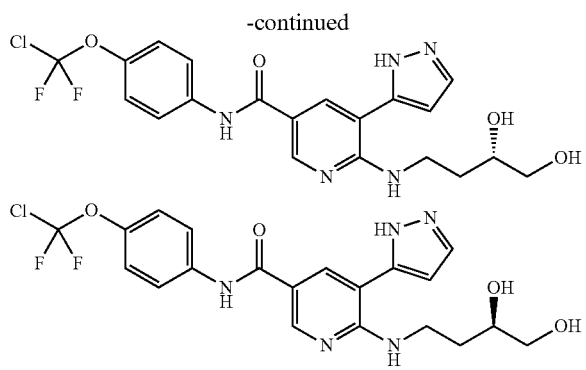

In another embodiment are compounds of formula (Ig):

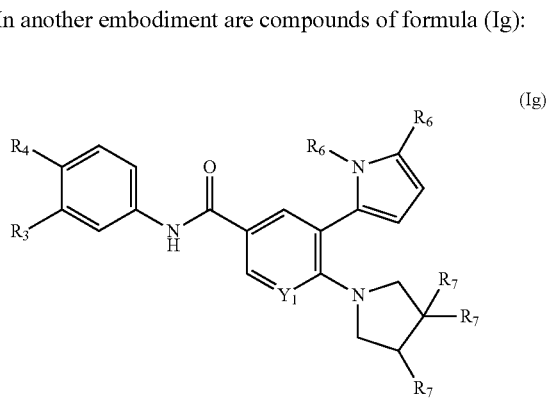
(Ig)

in which: $R_3$ is selected from hydrogen and halo; $R_4$ is selected from —$SF_5$ and —$Y_2$—$CF_2$—$Y_3$; $R_6$ is independently selected from hydrogen, hydroxy, methyl, methoxy, cyano, trifluoromethyl, hydroxy-methyl, halo, amino, fluoro-ethyl, ethyl, cyclopropyl and dimethyl-amino-carbonyl; $R_7$ at each occurrence is independently selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, cyano and amino-carbonyl; or two $R_7$ groups combine with the atom to which they are attached to form a ring selected from cyclopropyl, azetidin-3-yl and 3-azabicyclo[3.1.0]hexan-3-yl; $Y_1$ is selected from CH and N;

$Y_2$ is selected from $CF_2$, O and $S(O)_{0-2}$; $Y_3$ is selected from hydrogen, fluoro, chloro, methyl, difluoromethyl and trifluoromethyl; or the pharmaceutically acceptable salts thereof.

In another embodiment are compounds of formula (Ih):

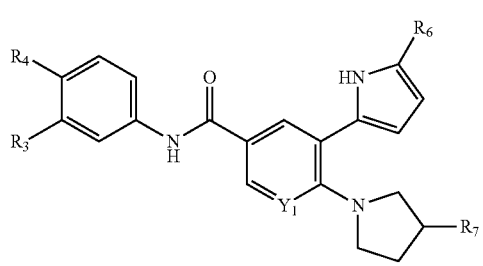
(Ih)

in which: $R_3$ is selected from hydrogen and halo; $R_4$ is selected from —$SF_5$ and —$Y_2$—$CF_2$—$Y_3$; $R_6$ at each occurrence is independently selected from hydrogen, hydroxy, methyl, methoxy, cyano, trifluoromethyl, hydroxy-methyl, halo, amino, fluoro-ethyl, ethyl, cyclopropyl and dimethyl-amino-carbonyl; $R_7$ is selected from hydroxy, methyl, methoxy, halo, hydroxy-methyl, amino, methyl-amino, amino-methyl, trifluoromethyl, 2-hydroxypropan-2-yl, methyl-carbonyl-amino, dimethyl-amino, cyano and amino-carbonyl; $Y_1$ is selected from N and $CR_5$; wherein $R_5$ is selected from hydrogen, methoxy and imidazolyl; wherein said imidazolyl is unsubstituted or substituted with methyl; $Y_2$ is selected from $CF_2$, O and $S(O)_{0-2}$; and $Y_3$ is selected from hydrogen, halo, methyl, difluoromethyl and trifluoromethyl; or the pharmaceutically acceptable salts thereof.

In a further embodiment are compounds, or the pharmaceutically acceptable salt thereof, selected from:

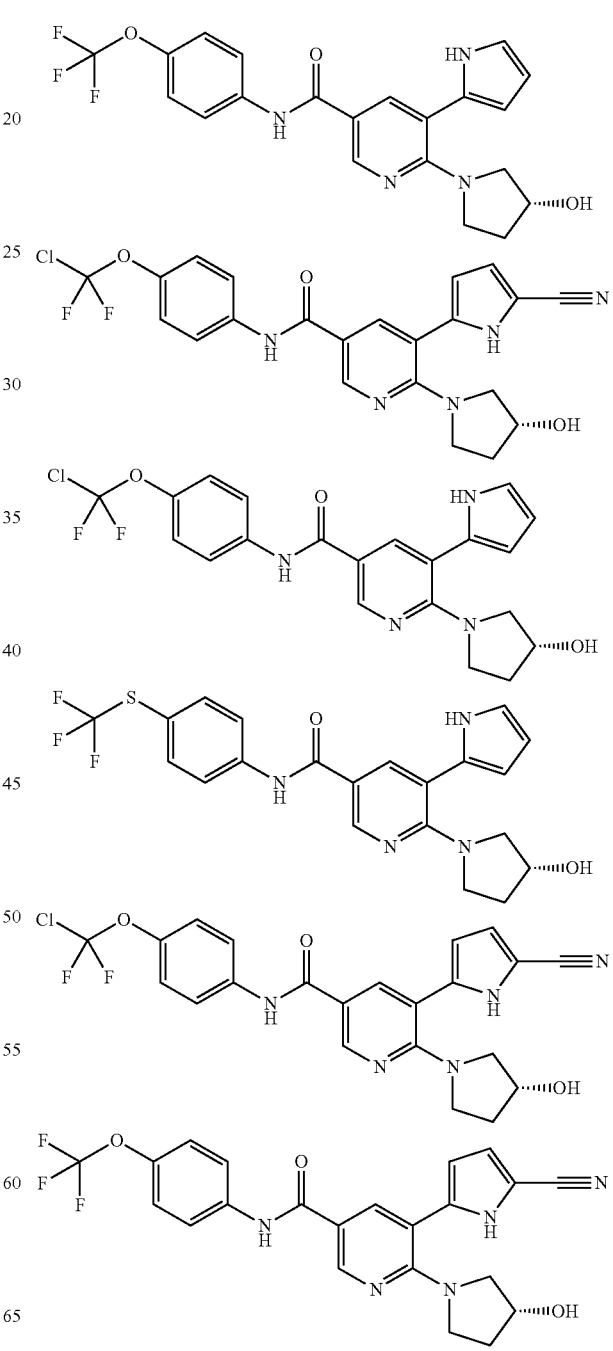

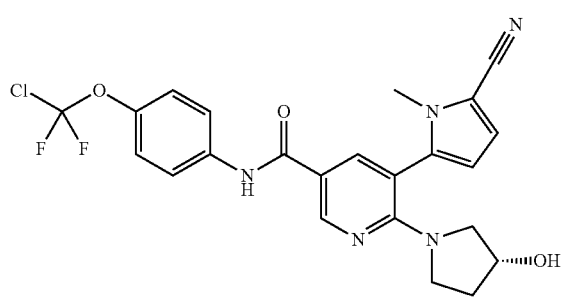

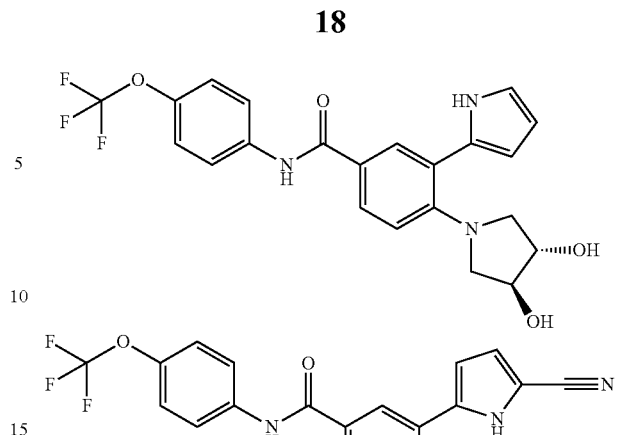

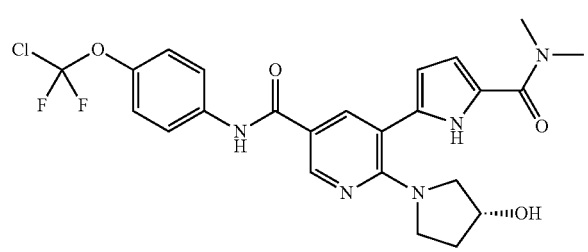 [SMILES: CN(C)C(=O)c1ccc(-c2cc(C(=O)Nc3ccc(OC(F)(F)Cl)cc3)cnc2N2CC[C@@H](O)C2)[nH]1]

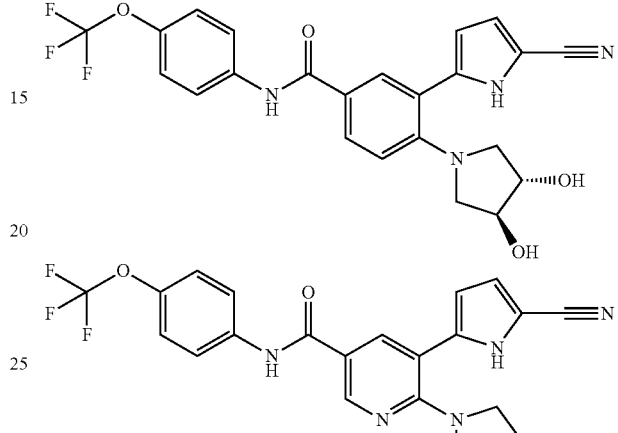

In another embodiment are compounds of formula (Ii):

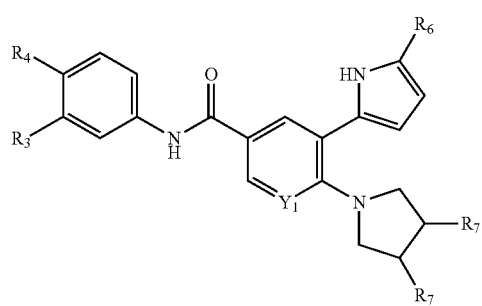

(Ii)

in which: R₃ is selected from hydrogen and halo; R₄ is selected from —SF₅ and —Y₂—CF₂—Y₃; R₆ at each occurrence is independently selected from hydrogen, hydroxy, methyl, methoxy, cyano, trifluoromethyl, hydroxy-methyl, halo, amino, fluoro-ethyl, ethyl and cyclopropyl; each R₇ is independently selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, cyano and amino-carbonyl; Y₁ is selected from N and CR₅; wherein R₅ is selected from hydrogen, methoxy and imidazolyl; wherein said imidazolyl is unsubstituted or substituted with methyl; Y₂ is selected from CF₂, O and S(O)₀₋₂; and Y₃ is selected from hydrogen, halo, methyl, difluoromethyl and trifluoromethyl; or the pharmaceutically acceptable salts thereof.

In a further embodiment are compounds, or the pharmaceutically acceptable salt thereof, selected from:

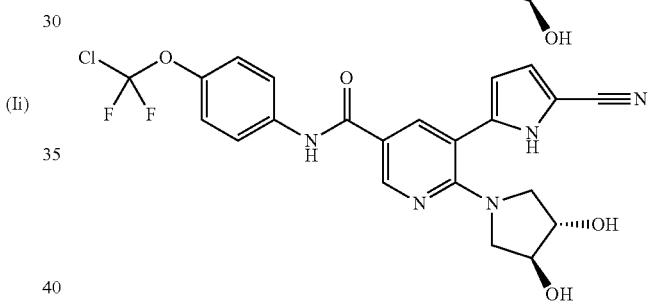

In another embodiment are compounds in which: R₁ is selected from thiazolyl, isoxazolyl, furanyl and thienyl; wherein said thiazolyl, isoxazolyl, furanyl or thienyl of R₁ is unsubstituted or substituted with 1 to 3 R₆ groups; R₂ is selected from pyrrolidinyl, piperidinyl, azetidinyl, morpholino, piperazinyl, 2-oxa-6-azaspiro[3.4]-octanyl, 3-azabicyclo[3.1.0]hexan-3-yl, pyrrolo[3,4-c]pyrazol-5(1H,4H, 6H)-yl, hexahydropyrrolo[3,4-c]pyrrolyl, 6-oxo-2,7-diazaspiro[4.4]-nonanyl, 1H-pyrrolo[3,4-c]pyridinyl, 1,4-oxazepan-4-yl, 2-oxooxazolidinyl, 1,4-diazepanyl, tetrahydro-2H-pyranyl, 3,6-dihydro-2H-pyranyl, 3,8-dioxa-10-azabicyclo[4.3.1]decanyl, —OR₅ᵦ and —NR₅ₐR₅ᵦ; wherein said pyrrolidinyl, piperidinyl, azetidinyl, morpholino, piperazinyl, 1,4-oxazepan-4-yl, pyrrolo[3,4-c]pyrazol-5(1H,4H,6H)-yl, 2-oxa-6-azaspiro[3.4]-octanyl, 3-azabicyclo[3.1.0]hexan-3-yl, hexahydropyrrolo[3,4-c]pyrrolyl, 6-oxo-2,7-diazaspiro[4.4]-nonanyl, 1H-pyrrolo[3,4-c] pyridinyl, 2-oxooxazolidinyl, 1,4-diazepanyl, tetrahydro-2H-pyranyl, 3,6-dihydro-2H-pyranyl, or 3,8-dioxa-10-azabicyclo[4.3.1]decanyl is unsubstituted or substituted with 1 to 3 R₇ groups; R₃ is selected from hydrogen and halo; R₄ is selected from —SF₅ and —Y₂—CF₂—Y₃; R₅ₐ is selected from hydrogen and C₁₋₄alkyl; R₅ᵦ is selected from ethyl, hydroxy-ethyl, hydroxy-propyl, dimethyl-amino-propyl and tetrahydro-2H-pyran-4-yl; R₆ at each occurrence is independently selected from hydrogen, hydroxy, methyl, methoxy, cyano, trifluoromethyl, hydroxy-methyl, halo, amino, fluoro-ethyl, ethyl and cyclopropyl; $R_7$ at each occurrence is independently selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, cyano and amino-carbonyl; or two $R_7$ groups combine with the atom to which they are attached to form a ring selected from cyclopropyl, azetidin-3-yl and 3-azabicyclo[3.1.0]hexan-3-yl; Y is selected from CH and N; $Y_1$ is selected from N and $CR_5$; wherein $R_5$ is selected from hydrogen, methoxy and imidazolyl; wherein said imidazolyl is unsubstituted or substituted with methyl; $Y_2$ is selected from $CF_2$, O and $S(O)_{0-2}$; and $Y_3$ is selected from hydrogen, halo, methyl, difluoromethyl and trifluoromethyl; or the pharmaceutically acceptable salts thereof.

In a further embodiment are compounds, or the pharmaceutically acceptable salt thereof, selected from:

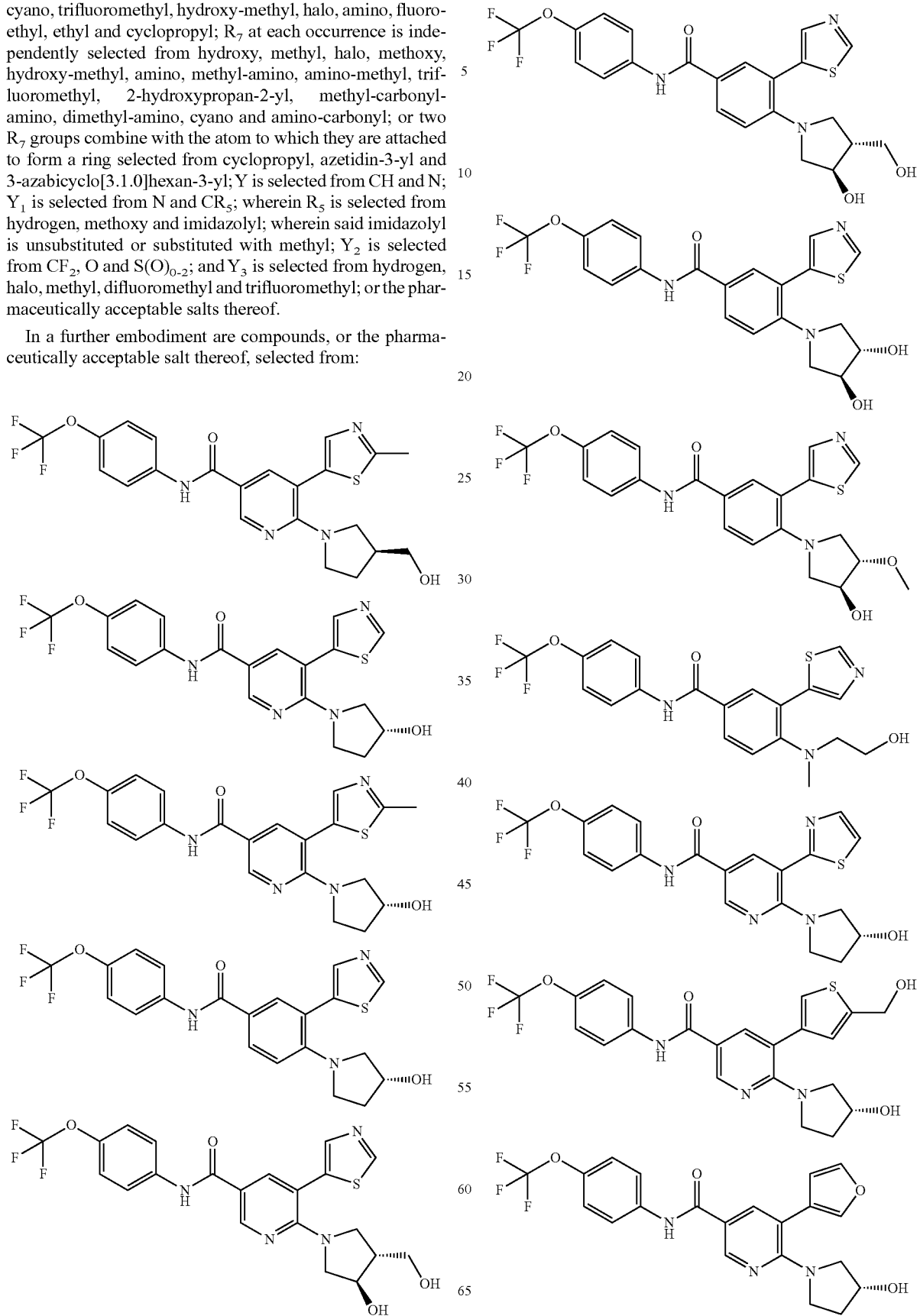

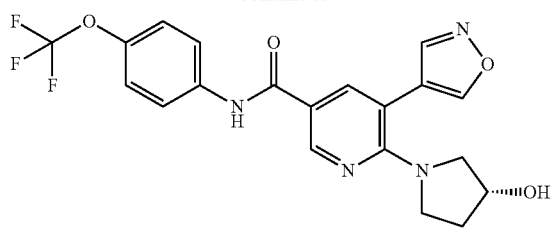

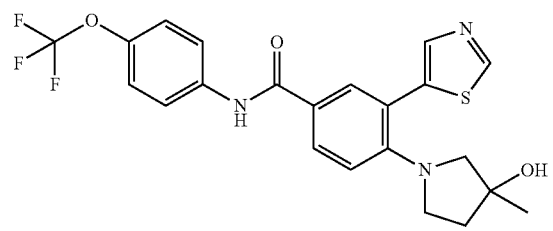

In another embodiment are compounds of formula (Ij):

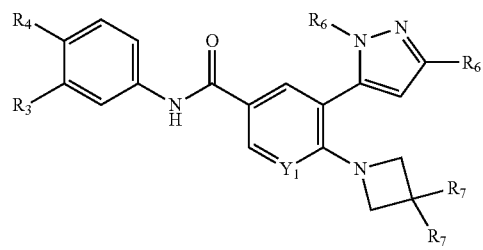

in which: $R_3$ is selected from hydrogen and halo; $R_4$ is selected from —$SF_5$ and —$Y_2$—$CF_2$—$Y_3$; $R_6$ at each occurrence is independently selected from hydrogen, hydroxy, methyl, methoxy, cyano, trifluoromethyl, hydroxy-methyl, halo, amino, fluoro-ethyl, ethyl and cyclopropyl; $R_7$ is selected from hydroxy, halo, methyl, methoxy, hydroxy-methyl, amino, methyl-amino, amino-methyl, trifluoromethyl, 2-hydroxypropan-2-yl, methyl-carbonyl-amino, dimethyl-amino, cyano and amino-carbonyl; or two $R_7$ groups combine with the atom to which they are attached to form a ring selected from cyclopropyl, azetidin-3-yl and 3-azabicyclo [3.1.0]hexan-3-yl; $Y_1$ is selected from CH and N; $Y_2$ is selected from $CF_2$, O and $S(O)_{0-2}$; $Y_3$ is selected from hydrogen, fluoro, chloro, methyl, difluoromethyl and trifluoromethyl; or the pharmaceutically acceptable salts thereof.

In a further embodiment are compounds, or the pharmaceutically acceptable salt thereof, selected from:

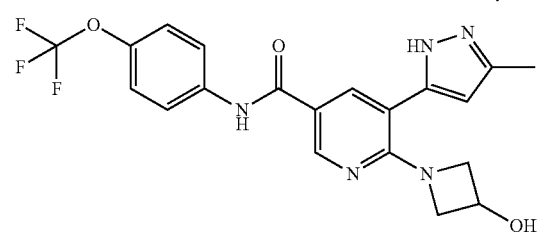

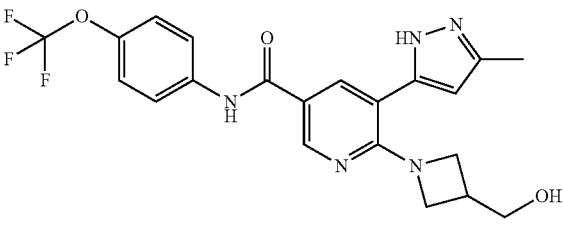

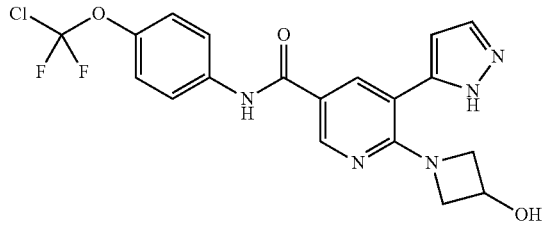

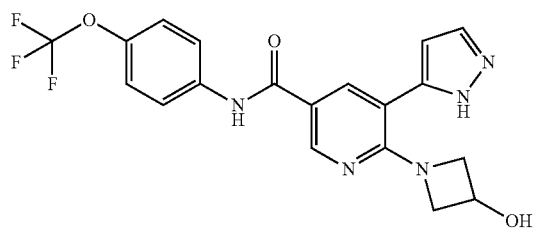

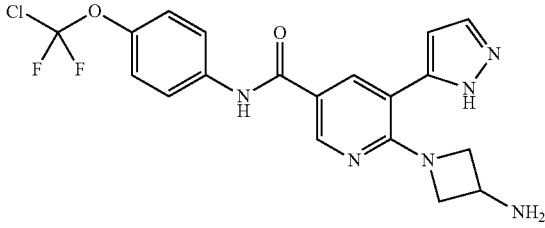

-continued

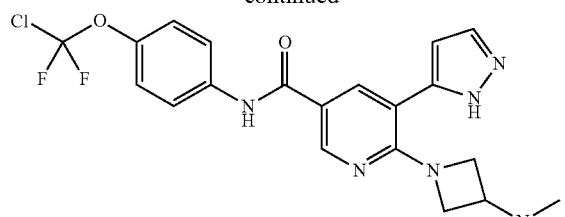
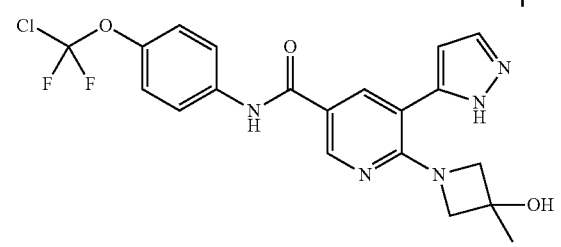
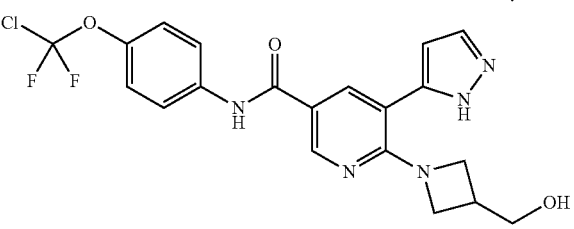
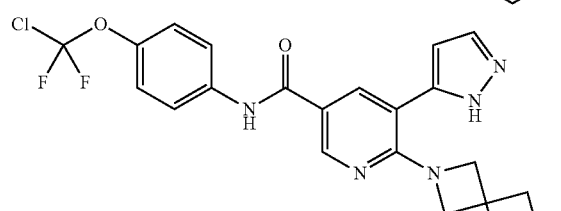
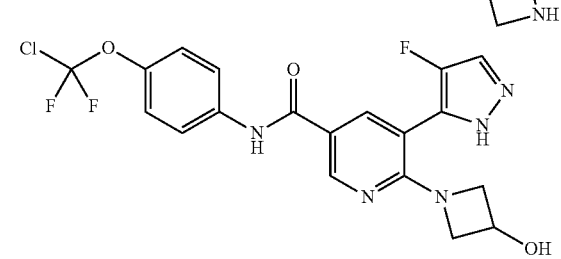
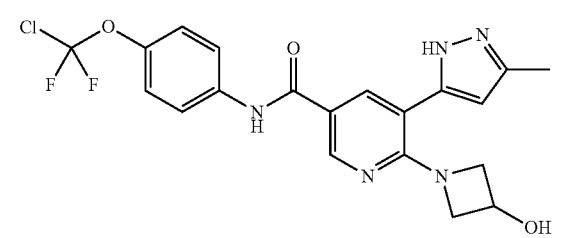
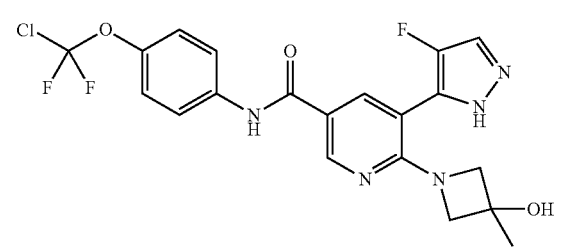

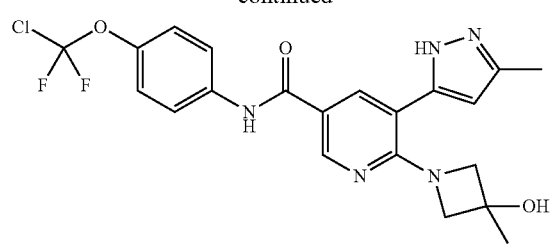
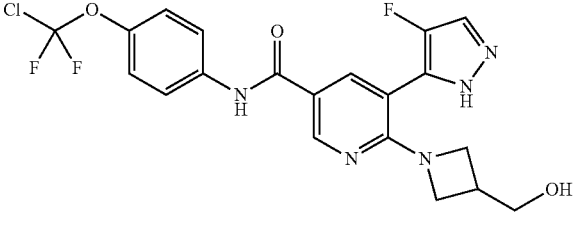
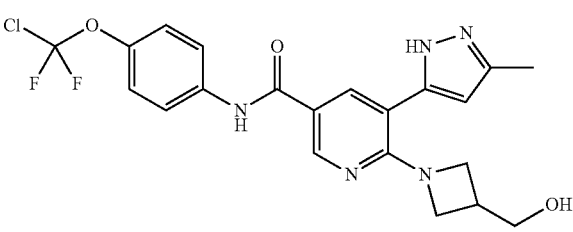

In another embodiment are compounds of formula (Ik):

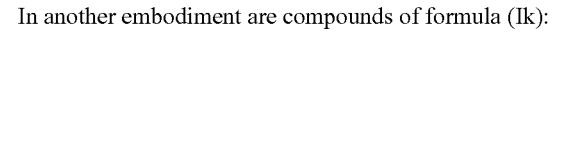

(Ik)

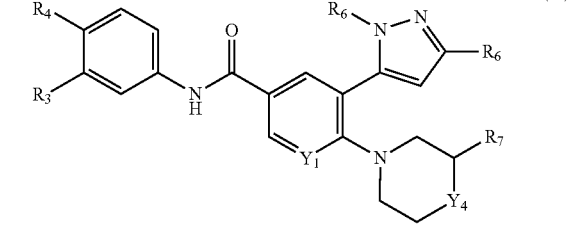

in which: $R_3$ is selected from hydrogen and halo; $R_4$ is selected from —$SF_5$ and —$Y_2$—$CF_2$—$Y_3$; $R_6$ at each occurrence is independently selected from hydrogen, hydroxy, methyl, methoxy, cyano, trifluoromethyl, hydroxy-methyl, halo, amino, fluoro-ethyl, ethyl and cyclopropyl; $R_7$ is selected from hydrogen, hydroxy, halo, methyl, methoxy, hydroxy-methyl, amino, methyl-amino, amino-methyl, difluoromethyl, fluoroethyl, trifluoromethyl, 2-hydroxypropan-2-yl, cyclopropyl, methyl-carbonyl-amino, dimethyl-amino, cyano and amino-carbonyl; or two $R_7$ groups combine with the atom to which they are attached to form a ring selected from cyclopropyl, azetidin-3-yl and 3-azabicyclo[3.1.0]hexan-3-yl; $Y_1$ is selected from CH and N; $Y_2$ is selected from $CF_2$, O and $S(O)_{0-2}$; $Y_3$ is selected from hydrogen, fluoro, chloro, methyl, difluoromethyl and trifluoromethyl; and $Y_4$ is selected from O, NH, $NR_7$ and $CR_7R_7$; or the pharmaceutically acceptable salts thereof.

In a further embodiment are compounds, or the pharmaceutically acceptable salt thereof, selected from:

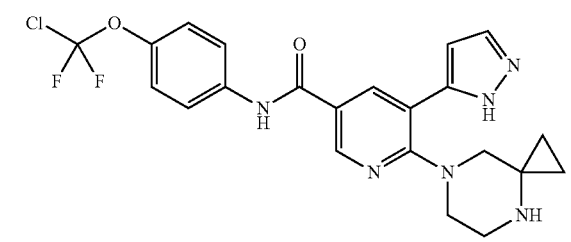
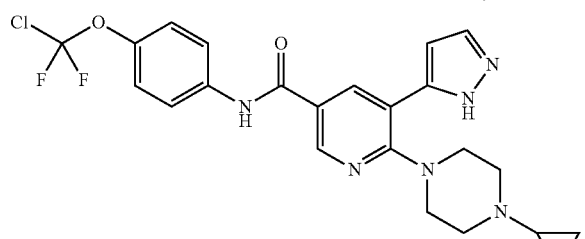
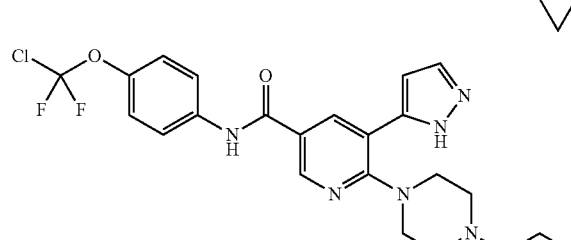
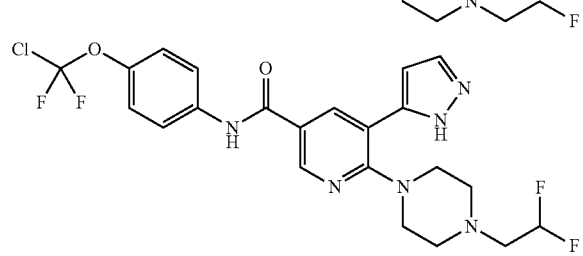
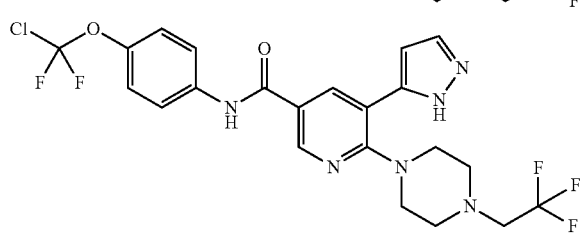
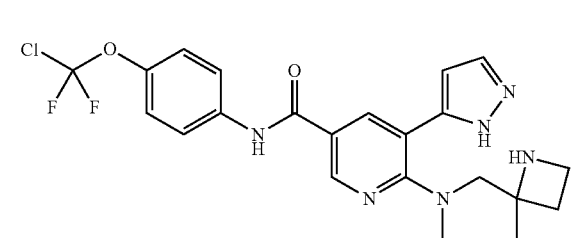
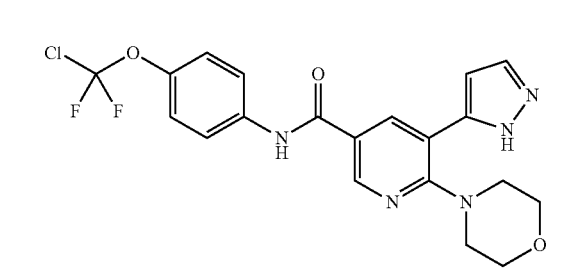
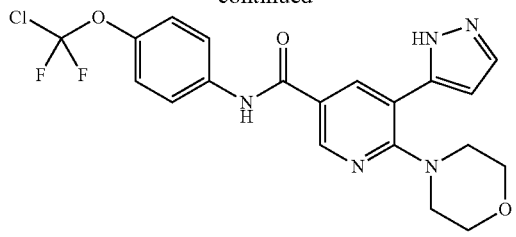
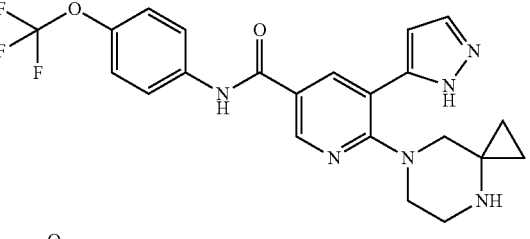
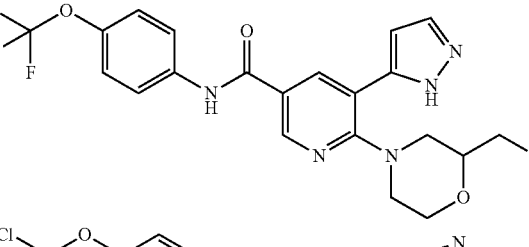
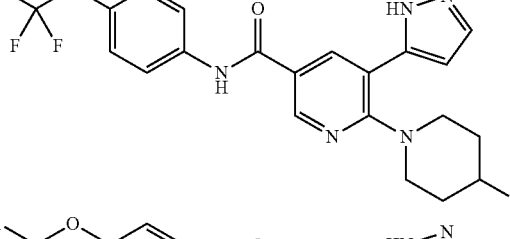
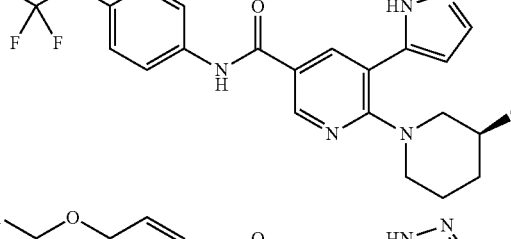
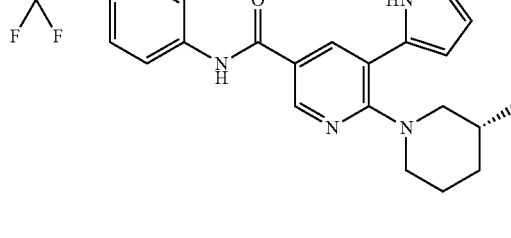
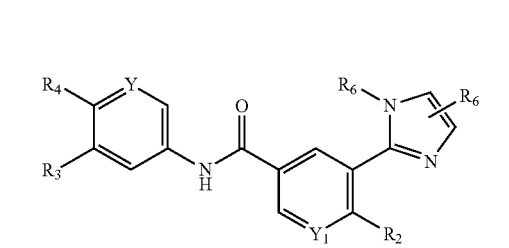
In another embodiment are compounds of formula (Im):
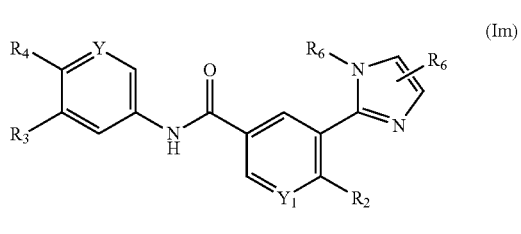

in which: $R_2$ is selected from pyrrolidinyl, piperidinyl, azetidinyl, morpholino, piperazinyl, 2-oxa-6-azaspiro[3.4]-octanyl, 3-azabicyclo[3.1.0]hexan-3-yl, pyrrolo[3,4-c]pyrazol-5(1H,4H,6H)-yl, hexahydropyrrolo[3,4-c]pyrrolyl, 6-oxo-2,7-diazaspiro[4.4]-nonanyl, 1H-pyrrolo[3,4-c]pyridinyl, 1,4-oxazepan-4-yl, 2-oxooxazolidinyl, 1,4-diazepanyl, tetrahydro-2H-pyranyl, 3,6-dihydro-2H-pyranyl, 3,8-dioxa-10-azabicyclo[4.3.1]decanyl, $-OR_{5b}$ and $-NR_{5a}R_{5b}$; wherein said pyrrolidinyl, piperidinyl, azetidinyl, morpholino, piperazinyl, 1,4-oxazepan-4-yl, pyrrolo[3,4-c]pyrazol-5(1H,4H,6H)-yl, 2-oxa-6-azaspiro[3.4]-octanyl, 3-azabicyclo[3.1.0]hexan-3-yl, hexahydropyrrolo[3,4-c]pyrrolyl, 6-oxo-2,7-diazaspiro[4.4]-nonanyl, 1H-pyrrolo[3,4-c]pyridinyl, 2-oxooxazolidinyl, 1,4-diazepanyl, tetrahydro-2H-pyranyl, 3,6-dihydro-2H-pyranyl, or 3,8-dioxa-10-azabicyclo[4.3.1]decanyl is unsubstituted or substituted with 1 to 3 $R_7$ groups; $R_3$ is selected from hydrogen and halo; $R_4$ is selected from $-SF_5$ and $-Y_2-CF_2-Y_3$; $R_6$ at each occurrence is independently selected from hydrogen, hydroxy, methyl, methoxy, cyano, trifluoromethyl, hydroxy-methyl, halo, amino, fluoro-ethyl, ethyl and cyclopropyl; $R_7$ at each occurrence is independently selected from hydroxy, methyl, halo, methoxy, hydroxy-methyl, amino, methyl-amino, amino-methyl, difluoromethyl, fluoroethyl, trifluoromethyl, 2-hydroxypropan-2-yl, methyl-carbonyl-amino, dimethyl-amino, cyclopropyl, cyano and amino-carbonyl; or two $R_7$ groups combine with the atom to which they are attached to form a ring selected from cyclopropyl, azetidin-3-yl and 3-azabicyclo[3.1.0]hexan-3-yl; Y is selected from CH and N; $Y_1$ is selected from N and $CR_5$; wherein $R_5$ is selected from hydrogen, methoxy and imidazolyl; wherein said imidazolyl is unsubstituted or substituted with methyl; $Y_2$ is selected from $CF_2$, O and $S(O)_{0-2}$; and $Y_3$ is selected from hydrogen, halo, methyl, difluoromethyl and trifluoromethyl; or the pharmaceutically acceptable salts thereof.

In a further embodiment are compounds, or the pharmaceutically acceptable salt thereof, selected from:

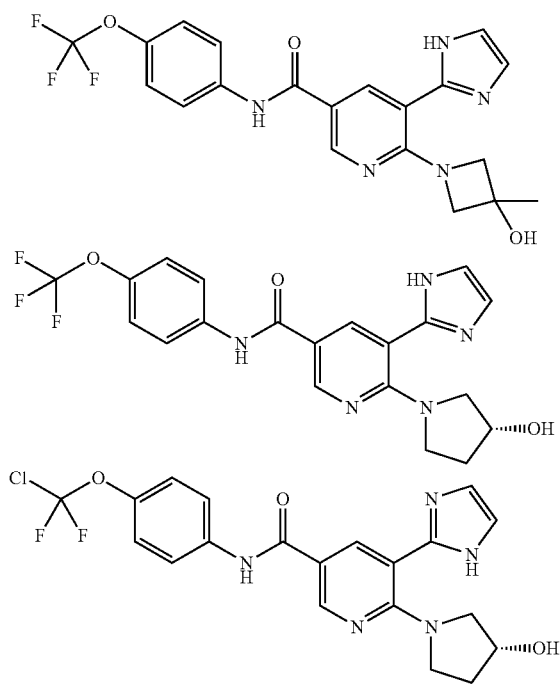

-continued

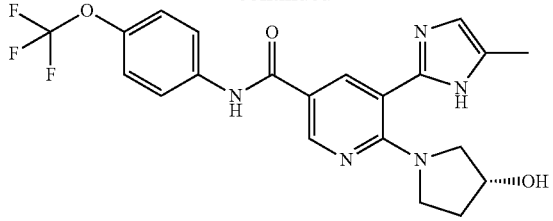

Pharmacology and Utility

On the basis of the inhibitory studies described in the "Assay" section below, a compound of formula (I) according to the invention shows therapeutic efficacy especially against disorders dependent on BCR-ABL1 activity. In particular, compounds of the present invention inhibit the allosteric or myristoyl binding site of BCR-ABL1 (including wild-type BCR-ABL1 and/or mutations thereof).

Combining an ATP-competitive inhibitor of BCR-ABL1 with an allosteric inhibitor of BCR-ABL1 delays acquired resistance in BCR-ABL1+KCL-22 cells, in vitro. Surprisingly, BCR-ABL1+KCL-22 cells treated every 3-4 days with a compound of the invention showed an acquired resistance after approximately 28 days whereas these same cells treated every 3-4 days with nilotinib or dasatinib showed an acquired resistance after only 18-21 days. Even more surprisingly, when BCR-ABL1+KCL-22 cells were treated every 3-4 days with a combination of a compound of the invention and either nilotinib or dasatinib, no acquired resistance was observed in at least the first 60 days. Therefore, myristoyl-binding site compounds of the present invention, in combination with BCR-ABL1 inhibitors that bind to the ATP binding site are especially important for the treatment of proliferative diseases involving upregulation of ABL1 kinase activity, as in the case of BCR-ABL1 fusion proteins in CML and subsets of other haematological malignancies such as ALL and AML.

Carcinoma cells utilize invapodia to degrade the extra cellular matrix during tumor invasion and metastasis. ABL kinase activity is required for Src-induced invapodia formation, regulating distinct stages of invapodia assembly and function. The compounds of the invention, therefore, as inhibitors of ABL, have the potential to be used as therapies for the treatment of metastatic invasive carcinomas.

An allosteric inhibitor of c-ABL kinase can be used to treat brain cancers: including Glioblastoma which is the most common & most aggressive malignant primary brain tumor in which the expression of c-ABL is immunohistochemically detectable in a subset of patients (Haberler C, Gelpi E, Marosi C, Rössler K, Birner P, Budka H, Hainfellner J A. Immunohistochemical analysis of platelet-derived growth factor receptor-alpha, -beta, c-kit, c-abl, and arg proteins in glioblastoma: possible implications for patient selection for imatinib mesylate therapy. J Neurooncol. 2006 January; 76(2):105-9). However, clinical trials with Gleevec® failed in patients with glioblastoma (Reardon D A, Dresemann G, Taillibert S, Campone M, van den Bent M, Clement P, Blomquist E, Gordower L, Schultz H, Raizer J, Hau P, Easaw J, Gil M, Tonn J, Gijtenbeek A, Schlegel U, Bergstrom P, Green S, Weir A, Nikolova Z. Multicentre phase II studies evaluating imatinib plus hydroxyurea in patients with progressive glioblastoma. Br J Cancer. 2009 Dec. 15; 101(12):1995-2004; Razis E, Selviaridis P, Labropoulos S, Norris J L, Zhu M J, Song D D, Kalebic T, Torrens M, Kalogera-Fountzila A, Karkavelas G, Karanastasi S, Fletcher J A, Fountzilas G. Phase II study of neoadjuvant imatinib in glioblastoma: evaluation of clinical and molecular effects of the treatment. Clin Cancer Res. 2009

Oct. 1; 15(19):6258-66; Dresemann G. Imatinib and hydroxyurea in pretreated progressive glioblastoma multiforme: a patient series. Ann Oncol. 2005 Oct.; 16(10):1702-8), possibly because of the poor brain intratumoral exposure of the drug and in the absence of disturbed blood-brain barrier (Holdhoff et al, J Neurooncol. 2010; 97(2):241-5). The transport of Gleevec® across the blood-brain barrier is in fact shown in preclinical studies to be limited by active efflux transporters such as P-glycoprotein. This is also the case for Dasatinib (Chen Y, Agarwal S, Shaik N M, Chen C, Yang Z, Elmquist W F. P-glycoprotein and breast cancer resistance protein influence brain distribution of dasatinib. J Pharmacol Exp Ther. 2009 September; 330(3):956-63). Irradiation is known to enhance the blood-brain barrier opening. In mouse models, glioblastoma multiforme response to Gleevec® correlated with an increase in tumor growth delay and survival when Gleevec® was administered in conjunction with daily irradiation (Geng L, Shinohara E T, Kim D, Tan J, Osusky K, Shyr Y, Hallahan D E. STI571 (Gleevec) improves tumor growth delay and survival in irradiated mouse models of glioblastoma. Int J Radiat Oncol Biol Phys. 2006 Jan. 1; 64(1):263-71). Therefore a new c-Abl inhibitor with high brain exposure represents a solid therapeutic approach for glioblastoma and other brain cancers.

CNS-CML: In some CML patients treated with Gleevec®, CNS Blast crisis and failure have been reported and can be explained by the poor brain exposure of Gleevec®. (Kim H J, Jung C W, Kim K, Ahn J S, Kim W S, Park K, Ko Y H, Kang W K, Park K. Isolated blast crisis in CNS in a patient with chronic myelogenous leukemia maintaining major cytogenetic response after imatinib. J Clin Oncol. 2006 Aug. 20; 24(24):4028-9; Radhika N, Minakshi M, Rajesh M, Manas B R, Deepak Kumar M. Central nervous system blast crisis in chronic myeloid leukemia on imatinib mesylate therapy: report of two cases. Indian J Hematol Blood Transfus. 2011 Mar.; 27(1):51-4). In fact, in CML patients, Gleevec®'s concentration is in fact much lower (~100 fold) in the CNS than in plasma (Leis J F, Stepan D E, Curtin P T, Ford J M, Peng B, Schubach S, Druker B J, Maziarz R T. Central nervous system failure in patients with chronic myelogenous leukemia lymphoid blast crisis and Philadelphia chromosome positive acute lymphoblastic leukemia treated with imatinib (STI-571). Leuk Lymphoma. 2004 April; 45(4):695-8). Therefore, c-ABL inhibitors from the present invention which show a high brain exposure represent a valid approach for development of therapies against CML including CNS-CML.

Compounds of the invention can be useful in the treatment of viruses. For example, viral infections can be mediated by ABL1 kinase activity, as in the case of pox-viruses and the Ebola virus. Gleevec® and Tasigna® have been shown to stop the release of Ebola viral particles from infected cells, in vitro (Kalman, Daniel; Bornmann, William Gerard, Methods of use of non-ATP competitive tyrosine kinase inhibitors to treat pathogenic infection, PCT Int. Appl. 2007, WO 2007002441; Garcia Mayra; Cooper Arik; Shi Wei; Bornmann William; Carrion Ricardo; Kalman Daniel; Nabel Gary J. Productive Replication of Ebola Virus Is Regulated by the c-ABL1 Tyrosine Kinase. Science translational medicine 2012; 4:123ra24). Compounds of the present invention that inhibit c-ABL kinase, therefore, can be expected to reduce the pathogen's ability to replicate.

Compounds of the invention can also be useful in the treatment of neural degeneration. While native c-ABL tyrosine kinase remains relatively quiescent in healthy adult brain, it can be activated in the brain of patients with CNS diseases, including neurodegenerative diseases such as, Alzheimer's disease (AD), Parkinson's disease (AD), frontotemporal dementia (FTD), Picks disease, Niemann-Pick type C disease (NPC) and other degenerative, inflammatory and autoimmune diseases and ageing.

Parkinson's disease is the second most prevalent chronic neurodegenerative disease with the most common familial autosomal-recessive form being caused by mutations in the E3 ubiquitin ligase, parkin. Recent studies showed that activated c-ABL was found in the striatum of patients with sporadic Parkinson's disease. Concomitantly, parkin was tyrosine-phosphorylated, causing loss of its ubiquitin ligase and cytoprotective activities as indicated by the accumulation of parkin substrates (Ko H S, Lee Y, Shin J H, Karuppagounder S S, Gadad B S, Koleske A J, Pletnikova O, Troncoso J C, Dawson V L, Dawson T M. Phosphorylation by the c-Abl protein tyrosine kinase inhibits parkin's ubiquitination and protective function. Proc Natl Acad Sci USA. 2010 Sep. 21; 107(38):16691-6; Imam S Z, Zhou Q, Yamamoto A, Valente A J, Ali S F, Bains M, Roberts J L, Kahle P J, Clark R A, Li S. Novel regulation of parkin function through c-Abl-mediated tyrosine phosphorylation: implications for Parkinson's disease. J Neurosci. 2011 Jan. 5; 31(1):157-63). These two studies also showed that in cell or animal models of Parkinson's disease, pharmacological inhibition of c-ABL kinase or genetic ABL knockdown prevented tyrosine phosphorylation of parkin and restored its E3 ligase activity and cytoprotective function both in vitro and in vivo. These results indicate that c-ABL-dependent tyrosine phosphorylation of parkin is a major post-translational modification that leads to loss of parkin function and disease progression in sporadic PD. Therefore, the ability of compounds of the invention to inhibit the myristate-binding site of ABL1, can be expected to offer new therapeutic opportunities for blocking the progression of Parkinson's disease.

Alzheimer's disease is characterized by two main hallmarks: extracellular deposits of the neurotoxic amyloid-β which leads to amyloid plaque development, and intracellular accumulation of hyperphosphorylated tau which contributes to the development of neurofibrillary tangles (NFTs).

Amyloid-β level is reduced following intrathecal treatment with Gleevec® in the brain of wild-type guinea-pigs and in cell models (Netzer W J, Dou F, Cai D, Veach D, Jean S, Li Y, Bornmann W G, Clarkson B, Xu H, Greengard P. Gleevec inhibits beta-amyloid production but not Notch cleavage. Proc Natl Acad Sci USA. 2003 Oct. 14; 100(21):12444-9). The same group proposed that Gleevec® achieves its amyloid-β-lowering effect via a new mechanism preventing GSAP interaction with the gamma-secretase substrate, APP-CTF (He G, Luo W, Li P, Remmers C, Netzer W J, Hendrick J, Bettayeb K, Flajolet M, Gorelick F, Wennogle L P, Greengard P. Gamma-secretase activating protein is a therapeutic target for Alzheimer's disease. Nature. 2010 Sep. 2; 467 (7311):95-8). In this study, Gleevec®'s effect to inhibit GSAP/APP-CTF was only seen at micromolar concentrations. Another group showed that tyrosine phosphorylation of the intracellular domain of APP (i.e. Tyr682) regulates the amyloidogenic APP processing accelerating amyloid-β formation in vivo (Barbagallo A P, Weldon R, Tamayev R, Zhou D, Giliberto L, Foreman O, D'Adamio L. Tyr(682) in the intracellular domain of APP regulates amyloidogenic APP processing in vivo. PLoS One. 2010 Nov. 16; 5(11):e15503). Other studies showed that APP is tyrosine-phosphorylated in cells expressing a constitutively active form of the ABL oncogene (Zambrano N, Bruni P, Minopoli G, Mosca R, Molino D, Russo C, Schettini G, Sudol M, Russo T. The beta-amyloid precursor protein APP is tyrosine-phosphorylated in cells expressing a constitutively active form of the Abl protoncogene. J Biol Chem. 2001 Jun. 8; 276(23):19787-92). These data together suggest a c-ABL-dependent amyloidogenic APP processing for the formation of the toxic amyloid-β peptide and subsequent amyloid plaques. Therefore a c-ABL inhibitor would be expected to lower amyloid plaque formation in Alzheimer's patients.

Tau has been shown to be phosphorylated by c-Abl kinase at tyrosines 18, 197, 310, and 394 in cell models, and tau pY394 has been shown to be present in the lesions NFTs in the brain of AD patients.

c-ABL is activated in the brain of patients with sporadic Alzheimer's disease as shown by its phosphorylation either at Y412, a indicator of activation, which co-localizes granulovacuolar degeneration, or at T735 which co-localized with the typical lesions, amyloid plaques, neurofibrillary tangles (NFTs) in addition to GVD. Amyloid-β and oxidative stress activate c-ABL kinase in neuronal cultures and intracerebral injection of fibrillar amyloid peptide leads to increased expression of c-ABL and a downstream effector p73. Transgenic mice (APP/Swe mouse model of AD), showed higher levels of c-ABL in their brain and, when these mice were treated with the c-ABL inhibitor Gleevec®, tau phosphorylation was decreased in their brains. A transgenic mouse model expressing constitutively active c-ABL in forebrain neurons exhibited neuronal loss, severe neuroinflammation, and tyrosine phosphorylation of tau in the brain (For review, see Schlatterer S D, Acker C M, Davies P. c-Abl in neurodegenerative disease. J Mol Neurosci. 2011 November; 45(3): 445-52).

Based on all these results, evidence exists for a role for c-ABL kinase in Alzheimer's pathogenesis for development of both lesions, amyloid plaques and neurofibrillary tangles.

Further, activated c-ABL is also present in other tauopathies besides sporadic Alzheimer's including in the brain of patients with frontotemporal dementia with N279K and P301L mutations, Pick's disease, and Guam Parkinson-dementia (Schlatterer S D, Acker C M, Davies P. c-Abl in neurodegenerative disease. J Mol Neurosci. 2011 November; 45(3):445-52).

Therefore, compounds of the present invention, by inhibiting c-ABL in the CNS, represent a valid approach for development of therapies against Alzheimer's disease, as well as other β-amyloidoses, such as vascular dementia and other tauopathies, such as frontotemporal dementia and picks disease.

Niemann-Pick type C (NPC) disease is a fatal autosomal recessive disorder characterized by the accumulation of free cholesterol and glycosphingolipids in the endosomal-lysosomal system, and by a progressive neuronal death in particular of cerebellar Purkinje neurons. In a mouse model of NPC, the proapoptotic c-ABL, the downstream target as well as p73 target genes are expressed in the cerebellums. Inhibition of c-ABL with Gleevec® prevented from loss of Purkinje neurons, improved neurological symptoms, and increased the survival. This prosurvival effect of Gleevec® correlated with reduced mRNA levels of p73 proapoptotic target genes (Alvarez A R, Klein A, Castro J, Cancino G I, Amigo J, Mosqueira M, Vargas L M, Yévenes L F, Bronfman F C, Zanlungo S. Imatinib therapy blocks cerebellar apoptosis and improves neurological symptoms in a mouse model of Niemann-Pick type C disease. FASEB J. 2008 Oct.; 22(10): 3617-27). Therefore, compounds of the present invention, by inhibiting c-ABL kinase, represent a valid approach for the development of therapies against diseases caused by the proapoptotic c-ABL/p73 pathway, such as NPC.

In prion disease models, Gleevec® showed beneficial effects: It delayed prion neuroinvasion by inhibiting prion propagation from the periphery to the CNS (Yun S W, Ertmer A, Flechsig E, Gilch S, Riederer P, Gerlach M, Schätzl H M, Klein M A. The tyrosine kinase inhibitor imatinib mesylate delays prion neuroinvasion by inhibiting prion propagation in the periphery. J Neurovirol. 2007 Aug.; 13(4):328-37). Gleevec® and ABL deficiency induced cellular clearance of PrPSc in prion-infected cells (Ertmer A, Gilch S, Yun S W, Flechsig E, Klebl B, Stein-Gerlach M, Klein M A, Schätzl H M. The tyrosine kinase inhibitor STI571 induces cellular clearance of PrPSc in prion-infected cells. J Biol Chem. 2004 Oct. 1; 279(40):41918-27). Therefore, novel c-Abl inhibitors from the present invention also represent a valid therapeutic approach for the treatment of prion diseases such as Creutzfeldt-Jacob disease.

X-linked recessive Emery-Dreifuss muscular dystrophy is caused by mutations of emerin, a nuclear-membrane protein with roles in nuclear architecture, gene regulation and signaling. A recent study has shown that emerin is tyrosine-phosphorylated directly by c-ABL in cell models, and that the phosphorylation status of emerin changes emerin binding to other proteins such as BAF. This, in turn, may explain the mislocalization of mutant emerin from nuclear to cytosolic compartments and consequently changes in downstream effector and signal integrator for signaling pathway(s) at the nuclear envelope (Tifft K E, Bradbury K A, Wilson K L. Tyrosine phosphorylation of nuclear-membrane protein emerin by Src, Abl and other kinases. J Cell Sci. 2009 Oct. 15; 122(Pt 20):3780-90). Changes in emerin-lamin interactions during both mitosis and interphase are of relevance for the pathology of muscular dystrophies. In addition, results from another study demonstrate that Gleevec® attenuates skeletal muscle dystrophy in mdx mice (Huang P, Zhao X S, Fields M, Ransohoff R M, Zhou L. Imatinib attenuates skeletal muscle dystrophy in mdx mice. FASEB J. 2009 Aug.; 23(8):2539-48).

Therefore, novel c-ABL inhibitors from the present invention also represent therapeutic approaches for treatment of skeletal and muscular dystrophies.

Furthermore, c-ABL kinase plays a role in inflammation and oxidative stress, two mechanisms that are implicated in a variety of human diseases ranging from acute CNS diseases, such as stroke and traumatic brain or spinal cord injuries, chronic CNS diseases, such as Alzheimer's, Parkinson's, Huntington's and motoneuron diseases, to non-CNS inflammatory and autoimmune diseases, such as diabetes, pulmonary fibrosis.

For example, Gleevec® prevents fibrosis in different preclinical models of systemic sclerosis and induces regression of established fibrosis (Akhmetshina A, Venalis P, Dees C, Busch N, Zwerina J, Schett G, Distler O, Distler J H. Treatment with imatinib prevents fibrosis in different preclinical models of systemic sclerosis and induces regression of established fibrosis. Arthritis Rheum. 2009 January; 60(1):219-24) and it shows antifibrotic effects in bleomycin-induced pulmonary fibrosis in mice (Aono Y, Nishioka Y, Inayama M, Ugai M, Kishi J, Uehara H, Izumi K, Sone S. Imatinib as a novel antifibrotic agent in bleomycin-induced pulmonary fibrosis in mice. Am J Respir Crit Care Med. 2005 Jun. 1; 171(11):1279-85). Another study showed that both imatinib and nilotinib attenuated bleomycin-induced acute lung injury and pulmonary fibrosis in mice (Rhee C K, Lee S H, Yoon H K, Kim S C, Lee S Y, Kwon S S, Kim Y K, Kim K H, Kim T J, Kim J W. Effect of nilotinib on bleomycin-induced acute lung injury and pulmonary fibrosis in mice. Respiration. 2011; 82(3):273-87). Although in these studies the authors were focusing on the implication the mechanism related to PDGFRs, of interest, in the study by Rhee et al. (Respiration. 2011; 82(3):273-87), nilotinib which is a more potent c-ABL inhibitor than imatinib showed superior therapeutic antifibrotic effects, thus supporting the therapeutic applicability of c-ABL inhibitors for treatment of human diseases with pulmonary inflammation. In another study, exposure of mice to hyperoxia increased c-Abl activation which is required for dynamin 2 phosphorylation and reactive oxygen species production and pulmonary leak (Singleton P A, Pendyala S, Gorshkova I A, Mambetsariev N, Moitra J, Garcia J G, Natarajan V. Dynamin 2 and c-Abl are novel regulators of hyperoxia-mediated NADPH oxidase activation and reactive oxygen species production in caveolin-enriched microdomains of the endothelium. J Biol Chem. 2009 Dec. 11; 284(50): 34964-75).

Therefore, these data indicate that new c-ABL inhibitors from the present invention have therapeutic applicability for treatment of human diseases with pulmonary inflammation.

c-ABL activation by insulin, via a modification of FAK response, may play an important role in directing mitogenic versus metabolic insulin receptor signaling (Genua M, Pandini G, Cassarino M F, Messina R L, Frasca F. c-Abl and insulin receptor signalling. Vitam Horm. 2009; 80:77-105). c-Abl inhibitors such as Gleevec® have been shown to reverse type 1 diabetes in nonobese diabetic mice (Louvet C, Szot G L, Lang J, Lee M R, Martinier N, Bollag G, Zhu S, Weiss A, Bluestone J A. Tyrosine kinase inhibitors reverse type 1 diabetes in nonobese diabetic mice. Proc Natl Acad Sci USA. 2008 Dec. 2; 105(48):18895-900). Amelioration of diabetes by Gleevec® was mimicked by siRNA-mediated knockdown of c-ABL mRNA (Hagerkvist R, Sandler S, Mokhtari D, Welsh N. Amelioration of diabetes by imatinib mesylate (Gleevec): role of beta-cell NF-kappaB activation and anti-apoptotic preconditioning. FASEB J. 2007 February; 21(2):618-28).

Therefore, the new c-ABL inhibitors from the present invention have therapeutic applicability for treatment of human diabetes.

A c-ABL inhibitor from the present invention can be used in combination with one or more of the existing treatment for the above diseases: for example a c-ABL inhibitor from the present invention can be used in combination with Levodopa or other L-DOPA-containing medicaments or a dopamine agonist for the treatment of Parkinson's disease or in combination with a cholinesterase inhibitor such as Exelon capsule or transdermal patch for the treatment of Alzheimer's disease.

In chronic myelogenous leukemia (CML), a reciprocal balanced chromosomal translocation in hematopoietic stem cells (HSCs) produces the BCR-ABL1 hybrid gene. The latter encodes the oncogenic BCR-ABL1 fusion protein. Whereas ABL encodes a tightly regulated protein tyrosine kinase, which plays a fundamental role in regulating cell proliferation, adherence and apoptosis, the BCR-ABL1 fusion gene encodes as constitutively activated kinase. This activated kinase transforms HSCs to produce a phenotype exhibiting deregulated clonal proliferation, reduced capacity to adhere to the bone marrow stroma and a reduced apoptotic response to mutagenic stimuli, resulting in progressively more malignant transformations. The resulting granulocytes fail to develop into mature lymphocytes and are released into the circulation, leading to a deficiency in the mature cells and increased susceptibility to infection. ATP-competitive inhibitors of BCR-ABL1 have been demonstrated to prevent the kinase from activating mitogenic and anti-apoptotic pathways (for example, P-3 kinase and STATS), leading to the death of the BCR-ABL1 phenotype cells and thereby providing an effective therapy against CML. The compounds of the invention, as BCR-ABL1 inhibitors, including mutants thereof, are thus especially appropriate for the therapy of diseases related to its over-expression, such as ALL or CML leukemias.

Compounds of the invention have also been demonstrated to have anti-tumor activity, in vivo: The in vivo antitumor activity is tested, for example using leukemic cell lines such as Ba/F3-BCR-ABL1, KCL-22, K-562, MEG-01, KYO-1, LAMA-84, KU812, EM-2, CML-T1, BV-173, or ALL-SIL.

The present invention includes a method to treat cancer, comprising administering to a subject in need of such treatment an effective amount of a compound of the invention or a pharmaceutical composition.

A further embodiment comprises administering to the subject an additional therapeutic agent.

In a further embodiment, the additional therapeutic agent is a different BCR-ABL1 inhibitor selected from imatinib, nilotinib, dasatinib, dosutinib, ponatinib and bafetinib.

In another embodiment is a method to treat a condition mediated by BCR-ABL1, comprising administering to a subject in need thereof an effective amount of a compound of the invention or a pharmaceutical composition.

In a further embodiment, the BCR-ABL1 contains one or more mutations (U Jane F. Apperley. Part 1: Mechanism of resistance to imatinib in chronic myeloid leukaemia. Lancet Oncology 2007; 8:1018). Examples of such mutations include V299L, T315I, F317I, F317L, Y253F, Y253H, E255K, E255V, F359C and F359V.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an ABL1/BCR-ABL1-mediated disorder, comprising the step of: administering to a patient in need thereof a therapeutically effective amount of a chemothereutic agent in combination with a therapeutically effective amount of a compound of compound of formula (I) as defined in the Summary of the Invention.

In another aspect, the present invention relates to a method of treating a ABL1/BCR-ABL1-mediated disorder, comprising the step of: administering to a patient in need thereof a therapeutically effective amount of a chemothereutic agent in combination with a therapeutically effective amount of a compound of compound of formula (I).

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution, suspension or solid dispersion in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17-beta-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C.sub.14 to about C.sub.20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula (I) (or a pharmaceutical composition comprising a compound of the formula (I) in the treatment of one or more of the diseases mentioned herein; wherein the response to treatment is beneficial as demonstrated, for example, by the partial or complete removal of one or more of the symptoms of the disease up to complete cure or remission.

Philadelphia chromosome positive (Ph+) ALL accounts for 15-30% of adult ALL and up to 5% of pediatric ALL (Faderl S, Garcia-MAnero G, Thomas D, et al. Philadelphia Chromosome Positive Acute Lymphoblastic Leukemia-Current Concepts and Future Perspectives. Rev Clin Exp Hematol 2002; 6:142-160). Pediatric Ph+ALL is characterized by an older age (median 9-10 years versus approximately 4 years for all ALL patients) and higher WBC counts at diagnosis. In both adults and children, Ph+ALL is characterized by a reciprocal translocation between chromosomes 9 and 22 (t(9;22)(q34;q11)) resulting in fusion of the BCR gene on chromosome 22 with ABL gene sequences translocated from chromosome 9, resulting in expression of the BCR-ABL1 protein. There are 2 primary variants of BCR-ABL1, p190BCR-ABL1, detectable in approximately 85% of Ph+ALL patients, and p210 BCR-ABL1, typical of CML, identified in approximately 15% of Ph+ALL patients (Dombret H, Galbert J, Boiron J, et al. Outcome of Treatment in Adults with Philadelphia chromosome-positive acute lymphoblastic leukemia-Results of the prospective multicenter LALA-94 trial. Blood 2002; 100:2357-2366; Faderl S, Garcia-MAnero G, Thomas D, et al. Philadelphia Chromosome Positive Acute Lymphoblastic Leukemia-Current Concepts and Future Perspectives. Rev Clin Exp Hematol 2002; 6:142-160).

The treatment of ALL is based on each patient's risk classification, with increasingly intensive treatment for patients who are at higher risk of relapse; this strategy maximizes remission rates while limiting unnecessary toxicities. Progress has been incremental, from the introduction of combination chemotherapy and treatment for pre-symptomatic central nervous system leukemia to newer, intensive treatment regimens for patients at high risk for relapse (C. H. Pui and W. E. Evans. Acute Lymphoblastic Leukemia New Engl J Med 1998; 339:605-615). Prior to the development of imatinib, Ph+ALL patients were treated with intensive chemotherapy followed by hematopoietic stem cell transplant (HSCT), ideally with a matched related donor, as this was shown to result in improved EFS versus either HSCT with other donors or chemotherapy alone. Overall, and in contrast to the majority of pediatric patients with ALL, patients with Ph+ALL have had a dire prognosis with low rates of event free survival (EFS) (Arico M, Valsecchi M G, Camitta B, Schrappe M, Chessells J, Baruchel A, Gaynon P, Silverman L, Janka-Schaub G, Kamps W, et al. New Engl J Med 2000; 342:998-1006).

A compound of formula (I) can also be used in combination with other antineoplastic compounds. Such compounds include, but are not limited to ribonucleotide reductase inhibitors, topoisomerase I inhibitors; topoisomerase II inhibitors; microtubule active compounds; alkylating compounds; histone deacetylase inhibitors; mTOR inhibitors, such as RAD001; antineoplastic antimetabolites; platin compounds; compounds targeting/decreasing a protein or lipid kinase activity methionine aminopeptidase inhibitors; biological response modifiers; inhibitors of Ras oncogenic isoforms; telomerase inhibitors; proteasome inhibitors; compounds used in the treatment of hematologic malignancies, such as FLUDARABINE; compounds which target, decrease or inhibit the activity of PKC, such as midostaurin; HSP90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics, HSP990 and AUY922; temozolomide (TEMODAL®); kinesin spindle protein inhibitors, such as SB715992 or SB743921 from GlaxoSmithKline, or pentamidine/chlorpromazine from CombinatoRx; PI3K inhibitors, such as BEZ235, BKM120 or BYL719; MEK inhibitors such as ARRY142886 from Array PioPharma, AZD6244 from AstraZeneca, PD181461 from Pfizer, leucovorin, EDG binders, antileukemia compounds, S-adenosylmethionine decarboxylase inhibitors, antiproliferative antibodies or other chemotherapeutic compounds. Further, alternatively or in addition they may be used in combination with ionizing radiation The term "ribonucleotide reductase inhibitors" refers to pyrimidine or purine nucleoside analogues including, but not limited to, fludarabine and/or cytosine arabinoside (ara-C), 6-thioguanine, 5-fluorouracil, cladribine, 6-mercaptopurine (especially in combination with ara-C against ALL), clofarabine, nelarabine (a prodrug of 9-β-arabinofuranosylguanine, ara-G), pentostatin, hydroxyurea or 2-hydroxy-1H-isoindole-1,3-dione derivatives (Nandy et al., Acta Oncologica 1994; 33:953-961.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, in the form as it is marketed. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds such as LDH589 disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity" as used herein includes, but is not limited to, protein tyrosine kinase and/or serine and/or threonine kinase inhibitors or lipid kinase inhibitors, for example:

a) compounds targeting, decreasing or inhibiting the activity of members of the ABL1 family, their gene-fusion products (e.g. BCR-ABL1 kinase) and mutants, such as compounds which target decrease or inhibit the activity of ABL1 family members and their gene fusion products, e.g. imatinib, nilotinib, dasatinib, bosutinib, ponatinib, bafetinib, PD180970, AG957, NSC 680410 and PD173955;

b) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors. Example HSP90 inhibitors are HSP990 and AUY922.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt.

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4th Edition, Vol. 1, pp. 248-275 (1993).

The term "S-adenosylmethionine decarboxylase inhibitors" as used herein includes, but is not limited to the compounds disclosed in U.S. Pat. No. 5,461,076.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Where temperatures are given hereinbefore or hereinafter, "about" has to be added, as minor deviations from the numeric values given, e.g. variations of ±10%, are tolerable. All reactions may take place in the presence of one or more diluents and/or solvents. The starting materials may be used in equimolar amounts; alternatively, a compound may be used in excess, e.g. to function as a solvent or to shift equilibrium or to generally accelerate reaction rates. Reaction aids, such as acids, bases or catalysts may be added in suitable amounts, as known in the field, required by a reaction and in line with generally known procedures.

Compounds of formula (I) can be prepared by proceeding as in the following Reaction Scheme I:

Reaction Scheme I:

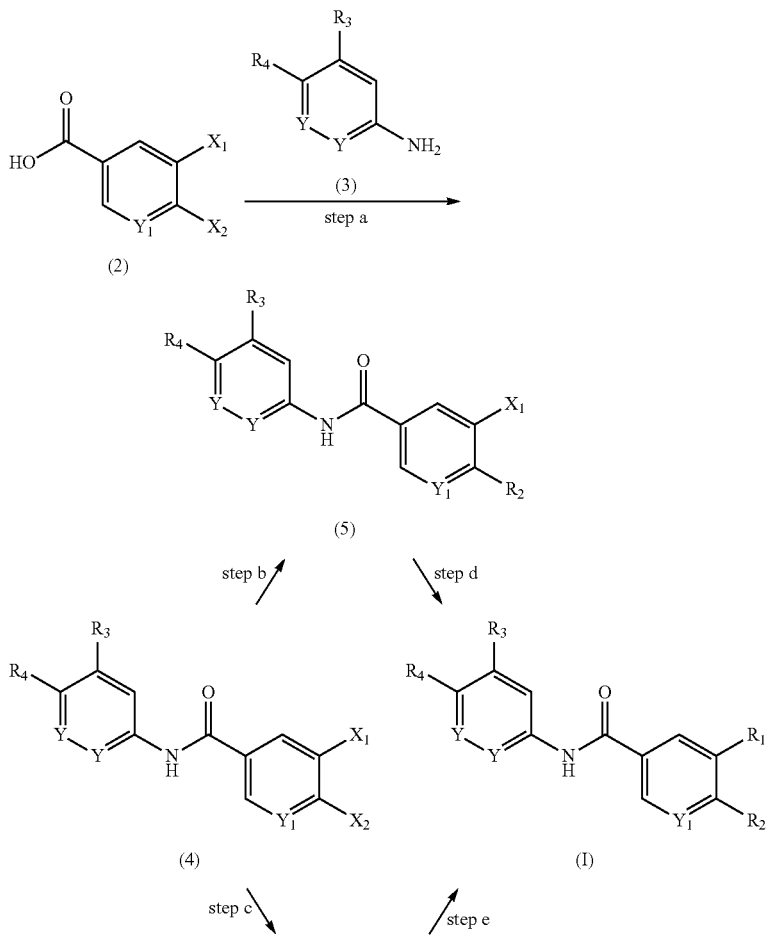

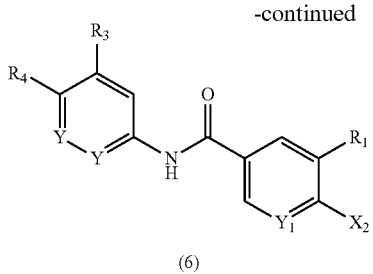

(6)

in which Y, $Y_1$, $R_1$, $R_2$, $R_3$ and $R_4$ are as defined for formula (I) in the Summary of the Invention and $X_1$ and $X_2$ represent halogen atoms, $X_1$ can be selected from chloro, bromo, or iodo and $X_2$ can be selected from chloro or fluoro.

Step a: A compound of formula (4) can be prepared by reacting the acid chloride from a compound of formula (2) with a compound of formula (3) in the presence of a suitable solvent (for example tetrahydrofuran, or the like), and an organic base (for example diisopropylethylamine, or the like). The reaction takes place from about 0° C. to about room temperature and can take up to about 2 hours to complete.

The acid chloride of a compound of formula (2) can be prepared with a chlorinating agent (for example thionyl chloride, or oxalyl chloride, or the like) in the presence of a catalyst (for example dimethylformamide, or the like) and a suitable solvent (for example toluene, or the like). The reaction takes place at about room temperature or by heating to about 85° C. and can take up to about 2 hours to complete.

Step b: A compound of formula (5) can be prepared by reacting a compound of formula (4) with $R_2$—H wherein $R_2$ is as defined in the Summary of the Invention, in the presence of a suitable solvent (for example 2-propanol, or dimethyl sulfoxide, or the like), and a suitable organic base (for example diisopropylethylamine, or triethylamine, or the like). The reaction takes place at about 90° C. to about 140° C. and can take from about 30 minutes to about 72 hours to complete.

Step c: A compound of formula (6) can be prepared by reacting a compound of formula (4), $X_1$ being preferably bromo or iodo, with $R_1$—$Z_1$, wherein $R_1$ is as defined herein, $Z_1$ being preferably a boronic acid or ester (Suzuki reaction), in the presence of a suitable solvent (for example dimethoxyethane, or a mixture of dimethoxyethane and water, or the like), a suitable inorganic base (for example sodium carbonate, or the like), and a palladium catalyst (for example bis(triphenylphosphine)palladium(II) dichloride, or 1,1'-bis(diphenylphosphino)ferrocene-palladium(II)dichloride dichloromethane complex, or tetrakis(triphenylphosphine)palladium(0), or the like) and optionally a cosolvent (for example, ethanol, or the like. The reaction takes place from about 80° C. to about 130° C. and can take from about 20 minutes to about 18 hours to complete.

Alternatively, step c can occur by reacting a compound of formula (4), $X_1$ being preferably bromo or iodo, with $R_1$—$Z_2$, wherein $R_1$ is as defined herein, $Z_2$ being preferably a trialkylstannyl reagent (Stille reaction), in the presence of a suitable solvent (for example dimethyl sulfoxide, or the like), and a palladium catalyst (for example tetrakis(triphenylphosphine)palladium(0). The reaction takes place at about 140° C. and can take up to about 24 hours to complete.

Step d: A compound of formula (I) can be prepared by reacting a compound of formula (5), $X_1$ being preferably bromo or iodo, with $R_1$—$Z_1$, wherein $R_1$ is as defined herein, $Z_1$ being preferably a boronic acid or ester (Suzuki reaction), in the presence of a suitable solvent (for example dimethoxyethane, or a mixture of dimethoxyethane and water, or the like), a inorganic base (for example sodium carbonate, or the like), and a palladium catalyst (for example bis(triphenylphosphine)palladium(II) dichloride, or 1,1'-bis(diphenylphosphino)ferrocene-palladium(II)dichloride dichloromethane complex, or tetrakis(triphenylphosphine)palladium(0), or the like) and optionally a cosolvent (for example, ethanol, or the like). The reaction takes place at about 80-130° C. and can take up to about 20 minutes to 2 hours to complete.

Step e: A compound of formula (I) can be prepared by reacting a compound of formula (6) with $R_2$—H wherein $R_2$ is as defined herein, in the presence of a suitable solvent (for example 2-propanol, or dimethyl sulfoxide, or the like), an organic base (for example diisopropylethylamine, or triethylamine, or the like). The reaction takes place at about 90-140° C. and can take up to about 30 minutes to 72 hours to complete.

Compounds of formula (I) can be prepared by proceeding as in the following Reaction Scheme II:

Reaction Scheme II:

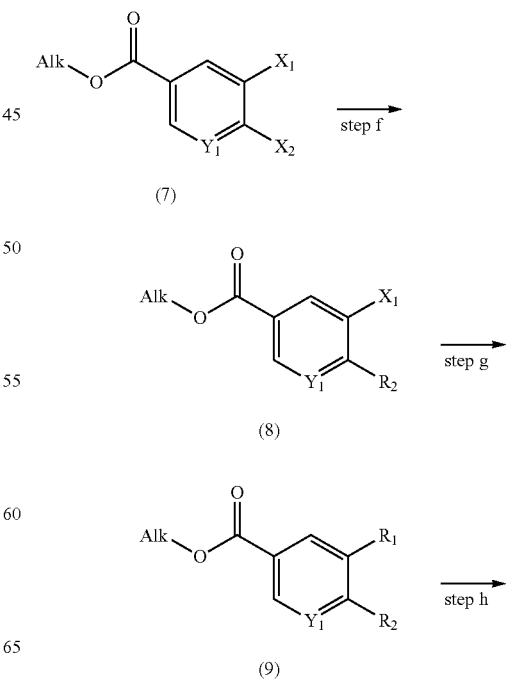

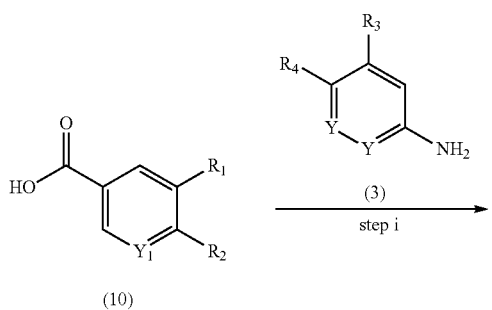

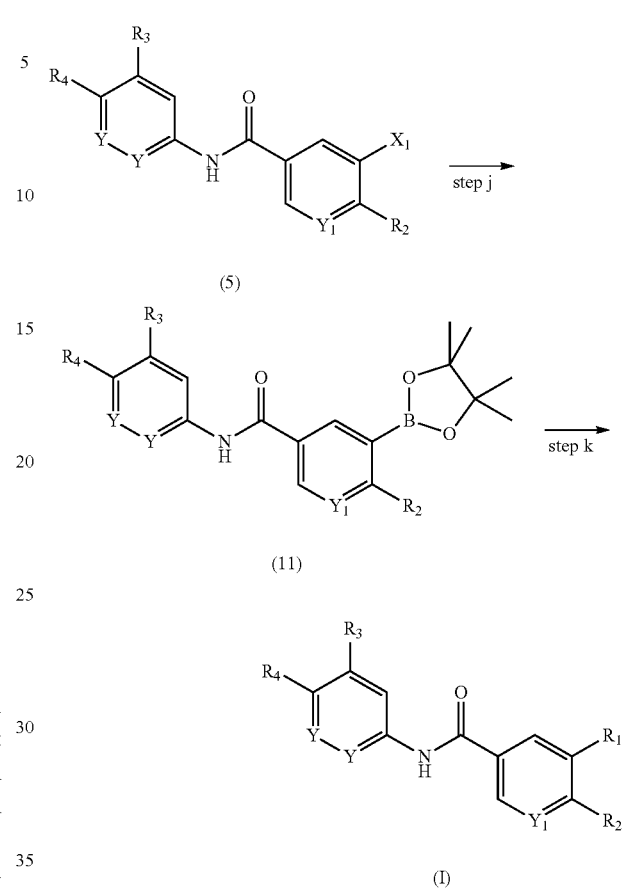

in which Y, $Y_1$, $R_1$, $R_2$, $R_3$ and $R_4$ are as defined for formula (I) in the Summary of the Invention and $X_1$ and $X_2$ represent halogen atoms, $X_1$ in particular chloro, bromo, or iodo, $X_2$ in particular chloro or fluoro and Alk is low alkyl chain in particular methyl.

Step f: A compound of formula (8) can be prepared by reacting a compound of formula (7) with $R_2$—H wherein $R_2$ is as defined herein, in analogy to Step b Step g: A compound of formula (9) can be prepared by reacting a compound of formula (8), $X_1$ being preferably bromo or iodo, with $R_1$—$Z_1$, where $R_1$ is as defined herein, $Z_1$ being preferably a boronic acid or ester (Suzuki reaction), in analogy to Step d.

Step h: A compound of formula (10) can be prepared by hydrolysis of the ester of a compound of formula (9) in the presence of a suitable solvent (for example water, or the like), an inorganic base (for example sodium hydroxide, or the like). The reaction takes place at room temperature and can take up to about 2 hours complete.

Step i: A compound of formula (I) can be prepared by reacting a compound of formula (10) with a compound of formula (3) in the presence of a coupling reagent (such as 1-ethyl-3-(3-dimethylaminopropyl)carbodiimide hydrochloride and hydroxybenzotriazole, or the like), a suitable base (such as N-methylmorpholine, diisopropylethylamine, or the like) and a suitable solvent (such as dichloromethane, dimethylformamide, or the like). The reaction takes place at room temperature and can take up to about 12 hours to complete.

Compounds of formula (I) can be prepared by proceeding as in the following Reaction Scheme III:

in which Y, $Y_1$, $R_1$, $R_2$, $R_3$ and $R_4$ are as defined for formula (I) in the Summary of the Invention and $X_1$ and $X_2$ represent halogen atoms, $X_1$ in particular chloro, bromo, or iodo, $X_2$ in particular chloro or fluoro.

Step j: A compound of formula (11) can be prepared by reacting a compound of formula (5), $X_1$ being preferably bromo, with bis(pinacolato)diboron, in the presence of a suitable solvent (for example dioxane, or the like), an inorganic base (for example tripotassium carbonate, or the like), and a palladium catalyst (for example bis(triphenylphosphine)palladium(II) dichloride, or the like). The reaction takes place at about 50-65° C. and can take up to 32 hours to complete.

Step k: A compound of formula (I) can be prepared by reacting a compound of formula (11) with $R_1$—$X_3$, $X_3$ being preferably bromo, in the presence of a suitable solvent (for example dimethoxyethane, or the like), a inorganic base (for example sodium carbonate, or the like), and a palladium catalyst (for example 2-dicyclohexylphosphino-2',6'-dimethoxybiphenyl-palladium diacetate, or the like). The reaction takes place at about 90-125° C. and can take up 20 minutes to 16 hours to complete.

Compounds of formula (I) can be prepared by proceeding as in the following Reaction Scheme IV:

Reaction Scheme IV:

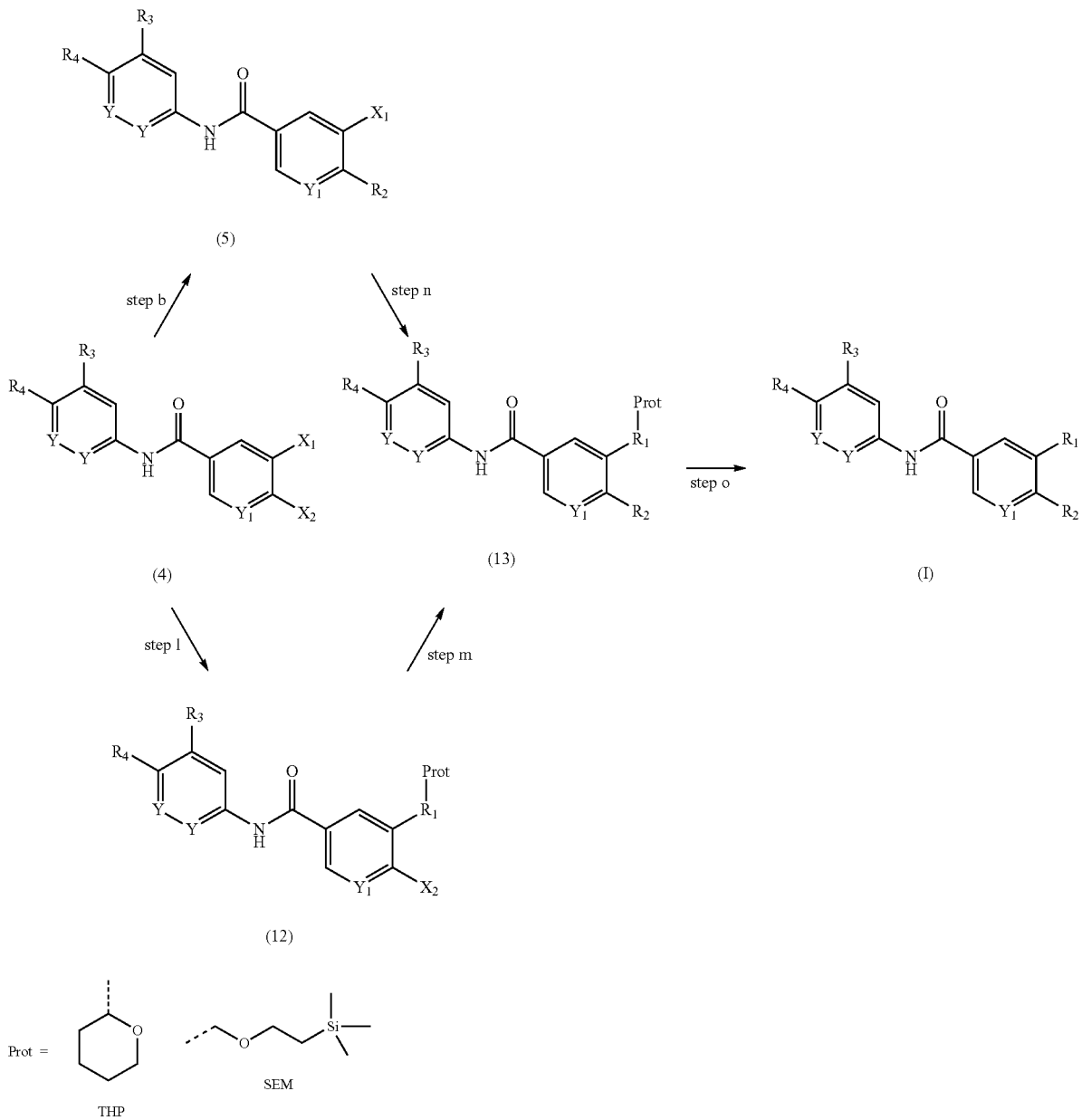

in which Y, $Y_1$, $R_1$, $R_2$, $R_3$ and $R_4$ are as defined for formula (I) in the Summary of the Invention and $X_1$ and $X_2$ represent halogen atoms, $X_1$ in particular chloro, bromo, or iodo, $X_2$ in particular chloro or fluoro, Prot represents a protecting group, in particular tetrahydro-2H-pyran-2-yl (THP) or 2-(trimethylsilyl)ethoxy]methyl (SEM).

Step l: A compound of formula (12) can be prepared by reacting a compound of formula (4) with Prot-$R_1$—$Z_1$ where $R_1$ is as defined herein, $Z_1$ being preferably a boronic acid or ester (Suzuki reaction), Prot is in particular THP or SEM, in analogy to Step c.

Step m: A compound of formula (13) can be prepared by reacting a compound of formula (12) with $R_2$—H wherein $R_2$ is as defined herein, in analogy to Step e.

Step n: A compound of formula (13) can be prepared by reacting a compound of formula (5) with Prot-$R_1$—$Z_1$ where $R_1$ is as defined herein, $Z_1$ being preferably a boronic acid or ester (Suzuki reaction), Prot is in particular THP or SEM, in analogy to Step d.

Step o: A compound of formula (I) can be prepared by reacting a compound of formula (13) with a deprotecting agent (for example tetra-n-butylammonium fluoride, or trifluoroacetic acid, or hydrochloric acid, or the like) in the presence of a suitable solvent (for example tetrahydrofuran, or dichloromethane, or the like). The reaction takes place at room temperature or to about 80° C. and can take up to about 2 to 24 hours to complete.

Compounds of formula (I), where $R_1$ is an imidazole substituted by a $R_6$ group (where $R_6$ is a methyl), can be prepared by proceeding as in the following Reaction Scheme V:

Reaction Scheme V:

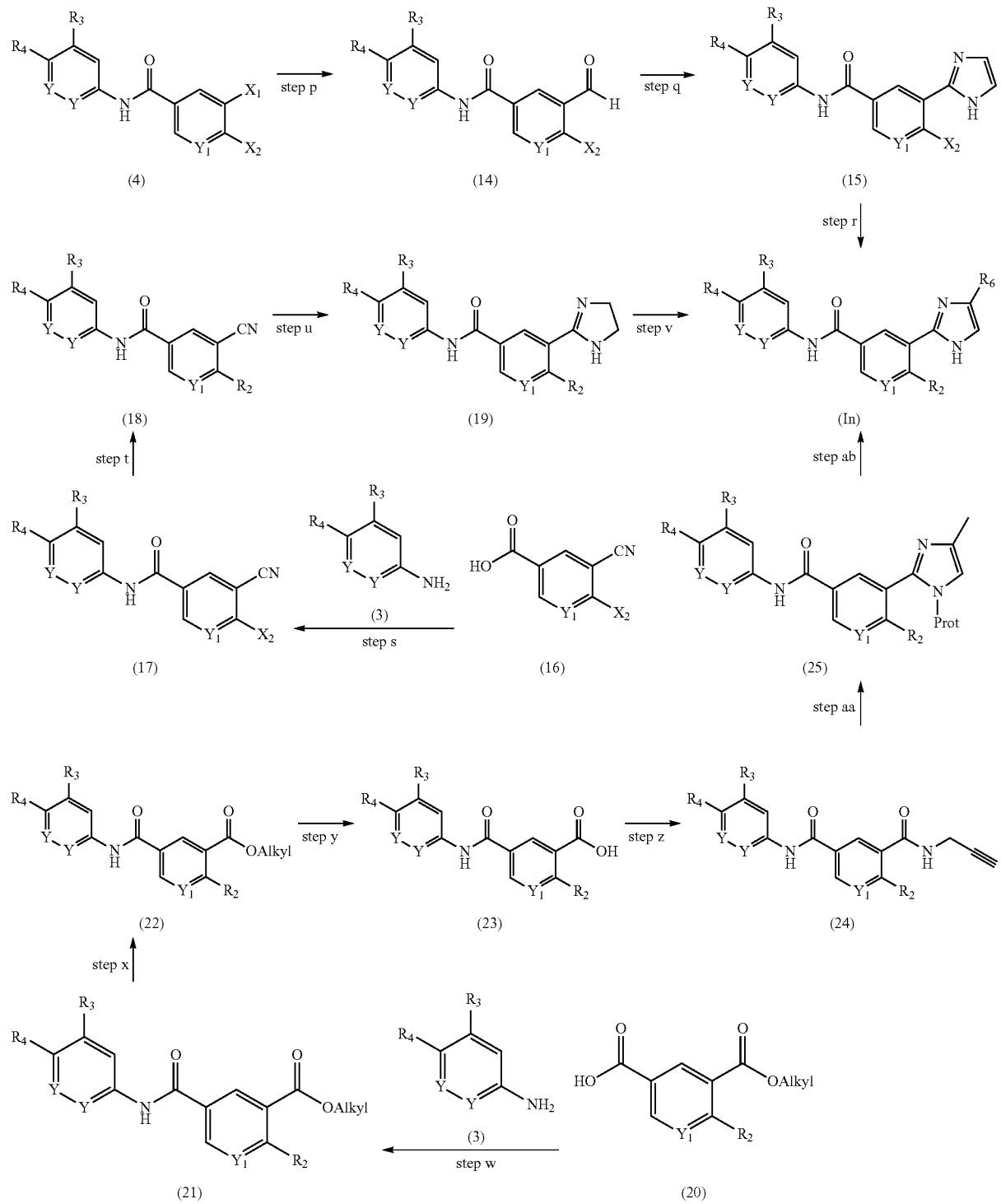

in which Y, $Y_1$, $R_2$, $R_3$ and $R_4$ are as defined for formula (I) in the Summary of the Invention, $X_1$ represents a halogen atom, in particular bromo or iodo, and $X_2$ represents a halogen atom, in particular chloro.

Step p: A compound of formula (14) can be prepared by reacting a compound of formula (4) with Grignard reagent (for example isopropyl magnesium chloride, or the like) in the presence of a suitable solvent (for example tetrahydrofuran, or the like), followed by the addition of dimethyl formamide. The reaction takes place at about −85° to −40° C. to about room temperature and can take up to about 3 hours to complete.

Step q: A compound of formula (15) can be prepared by reacting a compound of formula (14) with glyoxal and ammoniac in the presence of a suitable solvent (for example water/methanol, or the like). The reaction takes place at about 80° C. and can take up to about 2 hours to complete.

Step r: A compound of formula (In) can be prepared by reacting a compound of formula (15) with $R_2$—H wherein $R_2$ is as defined herein, in analogy to Step e.

Step s: A compound of formula (17) can be prepared by reacting the acid chloride from a compound of formula (16) with a compound of formula (3) in analogy to Step a.

Step t: A compound of formula (18) can be prepared by reacting a compound of formula (17) with $R_2$—H wherein $R_2$ is as defined herein, in analogy to Step e.

Step u: A compound of formula (19) can be prepared by reacting a compound of formula (18) with ethylenediamine, ammonium sulfide and sodium bisulfite. The reaction takes place at about 100° C. and can take up to about 18 hours to complete.

Step v: A compound of formula (In) can be prepared by reacting a compound of formula (19) with an oxidant (for example diacetoxyiodobenzene, or the like) and an inorganic base (for example potassium carbonate, or the like) in the presence of a suitable solvent (for example DMSO, or the like). The reaction takes place at about room temperature and can take up to about 18 hours to complete.

Step w: A compound of formula (21) can be prepared by reacting the acid chloride from a compound of formula (20) with a compound of formula (3) in analogy to Step a.

Step x: A compound of formula (22) can be prepared by reacting a compound of formula (21) with $R_2$—H wherein $R_2$ is as defined herein, in analogy to Step e.

Step y: A compound of formula (23) can be prepared by reacting a compound of formula (22) with an inorganic base (for example lithium hydroxide, or the like) in the presence of a suitable solvent (for example ethanol, or the like). The reaction takes place at about 50° C. and can take up to about 8 hours to complete.

Step z: A compound of formula (24) can be prepared by reacting a compound of formula (23) with a coupling reagent (for example O-(7-azabenzotriazol-1-yl)-N,N,N',N'-tetramethyluronium hexafluorophosphate, or the like), an organic base (for example, N,N-diisopropylethylamine, or the like) and propargylamine in the presence of a suitable solvent (for example dimethylformamide, or the like). The reaction takes place at about room temperature and can take up to about 3 hours to complete.

Step aa: A compound of formula (25) can be prepared by reacting a compound of formula (24) with a benzylic amine (for example methoxybenzylamine, or the like) and zinc trifluoromethanesulphonate in the presence of a suitable solvent (for example toluene, or the like), The reaction takes place at reflux and can take up to about 41 hours to complete.

Step ab: ab compound of formula (In) can be prepared by hydrogenation a compound of formula (25) with palladium, (for example palladium on carbon, or the like) and ammonium formate in the presence of a suitable solvent (for example ethanol, or the like). The reaction takes place at reflux and can take up to about 52 hours to complete.

Detailed examples of the synthesis of compounds of formula (I) can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula (I) can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Wherever compounds of the formula (I), and/or N-oxides, tautomers and/or (preferably pharmaceutically acceptable) salts thereof are mentioned, this comprises such modified formulae, while preferably the molecules of the formula (I), their N-oxides, their tautomers and/or their salts are meant.

Alternatively, the salt forms of the compounds of the invention can be prepared using salts of the starting materials or intermediates. In view of the close relationship between the novel compounds of the formula (I) in free form and those in the form of their salts, including those salts that can be used as intermediates, for example in the purification or identification of the novel compounds, any reference to the compounds or a compound of the formula (I) hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid. Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier M G, Langley D R, Kadow J F, Senter P D, Knipe J O, Tun M M, Vyas D M and Doyle T W (1994) Synthesis of etoposide phosphate, BMY-4048 1: a watersoluble clinically active prodrug of etoposide. Bioorg Med Chem Lett 4:2567-2572; and Rautio J, Kumpulainen H, Heimbach T, Oliyai R, Oh D, Järvinen T and Savolainen J (2008). For example, a compound of the invention can form a prodrug as shown:

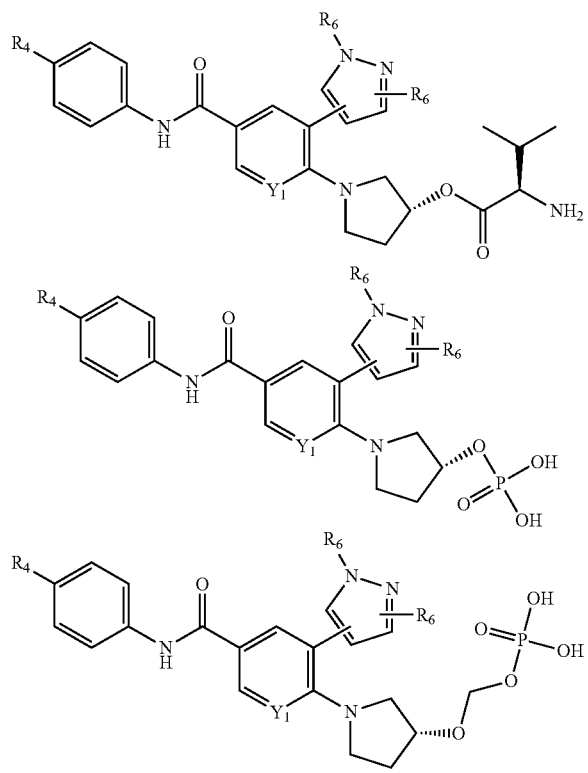

Protected derivatives of the compounds of the invention can be made by means known to those of ordinary skill in the art. If one or more other functional groups, for example carboxy, hydroxy, amino, sulfhydryl or the like are or need to be protected in a starting material as described herein or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which are groups that are added at a starting material or intermediate stage and removed to obtain a final compound. Also in the case of conversions of a compound of the formula (I) into a different compound of the formula (I), protecting groups may be introduced and removed, if useful or required. The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. Diastereomeric mixtures for example may be separated into their individual diastereomers by means of fractionated crystallization, chromatography, solvent distribution, and similar procedures. This separation may take place either at the level of a starting compound or in a compound of formula (I) itself. Enantiomers may be separated through the formation of diastereomeric salts, for example by salt formation with an enantiomer-pure chiral acid, or by means of chromatography, for example by HPLC, using chromatographic substrates with chiral ligands. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of formula (I) can be made by a process, which involves:

(a) those of reaction schemes I-V; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable pro-drug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following Examples illustrate the invention without limiting the scope thereof. In the Examples provided, temperatures are given in degrees Celsius. Unless otherwise indicated, the reactions take place at room temperature. Further, if not indicated otherwise, the analytical HPLC conditions are as follows:

Condition 1: UPLC-MS, column Acquity BEH C18, 1.7 μm, 2.1×50 mm, oven at 40° C., eluents: A=water+0.1% formic acid and B=MeCN+0.1% formic acid, gradient from 20% to 100% B in 4.3 min, flow 0.7 mL/min, detection UV/VIS (DAD), ESI (+/−).

Condition 2: LC-MS, column Ascentis® Express C18 2.7 μm 2.1×30 mm, 50° C., eluents: A=water+0.05% formic acid+3.75 mM ammonium acetate and B=MeCN+0.04% formic acid, gradient from 5% to 95% B in 3.7 min, flow 1.2 mL/min to 1.4 mL/min in 3.7 min, detection UV/VIS (DAD), ESI (+/−).

Condition 3: UPLC-MS, column Acquity HSS T3, 1.8 μm, 2.1×50 mm, oven at 50° C., eluents: A=water+0.05% formic acid+3.75 mM ammonium acetate and B=MeCN+0.04% formic acid, gradient from 2% to 98% B in 1.40 min, then 98% B for 0.75 min, flow 1.2 mL/min, detection UV/VIS (DAD), ESI (+/−).

Condition 4: HPLC, column Chromolith® Performance, RP-18e, 100×4.6 mm+precolumn 5×4.6 mm at RT, eluents: A=water+0.1% formic acid and B=MeCN+0.1% formic acid, gradient from 2% to 100% B in 8 min, then 100% B for 2 min, flow 2.0 mL/min, detection UV/VIS (DAD).

Condition 5: LC-MS, column Ascentis® Express C18 2.7 μm 2.1×30 mm, 50° C., eluents: A=water+0.05% TFA, and B=MeCN+0.04% TFA, gradient from 10% to 95% B in 3.0 min, then 95% B for 1.0 min, flow 1.2 mL/min, detection UV/VIS (DAD), ESI (+).

Condition 6: UPLC-MS, direct injection, detection UV/VIS (DAD), ESI (+/−).

Condition 7: HPLC, column CC125/4 Nucleosil® 100-3 C18HD, 4.0×125 mm, eluents: A=water+0.1% TFA and B=MeCN+0.1% TFA, gradient from 2% to 100% B in 7 min, then 100% B for 2 min and finally 100% to 2% B in 1 min, flow 1.0 mL/min, detection UV 215 nm.

Condition 8: similar condition as Condition 3, oven at 60° C. instead of 50° C.

Further, if not indicated otherwise, the preparative HPLC conditions are as follows:

Condition 9: Preparative HPLC, Column: XBridge C18 30×100 mm, 5 μm; flow rate 30 mL/min; mobile phase: A=water+0.1% formic acid; B=MeCN; variable gradient, from initial % B to final % B, and runtime as specified in the Examples.

Condition 10: Preparative HPLC Gilson system, column SunFire™ prep C18 OBD, 5 μm 30×100 mm, eluents: A=water+0.1% TFA and B=MeCN, gradient 5% B for 2 min, then 5% to 100% B in 20 min and finally 100% B in 3 min, flow 30 mL/min, detection UV/VIS.

Condition 11: Preparative HPLC, Gilson system, column Atlantis® prep C18 OBD, 5 μm 19×100 mm, eluents: A=water+0.1% TFA and B=MeCN, gradient 5% B for 2 min, then 5% to 100% B in 7 min and finally 100% B in 3 min, flow 23 mL/min, detection UV/VIS.

Preparative achiral SFC is done using the following system: Waters SFC THAR100; flow rate 100 mL/min; mobile phase: A=supercritical $CO_2$; B=MeOH; variable gradient, from initial % B to final % B runtime and columns as specified in the Examples. Details for the columns:

Column 2-EP: column 2-Ethylpyridine (250×30 mm, 5 μm, 60 Å), Princeton

Column 4-EP: column 4-Ethylpyridine (250×30 mm, 5 μm, 60 Å), Princeton

Column DEAP: column Diethyl amino (250×30 mm, 5 μm, 60 Å), Princeton

Column $NH_2$: column Amino Reprosil 70 NH2 (250×30 mm, 5 μm), Dr Maisch

Column Diol: column Diol (250×30 mm, 5 μm, 60 Å), Princeton

Column PFP: Column Pentafluorophenyl (250×30 mm, 5 μm, 120 Å), ES Industry $^1$H-NMR spectra were recorded on a 400 MHz, or a 600 MHz NMR spectrometer as indicated. Significant peaks are tabulated in the order: multiplicity (s, singlet; d, doublet; t, triplet; q, quartet; m, multiplet; br. s, broad singlet) and number of protons.

In the following Examples, the abbreviations given below are used: aq. (aqueous); DAD (diode array detector); dba (dibenzylideneacetone); DCE (1,2-dichloroethane); DCM (dichloromethane); DIPEA (diisopropyl-ethylamine); DMA (dimethylacetamide); DMF (N,N-dimethylformamide); DME (dimethoxyethane); DMSO (dimethyl sulfoxide); dppf (1,1'-bis(diphenylphosphino)ferrocene); eq. (equivalents); ESI (electrospray ionization); EtOAc (ethyl acetate); EtOH (ethanol); $Et_2O$ (diethyl ether); h (hour); HPLC (high performance liquid chromatography); HV (high vacuum); iPrOH (isopropanol); $iPr_2O$ (diisopropyl ether); LC (liquid chromatography); M (molar); MeCN (acetonitrile); MeOH (methanol); min (minutes); mL (milliliters); MP (macroporous); MPLC (medium pressure liquid chromatography); MS (mass spectrometry); MW (microwave); n-BuLi (n-butyllithium); NMP (N-methylpyrrolidinone); NMR (nuclear magnetic resonance); PL (polystyrene); PPh₃ (triphenylphosphine); RM (reaction mixture); RT (room temperature); sat. (saturated); sec (seconds); SFC (supercritical fluid chromatography); Si-Thiol (3-mercaptopropyl modified silica gel); SPE (solid phase extraction); SPhos (2-dicyclohexylphosphino-2', 6'-dimethoxybiphenyl); TBAF (tetra-n-butylammonium fluoride); TBME (methyl tert-butyl ether); TFA (trifluoroacetic acid); TEA (triethylamine); THF (tetrahydrofuran); $t_R$ (retention time); UPLC (ultra performance liquid chromatography) and UV (Ultraviolet).

Example 1

(R)-4-(3-Hydroxypyrrolidin-1-yl)-3-(thiazol-5-yl)-N-(4-(trifluoromethoxy)phenyl)benzamide

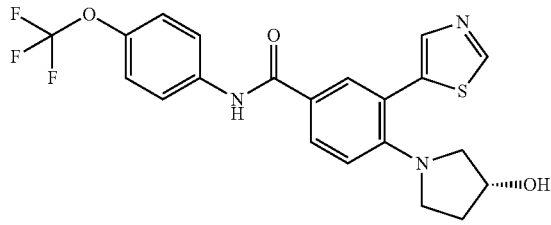 [SMILES: O=C(Nc1ccc(OC(F)(F)F)cc1)c1ccc(N2CC[C@@H](O)C2)c(-c2cncs2)c1]

A mixture of 4-fluoro-3-(thiazol-5-yl)-N-(4-(trifluoromethoxy)phenyl)benzamide (Stage 1.1, 50 mg, 0.131 mmol), (R)-pyrrolidin-3-ol (22.8 mg, 0.262 mmol) and TEA (72.9 µL, 0.523 mmol) in DMSO (98 µL) was stirred at 100° C. overnight. The RM was filtered and the filtrate was purified by preparative SFC (Column Diol, isocratic 30% in 6 min) to yield the title compound as a pale brown solid. UPLC-MS (Condition 1) $t_R$=1.05 min, m/z=450.3 [M+H]⁺, m/z=448.3 [M−H]⁻; ¹H-NMR (400 MHz, DMSO-d₆) δ ppm 1.68-1.82 (m, 1H) 1.82-1.99 (m, 1H) 2.79 (d, J=10.29 Hz, 1H) 3.06-3.14 (m, 1H) 3.14-3.21 (m, 1H) 3.24-3.33 (m, 1H) 4.24 (br. s, 1H) 4.80-5.00 (m, 1H) 6.98 (d, J=8.78 Hz, 1H) 7.35 (d, J=8.41 Hz, 2H) 7.76-8.02 (m, 5H) 9.17 (s, 1H) 10.18 (s, 1H).

Stage 1.1 4-Fluoro-3-(thiazol-5-yl)-N-(4-(trifluoromethoxy)phenyl)benzamide

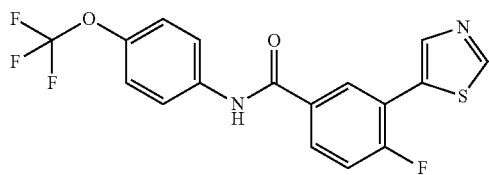 [SMILES: O=C(Nc1ccc(OC(F)(F)F)cc1)c1ccc(F)c(-c2cncs2)c1]

A mixture of 3-bromo-4-fluoro-N-(4-(trifluoromethoxy)phenyl)benzamide (Stage 1.2, 100 mg, 0.264 mmol), thiazole (113 mg, 1.322 mmol), KOAc (130 mg, 1.322 mmol) and Pd(OAc)₂ (0.297 mg, 1.322 µmol) were added to a vial, which was sealed and evacuated/purged with argon. DMA (0.81 mL) was added and the mixture was stirred at 130° C. for 20 h. The RM was diluted with THF (3 mL), treated with Si-Thiol (Silicycle, 1.44 mmol/g, 9.18 mg, 0.013 mmol) and filtered off. The filtrate was poured onto 1 M HCl (40 mL) and extracted 3 times with TBME. The combined extracts were washed 3 times with 1M HCl, sat. NaHCO₃ and brine, dried over Na₂SO₄ and the solvent was evaporated off under reduced pressure to give a crude product which was purified by flash chromatography (RediSep® Silica gel column, 4 g, cyclohexane/EtOAc from 10% to 40% EtOAc) to yield the title compound as an off-white solid. UPLC-MS (Condition 1) $t_R$=2.80 min, m/z=383.0 [M+H]⁺, m/z=381.0 [M−H]⁻; ¹H-NMR (400 MHz, DMSO-d₆) δ ppm 7.40 (m, J=8.31 Hz, 2H) 7.58 (dd, J=10.76, 8.80 Hz, 1H) 7.83-7.97 (m, 2H) 8.02 (ddd, J=8.62, 4.95, 2.32 Hz, 1H) 8.40 (dd, J=7.21, 2.32 Hz, 1H) 8.49 (s, 1H) 9.28 (s, 1H) 10.54 (s, 1H).

Stage 1.2 3-Bromo-4-fluoro-N-(4-(trifluoromethoxy)phenyl)benzamide

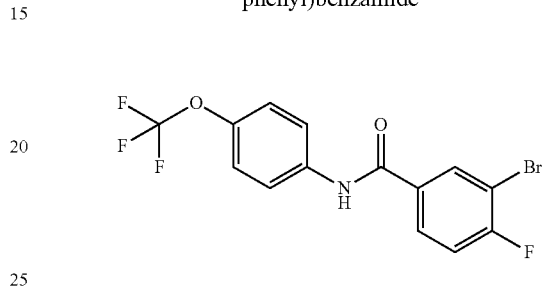

SOCl₂ (2.92 mL, 40.0 mmol) and DMF (0.5 mL) were added dropwise to a suspension of 3-bromo-4-fluorobenzoic acid (1.752 g, 8 mmol) in toluene (20 mL) and the RM was stirred at 80° C. for 1 h The solvent was evaporated off under reduced pressure and the residue was diluted with THF (15 mL). DIPEA (2.79 mL, 16.00 mmol) was added and the mixture was cooled to 0° C., treated with a solution of 4-trifluoromethoxyaniline (1.181 mL, 8.80 mmol) in THF (5 mL) and stirred for 1 h. The RM was treated with aq. 1 M HCl (50 mL), and extracted with TBME. The combined extracts were washed with aq. 1 M HCl, aq. 1 M NaOH and brine, dried over MgSO₄ and the solvent was evaporated off under reduced pressure to give a residue was crystallized from n-heptane/DCM to afford the title compound as a white solid. UPLC-MS (Condition 1) $t_R$=3.18 min, m/z=377.9/379.9 [M+H]⁺, m/z=375.9/377.9 [M−H]⁻; ¹H-NMR (400 MHz, DMSO-d₆) δ ppm 7.38 (d, J=8.6 Hz, 2H) 7.56 (t, J=8.7 Hz, 1H) 7.87 (d, J=9.0 Hz, 2H) 8.00-8.06 (m, 1H) 8.32 (dd, J=6.6, 2.2 Hz, 1H) 10.50 (s, 1H).

Example 2

4-(3-Hydroxy-3-methylpyrrolidin-1-yl)-3-(thiazol-5-yl)-N-(4-(trifluoromethoxy)phenyl)benzamide

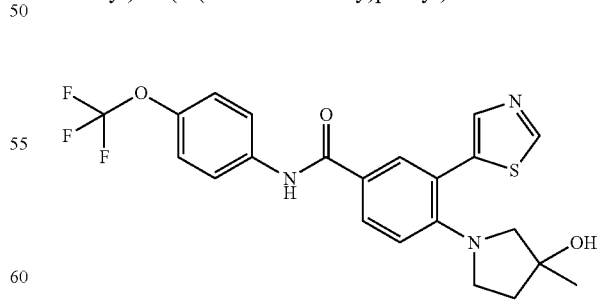

The title compound was prepared in an analogous fashion to that described in Example 1 using 4-fluoro-3-(thiazol-5-yl)-N-(4-(trifluoromethoxy)phenyl)benzamide (Stage 1.1) and 3-methylpyrrolidin-3-ol to afford a yellow solid. UPLC-MS (Condition 1) $t_R$=2.57 min, m/z=464.1 [M+H]⁺, m/z=462.1 [M−H]⁻; ¹H-NMR (400 MHz, DMSO-d₆) δ ppm 1.09-1.30 (m, 3H) 1.63-1.85 (m, 2H) 2.88 (s, 1H) 2.95 (s, 1H) 3.02-3.15 (m, 1H) 3.26-3.30 (m, 1H) 4.72 (s, 1H) 6.94 (d, J=8.80 Hz, 1H) 7.33 (d, J=9.05 Hz, 2H) 7.78-8.00 (m, 6H) 9.15 (s, 1H) 10.14 (s, 1H).

Example 3

4-((3S,4S)-3,4-Dihydroxypyrrolidin-1-yl)-3-(thiazol-5-yl)-N-(4-(trifluoromethoxy)phenyl)benzamide

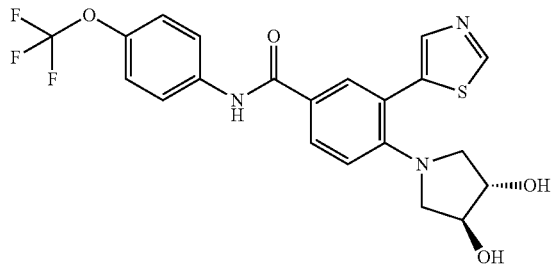 [SMILES: O=C(Nc1ccc(OC(F)(F)F)cc1)c1ccc(N2C[C@H](O)[C@@H](O)C2)c(-c2cncs2)c1]

A solution of 4-fluoro-3-(thiazol-5-yl)-N-(4-(trifluoromethoxy)phenyl)benzamide (Stage 1.1, 60 mg, 0.13 mmol), (3S,4S)-pyrrolidine-3,4-diol (28.2 mg, 0.273 mmol) and TEA (76 μL, 0.546 mmol) in DMSO (103 μL) was stirred at 105° C. for 90 h. The solvent was evaporated off under reduced pressure and the crude product was purified by preparative SFC (Column Diol, from 22% to 27% in 10 min) to afford the title compound as a yellow powder. UPLC-MS (Condition 1) $t_R$=2.18 min, m/z=466.0 [M+H]⁺, m/z=464.1 [M−H]⁻; ¹H-NMR (400 MHz, DMSO-d₆) δ ppm 2.86 (d, J=10.51 Hz, 2H) 3.36 (dd, J=10.51, 3.67 Hz, 2H) 3.90 (br. s, 2H) 5.05 (br. s, 2H) 6.93 (d, J=8.80 Hz, 1H) 7.33 (d, J=8.56 Hz, 2H) 7.78-7.98 (m, 5H) 9.16 (s, 1H) 10.12 (s, 1H).

Example 4

4-(trans-3-Hydroxy-4-methoxypyrrolidin-1-yl)-3-(thiazol-5-yl)-N-(4-(trifluoromethoxy)phenyl)benzamide

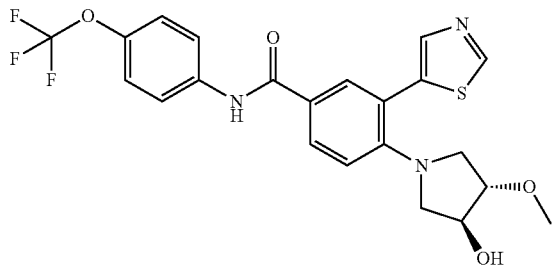 [SMILES: CO[C@H]1CN(c2ccc(C(=O)Nc3ccc(OC(F)(F)F)cc3)cc2-c2cncs2)C[C@@H]1O]

A solution of 4-fluoro-3-(thiazol-5-yl)-N-(4-(trifluoromethoxy)phenyl)benzamide (Stage 1.1, 58 mg, 0.132 mmol), (+/−)-trans-4-methoxy-pyrrolidinol hydrochloride (40.5 mg, 0.264 mmol) and TEA (73.6 μL, 0.528 mmol) in DMSO (99 μL) was stirred overnight at 105° C. Additional TEA (36.8 μL, 0.264 mmol) was added and the RM was stirred overnight. Additional (+/−)-trans-4-methoxy-pyrrolidinol hydrochloride (20.27 mg, 0.132 mmol) and TEA (36.8 μL, 0.264 mmol) were added and the RM was stirred at 120° C. overnight. The solvent was evaporated off under reduced pressure and the residue was purified by preparative SFC (Column Diol, isocratic 23% in 9 min) to yield the title compound as an orange solid. UPLC-MS (Condition 1) $t_R$=2.44 min, m/z=480.0 [M+H]⁺, m/z=478.1 [M−H]⁻; ¹H-NMR (400 MHz, DMSO-d₆) δ ppm 2.85 (dd, J=10.51, 1.96 Hz, 1H) 2.95-3.03 (m, 1H) 3.16 (s, 2H) 3.20-3.26 (m, 3H) 3.58-3.70 (m, 1H) 4.08 (br. s, 1H) 5.16 (br. s, 1H) 6.96 (d, J=8.56 Hz, 1H) 7.33 (d, J=8.31 Hz, 1H) 7.79-7.99 (m, 5H) 9.15 (d, J=0.73 Hz, 1H) 10.14 (s, 1H).

Example 5

4-(trans-3-Hydroxy-4-(hydroxymethyl)pyrrolidin-1-yl)-3-(thiazol-5-yl)-N-(4-(trifluoromethoxy)phenyl)benzamide

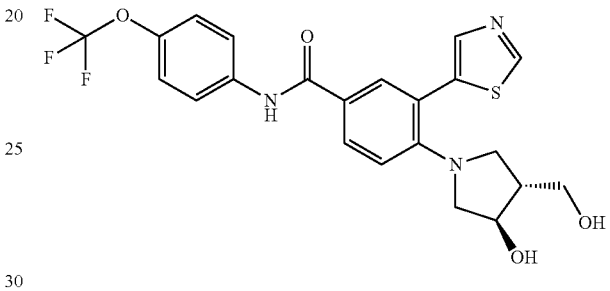

The title compound was prepared in an analogous fashion to that described in Example 4 using 4-fluoro-3-(thiazol-5-yl)-N-(4-(trifluoromethoxy)phenyl)benzamide (Stage 1.1) and trans-4-(hydroxymethyl)pyrrolidin-3-ol hydrochloride to afford an off-white solid. UPLC-MS (Condition 3) $t_R$=0.95 min, m/z=480.1 [M+H]⁺, m/z=478.2 [M−H]⁻; ¹H-NMR (400 MHz, DMSO-d₆) δ ppm 2.04-2.18 (m, 1H) 2.78 (dd, J=10.39, 3.79 Hz, 1H) 2.97 (dd, J=9.90, 5.01 Hz, 1H) 3.18 (dd, J=10.51, 5.62 Hz, 1H) 3.23-3.28 (m, 1H) 3.32-3.37 (m, 1H) 3.37-3.47 (m, 1H) 3.91-4.03 (m, 1H) 4.63 (t, J=5.14 Hz, 1H) 4.94 (d, J=4.16 Hz, 1H) 6.99 (d, J=8.80 Hz, 1H) 7.34 (d, J=8.56 Hz, 2H) 7.83-7.98 (m, 5H) 9.16 (d, J=0.73 Hz, 1H) 10.15 (s, 1H).

Example 6

(R)-6-(3-Hydroxypyrrolidin-1-yl)-5-(1H-pyrrol-2-yl)-N-(4-(trifluoromethoxy)phenyl)nicotinamide

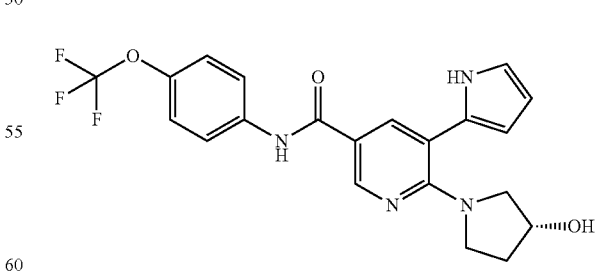

A mixture of (R)-5-bromo-6-(3-hydroxypyrrolidin-1-yl)-N-(4-(trifluoromethoxy)phenyl)nicotinamide (Stage 6.1, 100 mg, 0.224 mmol), tert-butyl 2-(4,4,5,5-tetramethyl-1,3,2-dioxaborolan-2-yl)-1H-pyrrole-1-carboxylate (131 mg, 0.448 mmol), Pd(PPh₃)₂Cl₂ (15.73 mg, 0.022 mmol), Na₂CO₃ (95 mg, 0.896 mmol), DME (951 μL), water (272 μL) and EtOH (136 µL) in a MW vial was sealed, evacuated/purged 3 times with argon and stirred at 80° C. for 16 h. MeOH (0.5 mL) was added and the RM was subjected to MW irradiation at 150° C. for 5 min, diluted with DME (3 mL) and treated with Si-Thiol (Silicycle, 1.44 mmol/g, 93 mg, 0.134 mmol) overnight. The RM was centrifuged, the supernatant was filtered and the solvent was evaporated off under reduced pressure to give a residue which was purified by preparative SFC (Column 2-EP, from 20% to 25% in 6 min) to afford the title compound as a grey solid. UPLC-MS (Condition 3) $t_R$ 1.02 min, m/z=433.4 [M+H]$^+$, m/z=477.3 [M+formic acid-H]$^-$; $^1$H-NMR (400 MHz, DMSO-d$_6$) δ ppm 1.67-1.77 (m, 1H) 1.77-1.88 (m, 1H) 2.97 (d, J=11.80 Hz, 1H) 3.23-3.32 (m, 2H) 3.39-3.49 (m, 1H) 4.15-4.24 (m, 1H) 4.79-4.89 (m, 1H) 6.06-6.13 (m, 2H) 6.76-6.84 (m, 1H) 7.34 (d, J=8.28 Hz, 2H) 7.82-7.92 (m, 2H) 8.02 (d, J=2.51 Hz, 1H) 8.69 (d, J=2.51 Hz, 1H) 10.17 (s, 1H) 11.14 (d, J=1.76 Hz, 1H).

Stage 6.1 (R)-5-Bromo-6-(3-hydroxypyrrolidin-1-yl)-N-(4-(trifluoromethoxy)phenyl)nicotinamide

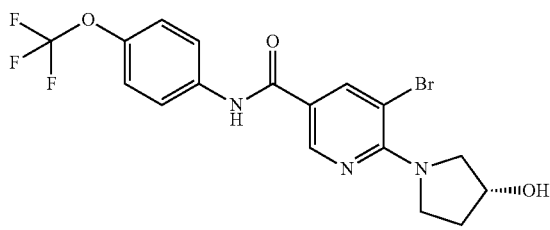

(R)-5-Bromo-6-(3-hydroxypyrrolidin-1-yl)-N-(4-(trifluoromethoxy)phenyl)nicotinamide (Stage 6.2, 2 g, 5.06 mmol) and (R)-pyrrolidin-3-ol (0.529 g, 6.07 mmol) in iPrOH (7.78 mL) were added to a MW vial and subjected to MW irradiation at 140° C. for 30 min. The RM was evaporated to dryness under reduced pressure then extracted from 0.5 M HCl (100 mL) and EtOAc (60 mL). Aq. layer was back extracted with EtOAc (60 mL) and the combined organic layers washed with HCl 0.5 M, water, dried over MgSO$_4$ and evaporated to dryness under reduced pressure. Trituration of the residue in cyclohexane/EtOAc mixture and filtration of the solid afforded the title compound as a yellow solid. UPLC-MS (Condition 1) $t_R$=2.64 min, m/z=445.9/447.9 [M+H]$^+$, m/z=444.0/446.0 [M–H]$^-$; $^1$H-NMR (400 MHz, DMSO-d$_6$) δ ppm 1.82-1.91 (m, 1H) 1.91-1.99 (m, 1H) 3.57 (d, J=11.49 Hz, 1H) 3.71 (ddd, J=10.94, 7.89, 3.42 Hz, 1H) 3.81-3.92 (m, 2H) 4.31-4.40 (m, 1H) 4.98 (d, J=3.18 Hz, 1H) 7.35 (d, J=8.31 Hz, 2H) 7.85 (d, J=9.29 Hz, 2H) 8.34 (d, J=2.20 Hz, 1H) 8.68 (d, J=2.20 Hz, 1H) 10.21 (s, 1H).

Stage 6.2 5-Bromo-6-chloro-N-(4-(trifluoromethoxy)phenyl)nicotinamide

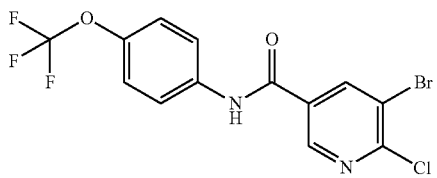 [SMILES: O=C(Nc1ccc(OC(F)(F)F)cc1)c1cnc(Cl)c(Br)c1]

SOCl$_2$ (1.089 mL, 14.92 mmol) and DMF (0.01 mL) were added dropwise to a suspension of 5-bromo-6-chloronicotinic acid (1.176 g, 4.97 mmol) in toluene (10 mL) and the RM was stirred at 85° C. for 2 h. The solvent was evaporated off under reduced pressure and the residue was diluted with THF (10 mL). DIPEA (1.74 mL, 9.95 mmol) was added and the mixture was cooled to −15° C. under argon atmosphere, treated with a solution of 4-trifluoromethoxyaniline (0.701 mL, 5.22 mmol) in THF (10 mL) and stirred at RT for 1 h. The solvent was off under reduced pressure and the residue was treated with aq. 1M HCl (50 mL), and extracted with TBME/EtOAc (4:1). The combined extracts were washed with aq. 1 M HCl, sat. aq. Na$_2$CO$_3$ and brine, dried over MgSO$_4$ and the solvent was evaporated off under reduced pressure to give the crude product was purified by flash chromatography (Biotage Silica gel column, 50 g, cyclohexane/EtOAc from 5% to 25% EtOAc) to afford the title compound as an off-white solid. UPLC-MS (Condition 1) $t_R$=3.09 min, m/z=394.9/396.8 [M+H]$^+$, m/z=393.0/394.9 [M–H]$^-$; $^1$H-NMR (400 MHz, DMSO-d$_6$) δ ppm 7.40 (d, J=8.6 Hz, 2H) 7.86 (d, J=9.0 Hz, 2H) 8.73 (d, J=2.2 Hz, 1H) 8.92 (d, J=2.0 Hz, 1H) 10.69 (s, 1H).

Example 7

(R)-5-(Furan-3-yl)-6-(3-hydroxypyrrolidin-1-yl)-N-(4-(trifluoromethoxy)phenyl)nicotinamide

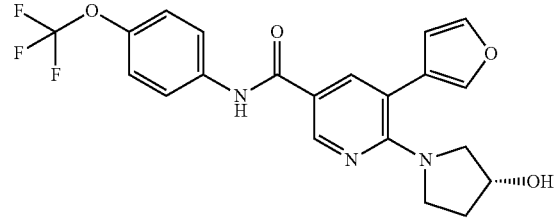 [SMILES: O=C(Nc1ccc(OC(F)(F)F)cc1)c1cnc(N2CC[C@@H](O)C2)c(-c2ccoc2)c1]

A mixture of (R)-5-bromo-6-(3-hydroxypyrrolidin-1-yl)-N-(4-(trifluoromethoxy)phenyl)nicotinamide (Stage 6.1, 60 mg, 0.134 mmol), furan-3-ylboronic acid (22.6 mg, 0.202 mmol), Pd(PPh$_3$)$_2$Cl$_2$ (9.44 mg, 0.013 mmol), Na$_2$CO$_3$ (42.8 mg, 0.403 mmol), DME (570 µL), water (163 µL) and EtOH (81 µL) in a MW vial was sealed, evacuated/purge with argon and subjected to MW irradiation at 120° C. for 10 min. The RM was diluted with THF (1 mL), treated with Si-Thiol (Silicycle, 1.44 mmol/g, 46.7 mg, 0.067 mmol), filtered and the filtrate was evaporated off under reduced pressure to give a residue which was purified by preparative HPLC (Condition 9, 25% for 0.2 min then 25% to 55% in 14 min) to yield the title compound as a white solid. LC-MS (Condition 2) $t_R$=1.92 min, m/z=434.1-435.2 [M+H]$^+$, m/z=432 [M–H]$^-$; $^1$H-NMR (400 MHz, DMSO-d$_6$) δ ppm 1.72-1.81 (m, 1H) 1.82-1.92 (m, 1H) 3.07 (d, J=11.49 Hz, 1H) 3.30-3.45 (m, 1H) 3.48-3.57 (m, 2H) 4.21-4.27 (m, 1H) 6.68 (s, 1H) 7.34 (d, J=8.56 Hz, 2H) 7.76 (t, J=1.59 Hz, 1H) 7.83 (s, 1H) 7.84-7.88 (m, 2H) 7.98 (d, J=2.45 Hz, 1H) 8.70 (d, J=2.45 Hz, 1H) 10.16 (s, 1H).

Example 8

(R)-6-(3-Hydroxypyrrolidin-1-yl)-5-(isoxazol-4-yl)-N-(4-(trifluoromethoxy)phenyl)nicotinamide

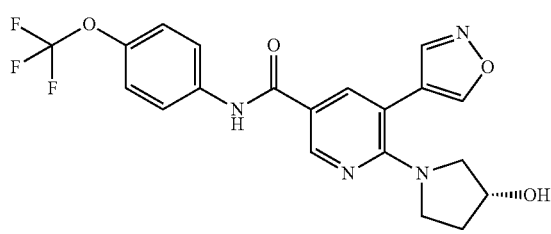

The title compound was prepared in an analogous fashion to that described in Example 7 using (R)-5-bromo-6-(3-hydroxypyrrolidin-1-yl)-N-(4-(trifluoromethoxy)phenyl)nicotinamide (Stage 6.1) and 4-(4,4,5,5-tetramethyl-1,3,2-dioxaborolan-2-yl)isoxazole to afford a white solid. LC-MS (Condition 2) $t_R$=1.80 min, m/z=435.2-436.2 [M+H]$^+$, m/z=433 [M−H]$^−$; $^1$H-NMR (400 MHz, DMSO-d$_6$) δ ppm 1.74-1.82 (m, 1H) 1.84-1.94 (m, 1H) 3.01 (d, J=11.25 Hz, 1H) 3.29-3.53 (m, 3H) 4.22-4.28 (m, 1H) 7.35 (d, J=8.80 Hz, 2H) 7.86 (d, J=9.05 Hz, 2H) 8.03 (d, J=2.20 Hz, 1H) 8.75 (d, J=2.20 Hz, 1H) 8.85 (s, 1H) 9.12 (s, 1H) 10.17 (s, 1H).

Example 9

(R)-6-(3-Hydroxypyrrolidin-1-yl)-5-(thiazol-2-yl)-N-(4-(trifluoromethoxy)phenyl)nicotinamide

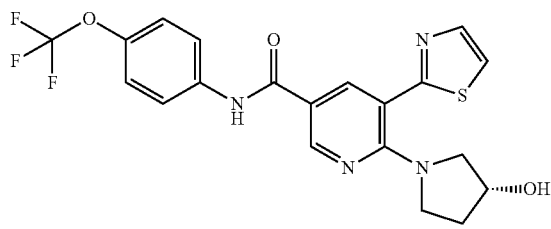 [SMILES: O=C(Nc1ccc(OC(F)(F)F)cc1)c1cnc(N2CC[C@@H](O)C2)c(-c2nccs2)c1]

(R)-6-(3-Hydroxypyrrolidin-1-yl)-5-(4,4,5,5-tetramethyl-1,3,2-dioxaborolan-2-yl)-N-(4-(trifluoromethoxy)phenyl)nicotinamide (Stage 9.1, 50 mg, 0.101 mmol), 2-bromothiazole (24.9 mg, 0.152 mmol), PdCl$_2$(dppf)-(CH$_2$Cl$_2$) (8.28 mg, 10.14 μmol), Na$_2$CO$_3$ (32.2 mg, 0.304 mmol), DME (522 μL) and water (92 μL) were added to a MW vial, which was sealed, evacuated/purged with argon, and RM was stirred at 90° C. for 16 h. The RM was diluted with THF (2 mL), treated with Si-Thiol (1.27 mmol/g, 39.9 mg, 0.051 mmol), filtered and the filtrate was evaporated off under reduced pressure to give a residue which was purified by preparative HPLC (Condition 9, 40% for 0.2 min then 40% to 70% in 14 min) to yield the title compound as a white solid. UPLC-MS (Condition 1) $t_R$=2.51 min, m/z=451-452 [M+H]$^+$, m/z=449-450 [M−H]; $^1$H-NMR (400 MHz, DMSO-d$_6$) δ ppm 1.71-1.80 (m, 1H) 1.81-1.92 (m, 1H) 2.94 (d, J=11.74 Hz, 1H) 3.25-3.30 (m, 2H) 3.43-3.53 (m, 1H) 4.18-4.26 (m, 1H) 4.81-4.94 (m, 1H) 7.35 (d, J=8.56 Hz, 2H) 7.83-7.88 (m, 2H) 7.89 (d, J=3.42 Hz, 1H) 7.94 (d, J=3.42 Hz, 1H) 8.19 (d, J=2.45 Hz, 1H) 8.82 (d, J=2.20 Hz, 1H) 10.25 (s, 1H).

Stage 9.1 (R)-6-(3-Hydroxypyrrolidin-1-yl)-5-(4,4,5,5-tetramethyl-1,3,2-dioxaborolan-2-yl)-N-(4-(trifluoromethoxy)phenyl)nicotinamide

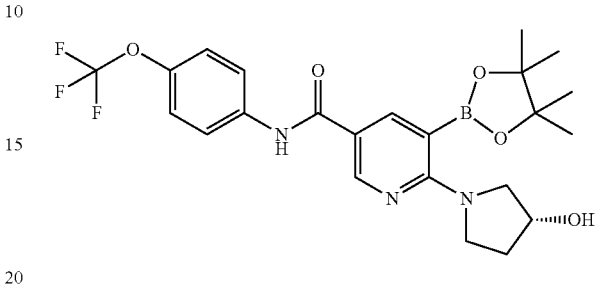

(R)-5-Bromo-6-(3-hydroxypyrrolidin-1-yl)-N-(4-(trifluoromethoxy)phenyl)nicotinamide (Stage 6.1, 376 mg, 0.843 mmol), bis(pinacolato)diboron (856 mg, 3.37 mmol), SPhos (25.9 mg, 0.063 mmol), Pd(OAc)$_2$ (5.68 mg, 0.025 mmol) and finely ground K$_3$PO$_4$ (537 mg, 2.53 mmol) were added to a MW vial, which was sealed and evacuated/purged with argon. Dioxane (3.371 mL) was added and the RM was stirred at 50° C. for 3 days. A second portion of bis(pinacolato) diboron (428 mg, 1.685 mmol) was then added and the reaction was stirred at 50° C. for 16 h and then at 65° C. overnight. Water (30 mL) was added and the mixture was extracted with EtOAc/TBME (1:1). The combined extracts were washed with brine, dried over Na$_2$SO$_4$ and the solvent was evaporated off under reduced pressure to give a crude product which was purified by flash chromatography (RediSep® Silica gel column, 24 g, cyclohexane/EtOAc-EtOH+0.1% NH$_4$OH (9:1) from 20% to 70% EtOAc-EtOH+0.1% NH$_4$OH (9:1)) to afford the title compound as a grey solid. UPLC-MS (Condition 1) $t_R$=2.42 min, m/z=493.1 [M+H]$^+$, m/z=491.1 [M−H]$^−$; $^1$H-NMR (400 MHz, DMSO-d$_6$) δ ppm 1.33 (d, J=5.38 Hz, 12H) 1.80-1.93 (m, 1H) 1.99 (s, 1H) 3.27 (s, 1H) 3.40-3.59 (m, 1H) 3.59-3.78 (m, 2H) 4.37 (br. s, 1H) 4.96 (d, J=3.18 Hz, 1H) 7.34 (d, J=8.56 Hz, 2H) 7.80-7.90 (m, 2H) 8.18 (d, J=2.69 Hz, 1H) 8.76 (d, J=2.69 Hz, 1H) 10.19 (s, 1H).

Example 10

(R)-6-(3-Hydroxypyrrolidin-1-yl)-5-(thiazol-5-yl)-N-(4-(trifluoromethoxy)phenyl)nicotinamide

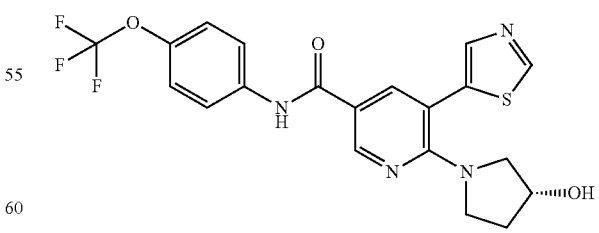

(R)-6-(3-Hydroxypyrrolidin-1-yl)-5-(4,4,5,5-tetramethyl-1,3,2-dioxaborolan-2-yl)-N-(4-(trifluoromethoxy)phenyl) nicotinamide (Stage 9.1, 60 mg, 0.122 mmol), 5-bromothiazole (29.9 mg, 0.182 mmol), PdCl$_2$(dppf)-(CH$_2$Cl$_2$) (9.93 mg, 0.012 mmol), Na$_2$CO$_3$ (38.7 mg, 0.365 mmol) DME (627

μL) and water (111 μL) were added to a MW vial, which was sealed, evacuated/purged with argon and was subjected to MW irradiation at 125° C. for 10 min. Additional 5-bromothiazole, (29.9 mg, 0.182 mmol) was added MW irradiation was continued at 125° C. for 10 min. The RM was stirred with Si-Thiol (1.27 mmol/g, 47.9 mg, 0.061 mmol), filtered and the filtrate was evaporated off under reduced pressure to give a residue which was purified by preparative HPLC (Condition 9, 25% for 0.2 min then 25% to 55% in 14 min) to afford the title compound as a white solid. UPLC-MS (Condition 1) $t_R$=2.17 min, m/z=451.0-452.0 [M+H]$^+$, m/z=449.0-450.0 [M−H]$^−$; $^1$H-NMR (400 MHz, DMSO-d$_6$) δ ppm 1.70-1.79 (m, 1H) 1.80-1.91 (m, 1H) 3.00 (d, J=11.49 Hz, 1H) 3.25-3.31 (m, 2H) 3.42-3.51 (m, 1H) 4.19-4.25 (m, 1H) 4.74-4.99 (m, 1H) 7.34 (d, J=8.56 Hz, 2H) 7.82-7.88 (m, 2H) 7.91 (s, 1H) 8.08 (d, J=2.45 Hz, 1H) 8.78 (d, J=2.45 Hz, 1H) 9.19 (s, 1H), 10.19 (s, 1H).

Example 11

(R)-6-(3-Hydroxypyrrolidin-1-yl)-5-(2-methylthiazol-5-yl)-N-(4-(trifluoromethoxy)phenyl)nicotinamide

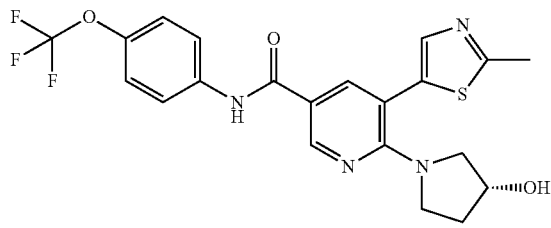 [SMILES: Cc1ncc(-c2cc(C(=O)Nc3ccc(OC(F)(F)F)cc3)cnc2N2CC[C@@H](O)C2)s1]

(R)-5-Bromo-6-(3-hydroxypyrrolidin-1-yl)-N-(4-(trifluoromethoxy)phenyl)nicotinamide (Stage 6.1, 60 mg, 0.134 mmol), 2-methyl-5-(4,4,5,5-tetramethyl-1,3,2-dioxaborolan-2-yl)thiazole (45.4 mg, 0.202 mmol), Pd$_2$(dba)$_3$ (2.463 mg, 2.69 μmol), 2-dichlohexylphosphino-2'-6'-dimethoxybiphenyl (4.42 mg, 10.76 μmol) and K$_3$PO$_4$ (86 mg, 0.403 mmol) were added to a MW vial, which was sealed and evacuated/purged with argon. Dioxane was added and the RM was stirred at 100° C. for 16 h. Additional 2-methylthiasole-5-boronic acid pinacol ester (15.14 mg, 0.067 mmol) and Pd$_2$(dba)$_3$ (2.463 mg, 2.69 μmol) were added and RM was stirred at 100° C. overnight. The RM was diluted with THF (1 mL), treated with Si-Thiol (Silicycle, 1.44 mmol/g, 93 mg, 0.134 mmol), filtered and the filtrate was evaporated off under reduced pressure to give a residue which was purified by preparative HPLC (Condition 9, 30% for 0.2 min then 30% to 60% in 12 min) to yield the title compound as a white solid. UPLC-MS (Condition 1) $t_R$=2.35 min, m/z=465.1-466.1 [M+H]$^+$, m/z=463.1-464.2 [M−H]$^−$; $^1$H-NMR (400 MHz, DMSO-d$_6$) δ ppm 1.71-1.80 (m, 1H) 1.81-1.92 (m, 1H) 2.70 (s, 3H) 3.03-3.09 (m, 1H) 3.25-3.40 (m, 2H) 3.45-3.55 (m, 1H) 4.20-4.27 (m, 1H) 4.88 (d, J=3.18 Hz, 1H) 7.34 (d, J=8.80 Hz, 2H) 7.60 (s, 1H) 7.85 (d, J=9.05 Hz, 2H) 8.04 (d, J=2.45 Hz, 1H) 8.76 (d, J=2.20 Hz, 1H) 10.18 (s, 1H).

Example 12

(R)-5-(5-(Hydroxymethyl)thiophen-3-yl)-6-(3-hydroxypyrrolidin-1-yl)-N-(4-(trifluoromethoxy)phenyl)nicotinamide

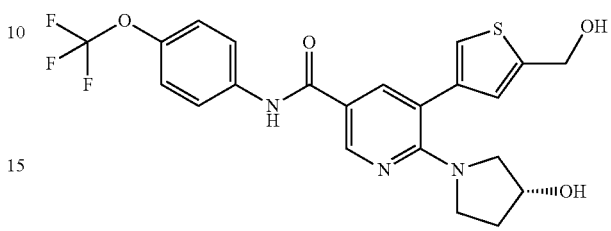

A mixture of (R)-5-chloro-6-(3-hydroxypyrrolidin-1-yl)-N-(4-(trifluoromethoxy)phenyl)nicotinamide (Stage 12.1, 50 mg, 0.124 mmol), (4-(4,4,5,5-tetramethyl-1,3,2-dioxaborolan-2-yl)thiophen-2-yl)methanol (45 mg, 0.187 mmol), 2 M Na$_2$CO$_3$ (0.124 mL, 0.249 mmol) and DME (2.5 mL) were added to a MW vial, which was sealed and evacuated/purged with argon. PdCl$_2$(dppf)-(CH$_2$Cl$_2$) was added (10 mg, 0.012 mmol) and the mixture was stirred at 140° C. for 30 min. The RM was filtered through a PL-Thiol MP SPE cartridge (StratoSpheres™), the cartridge was washed with MeOH and the solvent was evaporated off under reduced pressure to give a residue which was purified by preparative LC-MS to afford the title compound. LC-MS (Condition 5) $t_R$ 1.55 min, m/z=479.9 [M+H]$^+$.

Stage 12.1 (R)-5-Chloro-6-(3-hydroxypyrrolidin-1-yl)-N-(4-(trifluoromethoxy)phenyl)nicotinamide

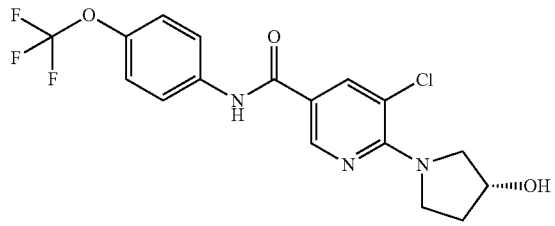 [SMILES: O=C(Nc1ccc(OC(F)(F)F)cc1)c1cnc(N2CC[C@@H](O)C2)c(Cl)c1]

A mixture of 5,6-dichloro-N-(4-(trifluoromethoxy)phenyl)nicotinamide (prepared from 5,6-dichloronicotinic acid in an analogous fashion to that described in Stage 6.2, 1.5 g, 4.27 mmol) and (R)-pyrrolidin-3-ol (447 mg, 5.13 mmol), iPrOH (10 mL) and DIPEA (1.104 g, 8.54 mmol) were subjected to MW irradiation at 140° C. for 60 min. The RM was quenched with water (100 mL) and extracted with EtOAc (3×100 mL). The combined organic extracts were washed with brine (100 mL), dried over MgSO$_4$, filtered and the filtrate was evaporated off under reduced pressure to afford the title compound as a beige powder. $^1$H-NMR (400 MHz, DMSO-d$_6$) δ ppm 1.85-1.97 (m, 2H) 3.59 (d, J=12 Hz, 1H)

3.7-3.8 (m, 1H) 3.8-3.95 (m, 2H) 4.35-4.40 (m, 1H) 5.00 (s, 1H) 7.35 (d, J=2 Hz, 2H) 7.86 (d, J=2 Hz, 2H) 8.17 (s, 1H) 8.66 (s, 1H) 10.22 (s, 1H).

Example 13

(S)-6-(3-Hydroxy-3-methylpyrrolidin-1-yl)-5-(1H-pyrazol-5-yl)-N-(4-(trifluoromethoxy)phenyl)nicotinamide

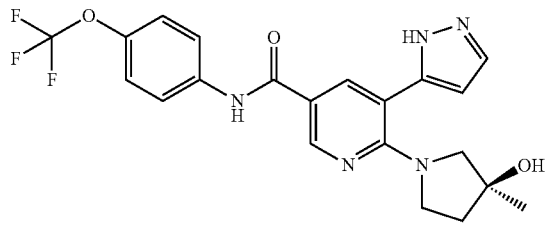 [SMILES: C[C@]1(O)CCN(c2ncc(C(=O)Nc3ccc(OC(F)(F)F)cc3)cc2-c2ccn[nH]2)C1]

(S)-6-(3-Hydroxy-3-methylpyrrolidin-1-yl)-N-(4-(trifluoromethoxy)phenyl)-5-(1-((2-(trimethylsilyl)ethoxy)methyl)-1H-pyrazol-5-yl)nicotinamide (Stage 13.1), ethylenediamine (57.3 µL, 0.848 mmol) and 1 M TBAF in THF (848 µL, 0.848 mmol) was added to a MW vial, which was sealed and the RM was stirred at 80° C. for 24 h. The solvent was evaporated off under reduced pressure to give a residue which was dissolved in EtOAc (30 mL), washed 3 times with sat. aq. NaHCO₃ and brine, dried over Na₂SO₄ and the solvent was evaporated off under reduced pressure to give a crude product was purified by preparative SFC (Column 2-EP, from 20% to 25% in 6 min) to yield the title compound as a white solid. HPLC Chiral (CHIRALCEL® OD-H, 250×4.6 mm, eluent: n-heptane/EtOH/MeOH (80:12:8), 1 mL/min, UV 210 nm) $t_R$=13.92 min, UPLC-MS (Condition 3) $t_R$=0.93 min, m/z=448.2 [M+H]⁺, m/z=446.0 [M−H]⁻; ¹H-NMR (400 MHz, DMSO-d₆) δ ppm 1.19 (s, 3H) 1.65-1.81 (m, 2H) 3.01 (d, J=11.54 Hz, 1H) 3.07 (d, J=10.92 Hz, 1H) 3.24-3.33 (m, 1H) 3.43-3.53 (m, 1H) 4.64-4.75 (m, 1H) 6.34-6.41 (m, 1H) 7.34 (d, J=8.66 Hz, 2H) 7.52-7.84 (m, 1H) 7.86 (d, J=9.16 Hz, 2H) 8.00-8.07 (m, 1H) 8.69-8.78 (m, 1H) 10.19 (s, 1H) 12.89-13.13 (m, 1H).

Stage 13.1 (S)-6-(3-Hydroxy-3-methylpyrrolidin-1-yl)-N-(4-(trifluoromethoxy)phenyl)-5-(1-((2-(trimethylsilyl)ethoxy)methyl)-1H-pyrazol-5-yl)nicotinamide

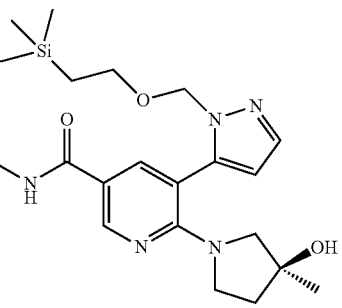

(S)-5-Bromo-6-(3-hydroxy-3-methylpyrrolidin-1-yl)-N-(4-(trifluoromethoxy)phenyl)nicotinamide (Stage 13.2, 60 mg, 0.130 mmol), 5-(4,4,5,5-tetramethyl-1,3,2-dioxaborolan-2-yl)-1-((2-(trimethylsilyl)ethoxy)methyl)-1H-pyrazole (85 mg, 0.261 mmol), Pd(PPh₃)₂Cl₂ (10.98 mg, 0.016 mmol), Na₂CO₃ (55.3 mg, 0.521 mmol), DME (553 µL), water (158 µL) and EtOH (79 µL) were added to a MW vial, which was sealed, evacuated/purged with argon and subjected to MW irradiation at 125° C. for 20 min. The RM was diluted with DME (2 mL), treated with Si-Thiol (Silicycle, 1.44 mmol/g, 54.3 mg, 0.078 mmol), centrifuged, the supernatant was filtered and the solvent was evaporated off under reduced pressure to give a residue which was purified by flash chromatography (RediSep® Silica gel column, 4 g, cyclohexane/EtOAc, from 10% to 60% EtOAc) to yield the title compound as a colorless oil. UPLC-MS (Condition 3) $t_R$=1.26 min, m/z=578.3 [M+H]+, m/z=622.3 [M+formic acid-H]−.

Stage 13.2 (S)-5-Bromo-6-(3-hydroxy-3-methylpyrrolidin-1-yl)-N-(4-(trifluoromethoxy)phenyl)nicotinamide

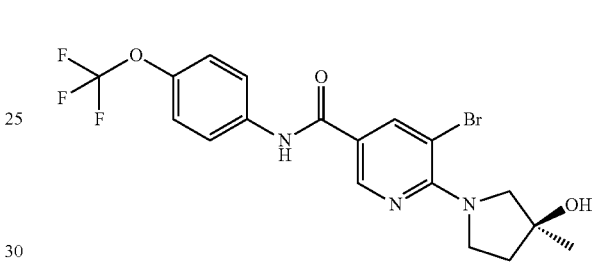

The title compound was obtained after chiral separation (preparative HPLC, Chiralcel OD 20 µm 00CM-EK002, 50×5 cm, mobile phase: n-heptane/EtOH (90:10) (v/v), flow rate: 50 mL/min) of racemic 5-bromo-6-(3-hydroxy-3-methylpyrrolidin-1-yl)-N-(4-(trifluoromethoxy)phenyl)nicotinamide (Stage 13.3) (2.18 g, 4.74 mmol) to afford a white solid. UPLC-MS (Condition 3) $t_R$=1.14 min, m/z=460.3/462.3 [M+H]+, m/z=458.1/460.1 [M−H]−; ¹H-NMR (400 MHz, DMSO-d₆) δ ppm 1.32 (s, 3H) 1.74-1.91 (m, 2H) 3.60 (d, J=11.32 Hz, 1H) 3.66 (d, J=11.32 Hz, 1H) 3.69-3.74 (m, 1H) 3.86-3.95 (m, 1H) 4.79 (s, 1H) 7.33 (d, J=8.59 Hz, 2H) 7.79-7.87 (m, 2H) 8.31 (d, J=1.95 Hz, 1H) 8.65 (d, J=1.95 Hz, 1H) 10.20 (s, 1H). Chiral HPLC: Column: Chiralcel OD-H 5 µm, 4.6×250 mm, eluent n-heptane/EtOH (9:1), flow at 1.1 mL/min, $t_R$=11.29 min, ee=99.0% (UV-210 nm).

Stage 13.3 5-Bromo-6-(3-hydroxy-3-methylpyrrolidin-1-yl)-N-(4-(trifluoromethoxy)phenyl)nicotinamide

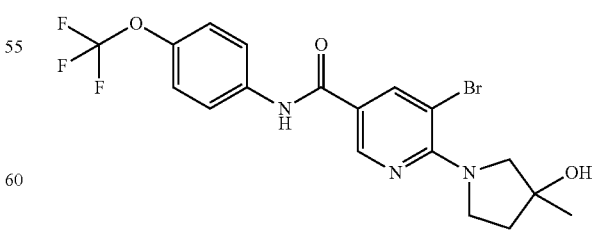

The title compound was prepared in an analogous fashion to that described in Stage 6.1 using 5-bromo-6-chloro-N-(4-(trifluoromethoxy)phenyl)nicotinamide (Stage 6.2) and 3-methylpyrrolidin-3-ol hydrochloride to afford a white solid. UPLC-MS (Condition 1) $t_R$=2.79 min, m/z=460.9/461.9 [M+H]$^+$, m/z=458.0/460 [M−H]$^−$; $^1$H-NMR (400 MHz, DMSO-d$_6$) δ ppm 1.34 (s, 3H) 1.76-1.93 (m, 2H) 3.63 (d, 1H) 3.68 (d, 1H) 3.70-3.76 (m, 1H) 3.88-3.97 (m, 1H) 4.82 (s, 1H) 7.35 (d, J=8.31 Hz, 2H) 7.85 (d, J=9.05 Hz, 2H) 8.33 (d, J=2.20 Hz, 1H) 8.67 (d, J=2.20 Hz, 1H) 10.22 (s, 1H).

Example 14

(R)-6-(3-Hydroxy-3-methylpyrrolidin-1-yl)-5-(1H-pyrazol-5-yl)-N-(4-(trifluoromethoxy)phenyl)nicotinamide

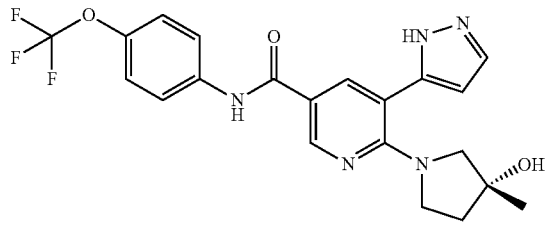 [SMILES: C[C@@]1(O)CCN(c2ncc(C(=O)Nc3ccc(OC(F)(F)F)cc3)cc2-c2ccn[nH]2)C1]

The title compound was prepared in an analogous fashion to that described in Example 15 using (R)-5-bromo-6-(3-hydroxy-3-methylpyrrolidin-1-yl)-N-(4-(trifluoromethoxy)phenyl)nicotinamide (Stage 14.1) and (1H-pyrazol-3-yl)boronic acid to afford a white solid. HPLC Chiral (CHIRALCEL® OD-H, 250×4.6 mm, eluent: n-heptane/EtOH/MeOH (80:12:8), 1 mL/min, UV 210 nm) $t_R$=5.49 min, UPLC-MS (Condition 3) $t_R$=0.93 min, m/z=448.3 [M+H]$^+$, m/z=446.1 [M−H]$^−$, 492.1 [M+formic acid-H]$^−$; $^1$H-NMR (400 MHz, DMSO-d$_6$) δ ppm 1.20 (s, 3H) 1.65-1.81 (m, 2H) 2.99 (d, J=10.54 Hz, 1H) 3.06 (d, J=11.80 Hz, 1H) 3.24-3.33 (m, 1H) 3.48 (td, J=10.20, 7.22 Hz, 1H) 4.68 (s, 1H) 6.38 (d, J=2.01 Hz, 1H) 7.33 (d, J=9.16 Hz, 2H) 7.75 (br. s, 1H) 7.83-7.90 (m, 2H) 8.03 (d, J=2.51 Hz, 1H) 8.73 (d, J=2.38 Hz, 1H) 10.19 (br. s, 1H) 12.96 (br. s, 1H).

Stage 14.1 (R)-5-Bromo-6-(3-hydroxy-3-methylpyrrolidin-1-yl)-N-(4-(trifluoromethoxy)phenyl)nicotinamide

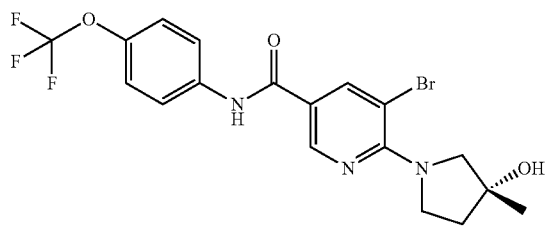 [SMILES: C[C@@]1(O)CCN(c2ncc(C(=O)Nc3ccc(OC(F)(F)F)cc3)cc2Br)C1]

The title compound was obtained after chiral separation (preparative HPLC, Chiralcel OD 20 μm 00CM-EK002, 50×5 cm, mobile phase: n-heptane/EtOH (90:10) (v/v), flow rate: 50 mL/min) of racemic 5-bromo-6-(3-hydroxy-3-methylpyrrolidin-1-yl)-N-(4-(trifluoromethoxy)phenyl)nicotinamide (Stage 13.3) (2.18 g, 4.74 mmol) to afford a white solid. UPLC-MS (Condition 3) $t_R$=1.14 min, m/z=460.3/462.3 [M+H]$^+$, m/z=458.1/460.1 [M−H]$^−$; $^1$H-NMR (400 MHz, DMSO-d$_6$) δ ppm 1.32 (s, 3H) 1.71-1.95 (m, 2H) 3.60 (d, J=10.93 Hz, 1H) 3.66 (d, J=10.93 Hz, 1H) 3.69-3.74 (m, 1H) 3.85-3.95 (m, 1H) 4.79 (s, 1H) 7.33 (d, J=8.59 Hz, 2H) 7.80-7.86 (m, 2H) 8.31 (d, J=2.34 Hz, 1H) 8.65 (d, J=1.95 Hz, 1H) 10.20 (s, 1H). Chiral HPLC: Column: Chiralcel OD-H 5 μm, 4.6×250 mm, eluent n-heptane/EtOH (9:1), flow at 1.1 mL/min, $t_R$=16.66 min, ee=99.4% (UV-210 nm).

Example 15

5-(1H-Pyrazol-5-yl)-6-(pyrrolidin-1-yl)-N-(4-(trifluoromethoxy)phenyl)nicotinamide

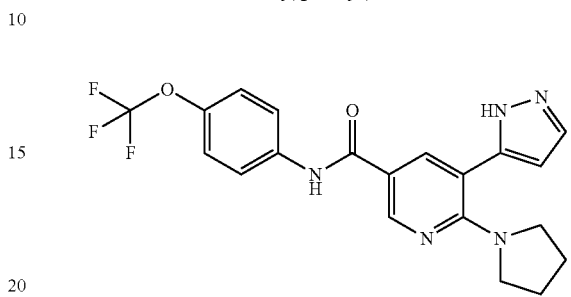

5-Bromo-6-(pyrrolidin-1-yl)-N-(4-(trifluoromethoxy)phenyl)nicotinamide (Stage 15.1, 60 mg, 0.139 mmol) and (1H-pyrazol-3-yl)boronic acid (62.4 mg, 0.558 mmol), Pd(PPh$_3$)$_2$Cl$_2$ (11.75 mg, 0.017 mmol), Na$_2$CO$_3$ (73.9 mg, 0.697 mmol), DME (592 μL), water (169 μL) and EtOH (85 μL) were added to a MW vial, which was sealed, evacuated/purged with argon and subjected to MW irradiation at 130° C. for 30 min. Additional 1-H-Pyrazole-3-boronic acid, (31.2 mg, 0.279 mmol) was added to the RM and was subjected to further MW irradiation at 130° C. for 30 min. The RM was diluted with THF (2 mL), treated with Si-Thiol (1.44 mmol/g, 58.1 mg, 0.084 mmol)., centrifuged, the supernatant was filtered and the solvent was evaporated off under reduced pressure to give a residue which was purified by preparative SFC (Column 2-EP, from 10% to 15% in 6 min) to yield the title compound as a white solid. UPLC-MS (Condition 3) $t_R$=1.02 min, m/z=418.4 [M+H]$^+$, m/z=462.2 [M+formic acid-H]$^−$; $^1$H-NMR (400 MHz, DMSO-d$_6$) δ ppm 1.64-1.90 (m, 4H) 3.19 (t, J=6.21 Hz, 4H) 6.40 (d, J=1.88 Hz, 1H) 7.35 (d, J=8.66 Hz, 2H) 7.75 (br. s, 1H) 7.87 (d, J=9.03 Hz, 2H) 8.04 (d, J=2.26 Hz, 1H) 8.75 (d, J=2.38 Hz, 1H) 10.22 (br. s, 1H) 12.70-13.19 (m, 1H).

Stage 15.1 5-Bromo-6-(pyrrolidin-1-yl)-N-(4-(trifluoromethoxy)phenyl)nicotinamide

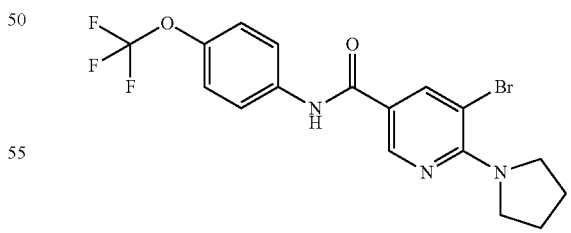

5-Bromo-6-chloro-N-(4-(trifluoromethoxy)phenyl)nicotinamide (Stage 6.2, 1 g, 2.53 mmol), pyrrolidine (0.544 g, 5.06 mmol), DIPEA (1.325 mL, 7.58 mmol) and iPrOH (2.53 mL) were added to a MW vial and subjected to MW irradiation at 140° C. for 1 h. The mixture was treated with aqueous HCl (40 mL of 0.5 M) was added and extracted with EtOAc The combined extracts were washed with 0.5 M HCl (40 mL) and brine, dried over Na$_2$SO$_4$ and the solvent was evaporated off under reduced pressure to give a residue was crystallized from cyclohexane/EtOAc to yield the title compound as an off-white solid. UPLC-MS (Condition 3) $t_R$=1.34 min, m/z=430.1/432.1 [M+H]$^+$, m/z=428.3/430.3 [M−H]$^−$; $^1$H-NMR (400 MHz, DMSO-$d_6$) δ ppm 1.76-2.01 (m, 4H) 3.60-3.80 (m, 4H) 7.33 (d, J=8.20 Hz, 2H) 7.72-7.91 (m, 2H) 8.32 (d, J=1.95 Hz, 1H) 8.66 (d, J=1.95 Hz, 1H) 10.20 (s, 1H).

Example 16

(S)-6-(3-(Hydroxymethyl)pyrrolidin-1-yl)-5-(2-methylthiazol-5-yl)-N-(4-(trifluoromethoxy)phenyl)nicotinamide

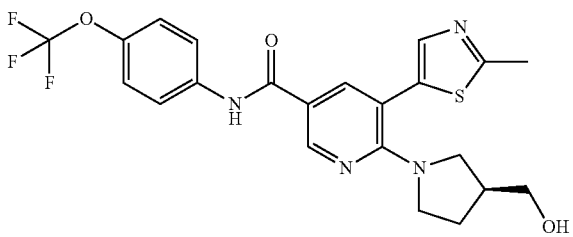 [SMILES: Cc1ncc(-c2cc(C(=O)Nc3ccc(OC(F)(F)F)cc3)cnc2N2CC[C@H](CO)C2)s1]

(S)-5-Bromo-6-(3-(hydroxymethyl)pyrrolidin-1-yl)-N-(4-(trifluoromethoxy)phenyl)nicotinamide (Stage 16.1, 92 mg, 0.2 mmol), 2-methyl-5-(4,4,5,5-tetramethyl-1,3,2-dioxaborolan-2-yl)thiazole (90 mg, 0.4 mmol), Na$_2$CO$_3$ (53 mg, 0.5 mmol), dioxane (1 mL) and water (0.6 mL). were added to a MW vial, which was sealed and evacuated/purged with argon. Pd(Ph$_3$P)$_4$ (11.56 mg, 0.01 mmol) was added and the RM was stirred at 80° C. for 18 h. The RM was dissolved in EtOAc, washed with brine, dried over Na$_2$SO$_4$ and the solvent was evaporated off under reduced pressure to give a residue. The residue, 2-methyl-5-(4,4,5,5-tetramethyl-1,3,2-dioxaborolan-2-yl)thiazole (90 mg, 0.4 mmol), Na$_2$CO$_3$ (53 mg, 0.5 mmol), dioxane (1 mL) and water (0.6 mL) added to an MW vial which was sealed and evacuated/purged with argon. Pd(Ph$_3$P)$_4$ (11.56 mg, 0.01 mmol) was added and the RM was stirred at 80° C. for 18 h. After cooling the RM was dissolved in EtOAc, washed with brine, dried over Na$_2$SO$_4$ and the solvent was evaporated off under reduced pressure to give a crude product was purified by flash chromatography (RediSep® Silica gel column, DCM/MeOH from 2% to 5% MeOH) followed by reverse phase chromatography (MPLC, Lichroprep® 15-25 µm column, water+0.1% formic acid/MeCN+0.1% formic acid, gradient 10% to 40% MeCN+0.1% formic acid). The fractions containing pure product were combined, treated with excess aqueous NaHCO$_3$ and extracted with EtOAc. The combined extracts were dried over Na$_2$SO$_4$ and the solvent was evaporated off under reduced pressure to give a residue which was dissolved in MeOH and the solvent was evaporated off under reduced pressure to afford the title compound as an off-white amorphous solid. HPLC (Condition 4) $t_R$=5.1 min, UPLC-MS (Condition 6) m/z=479.1 [M+H]$^+$; $^1$H-NMR (400 MHz, DMSO-$d_6$) δ ppm 1.59 (m, J=7.40 Hz, 1H) 1.85 (m, J=6.30 Hz, 1H) 2.15-2.31 (m, 1H) 2.68 (s, 3H) 3.03-3.19 (m, 1H) 3.21-3.40 (m, 5H) 4.63 (t, J=5.28 Hz, 1H) 7.33 (d, J=8.99 Hz, 2H) 7.60 (s, 1H) 7.83 (d, J=8.99 Hz, 2H) 8.03 (d, J=2.35 Hz, 1H) 8.73 (m, J=1.00 Hz, 1H) 10.17 (s, 1H).

Stage 16.1 (S)-5-Bromo-6-(3-(hydroxymethyl)pyrrolidin-1-yl)-N-(4-(trifluoromethoxy)phenyl)nicotinamide

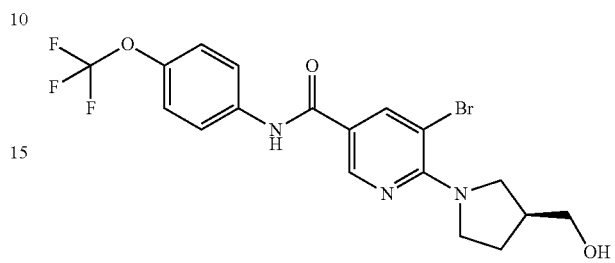

5-Bromo-6-chloro-N-(4-(trifluoromethoxy)phenyl)nicotinamide (Stage 6.2, 500 mg, 1.264 mmol), (S)-beta-prolinol hydrochloride (226 mg, 1.643 mmol), DIPEA (662 µL, 3.79 mmol) and iPrOH (1.945 mL) were added to a MW vial and subjected to MW irradiation at 140° C. for 60 min. The solvent was evaporated off under reduced pressure and the residue was treated with aq. 0.5 M HCl (20 mL) and extracted with EtOAc. The combined extracts were washed with 0.5 M HCl (10 mL) and water, dried over MgSO$_4$ and the solvent was evaporated off under reduced pressure to give the product which was triturated with cyclohexane, filtered and dried to afford the title compound as a white solid. UPLC-MS (Condition 1) $t_R$=2.76 min, m/z=460.0/462.0 [M+H]$^+$, m/z=458.0/460.0 [M−H]$^−$; $^1$H-NMR (400 MHz, DMSO-$d_6$) δ ppm 1.59-1.76 (m, 1H) 1.92-2.04 (m, 1H) 2.26-2.44 (m, 1H) 3.37-3.50 (m, 2H) 3.56 (dd, J=11.00, 7.34 Hz, 1H) 3.67-3.85 (m, 3H) 4.71 (br. s, 1H) 7.35 (d, J=8.56 Hz, 2H) 7.85 (d, 1H) 8.34 (d, J=1.96 Hz, 1H) 8.68 (d, J=1.96 Hz, 1H) 10.21 (s, 1H).

Example 17

6-(trans-3-Hydroxy-4-(hydroxymethyl)pyrrolidin-1-yl)-5-(thiazol-5-yl)-N-(4-(trifluoromethoxy)phenyl)nicotinamide

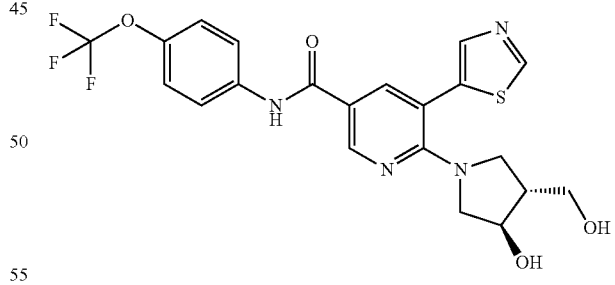

6-((3R,4R)-3-Hydroxy-4-(hydroxymethyl)pyrrolidin-1-yl)-5-(4,4,5,5-tetramethyl-1,3,2-dioxaborolan-2-yl)-N-(4-(trifluoromethoxy)phenyl)nicotinamide (Stage 17.1, 50 mg, 0.096 mmol), 5-bromothiazole (78 mg, 0.478 mmol), Pd(Ph$_3$P)$_4$ (11.04 mg, 9.55 µmol), K$_3$PO$_4$ (81 mg, 0.382 mmol) toluene (478 µL) were added to a MW vial, which was sealed, evacuated/purged with argon and the RM was stirred for 16 h at 110° C. The RM was diluted with DME (2 mL)/EtOAc (1 mL), treated with Si-Thiol (Silicycle, 1.44 mmol/g, 39.8 mg, 0.057 mmol), centrifuged, the supernatant was filtered and the solvent was evaporated off under reduced pressure to give a residue which was purified by preparative SFC (Column Diol, isocratic at 30% in 8 min) to afford the title compound as an amber wax. UPLC-MS (Condition 3) $t_R$=0.90 min, m/z=481.3 [M+H]$^+$; $^1$H-NMR (400 MHz, DMSO-d$_6$) δ ppm 2.05-2.15 (m, 1H) 2.99 (dd, J=10.79, 3.14 Hz, 1H) 3.18-3.23 (m, 1H) 3.22-3.28 (m, 1H) 3.39 (m, J=5.40 Hz, 2H) 3.52 (dd, J=11.30 Hz, 1H) 3.94-4.03 (m, 1H) 4.66 (t, J=5.27 Hz, 1H) 5.00 (d, J=4.27 Hz, 1H) 7.36 (d, J=8.41 Hz, 2H) 7.83-7.89 (m, 2H) 7.94 (d, J=0.50 Hz, 1H) 8.09 (d, J=2.38 Hz, 1H) 8.78 (d, J=2.38 Hz, 1H) 9.20 (d, J=0.50 Hz, 1H) 10.22 (s, 1H).

Stage 17.1 6-((3R,4R)-3-Hydroxy-4-(hydroxymethyl)pyrrolidin-1-yl)-5-(4,4,5,5-tetramethyl-1,3,2-dioxaborolan-2-yl)-N-(4-(trifluoromethoxy)phenyl)nicotinamide

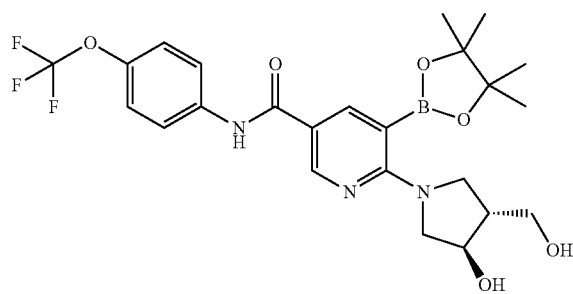 [SMILES: CC1(C)OB(c2cc(C(=O)Nc3ccc(OC(F)(F)F)cc3)cnc2N2C[C@H](CO)[C@@H](O)C2)OC1(C)C]

5-Bromo-6-((3R,4R)-3-hydroxy-4-(hydroxymethyl)pyrrolidin-1-yl)-N-(4-(trifluoromethoxy)phenyl)nicotinamide (Stage 17.2, 250 mg, 0.525 mmol), Bis(pinacolato)diboron (533 mg, 2.1 mmol), SPhos (16.16 mg, 0.039 mmol), Pd(OAc)$_2$ (3.54 mg, 0.016 mmol) and K$_3$PO$_4$ (334 mg, 1.575 mmol) were added to a MW vial, which was sealed and evacuated/purged with argon. Dioxane (2.1 mL) was added and the RM was stirred at 50-55° C. for 16 h. The RM was treated with water (20 mL) and extracted with EtOAc/TBME (1:1). The combined extracts were washed with brine and dried over Na$_2$SO$_4$ and the solvent was evaporated off under reduced pressure to give a crude product was purified by flash chromatography (RediSep® Silica gel column, 12 g, DCM/MeCN, from 25% to 100% MeCN) to afford the title compound as a colorless wax. UPLC-MS (Condition 3) $t_R$=1.03 min, m/z=524.4 [M+H]$^+$, m/z=522.4 [M–H]$^-$; $^1$H-NMR (400 MHz, DMSO-d$_6$) δ ppm 1.32 (s, 12H) 2.18-2.27 (m, 1H) 3.25-3.31 (m, 1H) 3.33-3.40 (m, 2H) 3.47 (s, 1H) 3.64-3.74 (m, 2H) 4.11 (s, 1H) 4.69 (t, J=5.14 Hz, 1H) 5.07 (d, J=4.16 Hz, 1H) 7.34 (d, J=8.31 Hz, 2H) 7.82-7.88 (m, 2H) 8.16 (d, J=2.69 Hz, 1H) 8.75 (d, J=2.45 Hz, 1H) 10.20 (s, 1H).

Stage 17.2 5-Bromo-6-((3R,4R)-3-hydroxy-4-(hydroxymethyl)pyrrolidin-1-yl)-N-(4-(trifluoromethoxy)phenyl)nicotinamide

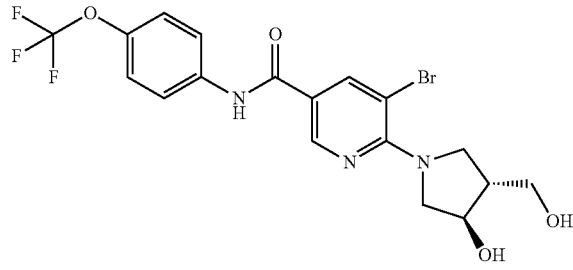 [SMILES: O=C(Nc1ccc(OC(F)(F)F)cc1)c1cnc(N2C[C@H](CO)[C@@H](O)C2)c(Br)c1]

The title compound was prepared in an analogous fashion to that described in Stage 6.1 using 5-bromo-6-chloro-N-(4-(trifluoromethoxy)phenyl)nicotinamide (Stage 6.2) and trans-4-(hydroxymethyl)pyrrolidin-3-ol hydrochloride to afford an off-white solid. UPLC-MS (Condition 3) $t_R$=0.98 min, m/z=476.2/478.2 [M+H]$^+$, m/z=474.0/476.0 [M–H]$^-$; $^1$H-NMR (400 MHz, DMSO-d$_6$) δ ppm 2.11-2.23 (m, 1H) 3.25-3.34 (m, 2H) 3.39-3.49 (m, 1H) 3.50-3.62 (m, 2H) 3.83-3.96 (m, 2H) 4.04-4.12 (m, 1H) 4.70 (t, J=5.27 Hz, 1H) 5.07 (d, J=4.37 Hz, 1H) 7.33 (d, J=8.75 Hz, 2H) 7.83 (d, J=9.00 Hz, 2H) 8.32 (d, J=2.06 Hz, 1H) 8.66 (d, J=1.80 Hz, 1H) 10.21 (s, 1H).

Example 18

6-Morpholino-5-(1H-pyrazol-5-yl)-N-(4-(trifluoromethoxy)phenyl)nicotinamide

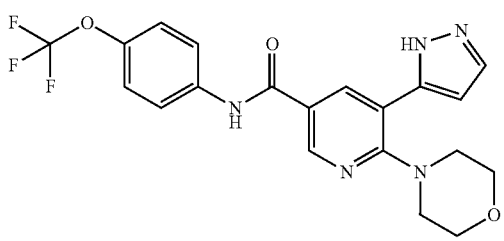 [SMILES: O=C(Nc1ccc(OC(F)(F)F)cc1)c1cnc(N2CCOCC2)c(-c2ccn[nH]2)c1]

5-Bromo-6-morpholino-N-(4-(trifluoromethoxy)phenyl)nicotinamide (Stage 18.1, 100 mg, 0.224 mmol), 1-(tetrahydro-2H-pyran-2-yl)-5-(4,4,5,5-tetramethyl-1,3,2-dioxaborolan-2-yl)-1H-pyrazole (125 mg, 0.448 mmol), Pd(Ph$_3$P)$_4$ (25.9 mg, 0.022 mmol) and K$_3$PO$_4$ (190 mg, 0.896 mmol) and toluene (1.121 mL) were added to a MW vial, which was sealed, evacuated/purged with argon and the RM was stirred for 16 h at 110° C. The RM was diluted with DME (2 mL), treated with Si-Thiol (Silicycle, 1.44 mmol/g, 93 mg, 0.134 mmol), centrifuged, the supernatant was filtered and the solvent was evaporated off under reduced pressure to give a residue which was purified by flash chromatography (RediSep® Silica gel column, 4 g, cyclohexane/EtOAc from 10% to 60% EtOAc). The fractions containing pure product were combined and the solvent was evaporated off under reduced pressure to give a residue which was treated with TFA (500 μL, 6.49 mmol) and DCM (1.5 mL) and then stirred at RT for 4.5 h. The RM was diluted with DCM (30 mL) and washed with water, sat. aq. NaHCO3, brine and dried over Na$_2$SO$_4$. The solvent was evaporated off under reduced pressure to give a crude product which was purified by preparative SFC (Column Diol, from 20% to 25% in 6 min) to yield the title product as a white solid. UPLC-MS (Condition 3) $t_R$=1.0 min, m/z=434.2 [M+H]$^+$; $^1$H-NMR (400 MHz, DMSO-d$_6$) δ ppm 3.07-3.25 (m, 4H) 3.55-3.75 (m, 4H) 6.62-6.82 (m, 1H) 7.36 (d, J=8.53 Hz, 2H) 7.54-7.88 (m, 1H) 7.85-7.92 (m, 2H) 8.20-8.40 (m, 1H) 8.76 (d, J=2.13 Hz, 1H) 10.44 (br. s, 1H) 13.02-13.31 (m, 1H).

Stage 18.1 5-Bromo-6-morpholino-N-(4-(trifluoromethoxy)phenyl)nicotinamide

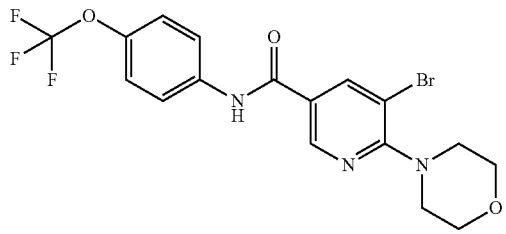 [SMILES: O=C(Nc1ccc(OC(F)(F)F)cc1)c1cnc(N2CCOCC2)c(Br)c1]

The title compound was prepared in an analogous fashion to that described in Stage 6.1 using 5-bromo-6-chloro-N-(4-(trifluoromethoxy)phenyl)nicotinamide (Stage 6.2) and morpholine to afford an off-white solid. UPLC-MS (Condition 3) $t_R$=1.20 min, m/z=445.9 [M+H]$^+$, m/z=443.9 [M−H]$^−$; $^1$H-NMR (400 MHz, DMSO-d$_6$) δ ppm 3.37-3.46 (m, 4H) 3.69-3.81 (m, 4H) 7.39 (d, J=8.78 Hz, 2H) 7.86 (d, J=9.16 Hz, 2H) 8.47 (d, J=2.13 Hz, 1H) 8.80 (d, J=2.13 Hz, 1H) 10.44 (s, 1H).

Example 19

6-((2-Hydroxyethyl)(methyl)amino)-5-(1H-pyrazol-5-yl)-N-(4-(trifluoromethoxy)phenyl)nicotinamide

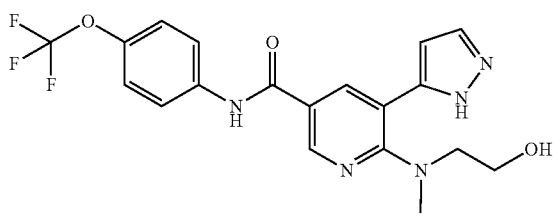 [SMILES: CN(CCO)c1ncc(C(=O)Nc2ccc(OC(F)(F)F)cc2)cc1-c1ccn[nH]1]

5-Bromo-6-((2-hydroxyethyl)(methyl)amino)-N-(4-(trifluoromethoxy)phenyl)nicotinamide (Stage 19.1, 87 mg, 0.2 mmol), 5-(4,4,5,5-tetramethyl-1,3,2-dioxaborolan-2-yl)-1-((2-(trimethylsilyl)ethoxy)methyl)-1H-pyrazole (130 mg, 0.401 mmol), Pd(PPh$_3$)$_2$Cl$_2$ (14.06 mg, 0.020 mmol), Na$_2$CO$_3$ (85 mg, 0.801 mmol), DME (850 μL), water (243 μL) and EtOH (121 μL) were added to a MW vial, which was sealed, evacuated/purged with argon and subjected to MW irradiation at 125° C. for 20 h. The RM was diluted with DME (3 mL), treated with Si-Thiol (Silicycle, 1.44 mmol/g, 83 mg, 0.120 mmol, centrifuged, the supernatant was filtered and the solvent was evaporated off under reduced pressure to give a residue which was purified by preparative SFC (Column NH$_2$, from 8% to 13% in 10 min). The resulting intermediate was treated with ethylene diamine (33.7 μL, 0.499 mmol) and 1 M TBAF in THF (1.496 mL, 1.496 mmol) and stirred at 75° C. for 24 h. The solvent was evaporated off under reduced pressure to give a, diluted with EtOAc (30 mL), washed 3 times with sat. aq. NaHCO$_3$, brine, dried over Na$_2$SO$_4$ and the solvent was evaporated off under reduced pressure to give a. The crude product was purified by preparative SFC (Column DEAP, isocratic 23% in 9 min) to yield the title product as yellow wax. UPLC-MS (Condition 3) $t_R$=0.92 min, m/z=422.2 [M+H]$^+$, m/z=420.1 [M−H]$^−$; $^1$H-NMR (400 MHz, DMSO-d$_6$) δ ppm 2.77 (s, 3H) 3.44 (t, J=5.87 Hz, 2H) 3.55 (q, J=5.46 Hz, 2H) 4.63 (br. s, 1H) 6.48 (d, J=2.20 Hz, 1H) 7.35 (d, J=8.56 Hz, 2H) 7.70-7.84 (m, 1H) 7.84-7.91 (m, 2H) 8.15 (d, J=1.96 Hz, 1H) 8.71 (d, J=2.20 Hz, 1H) 10.26 (s, 1H).

Stage 19.1 5-Bromo-6-((2-hydroxyethyl)(methyl)amino)-N-(4-(trifluoromethoxy)phenyl)nicotinamide

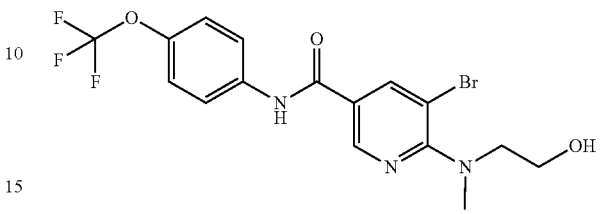

The title compound was prepared in an analogous fashion to that described in Stage 22.1 using 5-bromo-6-chloro-N-(4-(trifluoromethoxy)phenyl)nicotinamide (Stage 6.2) and 2-methylamino-ethanol to afford an off-white crystalline solid. HPLC (Condition 4) $t_R$=5.57 min, UPLC-MS (Condition 3) $t_R$=1.11 min, m/z=434.1 [M+H]$^+$.

Example 20

4-((2-Hydroxyethyl)(methyl)amino)-3-(thiazol-5-yl)-N-(4-(trifluoromethoxy)phenyl)benzamide

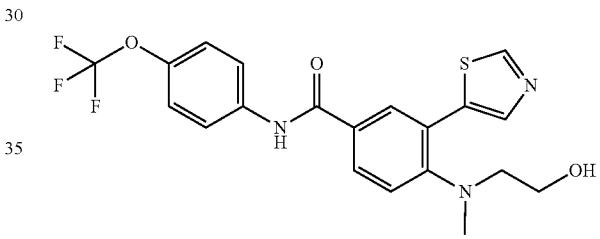

The title compound was prepared in an analogous fashion to that described in Example 1 using 4-fluoro-3-(thiazol-5-yl)-N-(4-(trifluoromethoxy)phenyl)benzamide (Stage 1.1) and (2-methylamino)ethanol to afford a light yellow powder. UPLC-MS (Condition 1) $t_R$=2.43 min, m/z=438.0 [M+H]$^+$, m/z=436.1 [M−H]$^−$; $^1$H-NMR (400 MHz, DMSO-d$_6$) δ ppm 2.68 (s, 3H) 3.02 (t, J=6.36 Hz, 2H) 3.50 (q, J=6.19 Hz, 2H) 4.53 (t, J=5.26 Hz, 1H) 7.36 (dd, J=8.80, 3.67 Hz, 3H) 7.82-7.95 (m, 3H) 8.15 (d, J=2.20 Hz, 1H) 8.35 (s, 1H) 9.13 (s, 1H) 10.34 (s, 1H).

Example 21

6-(Ethyl(2-hydroxyethyl)amino)-5-(1H-pyrazol-5-yl)-N-(4-(trifluoromethoxy)phenyl)nicotinamide

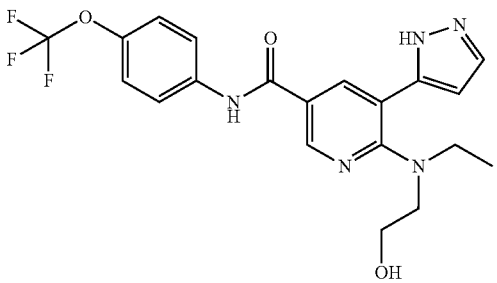 [SMILES: CCN(CCO)c1ncc(C(=O)Nc2ccc(OC(F)(F)F)cc2)cc1-c1ccn[nH]1]

The title compound was prepared in an analogous fashion to that described in Example 19 using 5-bromo-6-(ethyl(2-hydroxyethyl)amino)-N-(4-(trifluoromethoxy)phenyl)nicotinamide (Stage 21.1) and 5-(4,4,5,5-tetramethyl-1,3,2-dioxaborolan-2-yl)-1-((2-(trimethylsilyl)ethoxy)methyl)-1H-pyrazole to afford a yellow wax UPLC-MS (Condition 3) $t_R$=0.97 min, m/z=436.2 [M+H]$^+$, m/z=434.3 [M−H]$^−$; $^1$H-NMR (400 MHz, DMSO-d$_6$) δ ppm 0.93 (t, J=6.97 Hz, 3H) 3.26 (br. s, 2H) 3.36-3.44 (m, 2H) 3.44-3.52 (m, 2H) 4.59 (br. s, 1H) 6.53 (d, J=1.96 Hz, 1H) 7.34 (d, J=8.31 Hz, 2H) 7.80 (br. s, 1H) 7.84-7.90 (m, 2H) 8.13 (s, 1H) 8.71 (d, J=1.96 Hz, 1H) 10.28 (s, 1H) 12.94 (br. s, 1H).

Stage 21.1 5-Bromo-6-(ethyl(2-hydroxyethyl)amino)-N-(4-(trifluoromethoxy)phenyl)nicotinamide

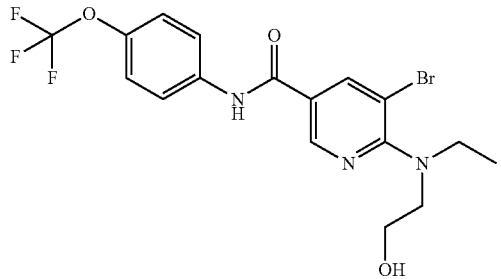 [SMILES: CCN(CCO)c1ncc(C(=O)Nc2ccc(OC(F)(F)F)cc2)cc1Br]

The title compound was prepared in an analogous fashion to that described in Stage 22.1 using 5-bromo-6-chloro-N-(4-(trifluoromethoxy)phenyl)nicotinamide (Stage 6.2) and 2-(ethylamino)ethanol to afford a white solid. (The RM was heated at 140° C. for 18 h). HPLC (Condition 4) $t_R$=5.92 min, UPLC-MS (Condition 3) $t_R$=1.19 min, m/z=450.1 [M+H]$^+$.

Example 22

(R)—N-(4-(Chlorodifluoromethoxy)phenyl)-6-(3-hydroxypyrrolidin-1-yl)-5-(1H-pyrrol-2-yl)nicotinamide

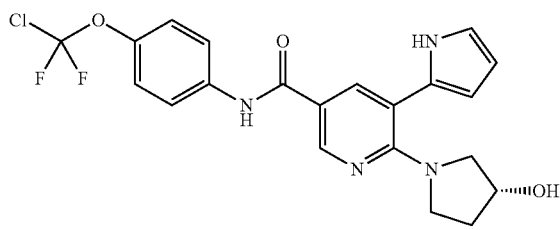 [SMILES: O=C(Nc1ccc(OC(F)(F)Cl)cc1)c1cnc(N2CC[C@@H](O)C2)c(-c2ccc[nH]2)c1]

The title compound was prepared in an analogous fashion to that described in Example 6 using (R)-5-bromo-N-(4-(chlorodifluoromethoxy)phenyl)-6-(3-hydroxypyrrolidin-1-yl)nicotinamide (Stage 22.1) and tert-butyl 2-(4,4,5,5-tetramethyl-1,3,2-dioxaborolan-2-yl)-1H-pyrrole-1-carboxylate to afford a grey solid. UPLC-MS (Condition 3) $t_R$=1.06 min, m/z=449.2 [M+H]$^+$, m/z=447.1 [M−H]$^−$; $^1$H-NMR (400 MHz, DMSO-d$_6$) δ ppm 1.64-1.77 (m, 1H) 1.77-1.93 (m, 1H) 2.98 (d, J=12.23 Hz, 1H) 3.21-3.29 (m, 2H) 3.37-3.51 (m, 1H) 4.19 (d, J=2.20 Hz, 1H) 4.81 (d, J=3.42 Hz, 1H) 6.02-6.18 (m, 2H) 6.70-6.88 (m, 1H) 7.32 (d, J=9.05 Hz, 2H) 7.79-7.94 (m, 2H) 8.02 (d, J=2.45 Hz, 1H) 8.70 (d, J=2.45 Hz, 1H) 10.15 (s, 1H) 11.10 (d, J=1.47 Hz, 1H).

Stage 22.1 (R)-5-Bromo-N-(4-(chlorodifluoromethoxy)phenyl)-6-(3-hydroxypyrrolidin-1-yl)nicotinamide

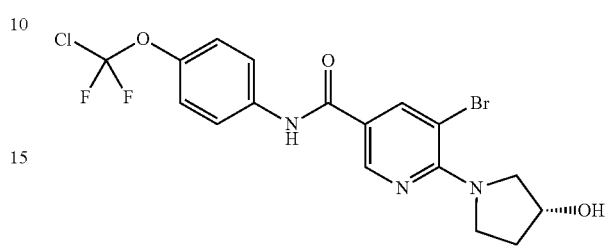

5-Bromo-6-chloro-N-(4-(chlorodifluoromethoxy)phenyl)nicotinamide (Stage 22.2, 206 mg, 0.5 mmol) and (R)-pyrrolidin-3-ol (52.3 mg, 0.6 mmol) were dissolved in iPrOH (1 mL). DIPEA (192 µL, 1.1 mmol) was added and the RM mixture was stirred at 140° C. for 1 h in a sealed vial. After cooling at RT, the RM was dissolved in EtOAc, washed with 0.5 M HCl and brine, dried over Na$_2$SO$_4$ and the solvent was evaporated off under reduced pressure to give a crude product which was purified by flash chromatography (RediSep® Silica gel column, n-heptane/EtOAc from 20% to 100% EtOAc). The resulting product was triturated under n-heptane, filtered and dried to afford the title compound as a white crystalline powder. HPLC (Condition 4) $t_R$=5.68 min, UPLC-MS (Condition 3) $t_R$=1.15 min, m/z=462.1 [M+H]$^+$.

Stage 22.2 5-Bromo-6-chloro-N-(4-(chlorodifluoromethoxy)phenyl)nicotinamide

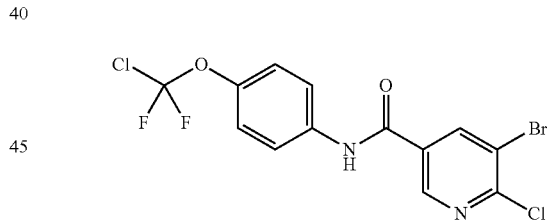

5-Bromo-6-chloro-nicotinic acid (8 g, 33.8 mmol) was suspended in toluene (70 mL). DMF (0.77 mL, 10.15 mmol) was added followed by slow addition of SOCl$_2$ (7.4 mL, 102 mmol) and the RM was stirred for 1 h at 80° C. After cooling at RT, the toluene was evaporated off under reduce pressure. The residue was dissolved in THF (70 mL) and cooled to −10-15° C. and treated with DIPEA (11.8 mL, 67.7 mmol) followed by the slow addition of a solution of 4-(chlorodifluoromethoxy)aniline (6.88 g, 35.5 mmol) in THF (70 mL) over 10 min. The RM was allowed to warm at RT and stirred for 1 h, the solvent was evaporated off under reduced pressure. The residue was dissolved in TBME, the solution was washed with 1 M HCl, 10% aq. NaHCO$_3$ and brine, dried over Na$_2$SO$_4$ and concentrated under reduced pressure until crystallization started. n-Heptane was then added and the product was filtered and dried to afford the title compound as a beige

Example 23

N-(4-(Chlorodifluoromethoxy)phenyl)-6-((2-hydroxyethyl)(methyl)amino)-5-(1H-pyrazol-5-yl)nicotinamide

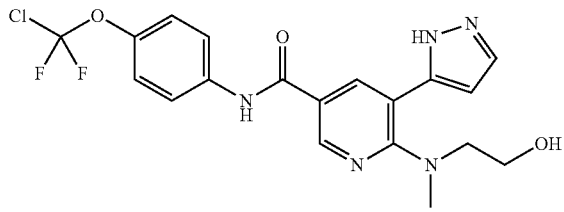 [SMILES: CN(CCO)c1ncc(C(=O)Nc2ccc(OC(F)(F)Cl)cc2)cc1-c1ccn[nH]1]

The title compound was prepared in an analogous fashion to that described in Example 26 using 5-bromo-N-(4-(chlorodifluoromethoxy)phenyl)-6-((2-hydroxyethyl)(methyl)amino)nicotinamide (Stage 23.1) and 1-(tetrahydro-2H-pyran-2-yl)-5-(4,4,5,5-tetramethyl-1,3,2-dioxaborolan-2-yl)-1H-pyrazole to afford a yellow resin. UPLC-MS (Condition 3) $t_R$=0.97 min, m/z=438.1 [M+H]$^+$, m/z=436.2 [M−H]$^-$; $^1$H-NMR (400 MHz, DMSO-d$_6$) δ ppm 2.77 (s, 3H) 3.37-3.49 (m, 2H) 3.49-3.65 (m, 2H) 4.62 (br. s, 1H) 6.47 (d, J=1.96 Hz, 1H) 7.33 (d, J=9.05 Hz, 2H) 7.72-7.85 (m, 1H) 7.85-7.96 (m, 2H) 8.14 (br. s, 1H) 8.71 (d, J=1.96 Hz, 1H) 10.26 (s, 1H) 12.58-13.18 (m, 1H).

Stage 23.1 5-Bromo-N-(4-(chlorodifluoromethoxy)phenyl)-6-((2-hydroxyethyl)(methyl)amino)nicotinamide

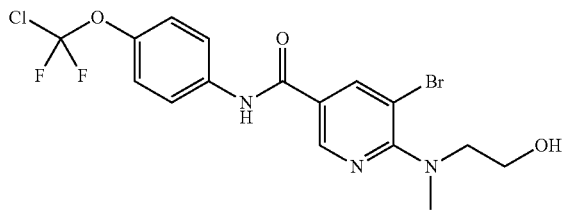 [SMILES: CN(CCO)c1ncc(C(=O)Nc2ccc(OC(F)(F)Cl)cc2)cc1Br]

The title compound was prepared in an analogous fashion to that described in Stage 22.1 using 5-bromo-6-chloro-N-(4-(chlorodifluoromethoxy)phenyl)nicotinamide (Stage 22.2) and 2-methylamino-ethanol to afford a white crystalline solid. HPLC (Condition 4) $t_R$=5.72 min, UPLC-MS (Condition 3) $t_R$=1.14 min, m/z=452.2 [M+H]$^+$.

Example 24

N-(4-(Chlorodifluoromethoxy)phenyl)-6-(ethyl(2-hydroxyethyl)amino)-5-(1H-pyrazol-5-yl)nicotinamide

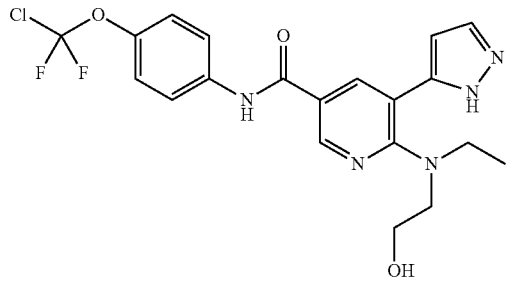 [SMILES: CCN(CCO)c1ncc(C(=O)Nc2ccc(OC(F)(F)Cl)cc2)cc1-c1ccn[nH]1]

The title compound was prepared in an analogous fashion to that described in Example 26 using 5-bromo-N-(4-(chlorodifluoromethoxy)phenyl)-6-(ethyl(2-hydroxyethyl)amino)nicotinamide (Stage 24.1) and 1-(tetrahydro-2H-pyran-2-yl)-5-(4,4,5,5-tetramethyl-1,3,2-dioxaborolan-2-yl)-1H-pyrazole to afford a yellow solid. UPLC-MS (Condition 3) $t_R$=1.02 min, m/z=452.2 [M+H]$^+$, m/z=450.1 [M−H]$^-$; $^1$H-NMR (400 MHz, DMSO-d$_6$) δ ppm 0.93 (t, J=7.09 Hz, 3H) 3.17-3.27 (m, 2H) 3.35-3.43 (m, 2H) 3.43-3.53 (m, 2H) 4.59 (br. s, 1H) 6.53 (d, J=1.96 Hz, 1H) 7.33 (d, J=9.05 Hz, 2H) 7.76 (br. s, 1H) 7.82-7.95 (m, 2H) 8.13 (d, J=2.45 Hz, 1H) 8.72 (d, J=2.45 Hz, 1H) 10.29 (s, 1H) 12.98 (br. s, 1H).

Stage 24.1 5-Bromo-N-(4-(chlorodifluoromethoxy)phenyl)-6-(ethyl(2-hydroxyethyl)amino)nicotinamide

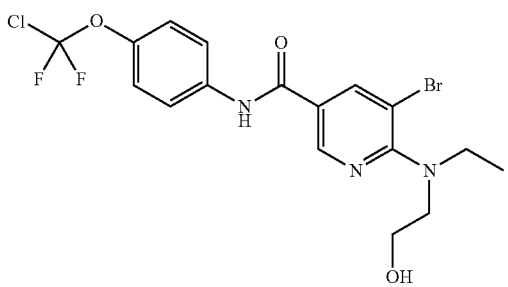 [SMILES: CCN(CCO)c1ncc(C(=O)Nc2ccc(OC(F)(F)Cl)cc2)cc1Br]

The title compound was prepared in an analogous fashion to that described in Stage 22.1 using 5-bromo-6-chloro-N-(4-(chlorodifluoromethoxy)phenyl)nicotinamide (Stage 22.2) and 2-ethylamino-ethanol to afford an off-white crystalline solid. (Reaction Time was 10 h). HPLC (Condition 4) $t_R$=6.1 min, UPLC-MS (Condition 3) $t_R$=1.21 min, m/z=466.2 [M+H]$^+$.

Example 25

(R)-6-(3-Hydroxypyrrolidin-1-yl)-5-(1H-pyrrol-2-yl)-N-(4-((trifluoromethyl)thio)phenyl)nicotinamide

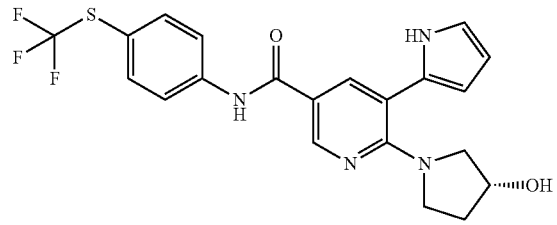

(R)-5-Bromo-6-(3-hydroxypyrrolidin-1-yl)-N-(4-((trifluoromethyl)thio)phenyl)nicotinamide (Stage 25.1, 100 mg, 0.216 mmol), tert-butyl 2-(4,4,5,5-tetramethyl-1,3,2-dioxaborolan-2-yl)-1H-pyrrole-1-carboxylate (127 mg, 0.433 mmol) Pd(PPH$_3$)$_2$Cl$_2$ (15.18 mg, 0.022 mmol), Na$_2$CO$_3$ (92 mg, 0.865 mmol), DME (918 μL), water (262 μL) and EtOH (131 μL) were added to a MW vial, which sealed, evacuated/purged with argon and the RM was stirred at 80° C. for 16 h. MeOH (0.5 mL) was added and the RM was subjected to MW irradiation at 150° C. for 5 min. The RM was diluted with DME (3 mL), treated with Si-Thiol (Silicycle, 1.43 mmol/g, 91 mg, 0.130 mmol), centrifuged, the supernatant was filtered and the solvent was evaporated off under reduced pressure to give a residue which was purified by flash chromatography (RediSep® Silica gel column, 12 g, cyclohexane/EtOAc from 40% to 100% EtOAc) followed by preparative SFC (Column DEAP, from 24% to 29% in 10 min) to afford the title compound as a grey solid. UPLC-MS (Condition 3) $t_R$=1.10 min, m/z=449.2 [M+H]$^+$, m/z=447.2 [M−H]$^-$; $^1$H-NMR (400 MHz, DMSO-d$_6$) δ ppm 1.74 (dd, J=6.48, 2.57 Hz, 1H) 1.83 (dd, J=8.68, 4.28 Hz, 1H) 2.98 (d, J=11.98 Hz, 1H) 3.22-3.29 (m, 2H) 3.37-3.50 (m, 1H) 4.19 (d, J=2.45 Hz, 1H) 4.81 (d, J=3.42 Hz, 1H) 5.94-6.17 (m, 2H) 6.67-6.87 (m, 1H) 7.67 (d, J=8.80 Hz, 2H) 7.83-7.99 (m, 2H) 8.02 (d, J=2.45 Hz, 1H) 8.71 (d, J=2.45 Hz, 1H) 10.25 (s, 1H) 11.11 (br. s, 1H).

Stage 25.1 (R)-5-Bromo-6-(3-hydroxypyrrolidin-1-yl)-N-(4-((trifluoromethyl)thio)phenyl)nicotinamide

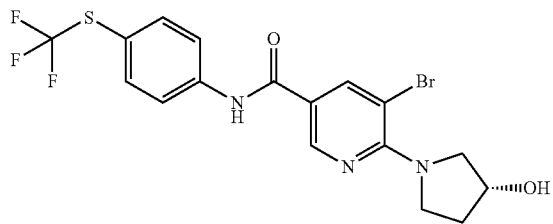 [SMILES: O=C(Nc1ccc(SC(F)(F)F)cc1)c1cnc(N2CC[C@@H](O)C2)c(Br)c1]

DIPEA (73 μL, 0.42 mmol) was added to a solution of 5-bromo-6-chloro-N-(4-((trifluoromethyl)thio)phenyl)nicotinamide (Stage 25.2, 123 mg, 0.3 mmol) and (R)-pyrrolidin-3-ol (31.4 mg, 0.36 mmol) in iPrOH (300 μL) in a vial, which was sealed and heated at 140° C. for 1 h. After cooling at RT, the RM was diluted with EtOAc, washed with brine, dried over Na$_2$SO$_4$ and the solvent evaporated off under reduced pressure to give a residue which was triturated with iPr$_2$O, filtered and dried to afford the title compound as a white crystalline powder. HPLC (Condition 4) $t_R$=5.9 min, UPLC-MS (Condition 3) $t_R$=1.21 min, m/z=464.1 [M+H]$^+$.

Stage 25.2 5-Bromo-6-chloro-N-(4-((trifluoromethyl)thio)phenyl)nicotinamide

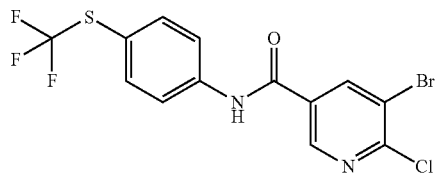

DMF (0.12 mL) was added followed by slow addition of SOCl$_2$ (0.73 mL, 10 mmol) to a mixture of 5-bromo-6-chloro-nicotinic acid (473 mg, 2 mmol) in toluene (5 mL), and the RM was then stirred at 80° C. for 1 h. After cooling at RT, the toluene was evaporated off under reduce pressure and the residue was dissolved in THF (0.4 mL). DIPEA (0.7 mL, 4 mmol) was added and the solution was cooled to 0° C. under nitrogen. 4-trifluoromethylsulfanyl-aniline (438 mg, 2.2 mmol) in THF (1 mL) was then added dropwise and the RM was stirred at 0° C. for 2 h. The RM was diluted with TBME (50 mL), treated with 1 M HCl and extracted with TBME. The combined extracts were washed with 1 M aq. NaOH and brine, dried over Na$_2$SO$_4$ and the solvent was evaporated off under reduced pressure and the product was crystallized from TBME/n-hexane to give the title compound as an off-white crystalline powder. HPLC (Condition 4) $t_R$=6.63 min, UPLC-MS (Condition 3) $t_R$=1.33 min, m/z=411.1 [M+H]$^+$.

Example 26

6-((2-Hydroxyethyl)(methyl)amino)-5-(1H-pyrazol-5-yl)-N-(4-((trifluoromethyl)thio)phenyl)nicotinamide

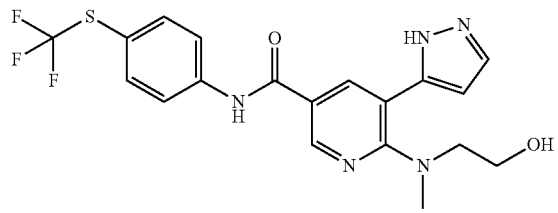 [SMILES: CN(CCO)c1ncc(C(=O)Nc2ccc(SC(F)(F)F)cc2)cc1-c1ccn[nH]1]

5-Bromo-6-((2-hydroxyethyl)(methyl)amino)-N-(4-((trifluoromethyl)thio)phenyl)nicotinamide (Stage 26.1, 113 mg, 0.25 mmol), 1-(tetrahydro-2H-pyran-2-yl)-5-(4,4,5,5-tetramethyl-1,3,2-dioxaborolan-2-yl)-1H-pyrazole (69.5 mg, 0.25 mmol), Pd(PPh$_3$)$_2$Cl$_2$ (0.018 g, 0.025 mmol), Na$_2$CO$_3$ (0.106 g, 1.000 mmol), DME (1.061 mL), water (0.303 mL) and EtOH (0.152 mL) were added to a MW vial, which was sealed, evacuated/purged with argon and subjected to MW irradiation at 125° C. for 20 min. The RM was diluted with DME (2 mL), treated with Si-Thiol (Silicycle, 1.43 mmol/g, 0.105 g, 0.150 mmol), centrifuged, the supernatant was filtered and the solvent was evaporated off under reduced pressure to give a residue which was purified by flash chromatography (RediSep® Silica gel column, 12 g, cyclohexane/EtOAc from 20% to 90% EtOAc). The resulting intermediate was treated with a mixture of TFA (0.963 mL, 12.50 mmol) and DCM (2.5 mL) and for stirred for 2 h at RT. The solvent was evaporated off under reduced pressure and the residue was basified with a solution of NH$_3$ 7 M in MeOH (2 mL, 14 mmol). The solvent was evaporated off under reduced pressure to give a crude product which was purified by preparative SFC (Column DEAP, isocratic 28% in 9 min) to afford the title compound as a yellow solid. UPLC-MS (Condition 3) $t_R$=1.01 min, m/z=438.2 [M+H]$^+$, m/z=436.2 [M−H]$^-$; $^1$H-NMR (400 MHz, DMSO-d$_6$) δ ppm 2.77 (s, 3H) 3.38-3.61 (m, 4H) 4.61 (br. s, 1H) 6.47 (s, 1H) 7.68 (d, J=8.56 Hz, 2H) 7.83 (br. s, 1H) 7.93 (d, J=8.80 Hz, 2H) 8.15 (br. s, 1H) 8.71 (br. s, 1H) 10.36 (s, 1H) 12.83-13.15 (m, 1H).

Stage 26.1 5-Bromo-6-((2-hydroxyethyl)(methyl)amino)-N-(4-((trifluoromethyl)thio)phenyl)nicotinamide

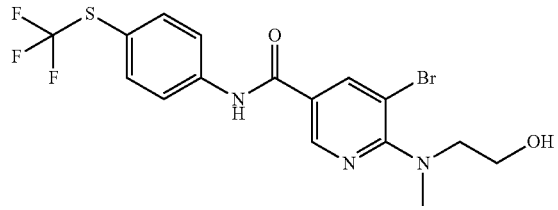

The title compound was prepared in an analogous fashion to that described in Stage 22.1 using 5-bromo-6-chloro-N-(4-((trifluoromethyl)thio)phenyl)nicotinamide (Stage 25.2) and 2-methylamino-ethanol to afford an off-white crystalline solid. HPLC (Condition 4) $t_R$=5.97 min, UPLC-MS (Condition 3) $t_R$=1.18 min, m/z=450.2 [M+H]$^+$.

Example 27

6-(Ethyl(2-hydroxyethyl)amino)-5-(1H-pyrazol-5-yl)-N-(4-((trifluoromethyl)thio)phenyl)nicotinamide

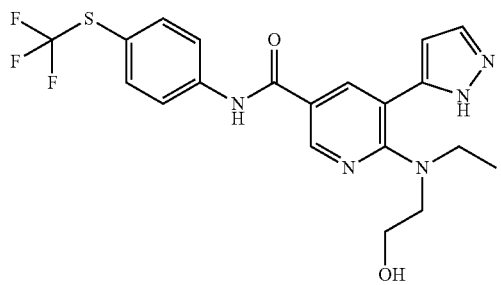 [SMILES: CCN(CCO)c1ncc(C(=O)Nc2ccc(SC(F)(F)F)cc2)cc1-c1ccn[nH]1]

The title compound was prepared in an analogous fashion to that described in Example 26 using 5-bromo-6-(ethyl(2-hydroxyethyl)amino)-N-(4-((trifluoromethyl)thio)phenyl)nicotinamide (Stage 27.1) and 1-(tetrahydro-2H-pyran-2-yl)-5-(4,4,5,5-tetramethyl-1,3,2-dioxaborolan-2-yl)-1H-to afford a white powder. UPLC-MS (Condition 3) $t_R$=1.09 min, m/z=452.2 [M+H]$^+$, m/z=450.1 [M–H]$^-$; $^1$H-NMR (400 MHz, DMSO-$d_6$) δ ppm 0.94 (t, J=6.97 Hz, 3H) 3.16-3.29 (m, 2H) 3.35-3.45 (m, 2H) 3.49 (d, J=5.14 Hz, 2H) 4.58 (br. s, 1H) 6.53 (br. s, 1H) 7.69 (d, J=8.56 Hz, 2H) 7.83 (br. s, 1H) 7.94 (d, J=8.80 Hz, 2H) 8.14 (br. s, 1H) 8.72 (br. s, 1H) 10.39 (s, 1H) 12.96 (br. s, 1H).

Stage 27.1 5-Bromo-6-(ethyl(2-hydroxyethyl)amino)-N-(4-((trifluoromethyl)thio)phenyl)nicotinamide

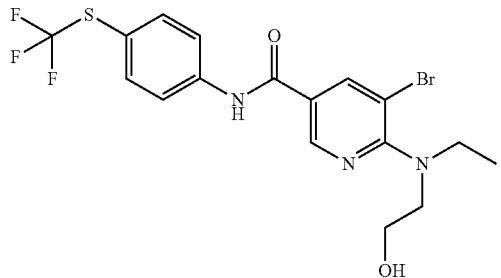

The title compound was prepared in an analogous fashion to that described in Stage 22.1 using 5-bromo-6-chloro-N-(4-((trifluoromethyl)thio)phenyl)nicotinamide (Stage 25.2) and 2-ethylamino-ethanol to afford a white crystalline solid. HPLC (Condition 4) $t_R$=6.33 min, UPLC-MS (Condition 3) $t_R$=1.25 min, m/z=466.2 [M+H]$^+$.

Example 28

4-((3S,4S)-3,4-Dihydroxypyrrolidin-1-yl)-3-(1H-pyrrol-2-yl)-N-(4-(trifluoromethoxy)phenyl)benzamide

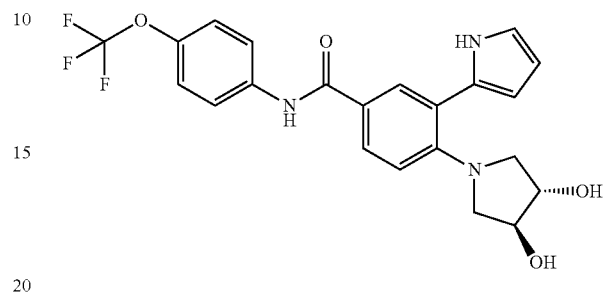

3-Bromo-4-((3S,4S)-3,4-dihydroxypyrrolidin-1-yl)-N-(4-(trifluoromethoxy)phenyl)benzamide (Stage 28.1, 100 mg, 0.217 mmol), tert-butyl 2-(4,4,5,5-tetramethyl-1,3,2-dioxaborolan-2-yl)-1H-pyrrole-1-carboxylate (127 mg, 0.434 mmol), Pd(PPh$_3$)$_2$Cl$_2$ (15.22 mg, 0.022 mmol), Na$_2$CO$_3$ (92 mg, 0.867 mmol), DME (920 µL), water (263 µL) and EtOH (131 µL) were added to a MW vial, which was sealed, evacuated/purged with argon and the RM was stirred at 80° C. for 16 h. MeOH (0.5 mL) was added and the RM was subjected to MW at 150° C. for 5 min. The RM was diluted with DME (3 mL), treated with Si-Thiol (Silicycle, 1.44 mmol/g, 90 mg, 0.130 mmol), centrifuged, the supernatant was filtered and the solvent was evaporated off under reduced pressure to give a residue which was purified by flash chromatography (RediSep® Silica gel column, 4 g, cyclohexane/EtOAc from 40% to 100% EtOAc) followed by preparative SFC (Column NH$_2$, from 25% to 30% in 10 min) to yield the title compound as a grey solid. UPLC-MS (Condition 3) $t_R$=0.98 min, m/z=448.1 [M+H]$^+$, m/z=446.1 [M–H]$^-$; 1H NMR (400 MHz, DMSO-$d_6$) δ ppm 2.82 (d, J=11.00 Hz, 2H) 3.28-3.34 (m, 6H) 3.86 (br. s, 2H) 4.97 (d, J=3.42 Hz, 2H) 6.03-6.07 (m, 1H) 6.07-6.12 (m, 1H) 6.75-6.77 (m, 1H) 6.78 (d, J=8.80 Hz, 1H) 7.31 (d, J=8.80 Hz, 2H) 7.82 (dd, J=8.80, 2.45 Hz, 1H) 7.85 (d, J=2.20 Hz, 1H) 7.86-7.91 (m, 2H) 10.07 (s, 1H) 10.97 (d, J=1.71 Hz, 1H).

Stage 28.1 3-Bromo-4-((3S,4S)-3,4-dihydroxypyrrolidin-1-yl)-N-(4-(trifluoromethoxy)phenyl)benzamide

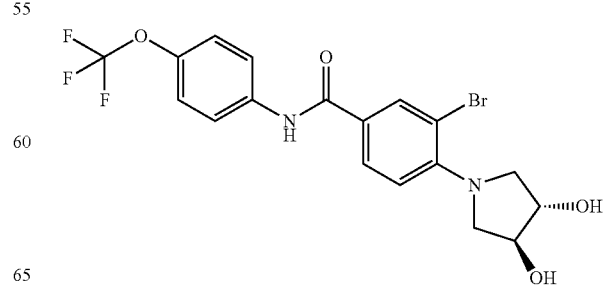

A solution of 3-bromo-4-fluoro-N-(4-(trifluoromethoxy)phenyl)benzamide (Stage 1.2, 500 mg, 1.322 mmol), (3S,4S)-pyrrolidine-3,4-diol (205 mg, 1.984 mmol) and TEA (553 µL, 3.97 mmol) in DMSO (994 µL) was stirred at 90° C. for 24 h. Additional (3S,4S)-pyrrolidine-3,4-diol, (68.2 mg, 0.661 mmol) and TEA (183 µL, 1.322 mmol) were added and mixture was stirred at 100° C. for 16 h. The cooled treated with 0.5 M HCl (20 mL) and extracted with TBME/EtOAc (1:1). The combined extracts were washed with 0.5 M HCl (20 mL) and brine, dried over MgSO$_4$ and the solvent was evaporated off under reduced pressure to give a residue which was crystallized from cyclohexane/EtOAc to afford the title compound as an off-white solid. UPLC-MS (Condition 1) $t_R$=2.41 min, m/z=460.9/462.9 [M+H]$^+$, m/z=459.0/461.0 [M−H]$^−$; $^1$H-NMR (400 MHz, DMSO-d$_6$) δ ppm 3.24 (d, J=10.76 Hz, 2H) 3.88 (dd, J=10.51, 3.67 Hz, 2H) 4.02 (br. s, 2H) 5.15 (d, J=3.18 Hz, 2H) 6.89 (d, J=8.80 Hz, 1H) 7.34 (d, J=8.31 Hz, 2H) 7.84 (dd, J=8.68, 2.08 Hz, 1H) 7.85-7.89 (m, 2H) 8.13 (d, J=2.20 Hz, 1H) 10.17 (s, 1H).

Example 29

3-(5-Cyano-1H-pyrrol-2-yl)-4-((3S,4S)-3,4-dihydroxypyrrolidin-1-yl)-N-(4-(trifluoromethoxy)phenyl)benzamide

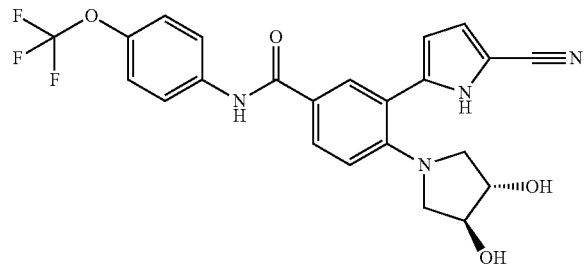 [SMILES: N#Cc1ccc(-c2cc(C(=O)Nc3ccc(OC(F)(F)F)cc3)ccc2N2C[C@H](O)[C@@H](O)C2)[nH]1]

3-Bromo-4-((3S,4S)-3,4-dihydroxypyrrolidin-1-yl)-N-(4-(trifluoromethoxy)phenyl)benzamide (Stage 28.1, 100 mg, 0.217 mmol), (1-(tert-butoxycarbonyl)-5-cyano-1H-pyrrol-2-yl)boronic acid (Stage 29.1, 103 mg, 0.436 mmol), Pd(PPh$_3$)$_2$Cl$_2$ (15.22 mg, 0.022 mmol), Na$_2$CO$_3$ (92 mg, 0.867 mmol), DME (920 µL), water (263 µL) and EtOH (131 µL) were added to a MW vial, which was sealed, evacuated/purged with argon and the RM was stirred at 70° C. for 16 h. MeOH (0.5 mL) was added and the RM was subjected to MW irradiation at 150° C. for 5 min. The RM was diluted with DME (3 mL), treated with Si-Thiol (Silicycle, 1.44 mmol/g, 90 mg, 0.130 mmol), centrifuged, the supernatant was filtered and the solvent was evaporated off under reduced pressure to give a residue which was purified by flash chromatography (RediSep® Silica gel column, 12 g, DCM/MeOH-1% NH$_4$OH, from 1% to 10% MeOH-1% NH$_4$OH) followed by preparative SFC (Column NH$_2$, from 26% to 31% in 10 min) to yield the title compound as an off-white solid. UPLC-MS (Condition 3) $t_R$=0.99 min, m/z=473.2 [M+H]$^+$, m/z=471.1 [M−H]$^−$; 1H NMR (400 MHz, DMSO-d$_6$) δ ppm 2.81 (d, J=10.76 Hz, 2H) 3.26-3.32 (m, 2H) 3.89 (br. s, 2H) 5.08 (d, J=2.93 Hz, 2H) 6.24 (d, J=3.67 Hz, 1H) 6.84 (d, J=8.93 Hz, 1H) 7.00 (d, J=3.67 Hz, 1H) 7.33 (d, J=8.44 Hz, 2H) 7.84-7.93 (m, 4H) 10.10 (s, 1H) 12.52 (br. s, 1H).

Stage 29.1 (1-(tert-Butoxycarbonyl)-5-cyano-1H-pyrrol-2-yl)boronic acid

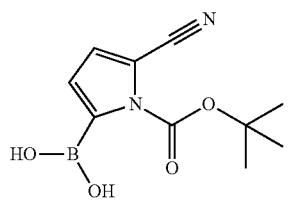 [SMILES: CC(C)(C)OC(=O)n1c(C#N)ccc1B(O)O]

To a solution of 2,2,6,6-tetramethylpiperidine (0.461 mL, 2.73 mmol) in THF (10 mL) at −78° C. under an argon atmosphere was added a solution of 1.6 M n-BuLi in n-hexane (1.951 mL, 3.12 mmol). The mixture was stirred at −78° C. for 15 min and then allowed to warm to RT. The mixture was cooled to −78° C. prior and a solution of tert-butyl 2-cyano-1H-pyrrole-1-carboxylate (500 mg, 2.60 mmol) in THF (2 mL) was added. The RM was stirred at −78° C. for 30 min and then trimethyl borate (1.450 mL, 13.01 mmol) was added. The RM was allowed to reach RT and stirred overnight. Sat. aq. NH$_4$Cl solution (10 mL) was added to the mixture and the mixture was extracted with Et$_2$O. The combined extracts were washed with 1 M HCl (2×10 mL), brine (10 mL) then the solvent was evaporated off under reduced pressure to give a residue which was crystallized from Et$_2$O/cyclohexane (1:3) to yield the title compound as an off-white solid (which was stored at −20° C.). UPLC-MS (Condition 3) $t_R$=0.72 min, m/z=237.1 [M+H]$^+$, m/z=281.1 [M+formic acid-H]$^−$.

Example 30

(R)-5-(5-Cyano-1H-pyrrol-2-yl)-6-(3-hydroxypyrrolidin-1-yl)-N-(4-(trifluoromethoxy)phenyl)nicotinamide

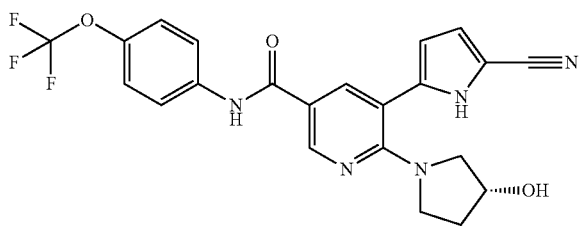 [SMILES: N#Cc1ccc(-c2cc(C(=O)Nc3ccc(OC(F)(F)F)cc3)cnc2N2CC[C@@H](O)C2)[nH]1]

The title compound was prepared in an analogous fashion to that described in Example 29 using (R)-5-bromo-6-(3-hydroxypyrrolidin-1-yl)-N-(4-(trifluoromethoxy)phenyl)nicotinamide (Stage 6.1) and (1-(tert-butoxycarbonyl)-5-cyano-1H-pyrrol-2-yl)boronic acid (Stage 29.1) to afford an off-white solid. UPLC-MS (Condition 3) $t_R$=1.03 min, m/z=458.1[M+H]$^+$, m/z=456.1 [M−H]$^−$; 1H NMR (400 MHz, DMSO-d$_6$) δ ppm 1.77 (m, J=6.48, 3.06 Hz, 1H) 1.82-1.92 (m, 1H) 2.95 (d, J=11.49 Hz, 1H) 3.26 (dd, J=11.74, 4.65 Hz, 1H) 3.31-3.34 (m, 1H) 3.40-3.50 (m, 1H) 4.19-4.28 (m, 1H) 4.88 (d, J=3.42 Hz, 1H) 6.31 (dd, J=3.67, 2.20 Hz, 1H) 7.01 (dd, J=3.67, 2.20 Hz, 1H) 7.34 (d, J=8.31 Hz, 2H)

7.82-7.89 (m, 2H) 8.07 (d, J=2.45 Hz, 1H) 8.76 (d, J=2.45 Hz, 1H) 10.16 (s, 1H) 12.59 (br. s, 1H).

Example 31

5-(5-Cyano-1H-pyrrol-2-yl)-6-((3S,4S)-3,4-dihydroxypyrrolidin-1-yl)-N-(4-(trifluoromethoxy)phenyl)nicotinamide

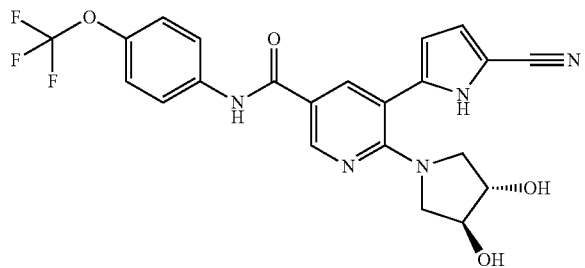

The title compound was prepared in an analogous fashion to that described in Example 29 using 5-bromo-6-((3S,4S)-3,4-dihydroxypyrrolidin-1-yl)-N-(4-(trifluoromethoxy)phenyl)nicotinamide (Stage 31.1) and (1-(tert-butoxycarbonyl)-5-cyano-1H-pyrrol-2-yl)boronic acid (Stage 29.1) to afford an off-white solid. UPLC-MS (Condition 3) $t_R$=0.94 min, m/z=474.1 [M+H]$^+$, m/z=472.1 [M−H]$^−$; 1H NMR (400 MHz, DMSO-d$_6$) δ ppm 3.02 (d, J=11.86 Hz, 2H) 3.46 (dd, J=11.86, 3.55 Hz, 2H) 3.89 (br. s, 2H) 5.09 (d, J=2.45 Hz, 2H) 6.29 (d, J=3.67 Hz, 1H) 7.03 (d, J=3.67 Hz, 1H) 7.35 (d, J=8.44 Hz, 2H) 7.82-7.90 (m, 2H) 8.07 (d, J=2.45 Hz, 1H) 8.75 (d, J=2.45 Hz, 1H) 10.18 (s, 1H) 12.65 (br. s, 1H).

Stage 31.1 5-Bromo-6-((3S,4S)-3,4-dihydroxypyrrolidin-1-yl)-N-(4-(trifluoromethoxy)phenyl)nicotinamide

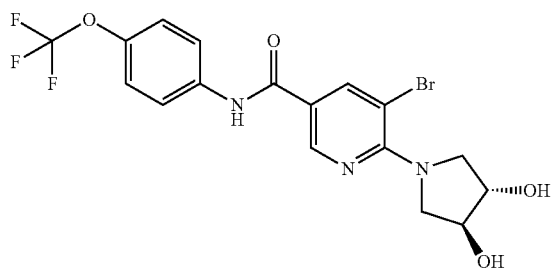 [SMILES: O=C(Nc1ccc(OC(F)(F)F)cc1)c1cnc(N2C[C@H](O)[C@@H](O)C2)c(Br)c1]

5-Bromo-6-chloro-N-(4-(trifluoromethoxy)phenyl)nicotinamide (Stage 6.2, 500 mg, 1.264 mmol, (3S,4S)-pyrrolidine-3,4-diol (157 mg, 1.517 mmol), DIPEA (442 μL, 2.53 mmol) and iPrOH (1.264 mL) were added to a MW vial, which was sealed and subjected to MW irradiation at 140° C. for 30 min. The solvent was evaporated off under reduced pressure to give a residue which was treated with 0.5 M HCl (10 mL) and extracted with EtOAc. The combined extracts were washed with HCl 0.5 M and brine, diluted with MeOH (20 mL), dried over MgSO$_4$ and the solvent was evaporated off under reduced pressure and the product was crystallized from EtOAc/MeOH afforded the title compound as a white solid. UPLC-MS (Condition 1) $t_R$=2.48 min, m/z=462.0/464.0 [M+H]$^+$, m/z=460.0/462.0 [M−H]$^−$; $^1$H-NMR (400 MHz, DMSO-d$_6$) δ ppm 3.56 (d, J=11.25 Hz, 2H) 3.94-4.06 (m, 4H) 4.79 (br. s, 2H) 7.34 (d, J=8.80 Hz, 2H) 7.88 (d, J=9.05 Hz, 2H) 8.38 (d, J=1.96 Hz, 1H) 8.71 (d, J=1.96 Hz, 1H) 10.34 (s, 1H).

Example 32

(R)-6-(3-Amino-3-(trifluoromethyl)pyrrolidin-1-yl)-5-(1H-pyrazol-5-yl)-N-(4-(trifluoromethoxy)phenyl)nicotinamide

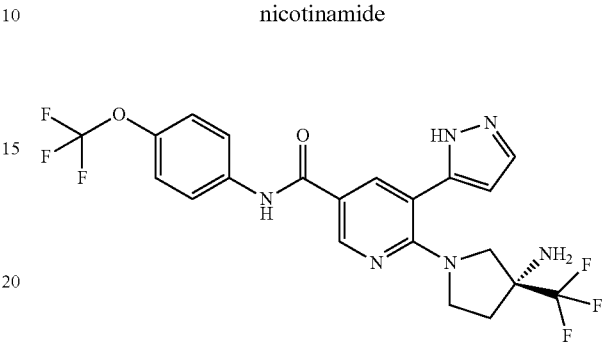

(R)-tert-butyl 3-(trifluoromethyl)pyrrolidin-3-ylcarbamate (92 mg, 0.362 mmol) and DIPEA (0.075 mL, 0.428 mmol) were added to a solution of 6-chloro-5-(1-(tetrahydro-2H-pyran-2-yl)-1H-pyrazol-5-yl)-N-(4-(trifluoromethoxy)phenyl)nicotinamide (Stage 32.1, 100 mg, 0.214 mmol) in iPrOH (1.5 mL) and the RM was stirred at 130° C. overnight. The mixture was filtered and the solvent was evaporated off under reduced pressure to give a residue which was treated with 2 N aqueous citric acid and extracted with DCM. The combined extracts were dried over Na$_2$SO$_4$ and the solvent was evaporated off under reduced pressure to give a residue which was treated with TFA (3 mL) in DCM (2 mL) and stirred for 4 h at RT. The solvent was evaporated off under reduced pressure and the residue was purified by SFC (Column 4-EP, from 17% to 22% in 6 min) and lyophilized in water/MeCN (min. vol.) to give the title compound as a beige powder. UPLC-MS (Condition 3) $t_R$=1.03 min, m/z=501.1 [M+H]$^+$, m/z=499.2 [M−H]$^−$; 1H NMR (600 MHz, DMSO-d$_6$) δ ppm 1.73-1.84 (m, 1H) 1.94-2.07 (m, 1H) 2.26 (br. s, 2H) 2.95-3.15 (m, 1H) 3.29-3.42 (m, 1H) 3.47-3.60 (m, 2H) 6.43 (br. s, 1H) 7.34 (d, J=8.47 Hz, 2H) 7.80-7.91 (m, 3H) 8.08 (s, 1H) 8.75 (br. s, 1H) 10.24 (s, 1H) 12.98 (br. s, 1H).

Stage 32.1 6-Chloro-5-(1-(tetrahydro-2H-pyran-2-yl)-1H-pyrazol-5-yl)-N-(4-(trifluoromethoxy)phenyl)nicotinamide

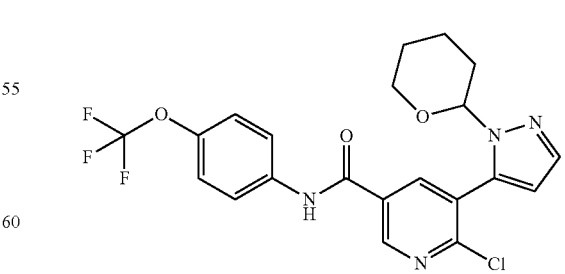

K$_3$PO$_4$ (5.70 g, 26.8 mmol), followed by 1-(tetrahydro-2H-pyran-2-yl)-5-(4,4,5,5-tetramethyl-1,3,2-dioxaborolan-2-yl)-1H-pyrazole (3.73 g, 13.42 mmol) and Pd(PPh$_3$)$_4$ (0.517 g, 0.447 mmol) were added to a solution of 6-chloro-5-iodo- N-(4-(trifluoromethoxy)phenyl)nicotinamide (Stage 32.2, 4.0 g, 8.95 mmol) in toluene (45 mL) under an argon atmosphere. The RM was stirred at 80° C. for 5 h, filtered through Hyflo®, washed with EtOAc (100 mL) and the solvent was evaporated off under reduced pressure to give a crude product was purified by flash chromatography (Silica gel column, 80 g, n-hexane/EtOAc from 9:1 to 1:1) and triturated under n-hexane, filtered and dried to afford the title compound as a beige solid. HPLC (Condition 7) $t_R$=7.569 min, UPLC-MS (Condition 3) $t_R$=1.19 min, m/z=466.9 [M+H]$^+$; $^1$H-NMR (400 MHz, DMSO-d$_6$) δ ppm 1.38-1.67 (m, 3H) 1.81-2.01 (m, 2H) 2.25-2.39 (m, 1H) 3.34-3.46 (m, 1H) 3.74-3.84 (m, 1H) 5.15 (d, J=8.21 Hz, 1H) 6.62 (s, 1H) 7.40 (d, J=8.21 Hz, 2H) 7.69 (s, 1H) 7.88 (d, J=8.99 Hz, 2H) 8.50 (s, 1H) 9.06 (s, 1H) 10.70 (s, 1H).

Stage 32.2 6-Chloro-5-iodo-N-(4-(trifluoromethoxy)phenyl)nicotinamide

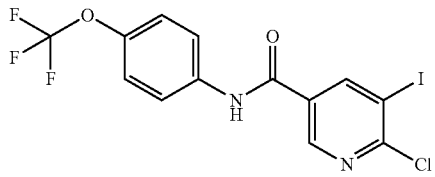 [SMILES: O=C(Nc1ccc(OC(F)(F)F)cc1)c1cnc(Cl)c(I)c1]

DMF (1.927 mL, 24.89 mmol) and SOCl$_2$ (18.17 mL, 249 mmol) were added to a suspension of 6-chloro-5-iodo-3-pyridinecarboxylic acid (24 g, 83 mmol) in toluene (165 mL) and the RM was stirred at 80° C. for 1 h. The solvent was evaporated off under reduced pressure and the residue was dissolved in THF (165 mL). DIPEA (29.0 mL, 166 mmol) was added, the mixture was cooled down to −15° C., treated dropwise with a solution of 4-(trifluoromethoxy)aniline (15.43 g, 87 mmol) in THF (165 mL) and stirred at RT for 1 h. The solvent was off under reduced pressure and the residue was dissolved in TBME (500 mL), washed with 1 M HCl, a sat. aq. solution of NaHCO$_3$ and brine, dried over Na$_2$SO$_4$ and the solvent was evaporated off under reduced pressure and the product was recrystallized from EtOAc/n-heptane to afford the title compound as a white solid. HPLC (Condition 4) $t_R$=6.36 min, UPLC-MS (Condition 3) $t_R$=1.23 min, m/z=441.1 [M−H]$^-$.

Example 33

6-(1-Amino-3-azabicyclo[3.1.0]hexan-3-yl)-5-(1H-pyrazol-5-yl)-N-(4-(trifluoromethoxy)phenyl)nicotinamide

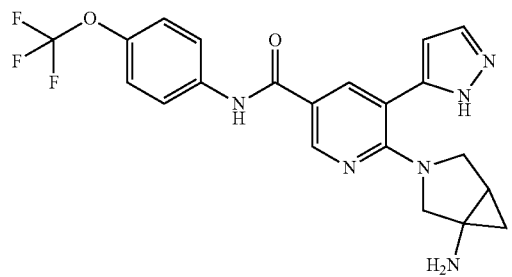 [SMILES: NC12CC1CN(c1ncc(C(=O)Nc3ccc(OC(F)(F)F)cc3)cc1-c1ccn[nH]1)C2]

DIPEA (96 µL, 0.55 mmol) was added to a mixture of 6-chloro-5-(1-(tetrahydro-2H-pyran-2-yl)-1H-pyrazol-5-yl)-N-(4-(trifluoromethoxy)phenyl)nicotinamide (Stage 32.1, 117 mg, 0.25 mmol) and (tert-butyl 3-azabicyclo[3.1.0]hexan-1-ylcarbamate, 59.2 mg, 1.2 mmol) in iPrOH (250 µL) in a vial, which was sealed and the RM mixture was stirred at 140° C. for 18 h. After cooling at RT, the RM was dissolved in EtOAc, washed with brine, dried over Na$_2$SO$_4$ and the solvent was evaporated off under reduced pressure to give a residue which was dissolved in DCM (1 mL), cooled to 0° C., treated with TFA (0.45 mL, 5.85 mmol) and was stirred at RT for 3 h. The RM was poured into 10% aq. Na$_2$CO$_3$ (10 mL) and extracted with EtOAc. The combined extracts were dried over Na$_2$SO$_4$ and the solvent was evaporated off under reduced pressure to give a crude product which was purified by preparative SFC (Column 2-EP, from 22% to 27% in 6 min) to afford the title compound as an amorphous white powder. HPLC (Condition 4) $t_R$=4.2 min, UPLC-MS (Condition 3) $t_R$=0.76 min, m/z=445.1 [M+H]$^+$; $^1$H-NMR (400 MHz, DMSO-d$_6$) δ ppm 0.56-0.71 (m, 1H) 0.96-1.10 (m, 1H) 1.61-1.79 (m, 1H) 2.26 (s, 1H) 3.22-3.37 (m, 1H) 3.44 (d, J=1.00 Hz, 1H) 3.70 (d, J=1.00 Hz, 1H) 6.40 (d, J=1.56 Hz, 1H) 7.32 (d, J=8.60 Hz, 2H) 7.84 (d, J=8.99 Hz, 3H) 8.07 (d, J=2.35 Hz, 1H) 8.71 (br. s, 1H) 10.24 (s, 1H) 13.00 (br. s, 1H).

Example 34

6-((1R,5S,6s)-6-Amino-3-azabicyclo[3.1.0]hexan-3-yl)-5-(1H-pyrazol-5-yl)-N-(4-(trifluoromethoxy)phenyl)nicotinamide

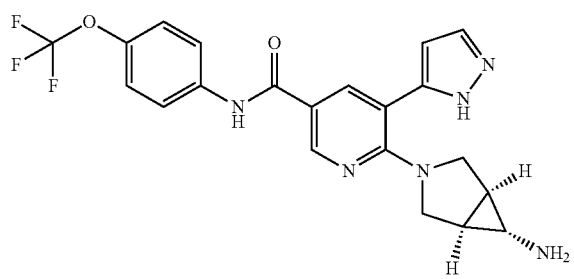 [SMILES: N[C@@H]1[C@H]2CN(c3ncc(C(=O)Nc4ccc(OC(F)(F)F)cc4)cc3-c3ccn[nH]3)C[C@@H]12]

The title compound was prepared in an analogous fashion to that described in Example 33 using 6-chloro-5-(1-(tetrahydro-2H-pyran-2-yl)-1H-pyrazol-5-yl)-N-(4-(trifluoromethoxy)phenyl)nicotinamide (Stage 32.1) and tert-butyl (1R,5S,6s)-3-azabicyclo[3.1.0]hexan-6-ylcarbamate to afford an amorphous white powder. HPLC (Condition 4) $t_R$=4.13 min, UPLC-MS (Condition 3) $t_R$=0.75 min, m/z=445.1 [M+H]$^+$; $^1$H-NMR (400 MHz, DMSO-d$_6$) δ ppm 1.77 (br. s, 2H) 2.14-2.33 (m, 3H) 3.18-3.27 (m, 1H) 3.50 (d, J=10.56 Hz, 1H) 6.39 (d, J=1.95 Hz, 1H) 7.32 (d, J=8.99 Hz, 2H) 7.84 (d, J=8.99 Hz, 3H) 8.04 (d, J=1.95 Hz, 1H) 8.71 (br. s, 1H) 10.21 (s, 1H) 12.88-13.10 (m, 1H).

Example 35

5-(1H-Pyrazol-5-yl)-6-(4,7-diazaspiro[2.5]octan-7-yl)-N-(4-(trifluoromethoxy)phenyl)nicotinamide

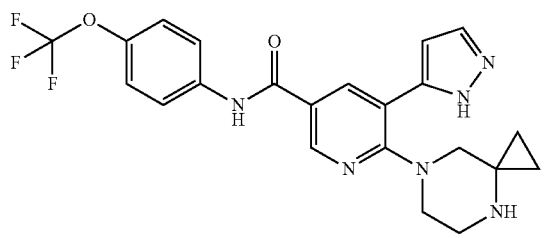 [SMILES: O=C(Nc1ccc(OC(F)(F)F)cc1)c1cnc(N2CCNC3(CC3)C2)c(-c2ccn[nH]2)c1]

The title compound was prepared in an analogous fashion to that described in Example 33 using 6-chloro-5-(1-(tetrahydro-2H-pyran-2-yl)-1H-pyrazol-5-yl)-N-(4-(trifluoromethoxy)phenyl)nicotinamide (Stage 32.1) and tert-butyl 4,7-diazaspiro[2.5]octane-4-carboxylate to afford an amorphous white powder. HPLC (Condition 4) $t_R$=4.17 min, UPLC-MS (Condition 3) $t_R$=0.78 min, m/z=459.1 [M+H]$^+$; $^1$H-NMR (400 MHz, DMSO-d$_6$) δ ppm 0.46-0.85 (m, 4H) 3.04 (br. s, 2H) 3.16-3.37 (m, 5H) 6.67 (br. s, 1H) 7.34 (d, J=8.60 Hz, 2H) 7.86 (d, J=9.38 Hz, 3H) 8.34 (br. s, 1H) 8.75 (s, 1H) 10.43 (s, 1H) 12.96-13.19 (m, 1H).

Example 36

6-(2-(Hydroxymethyl)morpholino)-5-(1H-pyrazol-5-yl)-N-(4-(trifluoromethoxy)phenyl)nicotinamide

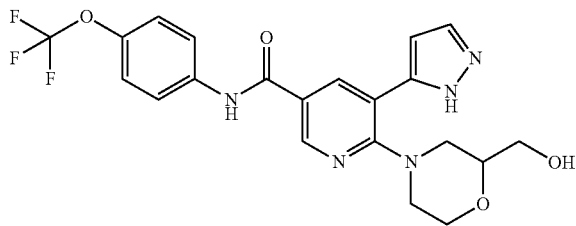 [SMILES: O=C(Nc1ccc(OC(F)(F)F)cc1)c1cnc(N2CCOC(CO)C2)c(-c2ccn[nH]2)c1]

A mixture of 6-chloro-5-(1-(tetrahydro-2H-pyran-2-yl)-1H-pyrazol-5-yl)-N-(4-(trifluoromethoxy)phenyl)nicotinamide (Stage 32.1, 150 mg, 0.321 mmol), 2-hydroxymethylmorpholine (75 mg, 0.643 mmol) and DIPEA (0.224 mL, 1.285 mmol) in iPrOH (0.6 mL) in a sealed vial was stirred at 140° C. for 4 h. The RM was dissolved in EtOAc, washed with water (3×20 mL), dried over Na$_2$SO$_4$ and the solvent was evaporated off under reduced pressure to give a residue which was dissolved in DCM (2.5 mL), treated with TFA (0.912 mL, 11.84 mmol) and stirred at RT for 2 h. The RM was diluted with EtOAc, washed with aq. sat. NaHCO$_3$ solution (2×40 mL) and with water (2×40 mL), dried over Na$_2$SO$_4$ and the solvent was evaporated off under reduced pressure to give a crude product which was purified by flash chromatography (RediSep® Silica gel column, 12 g, DCM/MeOH 9:1) followed by preparative HPLC (Condition 10). Fractions containing product were combined and the solvent was evaporated off under reduced pressure to give an aqueous residue which was treated with Na$_2$CO$_3$ (100 mg) and extracted with EtOAc. The combined extracts were washed with water (2×20 mL), dried over Na$_2$SO$_4$ and the solvent was evaporated off under reduced pressure to give a crude product which was purified by preparative SFC (Column 4-EP, from 20% to 25% in 6 min) to give the title compound as a white solid. HPLC (Condition 7) $t_R$=5.738 min, UPLC-MS (Condition 3) $t_R$=0.90 min, m/z=464.1 [M+H]$^+$; $^1$H-NMR (400 MHz, DMSO-d$_6$) δ ppm 2.54-2.67 (m, 1H) 2.73-2.86 (m, 1H) 3.22-3.30 (m, 1H) 3.35-3.45 (m, 2H) 3.47-3.68 (m, 3H) 3.70-3.84 (m, 1H) 4.52-4.77 (m, 1H) 6.60/6.69 (s, 1H) 7.34 (d, J=8.99 Hz, 2H) 7.79-7.96 (m, 3H) 8.20/8.35 (br. s, 1H) 8.74 (br. s, 1H) 10.36/10.41 (s, 1H) 13.03/13.19 (s, 1H).

Example 37

6-(3-Hydroxyazetidin-1-yl)-5-(1H-pyrazol-5-yl)-N-(4-(trifluoromethoxy)phenyl)nicotinamide

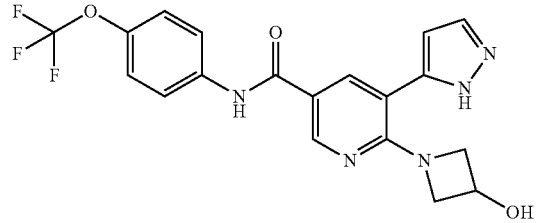 [SMILES: O=C(Nc1ccc(OC(F)(F)F)cc1)c1cnc(N2CC(O)C2)c(-c2ccn[nH]2)c1]

1-(Tetrahydro-2H-pyran-2-yl)-1H-pyrazole-5-boronic acid pinacol ester (209 mg, 0.752 mmol), K$_3$PO$_4$ (368 mg, 1.735 mmol) and Pd(PPh$_3$)$_4$ (33.4 mg, 0.029 mmol) were added to a mixture of 5-bromo-6-(3-hydroxyazetidin-1-yl)-N-(4-(trifluoromethoxy)phenyl)nicotinamide (Stage 37.1, 250 mg, 0.578 mmol) in toluene (2.5 mL) in a vial, which was sealed, purged with argon and the RM was stirred at 110° C. for 3 h. The cooled mixture was treated with brine (25 mL) and extracted with EtOAc. The combined extracts were washed with brine (25 mL), dried over Na$_2$SO$_4$ and the solvent was evaporated off under reduced pressure. The residue (100 mg, 0.199 mmol) was dissolved in DCM (0.5 mL), treated with TFA (0.3 mL, 3.89 mmol) and stirred at RT for 8 h. Aq. Na$_2$CO$_3$ (0.5 mL) was added and the solvent was evaporated off under reduced pressure to give a crude product which was purified by SFC (Column NH$_2$, from 21% to 26% over 6 min) and lyophilized in water/MeCN to give the title product. UPLC-MS (Condition 3) $t_R$=0.86 min, m/z=420.2 [M+H]$^+$; $^1$H-NMR (600 MHz, DMSO-d$_6$) δ ppm 3.53-3.59 (m, 2H) 3.91-4.00 (m, 2H) 4.35-4.42 (m, 1H) 6.43 (d, J=1.88 Hz, 1H) 7.35 (d, J=8.66 Hz, 2H) 7.79 (br. s, 1H) 7.86 (d, J=9.03 Hz, 2H) 8.09 (d, J=2.07 Hz, 1H) 8.71 (d, J=2.07 Hz, 1H) 10.26 (s, 1H).

Stage 37.1 5-Bromo-6-(3-hydroxyazetidin-1-yl)-N-(4-(trifluoromethoxy)phenyl)nicotinamide

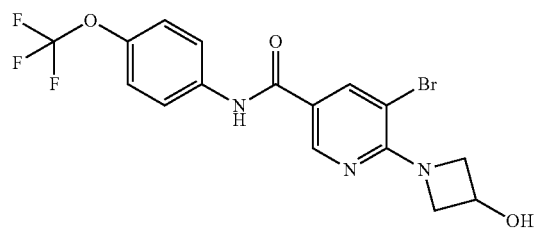 [SMILES: O=C(Nc1ccc(OC(F)(F)F)cc1)c1cnc(N2CC(O)C2)c(Br)c1]

DIPEA (3.67 mL, 21.0 mmol) was added to (R)-5-Bromo-6-(3-hydroxypyrrolidin-1-yl)-N-(4-(trifluoromethoxy)phenyl)nicotinamide (Stage 6.2, 2.77 g, 7.0 mmol) and 3-hydroxyazetidine HCl (0.920 g, 8.40 mmol) in iPrOH (7.0 mL) in a vial which was sealed and the RM mixture was stirred at 140° C. for 1.5 h. After cooling to RT, the RM was dissolved in EtOAc, washed with brine, dried over Na$_2$SO$_4$ and the solvent was evaporated off under reduced pressure to give the title product as a yellow foam. HPLC (Condition 4) t$_R$=5.37 min, UPLC-MS (Condition 3) t$_R$=1.09 min, m/z=432/434 [M+H]$^+$.

Example 38

6-(3-(Dimethylamino)azetidin-1-yl)-5-(1H-pyrazol-5-yl)-N-(4-(trifluoromethoxy)phenyl)nicotinamide

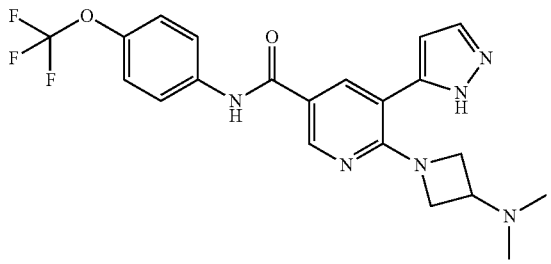 [SMILES: CN(C)C1CN(c2ncc(C(=O)Nc3ccc(OC(F)(F)F)cc3)cc2-c2ccn[nH]2)C1]

DIPEA (0.182 mL, 1.043 mmol) was added to 6-chloro-5-(1H-pyrazol-5-yl)-N-(4-(trifluoromethoxy)phenyl)nicotinamide (Stage 38.1, 70 mg, 0.174 mmol), N,N-dimethylazetidin-3-amine (60.1 mg, 0.348 mmol) and iPr$_2$O (1 mL) in a vial, which was sealed and the RM was stirred at 110° C. for 5 h. After cooling to RT, the RM was dissolved in EtOAc, washed with brine, dried over Na$_2$SO$_4$ and the solvent was evaporated off under reduced pressure to give a crude product which was purified by preparative HPLC (Condition 10). Fractions containing product were combined, treated with sat. aq. Na$_2$CO$_3$ and the MeCN was evaporated off under reduced pressure. The aq. phase was extracted with DCM (2×20 mL) and the combined extracts were dried over Na$_2$SO$_4$ and the solvent was evaporated off under reduced pressure to give the title compound as white crystals. HPLC (Condition 7) t$_R$=5.627 min, UPLC-MS (Condition 3) t$_R$=0.75 min, m/z=447.1 [M+H]$^+$; $^1$H-NMR (400 MHz, DMSO-d$_6$) δ ppm 2.01 (s, 6H) 2.90-3.05 (m, 1H) 3.49-3.62 (m, 2H) 3.70-3.87 (m, 2H) 6.36-6.51 (m, 1H) 7.34 (d, J=8.99 Hz, 2H) 7.80-7.92 (m, J=8.60 Hz, 3H) 8.08 (d, J=2.35 Hz, 1H) 8.69-8.79 (m, J=2.30 Hz, 1H) 10.24 (s, 1H) 12.90-13.21 (m, 1H).

Stage 38.1 6-Chloro-5-(1H-pyrazol-5-yl)-N-(4-(trifluoromethoxy)phenyl)nicotinamide

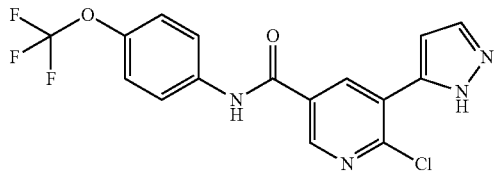 [SMILES: O=C(Nc1ccc(OC(F)(F)F)cc1)c1cnc(Cl)c(-c2ccn[nH]2)c1]

K$_3$PO$_4$ (5.70 g, 26.8 mmol), 1-(tetrahydro-2H-pyran-2-yl)-5-(4,4,5,5-tetramethyl-1,3,2-dioxaborolan-2-yl)-1H-pyrazole (3.73 g, 13.42 mmol) and Pd(PPh$_3$)$_4$ (0.517 g, 0.447 mmol) were added to a solution of 6-chloro-5-iodo-N-(4-(trifluoromethoxy)phenyl)nicotinamide (Stage 32.2, 4.0 g, 8.95 mmol) in toluene (45 mL) added under an argon atmosphere and the RM was stirred at 80° C. for 5 h. The RM was filtered through Hyflo®, which was washed with EtOAc. The filtrate and washings were combined and the solvent was evaporated off under reduced pressure to give a residue which was purified by flash chromatography (Silica gel column, 80 g, n-hexane/EtOAc from 9:1 to 1:1) and triturated under n-hexane, filtered and dried to afford a solid, a portion of which (1.5 g, 3.02 mmol) was treated with TFA (1.163 mL, 15.10 mmol) in DCM (20 mL) and stirred at RT for 4 h. TFA (1.16 mL) was added and the mixture was allowed to stand for 3 days at RT. The solvent was evaporated off under reduced pressure and the residue was diluted with EtOAc, treated with sat. aq. Na$_2$CO$_3$ and extracted with EtOAc. The combined organic layers were washed with brine (50 mL), dried over Na$_2$SO$_4$ and the solvent was evaporated off under reduced pressure to give a crude product which was purified by flash chromatography (Silica gel column, 40 g, n-hexane/EtOAc from 9:1 to 1:1) to afford the title product as beige crystals. UPLC-MS (Condition 3) t$_R$=1.02 min, m/z=383.1 [M+H]$^+$.

Example 39

6-(3-(Hydroxymethyl)azetidin-1-yl)-5-(1H-pyrazol-5-yl)-N-(4-(trifluoromethoxy)phenyl)nicotinamide

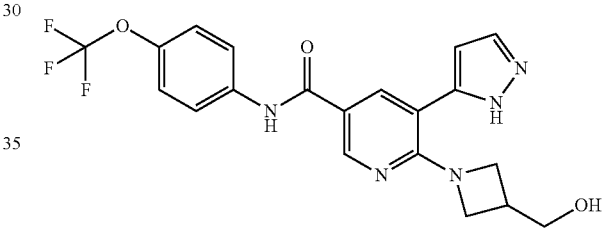

The title compound was prepared in an analogous fashion to that described in Example 37 using 5-bromo-6-(3-(hydroxymethyl)azetidin-1-yl)-N-(4-(trifluoromethoxy)phenyl)nicotinamide (Stage 39.1) and 1-(Tetrahydro-2H-pyran-2-yl)-1H-pyrazole-5-boronic acid pinacol ester. UPLC-MS (Condition 3) t$_R$=0.87 min, m/z=434.2 [M+H]$^+$; $^1$H-NMR (600 MHz, DMSO-d$_6$) δ ppm 2.59-2.68 (m, 1H) 3.47 (d, J=6.02 Hz, 2H) 3.53-3.61 (m, 2H) 3.77-3.87 (m, 2H) 6.45 (d, J=1.88 Hz, 1H) 7.35 (d, J=8.66 Hz, 2H) 7.79 (br. s, 1H) 7.86 (d, J=9.03 Hz, 2H) 8.10 (s, 1H) 8.69 (d, J=1.69 Hz, 1H) 10.28 (s, 1H).

Stage 39.1 5-Bromo-6-(3-(hydroxymethyl)azetidin-1-yl)-N-(4-(trifluoromethoxy)phenyl)nicotinamide

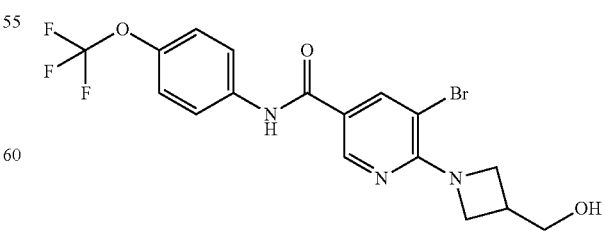

DIPEA (0.115 mL, 0.660 mmol) was added to a solution of 5-bromo-6-chloro-N-(4-(trifluoromethoxy)phenyl)nicotinamide (Stage 6.2, 119 mg, 0.3 mmol) and azetidin-3-yl-methanol, HCl salt (44.5 mg, 0.36 mmol) in iPrOH (0.3 mL) in a vial, which was sealed and the RM mixture stirred at 140° C. for 5 h. After cooling at RT, the RM was dissolved in EtOAc, washed with 0.5 M HCl and brine, dried over Na$_2$SO$_4$ and the solvent was evaporated off under reduced pressure to give a crude product which was purified by flash chromatography (Silica gel column, n-hexane/EtOAc from 50% to 100% EtOAc) and crystallized from n-pentane/EtOAc to afford the title product as white crystals. HPLC (Condition 4) t$_R$=5.33 min, UPLC-MS (Condition 3) t$_R$=1.06 min, m/z=446.2 [M+H]$^+$.

Example 40

6-(3-Hydroxy-3-methylazetidin-1-yl)-5-(1H-pyrazol-5-yl)-N-(4-(trifluoromethoxy)phenyl)nicotinamide

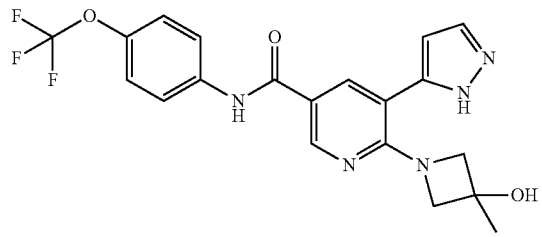 [SMILES: CC1(O)CN(c2ncc(C(=O)Nc3ccc(OC(F)(F)F)cc3)cc2-c2ccn[nH]2)C1]

The title compound was prepared in an analogous fashion to that described in Example 33 using 6-chloro-5-(1-(tetrahydro-2H-pyran-2-yl)-1H-pyrazol-5-yl)-N-(4-(trifluoromethoxy)phenyl)nicotinamide (Stage 32.1) and 3-methylazetidin-3-ol to afford an off-white powder. HPLC (Condition 4) t$_R$=4.52 min, UPLC-MS (Condition 3) t$_R$=0.88 min, m/z=434.2 [M+H]$^+$; $^1$H-NMR (400 MHz, DMSO-d$_6$) δ ppm 1.30 (s, 3H) 3.61 (s, 4H) 5.40 (s, 1H) 6.41 (s, 1H) 7.32 (d, J=8.60 Hz, 2H) 7.74-7.89 (m, 3H) 8.04 (d, J=2.35 Hz, 1H) 8.70 (s, 1H) 10.20 (s, 1H) 12.90-13.15 (m, 1H).

Example 41

6-(3-Hydroxyazetidin-1-yl)-5-(3-methyl-1H-pyrazol-5-yl)-N-(4-(trifluoromethoxy)phenyl)nicotinamide

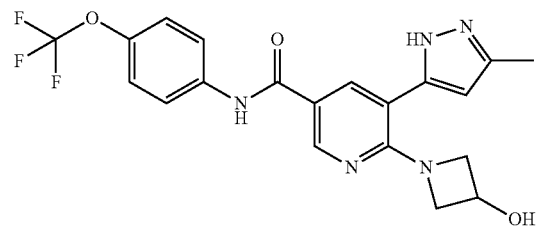 [SMILES: Cc1cc(-c2cc(C(=O)Nc3ccc(OC(F)(F)F)cc3)cnc2N2CC(O)C2)[nH]n1]

The title compound was prepared in an analogous fashion to that described in Example 37 using 5-bromo-6-(3-hydroxyazetidin-1-yl)-N-(4-(trifluoromethoxy)phenyl)nicotinamide (Stage 37.1) and 3-methyl-1-(tetrahydro-2H-pyran-2-yl)-5-(4,4,5,5-tetramethyl-1,3,2-dioxaborolan-2-yl)-1H-pyrazole (Stage 41.1) to afford a white lyophilizate. HPLC (Condition 7) t$_R$=5.50 min, UPLC-MS (Condition 3) t$_R$=0.89 min, m/z=434.2 [M+H]$^+$; $^1$H-NMR (400 MHz, DMSO-d$_6$) δ ppm 2.29 (s, 3H) 3.59-3.67 (m, 2H) 3.99-4.08 (m, 2H) 4.37-4.45 (m, 1H) 6.21 (s, 1H) 7.35 (d, J=8.99 Hz, 2H) 7.82-7.89 (m, J=9.40 Hz, 2H) 8.11 (d, J=1.96 Hz, 1H) 8.66 (d, J=2.35 Hz, 1H) 10.28 (s, 1H).

Stage 41.1 3-Methyl-1-(tetrahydro-2H-pyran-2-yl)-5-(4,4,5,5-tetramethyl-1,3,2-dioxaborolan-2-yl)-1H-pyrazole

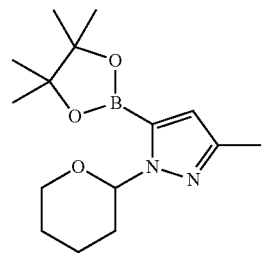

A mixture of 3-methylpyrazole (3.0 g, 35.4 mmol), 3,4-dihydro-2H-pyrane (4.97 mL, 53.2 mmol) and TFA (0.02 mL, 0.260 mmol) was stirred at 85° C. for 6 h under an argon atmosphere. The RM was cooled to RT and NaH 60% in mineral oil (0.061 g, 1.524 mmol) was and the RM was stirred for 10 min. The RM was purified by bulb-to-bulb distillation to give 3-methyl-1-(tetrahydro-2H-pyran-2-yl)-1H-pyrazole (b.p. 150-170° C., 12 mbar). A solution of n-1.6 M BuLi in n-hexane (3.38 mL, 5.41 mmol) was added dropwise over 10 min to a solution of 3-methyl-1-(tetrahydro-2H-pyran-2-yl)-1H-pyrazole (1.0 g, 5.41 mmol) in THF (12 mL) at −70° C. under a nitrogen atmosphere and The RM was stirred for 10 min and then treated dropwise with 2-methoxy-4,4,5,5-tetramethyl-1,3,2-dioxaborolane (0.898 g, 5.69 mmol) and stirred at −70° C. for 1 h. The RM was allowed to warm to RT, treated with n-hexane and the product was filtered, dissolved in water (10 mL) and acidified to pH 6 with 10% aqueous citric acid. The water was evaporated off under reduced pressure and the aqueous residue extracted with EtOAc, dried over Na$_2$SO$_4$ and the solvent was evaporated off under reduced pressure to give the title product as a yellow resin. UPLC-MS (Condition 3) t$_R$=0.56 min, m/z=211.2 [M+H]$^+$.

Example 42

6-(3-(Hydroxymethyl)azetidin-1-yl)-5-(3-methyl-1H-pyrazol-5-yl)-N-(4-(trifluoromethoxy)phenyl)nicotinamide

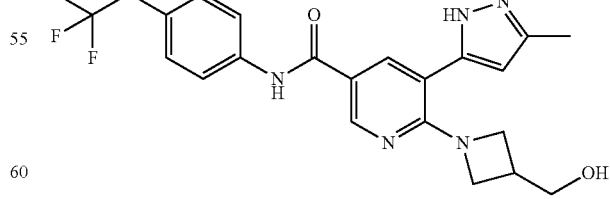

The title compound was prepared in an analogous fashion to that described in Example 41 using 5-bromo-6-(3-(hydroxymethyl)azetidin-1-yl)-N-(4-(trifluoromethoxy)phenyl)nicotinamide (Stage 39.1) and 3-methyl-1-(tetrahydro-2H-pyran-2-yl)-5-(4,4,5,5-tetramethyl-1,3,2-dioxaborolan-2- yl)-1H-pyrazole (Stage 41.1) to afford a beige lyophilizate. HPLC (Condition 7) $t_R$=5.488 min, UPLC-MS (Condition 3) $t_R$=0.89 min, m/z=448.1 [M+H]$^+$; $^1$H-NMR (400 MHz, DMSO-d$_6$) δ ppm 2.27 (s, 3H) 2.56-2.69 (m, 1H) 3.46 (d, J=6.26 Hz, 2H) 3.51-3.57 (m, 2H) 3.79 (t, J=8.6 Hz, 2H) 6.16 (s, 1H) 7.34 (d, J=8.60 Hz, 2H) 7.83-7.90 (m, J=9.00 Hz, 2H) 8.01 (d, J=2.35 Hz, 1H) 8.70 (d, J=2.35 Hz, 1H) 10.20 (br.s, 1H), 12.04 (br.s, 1H).

Example 43

5-(3-(Hydroxymethyl)-1H-pyrazol-5-yl)-6-(pyrrolidin-1-yl)-N-(4-(trifluoromethoxy)phenyl)nicotinamide

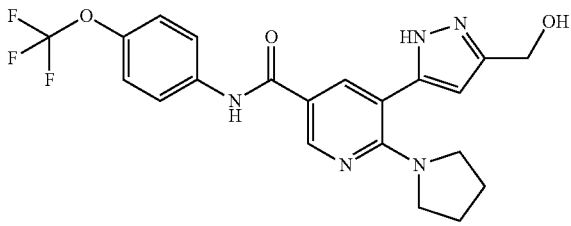 [SMILES: O=C(Nc1ccc(OC(F)(F)F)cc1)c1cnc(N2CCCC2)c(-c2cc(CO)n[nH]2)c1]

Pyrrolidine (0.230 mL, 2.78 mmol) and K$_2$CO$_3$ (0.524 g, 3.79 mmol) were added to a solution of 5-bromo-6-chloro-N-(4-(trifluoromethoxy)phenyl)nicotinamide (Stage 6.2, 1 g, 2.53 mmol) in MeCN (5 mL) and the RM was stirred at 100° C. for 4 h. The product was filtered, suspended in MeCN and water, filtered and the filtrate was evaporated off under reduced pressure to give a residue. The residue (100 mg, 0.232 mmol) was suspended in dioxane (1 mL), treated with tributyl(1-ethoxyvinyl)stannane (101 mg, 0.279 mmol) and Pd(Ph$_3$P)$_4$ (26.9 mg, 0.023 mmol) and stirred at 110° C. for 2 h. The solvent was evaporated off under reduced pressure, the residue was dissolved in dioxane (2 mL), and filtered through a PS-Thiol cartridge. This solution was treated with HCl (4 N) and stirred at RT for 4 h. The solvent was evaporated off under reduced pressure and the residue was dissolved in EtOH (2 mL), treated with NaOEt (0.5 mL from a solution of 100 mg sodium dissolved in 5 mL EtOH), stirred 30 min and the treated with diethyl oxalate (0.069 mL, 0.508 mmol). The RM was stirred for 4 h at 80° C. The solvent was evaporated off under reduced pressure and the residue was treated with sat. aq. NH$_4$Cl solution and extracted with DCM. The combined extracts were washed with brine, dried over Na$_2$SO$_4$ and the solvent was evaporated off under reduced pressure to give a residue which was dissolved in acetic acid (2 mL, 34.9 mmol), treated with hydrazine hydrate (0.030 mL, 0.956 mmol) and stirred at RT for 2 h. the solvent was evaporated off under reduced pressure to give a residue which was treated with MeCN/n-hexane and extracted with MeCN. The MeCN phase was separated and the solvent was evaporated off under reduced pressure to give a residue, which was dissolved in THF (1 mL), treated with LiAlH$_4$ (20 mg, 0.527 mmol) and stirred at RT for 4 h. Additional LiAlH$_4$ (3 eq.) were added and the RM was stirred overnight at RT. The RM was treated with an aq. solution of Rochelle salt's, filtered and the filtrate was evaporated off under reduced pressure to give a crude product which was purified by preparative SFC and lyophilized (water/MeCN) afforded the title product. UPLC-MS (Condition 3) $t_R$=0.9 min, m/z=448.1 [M+H]$^+$; $^1$H-NMR (600 MHz, DMSO-d$_6$) δ ppm 1.81 (br. s, 4H) 3.25 (br. s, 4H) 4.53 (s, 2H) 6.33 (s, 1H) 7.36 (d, J=8.66 Hz, 2H) 7.86 (d, J=9.03 Hz, 2H) 8.14 (s, 1H) 8.67 (s, 1H) 10.31 (br. s, 1H).

Example 44

5-(3-Cyano-1H-pyrazol-5-yl)-6-(pyrrolidin-1-yl)-N-(4-(trifluoromethoxy)phenyl)nicotinamide

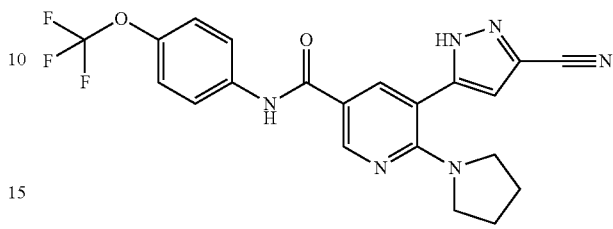

Tributyl(1-ethoxyvinyl)tin (2.065 g, 5.72 mmol) and Pd(PPh$_3$)$_4$ (0.551 g, 0.477 mmol) were added to a solution of 5-bromo-6-(pyrrolidin-1-yl)-N-(4-(trifluoromethoxy)phenyl)nicotinamide (Stage 15.1, 2.05 g, 4.77 mmol) in dioxane (20 mL). and stirred at 110° C. for 18 h. The solvent was evaporated off under reduced pressure and the residue was purified by flash chromatography (Silica gel 60, 1 kg, EtOAc/n-hexane (1:3). A solution this material (1 g, 2.373 mmol) in EtOH (10 mL) was treated with a solution of 4M HCl in dioxane (30 mL, 987 mmol) and stirred at RT overnight. The solvent was evaporated off under reduced pressure to give a residue, a portion of which (500 mg, 1.271 mmol) was dissolved in EtOH (10 mL), treated with a solution of sodium ethanolate (2.5 mL from a solution of 100 mg sodium dissolved in 5 mL EtOH), stirred for 30 min, then treated with diethyl oxalate (0.350 mL, 2.56 mmol) and stirred at 80° C. for 2 h. The solvent was evaporated off under reduced pressure and the residue was dissolved in acetic acid (10 mL, 175 mmol), treated with hydrazine monohydrate (0.150 mL, 4.78 mmol) and stirred at RT for 2 h. The solvent was evaporated off under reduced pressure and the residue was purified by flash chromatography (RediSep® Silica gel column, EtOAc/n-hexane 1:1). The residue (100 mg, 0.204 mmol) was treated with NH$_3$ 7 M in MeOH and stirred at 100° C. in a sealed vial. The solvent was evaporated off under reduced pressure and the residue was treated with POCl$_3$ (1 mL, 10.73 mmol) stirred overnight at RT and then at 80° C. for 4 h. The solvent was evaporated off under reduced pressure and the crude product was purified by preparative SFC and lyophilization (water/MeCN) afforded the title product. UPLC-MS (Condition 3) $t_R$=1.12 min, m/z=443.1 [M+H]$^+$; $^1$H-NMR (600 MHz, DMSO-d$_6$) δ ppm 1.75-1.86 (m, 4H) 3.18 (t, J=5.85 Hz, 4H) 7.10 (s, 1H) 7.34 (d, J=8.78 Hz, 2H) 7.85 (d, J=9.15 Hz, 2H) 8.09 (d, J=2.20 Hz, 1H) 8.82 (d, J=1.83 Hz, 1H) 10.18 (s, 1H) 14.24 (s, 1H).

Example 45

(R)—N-(4-(Chlorodifluoromethoxy)phenyl)-5-(5-cyano-1H-pyrrol-2-yl)-6-(3-hydroxypyrrolidin-1-yl)nicotinamide

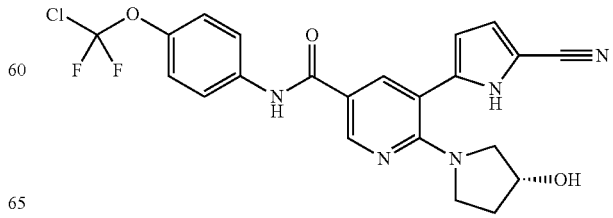

The title compound was prepared in an analogous fashion to that described in Example 29 using (R)-5-bromo-N-(4-(chlorodifluoromethoxy)phenyl)-6-(3-hydroxypyrrolidin-1-yl)nicotinamide (Stage 22.1) and (1-(tert-butoxycarbonyl)-5-cyano-1H-pyrrol-2-yl)boronic acid (Stage 29.1) to afford a beige solid. UPLC-MS (Condition 3) $t_R$=1.06 min, m/z=474.1 [M+H]$^+$, m/z=472.2 [M−H]$^-$; 1H NMR (400 MHz, DMSO-$d_6$) δ ppm 1.69-1.81 (m, 1H) 1.81-1.91 (m, 1H) 2.94 (d, J=11.74 Hz, 1H) 3.22-3.28 (m, 1H) 3.32 (d, J=3.42 Hz, 1H) 3.40-3.49 (m, 1H) 4.23 (br. s, 1H) 4.88 (br. s, 1H) 6.30 (d, J=3.67 Hz, 1H) 7.00 (d, J=3.67 Hz, 1H) 7.33 (d, J=9.05 Hz, 2H) 7.82-7.89 (m, 2H) 8.07 (d, J=2.20 Hz, 1H) 8.76 (d, J=2.20 Hz, 1H) 10.17 (s, 1H) 12.60 (br. s, 1H).

Example 46

N-(4-(Chlorodifluoromethoxy)phenyl)-5-(5-cyano-1H-pyrrol-2-yl)-6-((3S,4S)-3,4-dihydroxypyrrolidin-1-yl)nicotinamide

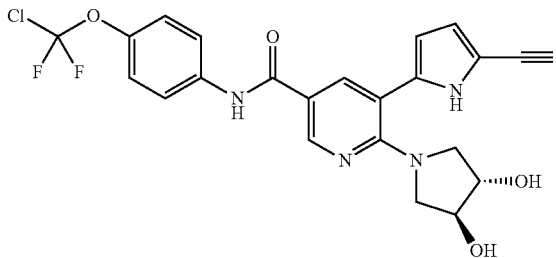

The title compound was prepared in an analogous fashion to that described in Example 29 using 5-bromo-N-(4-(chlorodifluoromethoxy)phenyl)-6-((3S,4S)-3,4-dihydroxypyrrolidin-1-yl)nicotinamide (Stage 46.1) and (1-(tert-butoxycarbonyl)-5-cyano-1H-pyrrol-2-yl)boronic acid (Stage 29.1) to afford a rose solid. UPLC-MS (Condition 3) $t_R$=0.97 min, m/z=490.0 [M+H]$^+$, m/z=487.9 [M−H]$^-$; 1H NMR (400 MHz, DMSO-$d_6$) δ ppm 3.02 (d, J=11.86 Hz, 2H) 3.46 (dd, J=11.86, 3.55 Hz, 2H) 3.90 (br. s, 2H) 5.09 (d, J=2.93 Hz, 2H) 6.29 (dd, J=3.67, 2.45 Hz, 1H) 7.03 (dd, J=3.67, 2.32 Hz, 1H) 7.34 (d, J=9.17 Hz, 2H) 7.83-7.90 (m, 2H) 8.07 (d, J=2.32 Hz, 1H) 8.76 (d, J=2.32 Hz, 1H) 10.18 (s, 1H) 12.63-12.68 (m, 1H).

Stage 46.1 5-Bromo-N-(4-(chlorodifluoromethoxy)phenyl)-6-((3S,4S)-3,4-dihydroxypyrrolidin-1-yl)nicotinamide

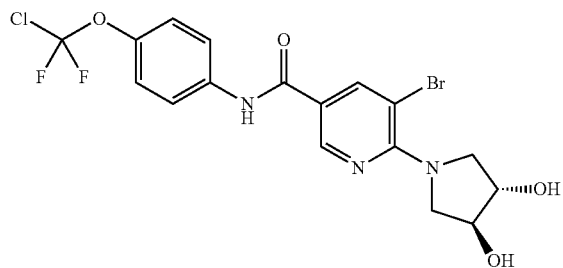 [SMILES: O=C(Nc1ccc(OC(F)(F)Cl)cc1)c1cnc(N2C[C@H](O)[C@@H](O)C2)c(Br)c1]

The title compound was prepared in an analogous fashion to that described in Stage 6.1 using 5-bromo-6-chloro-N-(4-(chlorodifluoromethoxy)phenyl)nicotinamide (Stage 22.2) and (3S,4S)-pyrrolidine-3,4-diol to afford an off-white solid. UPLC-MS (Condition 3) $t_R$=0.98 min, m/z=477.9 [M+H]$^+$, m/z=475.8 [M−H]$^-$; 1H NMR (400 MHz, DMSO-$d_6$) δ ppm 3.55 (d, J=11.13 Hz, 2H) 3.91-4.09 (m, 4H) 5.18 (d, J=2.81 Hz, 2H) 7.34 (d, J=9.05 Hz, 2H) 7.80-7.93 (m, 2H) 8.34 (d, J=1.96 Hz, 1H) 8.67 (d, J=1.96 Hz, 1H) 10.24 (s, 1H).

Example 47

(R)—N-(4-(Chlorodifluoromethoxy)phenyl)-5-(5-cyano-1-methyl-1H-pyrrol-2-yl)-6-(3-hydroxypyrrolidin-1-yl)nicotinamide

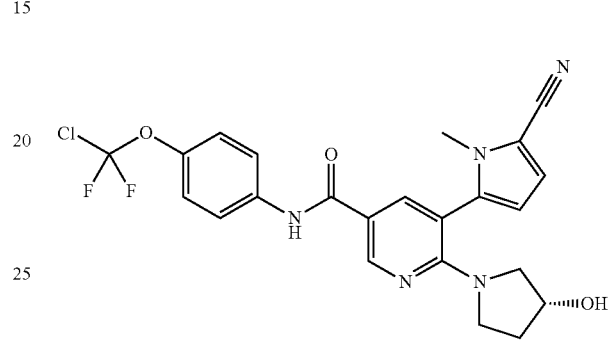

The title compound was prepared in an analogous fashion to that described in Stage 32.1 using (R)-5-bromo-N-(4-(chlorodifluoromethoxy)phenyl)-6-(3-hydroxypyrrolidin-1-yl)nicotinamide (Stage 22.1) and 5-cyano-1-methyl-1H-pyrrol-2-ylboronic acid to afford an off-white powder. HPLC (Condition 4) $t_R$=5.96 min, UPLC-MS (Condition 3) $t_R$=1.11 min, m/z=486 [M−H]$^-$.

Example 48

N-(4-(Chlorodifluoromethoxy)phenyl)-6-(3,3-difluoropyrrolidin-1-yl)-5-(1H-pyrazol-5-yl)nicotinamide

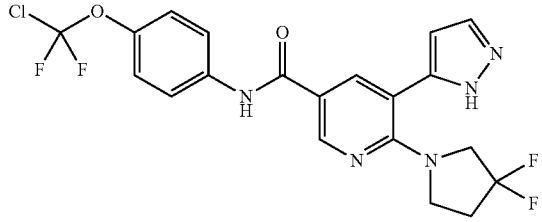 [SMILES: O=C(Nc1ccc(OC(F)(F)Cl)cc1)c1cnc(N2CCC(F)(F)C2)c(-c2ccn[nH]2)c1]

3,3-Difluoropyrrolidine hydrochloride (69.8 mg, 0.486 mmol) and DIPEA (0.170 mL, 0.972 mmol) were added to 6-chloro-N-(4-(chlorodifluoromethoxy)phenyl)-5-(1H-pyrazol-5-yl)nicotinamide (Stage 48.1, 100 mg, 0.243 mmol) in iPrOH (0.5 mL) and stirred at 140° C. for 3 h. The RM was treated with water, and extracted with EtOAc. The combined extracts were dried over $Na_2SO_4$ and the solvent was evaporated off under reduced pressure to give the crude material which was purified by crystallization from DCM/EtOAc to give the title product as a white solid. HPLC (Condition 7) $t_R$=6.746 min, UPLC-MS (Condition 3) $t_R$=1.11 min, m/z=470.1 [M+H]$^+$; 1H-NMR (400 MHz, DMSO-$d_6$) δ ppm 2.32-2.45 (m, 2H) 3.42-3.51 (m, 2H) 3.56 (t, J=13.29 Hz, 2H)

6.48 (s, 1H) 7.34 (d, J=8.60 Hz, 2H) 7.73-7.88 (m, 3H) 8.13 (d, J=2.35 Hz, 1H) 8.79 (s, 1H) 10.30 (s, 1H) 13.01 (br.s, 1H).

Stage 48.1 6-Chloro-N-(4-(chlorodifluoromethoxy) phenyl)-5-(1H-pyrazol-5-yl)nicotinamide

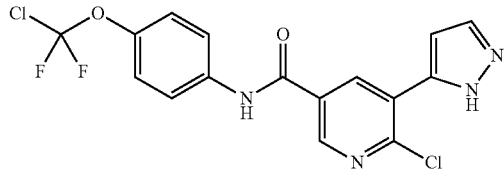 [SMILES: O=C(Nc1ccc(OC(F)(F)Cl)cc1)c1cnc(Cl)c(-c2ccn[nH]2)c1]

TFA (7.3 mL) was added to a solution of 6-chloro-N-(4-(chlorodifluoromethoxy)phenyl)-5-(1-(tetrahydro-2H-pyran-2-yl)-1H-pyrazol-5-yl)nicotinamide (Stage 48.2, 1.285 g, 2.366 mmol) in DCM (20 mL) and the RM was stirred at RT. The solvent was evaporated off under reduced pressure and the residue was dissolved in EtOAc (150 mL), washed with aq. sat. NaHCO₃ solution (2×50 mL) and water (2×50 mL) dried over Na₂SO₄ and the solvent was evaporated off under reduced pressure to give a residue was crystallized from iPr₂O/EtOAc to give the title product as a white solid. HPLC (Condition 7) $t_R$=6.797 min, UPLC-MS (Condition 3) $t_R$=1.05-min, m/z=398.9/401.0 [M+H]⁺.

Stage 48.2 6-Chloro-N-(4-(chlorodifluoromethoxy) phenyl)-5-(1-(tetrahydro-2H-pyran-2-yl)-1H-pyrazol-5-yl)nicotinamide

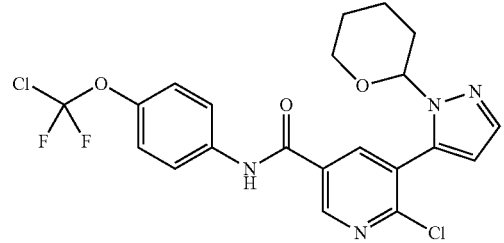 [SMILES: O=C(Nc1ccc(OC(F)(F)Cl)cc1)c1cnc(Cl)c(-c2ccnn2C2CCCCO2)c1]

1-(Tetrahydro-2H-pyran-2-yl)-1H-pyrazole-5-boronic acid pinacol ester (9.45 g, 34.0 mmol), Na₂CO₃ (39.2 mL, 78 mmol) and PdCl₂(dppf) (0.956 g, 1.307 mmol) were added to 6-chloro-N-(4-(chlorodifluoromethoxy)phenyl)-5-iodonicotinamide (Stage 48.3, 12 g, 26.1 mmol) in DME (160 mL). The mixture was evacuated/purged 3 times with argon, and stirred at 80° C. for 22 h. The RM was diluted with EtOAc (350 mL), washed with water (4×150 mL) and extracted with EtOAc. The combined extracts were dried over Na₂SO₄ and the solvent was evaporated off under reduced pressure to give the crude product which was purified by flash chromatography (Silica gel column, 850 g, EtOAc/n-hexane (1:2)) and crystallized from iPr₂O/EtOAc to give the title product as a white solid. HPLC (Condition 7) $t_R$=7.523 min, UPLC-MS (Condition 3) $t_R$=1.22 min, m/z=483/485 [M+H]⁺.

Stage 48.3 6-Chloro-N-(4-(chlorodifluoromethoxy) phenyl)-5-iodonicotinamide

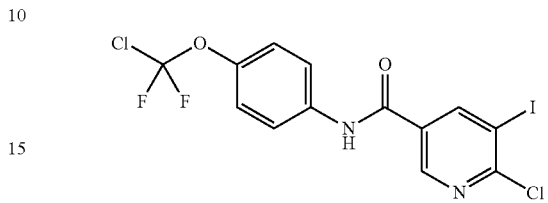

The title compound was prepared in an analogous fashion to that described in Stage 22.2 using 6-chloro-5-iodonicotinic acid and 4-(chlorodifluoromethoxy)aniline to afford an off-white powder. HPLC (Condition 4) $t_R$=6.47 min, UPLC-MS (Condition 3) $t_R$=1.26 min, m/z=456.8 [M−H]⁻.

Example 49

N-(4-(Chlorodifluoromethoxy)phenyl)-6-(3-hydroxy-3-methylpyrrolidin-1-yl)-5-(1H-pyrazol-5-yl) nicotinamide

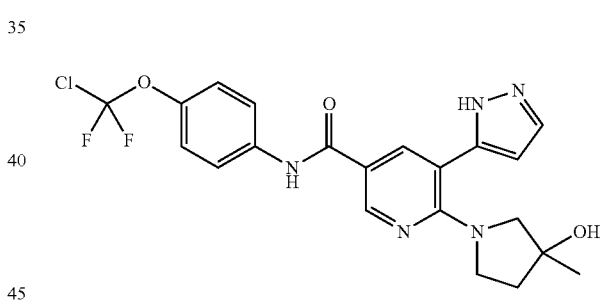

A mixture of 6-chloro-N-(4-(chlorodifluoromethoxy)phenyl)-5-(1-(tetrahydro-2H-pyran-2-yl)-1H-pyrazol-5-yl)nicotinamide (Stage 48.2, 500 mg, 1.035 mmol), 3-methylpyrrolidin-3-ol hydrochloride (244 mg, 1.77 mmol), DIPEA (0.723 mL, 4.14 mmol) and iPrOH (1.4 mL) in a MW vial was subjected to MW irradiation at 140° C. for 1.5 h. The cooled mixture was treated with aqueous HCl (37%) and MeOH (2 mL) and stirred for 1 h. The mixture was basified with sat. aq. NaHCO₃, extracted with EtOAc and the combined extracts were washed with water and brine, dried over Na₂SO₄ and the solvent was evaporated off under reduced pressure to give the crude product which was crystallized from toluene/EtOAc to afford the title product as a white solid. UPLC-MS (Condition 3) $t_R$=0.95 min, m/z=464.1 [M+H]⁺, m/z=508.1 [M+formic acid-H]⁻; 1H NMR (400 MHz, DMSO-d₆) δ ppm 1.20 (s, 3H) 1.60-1.85 (m, 2H) 2.93-3.12 (m, 2H) 3.25-3.31 (m, 1H) 3.42-3.54 (m, 1H) 4.61-4.76 (m, 1H) 6.31-6.42 (m, 1H) 7.33 (d, J=8.80 Hz, 2H) 7.51-7.84 (m, 1H) 7.87 (d, J=9.05 Hz, 2H) 8.03 (d, J=2.32 Hz, 1H) 8.73 (m, J=2.32 Hz, 1H) 10.19 (s, 1H) 12.86-13.15 (m, 1H).

Example 50

N-(4-(Chlorodifluoromethoxy)phenyl)-5-(1H-pyrazol-5-yl)-6-(2,6-diazaspiro[3.4]octan-6-yl)nicotinamide

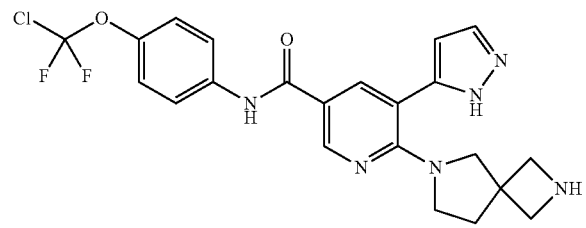 [SMILES: O=C(Nc1ccc(OC(F)(F)Cl)cc1)c1cnc(N2CCC3(CNC3)C2)c(-c2ccn[nH]2)c1]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and tert-butyl 2,6-diazaspiro[3.4]octane-2-carboxylate to afford an off-white powder. UPLC-MS (Condition 3) $t_R$=0.79 min, m/z=475.1 [M+H]$^+$; $^1$H-NMR (400 MHz, DMSO-d$_6$) δ ppm 2.04 (t, J=6.65 Hz, 2H) 3.14 (d, J=4.69 Hz, 3H) 3.46 (s, 2H) 3.76 (q, J=10.04 Hz, 4H) 6.39 (s, 1H) 7.31 (d, J=8.60 Hz, 2H) 7.78-7.92 (m, 3H) 8.08 (br. s, 1H) 8.74 (br. s, 1H) 10.27 (s, 1H) 12.90-13.01 (m, 1H).

Example 51

6-(3-(Aminomethyl)-3-fluoropyrrolidin-1-yl)-N-(4-(chlorodifluoromethoxy)phenyl)-5-(1H-pyrazol-5-yl)nicotinamide

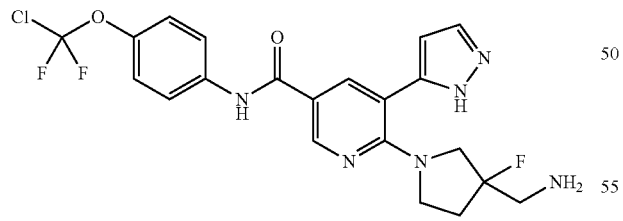

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and (3-fluoropyrrolidin-3-yl)methanamine to afford an off-white powder. HPLC (Condition 4) $t_R$=4.3 min, UPLC-MS (Condition 3) $t_R$=0.80 min, m/z=481 [M+H]$^+$; $^1$H-NMR (400 MHz, DMSO-d$_6$) δ ppm 1.92-2.10 (m, 2H) 3.03 (d, J=19.94 Hz, 2H) 3.11-3.67 (m, 6H) 6.41 (br. s, 1H) 7.31 (d, J=8.60 Hz, 2H) 7.79-7.91 (m, 3H) 8.08 (d, J=1.56 Hz, 1H) 8.73 (br. s, 1H) 10.23 (s, 1H) 12.90-13.16 (m, 1H).

Example 52

6-(trans-3-Amino-4-fluoropyrrolidin-1-yl)-N-(4-(chlorodifluoromethoxy)phenyl)-5-(1H-pyrazol-5-yl)nicotinamide

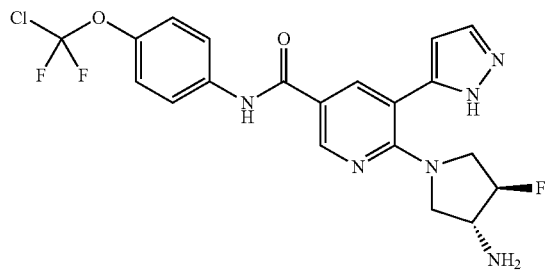 [SMILES: N[C@@H]1CN(c2ncc(C(=O)Nc3ccc(OC(F)(F)Cl)cc3)cc2-c2ccn[nH]2)C[C@H]1F]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and tert-butyl (trans-4-fluoropyrrolidin-3-yl)carbamate to afford an off-white powder. HPLC (Condition 4) $t_R$=4.58 min, UPLC-MS (Condition 3) $t_R$=0.83 min, m/z=467 [M+H]$^+$; $^1$H-NMR (400 MHz, DMSO-d$_6$) δ ppm 3.01 (br. s, 1H) 3.20-3.39 (m, 3H) 3.47 (d, J=10.56 Hz, 2H) 3.55-3.82 (m, 1H) 4.76-4.94 (m, 1H) 6.41 (br. s, 1H) 7.31 (d, J=8.99 Hz, 2H) 7.79-7.90 (m, 3H) 8.06 (s, 1H) 8.73 (br. s, 1H) 10.22 (s, 1H) 12.91-13.15 (m, 1H).

Example 53

N-(4-(Chlorodifluoromethoxy)phenyl)-6-((3S,4S)-3-(dimethylamino)-4-hydroxypyrrolidin-1-yl)-5-(1H-pyrazol-5-yl)nicotinamide

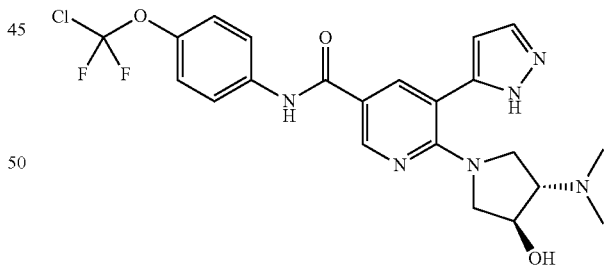

A mixture of 6-chloro-N-(4-(chlorodifluoromethoxy)phenyl)-5-(1H-pyrazol-5-yl)nicotinamide (Stage 48.1, 63 mg, 0.156 mmol), (3S,4S)-4-(dimethylamino) pyrrolidin-3-ol (50.8 mg, 0.250 mmol) and DIPEA (0.191 mL, 1.094 mmol) and iPrOH (1 mL) in a sealed vial was heated at 110° C. for 4 h The RM was treated with sat. aq. Na$_2$CO$_3$ (20 mL) and extracted with EtOAc. The combined extracts were washed with brine (10 mL), dried over Na$_2$SO$_4$ and the solvent was evaporated off under reduced pressure to give a crude product which was purified by preparative SFC (Column 4-EP, isocratic 25% in 15 min) followed by preparative HPLC (Condition 10). Fractions containing product were combined, treated with sat. aq. Na₂CO₃ and the MeCN was evaporated off under reduced pressure to give an aq. residue which was extracted with DCM. The combined extracts were dried over Na₂SO₄ and the solvent was evaporated off under reduced pressure to give the title product as a white foam. HPLC (Condition 7) t$_R$=5.71 min, UPLC-MS (Condition 3) t$_R$=0.78 min, m/z=493 [M+H]⁺; ¹H-NMR (400 MHz, DMSO-d₆) δ ppm 2.14 (s, 6H) 2.95-3.03 (m, 1H) 3.16-3.26 (m, 2H) 3.34-3.46 (m, 2H) 4.00-4.13 (m, 1H) 4.97-5.13 (m, 1H) 6.33-6.45 (m, 1H) 7.34 (d, J=8.99 Hz, 2H) 7.80-7.91 (m, J=9.40 Hz, 3H) 8.04 (s, 1H) 8.68-8.81 (m, 1H) 10.20 (s, 1H) 12.88-13.16 (m, 1H).

Example 54

6-(1-Amino-3-azabicyclo[3.1.0]hexan-3-yl)-N-(4-(chlorodifluoromethoxy)phenyl)-5-(1H-pyrazol-5-yl)nicotinamide

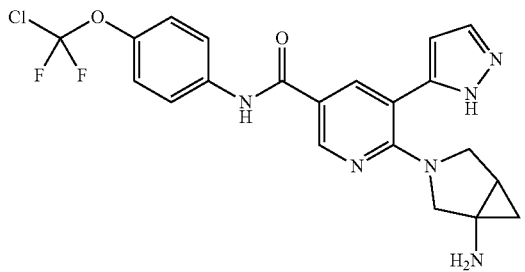 [SMILES: NC12CC1CN(c1ncc(C(=O)Nc3ccc(OC(F)(F)Cl)cc3)cc1-c1ccn[nH]1)C2]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and tert-butyl 3-azabicyclo[3.1.0]hexan-1-ylcarbamate to afford an off-white foam. HPLC (Condition 4) t$_R$=4.32 min, UPLC-MS (Condition 3) t$_R$=0.79 min, m/z=461.1 [M+H]⁺.

Example 55

6-((1R,5S,6s)-6-Amino-3-azabicyclo[3.1.0]hexan-3-yl)-N-(4-(chlorodifluoromethoxy)phenyl)-5-(1H-pyrazol-5-yl)nicotinamide

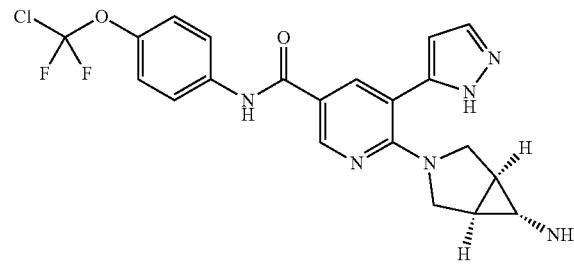

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and tert-butyl (1R,5S,6s)-3-azabicyclo[3.1.0]hexan-6-ylcarbamate to afford an off-white powder. HPLC (Condition 4) t$_R$=4.30 min, UPLC-MS (Condition 3) t$_R$=0.79 min, m/z=461.1 [M+H]⁺.

Example 56

N-(4-(Chlorodifluoromethoxy)phenyl)-5-(1H-pyrazol-5-yl)-6-(4,7-diazaspiro[2.5]octan-7-yl)nicotinamide

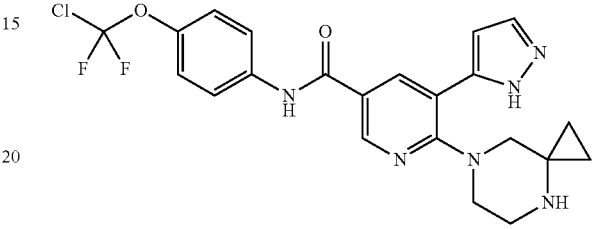

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and tert-butyl 4,7-diazaspiro[2.5]octane-4-carboxylate to afford an off-white powder. HPLC (Condition 4) t$_R$=4.44 min, UPLC-MS (Condition 3) t$_R$=0.81 min, m/z=475 [M+H]⁺; ¹H-NMR (400 MHz, DMSO-d₆) δ ppm 0.27-0.54 (m, 4H) 2.82 (br. s, 2H) 2.96-3.20 (m, 5H) 6.64 (br. s, 1H) 7.32 (d, J=8.21 Hz, 2H) 7.86 (d, J=8.99 Hz, 3H) 8.29 (br. s, 1H) 8.71 (br. s, 1H) 10.37 (br. s, 1H) 13.00 (br. s, 1H).

Example 57

N-(4-(Chlorodifluoromethoxy)phenyl)-6-(4-cyclopropylpiperazin-1-yl)-5-(1H-pyrazol-5-yl)nicotinamide The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and 1-cyclopropylpiperazine to afford an off-white powder. UPLC-MS (Condition 3) t$_R$=0.84 min, m/z=489 [M+H]⁺; ¹H-NMR (400 MHz, DMSO-d₆) δ ppm 0.22-0.45 (m, 4H) 1.56-1.66 (m, 1H) 2.56 (br. s, 4H) 3.12 (br. s, 4H) 6.67 (br. s, 1H) 7.33 (d, J=8.60

Hz, 2H) 7.79-7.91 (m, 3H) 8.32 (br. s, 1H) 8.72 (s, 1H) 10.39 (br. s, 1H) 12.98-13.19 (m, 1H).

Example 58

N-(4-(Chlorodifluoromethoxy)phenyl)-6-(4-(2-fluoroethyl)piperazin-1-yl)-5-(1H-pyrazol-5-yl)nicotinamide

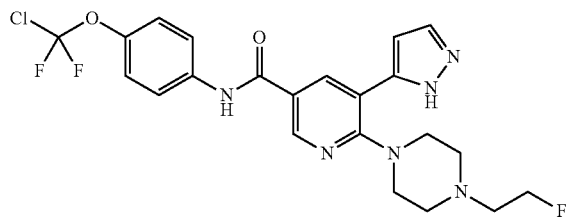 [SMILES: O=C(Nc1ccc(OC(F)(F)Cl)cc1)c1cnc(N2CCN(CCF)CC2)c(-c2ccn[nH]2)c1]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and 1-(2-fluoroethyl)piperazine to afford an off-white powder. HPLC (Condition 4) $t_R$=4.57 min, UPLC-MS (Condition 3) $t_R$=0.82 min, m/z=492.9 [M−H]$^-$; $^1$H-NMR (400 MHz, DMSO-d$_6$) δ ppm 2.54-2.71 (m, 2H) 3.09-3.21 (m, 4H) 3.24-3.35 (m, 4H) 4.46 (t, J=4.89 Hz, 1H) 4.58 (t, J=4.89 Hz, 1H) 6.66 (br. s, 1H) 7.33 (d, J=8.60 Hz, 2H) 7.86 (d, J=8.99 Hz, 3H) 8.28-8.37 (m, 1H) 8.73 (d, J=1.95 Hz, 1H) 10.39 (br. s, 1H) 12.96-13.11 (m, 1H).

Example 59

N-(4-(Chlorodifluoromethoxy)phenyl)-6-(4-(2,2-difluoroethyl)piperazin-1-yl)-5-(1H-pyrazol-5-yl)nicotinamide

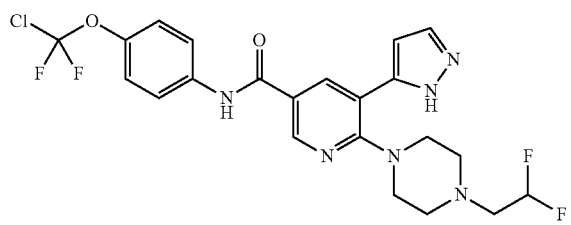 [SMILES: O=C(Nc1ccc(OC(F)(F)Cl)cc1)c1cnc(N2CCN(CC(F)F)CC2)c(-c2ccn[nH]2)c1]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and 1-(2,2-difluoroethyl)piperazine to afford an off-white powder. HPLC (Condition 4) $t_R$=4.72 min, UPLC-MS (Condition 3) $t_R$=1.05 min, m/z=513 [M+H]$^+$; $^1$H-NMR (400 MHz, DMSO-d$_6$) δ ppm 2.57 (br. s, 4H) 2.73 (td, J=15.64, 3.91 Hz, 2H) 3.09-3.22 (m, 4H) 6.13 (s, 1H) 6.67 (br. s, 1H) 7.33 (d, J=8.60 Hz, 2H) 7.86 (d, J=8.99 Hz, 3H) 8.33 (br. s, 1H) 8.73 (s, 1H) 10.40 (br. s, 1H) 12.98-13.22 (m, 1H).

Example 60

N-(4-(Chlorodifluoromethoxy)phenyl)-5-(1H-pyrazol-5-yl)-6-(4-(2,2,2-trifluoroethyl)piperazin-1-yl)nicotinamide

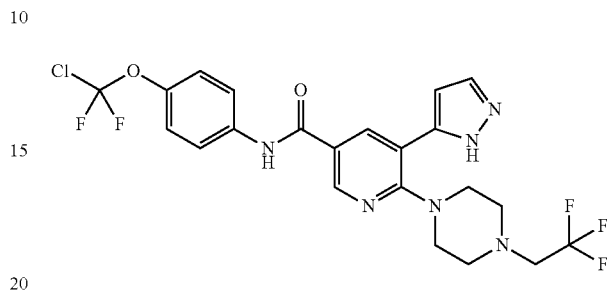

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and 1-(2,2,2-trifluoroethyl)piperazine to afford an off-white powder. HPLC (Condition 4) $t_R$=6.3 min, UPLC-MS (Condition 3) $t_R$=1.18 min, m/z=531 [M+H]$^+$; $^1$H-NMR (400 MHz, DMSO-d$_6$) δ ppm 2.59-2.70 (m, 4H) 3.08-3.26 (m, 6H) 6.59-6.73 (m, 1H) 7.33 (d, J=8.60 Hz, 2H) 7.86 (d, J=9.38 Hz, 3H) 8.27-8.37 (m, 1H) 8.73 (s, 1H) 10.40 (br. s, 1H) 13.02-13.18 (m, 1H).

Example 61

N-(4-(Chlorodifluoromethoxy)phenyl)-5-(1H-pyrazol-5-yl)-6-(1,6-diazaspiro[3.5]nonan-6-yl)nicotinamide

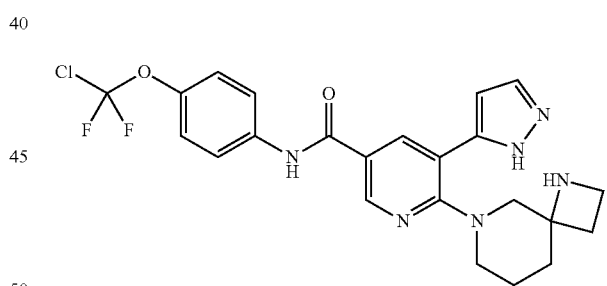

TFA (0.151 mL 1.964 mmol) was added to a solution of 1-benzyl-6-tert-butyl 1,6-diazaspiro[3.5]nonane-1,6-dicarboxylate (Stage 61.1, 105 mg, 0.275 mmol) in DCM (1 mL) and the RM was stirred at RT for 2 h. The solvent was evaporated off under reduced pressure and the residue was dissolved in iPrOH (1 mL), treated with DIPEA (0.343 mL, 1.964 mmol) and 6-chloro-N-(4-(chlorodifluoromethoxy)phenyl)-5-(1H-pyrazol-5-yl)nicotinamide (Stage 48.1, 80 mg, 0.196 mmol) and stirred at 120° C. for 20 h. The RM was treated with sat. aq. Na$_2$CO$_3$ and extracted with EtOAc. The combined extracts were washed with brine (10 mL), dried over Na$_2$SO$_4$ and the solvent was evaporated off under reduced pressure to give a residue which was purified by flash chromatography (Silica gel column, 4 g, DCM/EtOH from 99:1 to 97:3). The fractions containing the desired intermediate were combined and the solvent was evaporated off under reduced pressure to give a residue which was dissolved in MeOH and hydrogenated in the presence of Pd/C (55.2 mg). The RM was filtered through Hyflo®, washed with MeOH (2×10 mL) and the filtrate was evaporated to dryness under reduced pressure to give the crude product which was purified by preparative HPLC (Condition 10). Fractions containing product were combined, treated with sat. aq. Na$_2$CO$_3$ and the MeCN was evaporated off under reduced pressure to give an aq. residue which was extracted with DCM. The combined extracts were dried over Na$_2$SO$_4$ and the solvent was evaporated off under reduced pressure to give the title product as a white foam. HPLC (Condition 7) t$_R$=6.19 min, UPLC-MS (Condition 3) t$_R$=0.83 min, m/z=489.1 [M+H]$^+$; $^1$H-NMR (400 MHz, DMSO-d$_6$) δ ppm 1.37-1.69 (m, 4H) 1.81-1.97 (m, 2H) 2.93-3.06 (m, 2H) 3.19-3.28 (m, 4H) 6.60 (d, J=1.56 Hz, 1H) 7.35 (d, J=8.60 Hz, 2H) 7.75-7.95 (m, J=9.00 Hz, 3H) 8.28 (d, J=1.95 Hz, 1H) 8.74 (d, J=1.96 Hz, 1H) 10.39 (s, 1H).

Stage 61.1 1-Benzyl 6-tert-butyl 1,6-diazaspiro[3.5]nonane-1,6-dicarboxylate

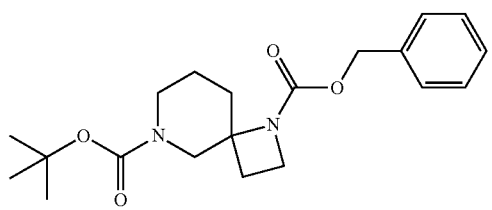 [SMILES: CC(C)(C)OC(=O)N1CCCC2(CCN2C(=O)OCc2ccccc2)C1]

A solution of benzyl chloroformate (0.148 mL, 1.039 mmol) in DCM (1 mL) was added to a mixture of tert-butyl-1,6-diazaspiro[3.5]nonane-6-carboxylate (200 mg, 0.866 mmol) and DIPEA (0.378 mL, 2.165 mmol) in DCM (3 mL) and the mixture was stirred at RT for 16 h. The solvent was evaporated off under reduced pressure and the crude product was purified by flash chromatography (Silica gel column, 4 g, n-hexane/DCM from 20% to 100% DCM) to give the title product as a yellow resin. UPLC-MS (Condition 3) t$_R$=1.21 min, m/z=361.1 [M+H]$^+$.

Example 62

N-(4-(Chlorodifluoromethoxy)phenyl)-6-morpholino-5-(1H-pyrazol-5-yl)nicotinamide

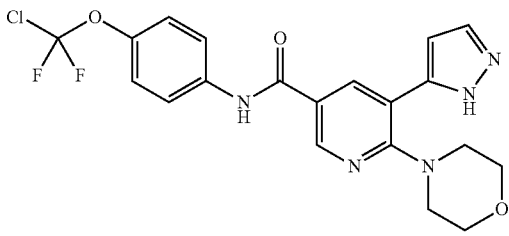 [SMILES: O=C(Nc1ccc(OC(F)(F)Cl)cc1)c1cnc(N2CCOCC2)c(-c2ccn[nH]2)c1]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and morpholine to afford a white powder. HPLC (Condition 4) t$_R$=5.62 min, UPLC-MS (Condition 3) t$_R$=1.03 min, m/z=450 [M+H]$^+$; $^1$H-NMR (400 MHz, DMSO-d$_6$) δ ppm 3.14 (d, J=1.17 Hz, 4H) 3.55-3.68 (m, 4H) 6.71 (br. s, 1H) 7.33 (d, J=8.60 Hz, 2H) 7.87 (d, J=8.99 Hz, 3H) 8.34 (br. s, 1H) 8.75 (s, 1H) 10.41 (br. s, 1H) 13.04 (br. s, 1H).

Example 63

N-(4-(Chlorodifluoromethoxy)phenyl)-6-(3-hydroxyazetidin-1-yl)-5-(1H-pyrazol-5-yl)nicotinamide

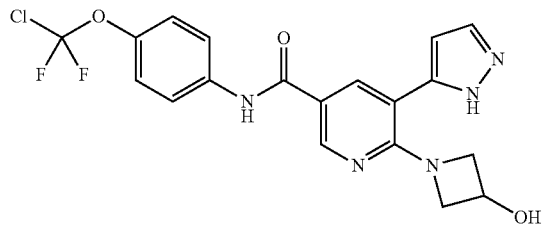 [SMILES: O=C(Nc1ccc(OC(F)(F)Cl)cc1)c1cnc(N2CC(O)C2)c(-c2ccn[nH]2)c1]

3-Hydroxyazetidine hydrochloride (53.2 mg, 0.486 mmol) and DIPEA (0.170 mL, 0.972 mmol) were added to a suspension of 6-chloro-N-(4-(chlorodifluoromethoxy)phenyl)-5-(1H-pyrazol-5-yl)nicotinamide (Stage 48.1, 100 mg, 0.243 mmol) in iPrOH (0.5 mL) and the RM was heated at 140° C. for 3 h. The RM was treated with water, extracted with EtOAc, and the combined extracts were dried over Na$_2$SO$_4$ and the solvent was evaporated off under reduced pressure to give. the crude product which was purified by flash chromatography (RediSep® Silica gel column, 24 g, DCM/MeOH 9:1) to give the title product as a yellow foam. HPLC (Condition 7) t$_R$=5.518 min, UPLC-MS (Condition 3) t$_R$=0.89 min, m/z=436 [M+H]$^+$; $^1$H-NMR (400 MHz, DMSO-d$_6$) δ ppm 3.49-3.57 (m, 2H) 3.87-3.99 (m, 2H) 4.32-4.44 (m, 1H) 5.53 (br.s, 1H) 6.40 (br.s, 1H) 7.33 (d, J=8.60 Hz, 2H) 7.81-7.91 (m, 3H) 8.06 (d, J=2.35 Hz, 1H) 8.70 (br.s, 1H) 10.23 (s, 1H) 13.01 (s, 1H).

Example 64

6-(3-Aminoazetidin-1-yl)-N-(4-(chlorodifluoromethoxy)phenyl)-5-(1H-pyrazol-5-yl)nicotinamide

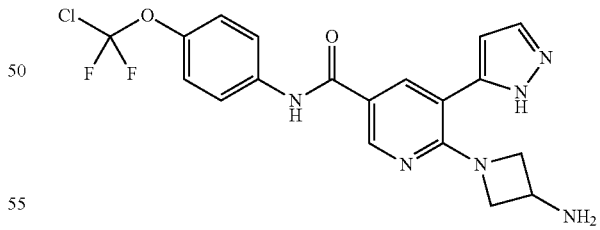

A mixture of 6-chloro-N-(4-(chlorodifluoromethoxy)phenyl)-5-(1-(tetrahydro-2H-pyran-2-yl)-1H-pyrazol-5-yl)nicotinamide (Stage 48.2, 70 mg, 0.143 mmol), tert-butyl azetidin-3-ylcarbamate (49.4 mg, 0.287 mmol), DIPEA (0.075 mL, 0.430 mmol) and iPrOH (1 mL) in a sealed vial was stirred at 120° C. for 2 h. The RM was treated with sat. aq. Na$_2$CO$_3$, extracted with EtOAc and the combined extracts were washed with brine (10 mL), dried over Na$_2$SO$_4$ and the solvent was evaporated off under reduced pressure to give a residue which was purified by flash chromatography (Silica gel column, 4 g, DCM/EtOH from 99:1 to 97:3). Fractions containing the desired intermediate were combined and the solvent was evaporated off under reduced pressure to give a residue which was dissolved in DCM (1 mL), treated with TFA (0.216 mL, 2.80 mmol) and stirred at RT for 3 h. The RM was treated with sat. aq. $Na_2CO_3$, and extracted with EtOAc. The combined extracts were washed with brine (20 mL), dried over $Na_2SO_4$ and the solvent was evaporated off under reduced pressure to give the crude product which was purified by preparative HPLC (Condition 11). Fractions containing the product were combined, treated with sat. aq. $Na_2CO_3$ and the MeCN was evaporated off under reduced pressure to give an aq. residue which was extracted with DCM. The combined extracts were dried over $Na_2SO_4$ and the solvent was evaporated off under reduced pressure to give the title product as a white solid. HPLC (Condition 7) $t_R$=5.545 min, UPLC-MS (Condition 3) $t_R$=0.77 min, m/z=435.1 $[M+H]^+$; $^1$H-NMR (400 MHz, DMSO-$d_6$) δ ppm 1.78-2.05 (m, 2H) 3.35-3.35 (m, 2H) 3.53-3.69 (m, 1H) 3.80-3.96 (m, 2H) 6.34-6.45 (m, 1H) 7.33 (d, J=8.60 Hz, 2H) 7.74 (br. s, 1H) 7.87 (d, J=8.99 Hz, 2H) 8.00-8.10 (m, 1H) 8.66-8.78 (m, 1H) 10.24 (br. s, 1H).

Example 65

N-(4-(Chlorodifluoromethoxy)phenyl)-6-(3-(dimethylamino)azetidin-1-yl)-5-(1H-pyrazol-5-yl)nicotinamide

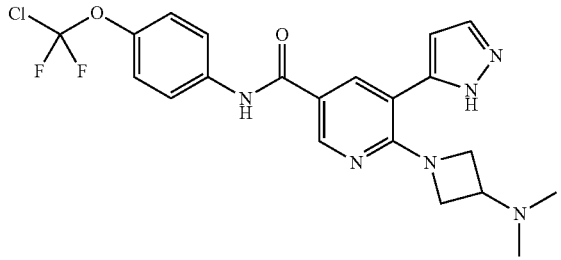 [SMILES: CN(C)C1CN(c2ncc(C(=O)Nc3ccc(OC(F)(F)Cl)cc3)cc2-c2ccn[nH]2)C1]

The title compound was prepared in an analogous fashion to that described in Example 38 using 6-chloro-N-(4-(chlorodifluoromethoxy)phenyl)-5-(1H-pyrazol-5-yl)nicotinamide (Stage 48.1) and N,N-dimethylazetidin-3-amine to afford a white solid. HPLC (Condition 7) $t_R$=5.768 min, UPLC-MS (Condition 3) $t_R$=0.78 min, m/z=463.1 $[M+H]^+$; $^1$H-NMR (400 MHz, DMSO-$d_6$) δ ppm 2.01 (s, 6H) 2.90-3.06 (m, 1H) 3.51-3.62 (m, 2H) 3.71-3.86 (m, 2H) 6.37-6.48 (m, 1H) 7.33 (d, J=8.60 Hz, 2H) 7.53-7.93 (m, J=9.4 Hz, 3H) 8.08 (d, J=2.35 Hz, 1H) 8.74 (d, J=1.95 Hz, 1H) 10.19-10.29 (m, 1H) 12.91-13.22 (m, 1H).

Example 66

N-(4-(Chlorodifluoromethoxy)phenyl)-6-(3-hydroxy-3-methylazetidin-1-yl)-5-(1H-pyrazol-5-yl)nicotinamide

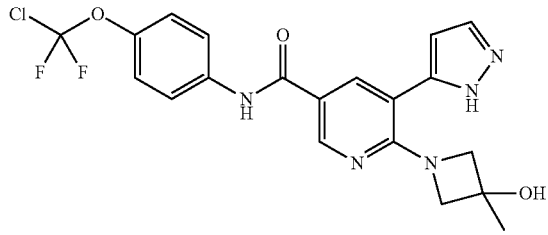 [SMILES: CC1(O)CN(c2ncc(C(=O)Nc3ccc(OC(F)(F)Cl)cc3)cc2-c2ccn[nH]2)C1]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and 3-methylazetidin-3-ol to afford a white powder. HPLC (Condition 4) $t_R$=4.8 min, UPLC-MS (Condition 3) $t_R$=0.94 min, m/z=449 $[M+H]^+$; $^1$H-NMR (400 MHz, DMSO-$d_6$) δ ppm 1.30 (s, 3H) 3.61 (s, 4H) 5.41 (s, 1H) 6.41 (br. s, 1H) 7.31 (d, J=8.60 Hz, 2H) 7.74-7.90 (m, 3H) 7.99-8.09 (m, 1H) 8.70 (br. s, 1H) 10.21 (s, 1H) 12.90-13.18 (m, 1H).

Example 67

N-(4-(Chlorodifluoromethoxy)phenyl)-6-(3-(hydroxymethyl)azetidin-1-yl)-5-(1H-pyrazol-5-yl)nicotinamide

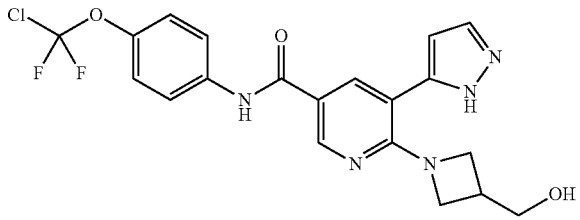 [SMILES: O=C(Nc1ccc(OC(F)(F)Cl)cc1)c1cnc(N2CC(CO)C2)c(-c2ccn[nH]2)c1]

The title compound was prepared in an analogous fashion to that described in Example 63 using 6-chloro-N-(4-(chlorodifluoromethoxy)phenyl)-5-(1H-pyrazol-5-yl)nicotinamide (Stage 48.1) and 3-azetidinemethanol hydrochloride to afford a yellow foam. HPLC (Condition 7) $t_R$=5.51 min, UPLC-MS (Condition 3) $t_R$=0.89 min, m/z=450.1 $[M+H]^+$; $^1$H-NMR (400 MHz, DMSO-$d_6$) δ ppm 2.55-2.68 (m, 1H) 3.43-3.49 (m, 2H) 3.49-3.56 (m, 2H) 3.73-3.82 (m, 2H) 4.66-4.73 (m, 1H) 6.42 (br.s, 1H) 7.33 (d, J=8.99 Hz, 2H) 7.79-7.91 (m, 3H) 8.04 (d, J=2.35 Hz, 1H) 8.75 (br.s, 1H) 10.21 (s, 1H) 13.02 (s, 1H).

Example 68

N-(4-(Chlorodifluoromethoxy)phenyl)-5-(1H-pyrazol-5-yl)-6-(2,6-diazaspiro[3.3]heptan-2-yl)nicotinamide

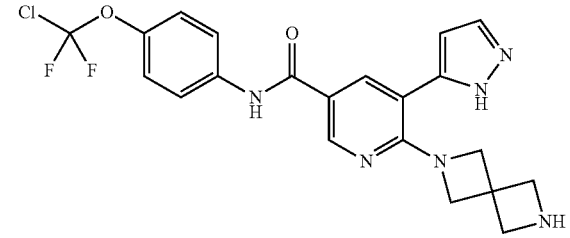 [SMILES: O=C(Nc1ccc(OC(F)(F)Cl)cc1)c1cnc(N2CC3(CNC3)C2)c(-c2ccn[nH]2)c1]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and tert-butyl 2,6-diazaspiro[3.3]heptane-2-carboxylate to afford a white powder. HPLC (Condition 4) $t_R$=4.17 min, UPLC-MS (Condition 3) $t_R$=0.77 min, m/z=461 $[M+H]^+$; $^1$H-NMR (400 MHz, DMSO-$d_6$) δ ppm 3.30 (br. s, 2H) 3.63 (s, 4H) 3.75-

3.92 (m, 4H) 6.41 (d, J=2.35 Hz, 1H) 7.26-7.35 (m, 2H) 7.77 (br. s, 1H) 7.81-7.89 (m, 2H) 8.05 (d, J=2.35 Hz, 1H) 8.71 (d, J=2.35 Hz, 1H) 10.22 (s, 1H).

Example 69

6-(3-Hydroxy-3-methylazetidin-1-yl)-5-(1H-imidazol-2-yl)-N-(4-(trifluoromethoxy)phenyl)nicotinamide

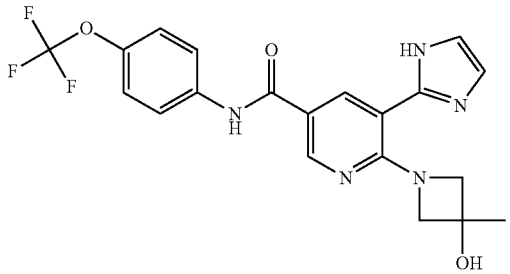 [SMILES: CC1(O)CN(c2ncc(C(=O)Nc3ccc(OC(F)(F)F)cc3)cc2-c2ncc[nH]2)C1]

DIPEA (0.139 mL, 0.794 mmol) was added to a mixture of 6-chloro-5-(1H-imidazol-2-yl)-N-(4-(trifluoromethoxy)phenyl)nicotinamide (Stage 69.1, 76 mg, 0.199 mmol) and 3-methylazetidin-3-ol HCl (27 mg, 0.218 mmol) in iPrOH (1 mL) and the RM was stirred at 140° C. 4.5 h. The solvent was evaporated off under reduced pressure and the residue was treated with water, extracted with EtOAc and the combined extracts were washed with water and brine, dried over MgSO$_4$/charcoal and the solvent was evaporated off under reduced pressure. The residue was purified by flash chromatography (Silica gel column, 15 g, EtOAc/EtOH from 95:5 to 9:1) and crystallized from n-hexane/EtOAc to give the title product as white crystals. UPLC-MS (Condition 3) $t_R$=0.7 min, m/z=434.2 [M+H]$^+$; $^1$H-NMR (600 MHz, DMSO-d$_6$) δ ppm 1.32 (s, 3H) 3.54-3.67 (m, 4H) 5.47 (s, 1H) 7.05 (s, 1H) 7.26 (s, 1H) 7.35 (d, J=8.66 Hz, 2H) 7.87 (d, J=9.03 Hz, 2H) 8.15 (d, J=2.07 Hz, 1H) 8.76 (d, J=2.07 Hz, 1H) 10.25 (s, 1H) 12.39 (br. s, 1H).

Stage 69.1 6-Chloro-5-(1H-imidazol-2-yl)-N-(4-(trifluoromethoxy)phenyl)nicotinamide

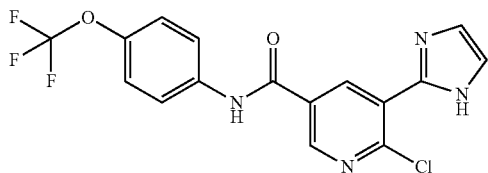 [SMILES: O=C(Nc1ccc(OC(F)(F)F)cc1)c1cnc(Cl)c(-c2ncc[nH]2)c1]

A solution of isopropyl magnesium chloride 2 M in THF (2.5 mL, 5 mmol) was added dropwise to a solution of 6-chloro-5-iodo-N-(4-(trifluoromethoxy)phenyl)nicotinamide (Stage 32.2, 885 mg, 2 mmol) in THF (15 mL) at a temperature between −70 and −85° C. under an argon atmosphere. The RM was then stirred at between −45 and −40° C. for 30 min, then cooled to −75° C. and treated dropwise with DMF (0.465 mL, 6.00 mmol). The RM allowed to slowly warm to RT, then treated with NH$_4$Cl aq. solution (15 mL) and extracted with a sat. EtOAc. The combined extracts were washed with a sat. NH$_4$Cl solution, with water and brine, dried over MgSO$_4$ and the solvent was evaporated off under reduced pressure. The residue was dissolved in MeOH (10 mL), treated with glyoxal 40% in water (0.178 mL, 3.89 mmol) and 25% aq. NH$_3$ (1.462 mL, 19.44 mmol) and the RM was stirred for at RT for 24 h. The solvent was evaporated off under reduced pressure and the residue was treated with water and extracted with EtOAc. The combined extracts were washed with water and brine, dried over Na$_2$SO$_4$ and the solvent was evaporated off under reduced pressure to give the crude product which was purified by column chromatography (Silica gel, 50 g, n-hexane/EtOAc 2:1 and 1:1) and recrystallized from n-hexane/EtOAC to afford the title product as white crystals. UPLC-MS (Condition 3) $t_R$ 0.88 min, m/z=383.1 [M+H]$^+$; $^1$H-NMR (600 MHz, DMSO-d$_6$) δ ppm 7.19 (s, 1H) 7.41 (d, J=7.72 Hz, 3H) 7.89 (d, J=8.85 Hz, 2H) 8.76 (d, J=2.07 Hz, 1H) 8.94 (d, J=2.07 Hz, 1H) 10.77 (s, 1H) 12.60 (br. s, 1H).

Example 70

(R)-6-(3-Hydroxypyrrolidin-1-yl)-5-(1H-imidazol-2-yl)-N-(4-(trifluoromethoxy)phenyl)nicotinamide

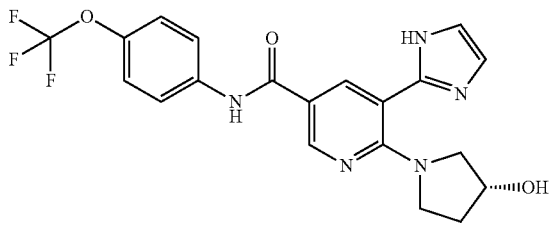 [SMILES: O=C(Nc1ccc(OC(F)(F)F)cc1)c1cnc(N2CC[C@@H](O)C2)c(-c2ncc[nH]2)c1]

A mixture of (R)-5-(4,5-dihydro-1H-imidazol-2-yl)-6-(3-hydroxypyrrolidin-1-yl)-N-(4-(trifluoromethoxy)phenyl)nicotinamide (Stage 70.1, 300 mg, 0.689 mmol), and K$_2$CO$_3$ (210 mg, 1.52 mmol) in DMSO (15 mL) was treated with diacetoxyiodobenzene (488 mg, 1.52 mmol) and stirred at RT overnight. The RM was then treated with EtOAc, washed with sat. aq. NaHCO$_3$ and brine. The solution was dried over anhydrous Na$_2$SO$_4$ and the solvent was evaporated off under reduced pressure. The crude product was purified by flash chromatography (RediSep® Silica gel column, DCM/(4% aq. NH$_3$ in MeOH) from 0 to 20% (4% aq. NH$_3$ in MeOH)) to afford the product as a pale-yellow solid. HPLC (Condition 4) $t_R$=3.88 min, UPLC-MS (Condition 8) $t_R$=0.74 min, m/z=434.1 [M+H]$^+$; $^1$H-NMR (600 MHz, DMSO-d$_6$) δ ppm 1.68-1.93 (m, 2H), 2.55-2.61 (m, 1H,) 2.80-2.92 (m, 1H), 3.16-3.31 (m, 2H), 3.37-3.43 (m, 1H), 4.17-4.26 (m, 1H), 4.81-4.94 (m, 1H), 6.95-7.29 (m, 2H), 7.35 (d, J=8.16 Hz, 2H), 7.88 (d, J=8.78 Hz, 2H), 8.13 (br. s, 1H), 8.79 (s, 1H), 10.23 (s, 1H).

Stage 70.1 (R)-5-(4,5-Dihydro-1H-imidazol-2-yl)-6-(3-hydroxypyrrolidin-1-yl)-N-(4-(trifluoromethoxy)phenyl)nicotinamide

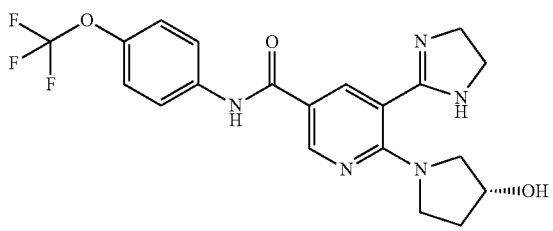 [SMILES: O=C(Nc1ccc(OC(F)(F)F)cc1)c1cnc(N2CC[C@@H](O)C2)c(C2=NCCN2)c1]

A stirred mixture of (R)-5-cyano-6-(3-hydroxypyrrolidin-1-yl)-N-(4-(trifluoromethoxy)phenyl)nicotinamide (Stage 70.2, 1 g, 2.55 mmol), NaHSO$_3$ (0.953 g, 15.3 mmol) and ethylenediamine (7.66 g, 1.27 mmol) was treated dropwise with 40% aq. ammonium silfide (4.34 mL, 25.5 mmol) and heated at 100° C. for 18 h. The cooled mixture was treated with EtOAc, washed with sat. aq. NaHCO₃ and brine, was dried over anhydrous Na₂SO₄ and the solvent was evaporated off under reduced pressure. The crude product was purified by flash chromatography (RediSep® Silica gel column, DCM/(5% aq. NH₃ in MeOH) from 0 to 40% (5% aq. NH₃ in MeOH)) to afford the product as a pale-yellow solid. HPLC (Condition 4) $t_R$=3.89 min, UPLC-MS (Condition 8) $t_R$=0.72 min, m/z=436.2 [M+H]⁺; ¹H-NMR (400 MHz, DMSO-d₆) δ ppm 1.67-1.98 (m, 3H) 3.40-3.75 (m, 8H) 4.30 (br. s, 1H) 4.91 (br. s, 1H) 7.31 (d, J=8.60 Hz, 2H) 7.78-7.91 (m, 2H) 8.06 (d, J=2.35 Hz, 1H) 8.71 (d, J=2.35 Hz, 1H) 10.17 (s, 1H).

Stage 70.2 (R)-5-Cyano-6-(3-hydroxypyrrolidin-1-yl)-N-(4-(trifluoromethoxy)phenyl)nicotinamide

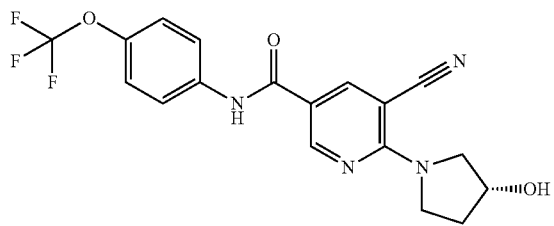 [SMILES: N#Cc1cc(C(=O)Nc2ccc(OC(F)(F)F)cc2)cnc1N1CC[C@@H](O)C1]

A stirred mixture of 6-chloro-5-cyano-N-(4-(trifluoromethoxy)phenyl)nicotinamide (Stage 70.3, 4.50 g, 13.2 mmol), (R)-3-Pyrrolidinol (1.38 g, 15.8 mmol) and DIPEA (3.74 g, 29.0 mmol) in iPrOH (20 mL) was heated at 110° C. for 60 min. The cooled RM was then evaporated to dryness under reduced pressure and the residue was dissolved in EtOAc, washed with sat. aq. NaHCO₃ and brine. The solution was dried over anhydrous Na₂SO₄ and the solvent was evaporated off under reduced pressure to give a crude product which was purified by crystallization from DCM/TBME to afford the product as a colorless crystalline solid. m.p. 234-236° C., HPLC (Condition 4) $t_R$=5.41 min, UPLC-MS (Condition 8) $t_R$=1.01 min, m/z=393.2 [M+H]⁺; ¹H-NMR (400 MHz, DMSO-d₆) δ ppm 1.00-1.25 (m, 1H), 1.80-2.06 (m, 1H), 3.67 (d, J=11.34 Hz, 1H), 3.82 (br. s, 3H), 4.01 (q, J=7.04 Hz, 1H), 4.40 (br. s, 1H), 7.34 (d, J=8.60 Hz, 2H), 7.83 (d, J=8.99 Hz, 2H), 8.51 (d, J=2.35 Hz, 1H), 8.83 (d, J=2.35 Hz, 1H), 10.23 (s, 1H).

Stage 70.3 6-Chloro-5-cyano-N-(4-(trifluoromethoxy)phenyl)nicotinamide

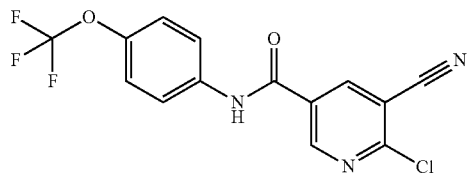 [SMILES: N#Cc1cc(C(=O)Nc2ccc(OC(F)(F)F)cc2)cnc1Cl]

A solution trimethylaluminium 2 M in toluene (20.77 mL, 41.5 mmol) was added to a stirred solution of 4-(trifluoromethoxy)aniline (2.247 mL, 16.62 mmol) in toluene (150 mL) under an argon atmosphere. After 30 min, a solution of 6-chloro-5-cyanonicotinic acid ethyl ester (3.5 g, 16.62 mmol) in toluene (10 mL) was added and the RM was stirred at 25° C. for 1 h. After cooling to 5° C., the RM was treated dropwise with a solution of sat. aq. NH₄Cl (50 mL) and EtOAc (50 mL) was added. The mixture was stirred for 60 min, filtered over Hyflo® and extracted with EtOAc. The combined extracts were dried over Na₂SO₄ and the solvent was evaporated off under reduced pressure to give a crude product which was purified by flash chromatography (RediSep® Silica gel column, n-heptane/EtOAc, from 0 to 30% EtOAc) and recrystallized from n-hexane/DCM to afford the title compound as a yellow crystalline solid. m.p. 198-200° C., HPLC (Condition 4) $t_R$=6.24 min, UPLC-MS (Condition 8) $t_R$=1.14 min, m/z=340.1 [M+H]⁺; ¹H-NMR (400 MHz, DMSO-d₆) δ ppm 7.15-7.34 (m, 2H), 7.67 (d, J=8.99 Hz, 2H), 8.02 (br. s, 1H), 8.53 (d, J=2.35 Hz, 1H), 9.05 (d, J=2.35 Hz, 1H).

Example 71

(R)—N-(4-(Chlorodifluoromethoxy)phenyl)-6-(3-hydroxypyrrolidin-1-yl)-5-(1H-imidazol-2-yl)nicotinamide

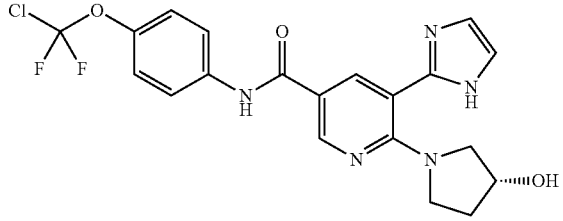 [SMILES: O=C(Nc1ccc(OC(F)(F)Cl)cc1)c1cnc(N2CC[C@@H](O)C2)c(-c2ncc[nH]2)c1]

The title compound was prepared in an analogous fashion to that described in Example 70 using (R)—N-(4-(chlorodifluoromethoxy)phenyl)-5-(4,5-dihydro-1H-imidazol-2-yl)-6-(3-hydroxypyrrolidin-1-yl)nicotinamide (Stage 71.1) to afford a yellow foam. HPLC (Condition 4) $t_R$=4.11 min, UPLC-MS (Condition 8) $t_R$=0.77 min, m/z=450.1 [M+H]⁺; ¹H-NMR (600 MHz, DMSO-d₆) δ ppm 1.68-1.79 (m, 2H), 1.80-1.90 (m, 1H,), 3.00 (m, J=11.2 Hz, 1H), 3.22-3.32 (m, 2H), 3.41-3.55 (m, 1H), 4.11-4.29 (m, 1H), 4.84 (br. s, 1H), 7.24 (s, 1H), 7.34 (d, J=8.41 Hz, 2H), 7.74 (s, 1H), 7.88 (d, J=8.53 Hz, 2H), 8.03 (s, 1H), 8.69 (s, 1H), 10.20 (s, 1H).

Stage 71.1 (R)—N-(4-(Chlorodifluoromethoxy)phenyl)-5-(4,5-dihydro-1H-imidazol-2-yl)-6-(3-hydroxypyrrolidin-1-yl)nicotinamide

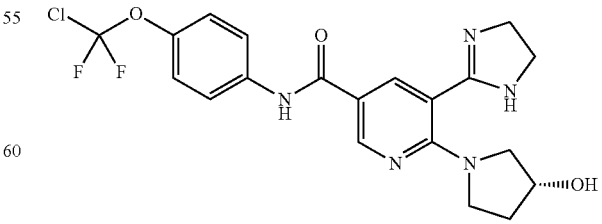

The title compound was prepared in an analogous fashion to that described in Stage 70.1 using (R)—N-(4-(chlorodifluoromethoxy)phenyl)-5-cyano-6-(3-hydroxypyrrolidin-1- yl)nicotinamide (Stage 71.2) to afford a yellow foam. HPLC (Condition 4) $t_R$=4.05 min, UPLC-MS (Condition 8) $t_R$=0.74 min.

Stage 71.2 (R)—N-(4-(Chlorodifluoromethoxy)phenyl)-5-cyano-6-(3-hydroxypyrrolidin-1-yl)nicotinamide

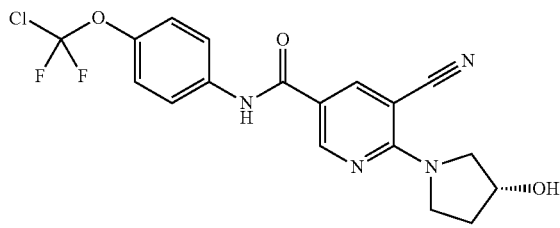 [SMILES: N#Cc1cc(C(=O)Nc2ccc(OC(F)(F)Cl)cc2)cnc1N1CC[C@@H](O)C1]

The title compound was prepared in an analogous fashion to that described in Stage 70.2 using 6-chloro-N-(4-(chlorodifluoromethoxy)phenyl)-5-cyanonicotinamide (Stage 71.3) to afford a colorless crystalline solid. m.p. 212-214° C., HPLC (Condition 4) $t_R$=5.63 min, UPLC-MS (Condition 8) $t_R$=1.06 min, m/z=409.2/407.1 [M+H]$^+$.

Stage 71.3 6-Chloro-N-(4-(chlorodifluoromethoxy)phenyl)-5-cyanonicotinamide

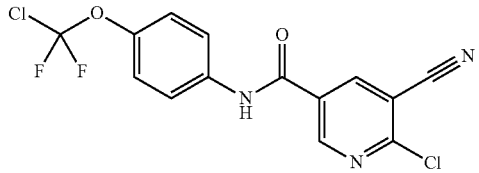 [SMILES: N#Cc1cc(C(=O)Nc2ccc(OC(F)(F)Cl)cc2)cnc1Cl]

The title compound was prepared in an analogous fashion to that described in Stage 70.3 using 6-chloro-5-cyanonicotinic acid ethyl ester to afford a pale-yellow crystalline solid. m.p. 185-188° C., HPLC (Condition 4) $t_R$=6.41 min, UPLC-MS (Condition 8) $t_R$=1.18 min, m/z=356 [M−H]$^+$.

Example 72

(R)-6-(3-Hydroxypyrrolidin-1-yl)-5-(5-methyl-1H-imidazol-2-yl)-N-(4-(trifluoromethoxy)phenyl)nicotinamide

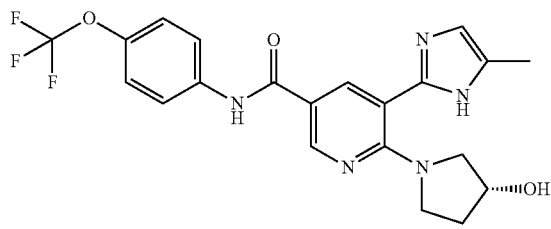 [SMILES: Cc1cnc(-c2cc(C(=O)Nc3ccc(OC(F)(F)F)cc3)cnc2N2CC[C@@H](O)C2)[nH]1]

Palladium on carbon 10% (5.63 mg) was added to a stirred mixture of (R)-6-(3-hydroxypyrrolidin-1-yl)-5-(1-(4-methoxybenzyl)-5-methyl-1H-imidazol-2-yl)-N-(4-(trifluoromethoxy)phenyl)nicotinamide (Stage 72.1, 300 mg, 0.053 mmol) and ammonium formate (33 mg, 0.529 mmol) in EtOH (5 mL) and the mixture was heated under reflux for 52 h. The RM was filtered through Hyflo® and the solvent was evaporated off under reduced pressure to give the crude product which was purified by SFC (Column DEAP, from 21% to 26% in 10 min) to afford the title compound as an amorphous solid. HPLC (Condition 4) $t_R$=4.01 min, UPLC-MS (Condition 8) $t_R$=0.76 min, m/z=448.2 [M+H]$^+$; $^1$H-NMR (600 MHz, DMSO-d$_6$) δ ppm 1.66-1.92 (m, 2H), 2.11-2.29 (m, 2H), 2.91 (br.s, 1H), 3.28 (br.s, 2H), 3.38-3.50 (m, 2H), 4.22 (br. s, 1H), 4.89 (br.s, 1H), 6.63-6.74 (m, 1H), 6.87-6.96 (m, 1H), 7.35 (d, J=8.59 Hz, 2H), 7.88 (d, J=8.92 Hz, 2H), 8.12 (s, 1H), 8.77 (s, 1H), 10.22 (s, 1H), 11.85-12.17 (m, 1H).

Stage 72.1 (R)-6-(3-Hydroxypyrrolidin-1-yl)-5-(1-(4-methoxybenzyl)-5-methyl-1H-imidazol-2-yl)-N-(4-(trifluoromethoxy)phenyl)nicotinamide

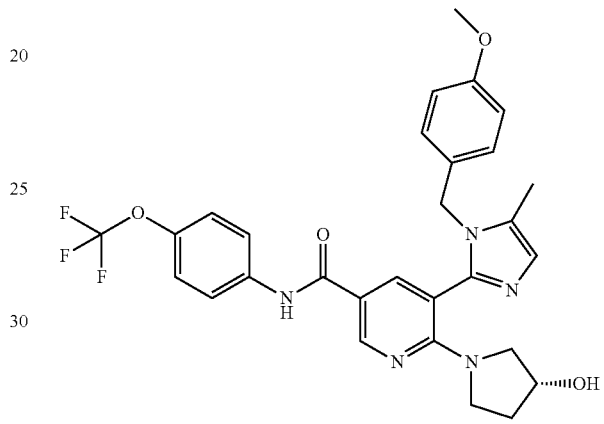

A stirred mixture of (R)-2-(3-hydroxypyrrolidin-1-yl)-N3-(prop-2-yn-1-yl)-N5-(4-(trifluoromethoxy)phenyl)pyridine-3,5-dicarboxamide (Stage 72.2, 0.50 g, 1.115 mmol) and 4-methoxybenzylamine (0.175 mL, 1.338 mmol) in toluene (30 mL) was treated with zinc trifluoromethanesulphonate (61 mg, 0.17 mmol) and heated under reflux for 41 h. The solvent was evaporated off under reduced pressure and the crude product was purified by flash chromatography (RediSep® Silica gel column, EtOAc 100%) to afford the title compound as a foam. HPLC (Condition 4) $t_R$=4.66 min, UPLC-MS (Condition 8) $t_R$=0.93 min, m/z=568.1 [M+H]$^+$; $^1$H-NMR (600 MHz, DMSO-d$_6$) δ ppm 1.72 (br. s, 1H), 2.19 (s, 3H), 2.74-3.09 (m, 2H), 2.85-3.07 (m, 1H), 3.15-3.31 (m, 2H), 3.64 (s, 3H), 4.15 (br. s, 1H), 4.90 (m, 3H), 6.72-6.86 (m, 5H), 7.35 (d, J=8.59 Hz, 2H), 7.85 (d, J=8.42 Hz, 2H), 7.19-8.03 (m, 1H), 8.78 (br. s, 1H), 10.05-10.20 (m, 1H).

Stage 72.2 (R)-2-(3-Hydroxypyrrolidin-1-yl)-N3-(prop-2-yn-1-yl)-N5-(4-(trifluoromethoxy)phenyl)pyridine-3,5-dicarboxamide

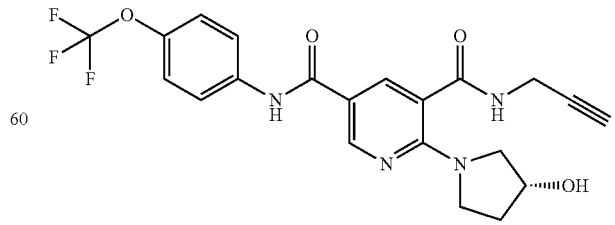

A mixture of (R)-2-(3-hydroxypyrrolidin-1-yl)-5-((4-(trifluoromethoxy)phenyl)carbamoyl)nicotinic acid (Stage 72.3, 1.50 g, 3.65 mmol), O-(7-azabenzotriazol-1-yl)-N,N,N',N'-tetramethyluronium hexafluorophosphate (HATU, 1.66 g, 4.38 mmol) and DIPEA (0.566 g, 4.38 mmol) in DMF (40 mL) was stirred at RT for 15 min and then propargylamine (0.35 mL, 5.47 mmol) was added. The mixture was stirred for 3 h and then treated with EtOAc, washed with sat. aq. solution of NaHCO₃ and brine. The organic phase was dried over Na₂SO₄ and the solvent was evaporated off under reduced pressure and the residue was crystallized from TBME/EtOAc to afford the product as a colorless crystalline solid. m.p. 246-248° C., HPLC (Condition 4) $t_R$=4.79 min, UPLC-MS (Condition 8) $t_R$=0.89 min, m/z=449.1 [M+H]⁺; ¹H-NMR (400 MHz, DMSO-d₆) δ ppm 1.78-2.01 (m, 2H), 3.15 (t, J=2.54 Hz, 1H), 3.24 (d, J=12.12 Hz, 1H), 3.43-3.69 (m, 3H), 4.03 (d, J=4.30 Hz, 2H), 4.33 (br. s, 1H), 4.96 (d, J=3.13 Hz, 1H), 7.34 (d, J=8.99 Hz, 2H), 7.79-7.90 (m, 2H), 8.04 (d, J=2.35 Hz, 1H), 8.75 (d, J=2.35 Hz, 1H), 8.96 (t, J=5.67 Hz, 1H), 10.20 (s, 1H).

Stage 72.3 (R)-2-(3-Hydroxypyrrolidin-1-yl)-5-((4-(trifluoromethoxy)phenyl)carbamoyl)nicotinic acid

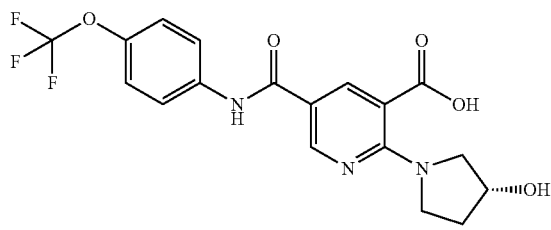 [SMILES: O=C(Nc1ccc(OC(F)(F)F)cc1)c1cnc(N2CC[C@@H](O)C2)c(C(=O)O)c1]

A mixture of (R)-2-(3-hydroxypyrrolidin-1-yl)-5-((4-(trifluoromethoxy)phenyl)carbamoyl)nicotinic acid ethyl ester (Stage 72.4, 3.20 g, 7.28 mmol) and LiOH in EtOH (18 mL)/water (6 mL) was stirred at 50° C. for 8 h. The solution was cooled to RT, acidified with citric acid monohydrate and resulting crystalline title compound was filtered and dried. m.p. 242-245° C., HPLC (Condition 4) $t_R$=4.45 min, UPLC-MS (Condition 8) $t_R$=0.80 min, m/z=412 [M+H]⁺; ¹H-NMR (400 MHz, DMSO-d₆) δ ppm 1.92 (br. s, 2H), 3.10 (d, J=12.12 Hz, 1H), 3.39 (br. s, 1H), 3.50-3.75 (m, 2H), 4.31 (br. s, 1H), 4.80-5.01 (m, 1H), 7.30 (d, J=8.60 Hz, 2H), 7.74-7.88 (m, 2H), 8.39 (d, J=2.35 Hz, 1H), 8.76 (d, J=2.35 Hz, 1H), 10.23 (s, 1H).

Stage 72.4 (R)-2-(3-Hydroxypyrrolidin-1-yl)-5-((4-(trifluoromethoxy)phenyl)carbamoyl)nicotinic acid ethyl ester

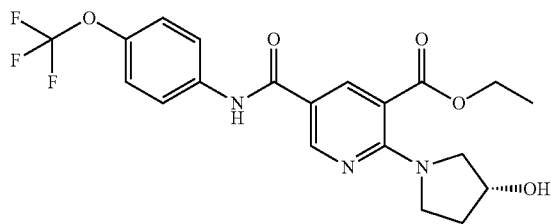 [SMILES: CCOC(=O)c1cc(C(=O)Nc2ccc(OC(F)(F)F)cc2)cnc1N1CC[C@@H](O)C1]

A mixture of 2-chloro-5-((4-(trifluoromethoxy)phenyl)carbamoyl)nicotinic acid ethyl ester (Stage 72.5, 3.00 g, 7.7 mmol), (R)-3-pyrrolidinol (0.807 g, 9.26 mmol) and DIPEA (2.19 g, 17.0 mmol) in iPrOH (50 mL) was stirred at 22° C. for 60 min. The solvent was evaporated off under reduced pressure and the residue was dissolved in EtOAc, washed with sat. aq. NaHCO₃ and brine, dried over anhydrous Na₂SO₄ and the solvent was evaporated off under reduced pressure to give the title compound as a foam. HPLC (Condition 4) $t_R$=5.63 min, UPLC-MS (Condition 8) $t_R$=1.06 min, m/z=440.1 [M+H]⁺; ¹H-NMR (400 MHz, DMSO-d₆) δ ppm 1.32 (t, J=7.04 Hz, 3H), 1.79-2.01 (m, 2H), 3.09 (d, J=11.73 Hz, 1H), 3.41 (d, J=8.21 Hz, 1H), 3.54 (dd, J=11.73, 4.30 Hz, 1H), 3.65 (dd, J=10.17, 3.52 Hz, 1H), 4.25-4.39 (m, 3H), 4.96 (d, J=3.13 Hz, 1H), 7.34 (d, J=8.21 Hz, 2H), 7.78-7.90 (m, 2H), 8.36 (d, J=2.35 Hz, 1H), 8.81 (d, J=2.35 Hz, 1H), 10.28 (s, 1H).

Stage 72.5 2-Chloro-5-((4-(trifluoromethoxy)phenyl)carbamoyl)nicotinic acid ethyl ester

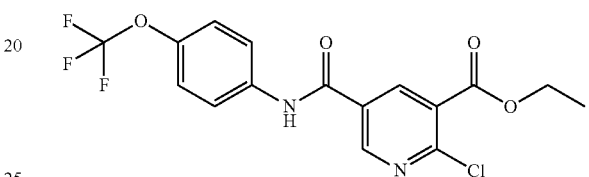

4-Trifluoromethoxyaniline (1.79 mL, 13.3 mmol) was added to a stirred solution of 2-chloropyridine-3,5-dicarboxylic acid ethyl ester (Stage 72.6, 3.20 g, 14 mmol), 1-hydroxybenzotriazole (3.20 g, 20.9 mmol) and 1-ethyl-3-(3-dimethylaminopropyl)-carbodiimide (2.94 g, 15.3 mmol) in DMF (50 mL). The mixture was stirred for 2 h and then treated with EtOAc, washed with a sat. aq. solution of NaHCO₃ and brine, dried over Na₂SO₄ and the solvent was evaporated off under reduced pressure and the crude product was purified by flash chromatography (RediSep® Silica gel column, n-heptane/EtOAc, from 0 to 50% EtOAc) and recrystallized from n-hexane/EtOAc to afford the title compound as a colorless crystalline solid. m.p. 135-137° C., HPLC (Condition 4) $t_R$=6.59 min, UPLC-MS (Condition 8) $t_R$=1.24 min, m/z=389.0 [M+H]⁺; ¹H-NMR (400 MHz, DMSO-d₆) δ ppm 1.35 (t, J=7.23 Hz, 3H), 4.39 (q, J=7.04 Hz, 2H), 7.39 (d, J=8.60 Hz, 2H), 7.76-7.92 (m, 2H), 8.69 (d, J=2.35 Hz, 1H), 9.08 (d, J=2.35 Hz, 1H), 10.76 (s, 1H).

Stage 72.6 2-Chloropyridine-3,5-dicarboxylic acid, ethyl ester

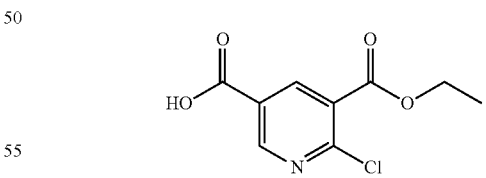

Sodium chlorite (6.48 g, 71.6 mmol) was added to a stirred solution of 2-chloro-5-formyl-3-pyridinecarboxylic acid ethyl ester (4.50 g, 21.1 mmol), NaH₂PO₄, dihydrate (2.91 g, 21.1 mmol) and 2-methyl-2-butene (6.50 g, 93 mmol) in tBuOH (200 mL) and water (60 mL) at 10-20° C. and the mixture was stirred at RT for 60 min. DCM (600 mL) was then added and the mixture was washed with brine, dried over Na₂SO₄ and the solvent was evaporated off under reduced pressure to afford the title compound as a colorless crystalline solid. m.p. 147-149° C., HPLC (Condition 4) $t_R$=4.19 min, UPLC-MS (Condition 8) $t_R$=0.70 min, m/z=230/227.1 [M+H]$^+$; $^1$H-NMR (400 MHz, DMSO-d$_6$) δ ppm 1.31 (t, J=7.04 Hz, 3H), 4.34 (q, J=7.04 Hz, 2H), 8.57 (d, J=2.35 Hz, 1H), 8.97 (d, J=2.35 Hz, 1H).

Example 73

(R)—N-(4-(Chlorodifluoromethoxy)phenyl)-5-(5-(dimethylcarbamoyl)-1H-pyrrol-2-yl)-6-(3-hydroxy-pyrrolidin-1-yl)nicotinamide

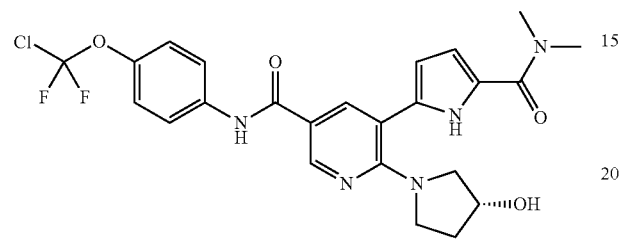

A mixture of 6-chloro-N-(4-(chlorodifluoromethoxy)phenyl)-5-(5-(dimethylcarbamoyl)-1H-pyrrol-2-yl)nicotinamide (Stage 73.1, 60 mg, 0.102 mmol), (R)-pyrrolidin-3-ol (17.82 mg, 0.205 mmol), DIPEA (71.5 μL, 0.409 mmol) and iPrOH (205 μL) in a sealed vial was subjected to MW irradiation at 140° C. for 1 h. The RM was purified by preparative SFC (Column NH$_2$, isocratic 24% in 6 min.) to yield the title compound as a white solid. UPLC-MS (Condition 3) $t_R$=1.03 min, m/z=520.1 [M+H]$^+$, m/z=564.2 [M+FA–H]$^-$; 1H NMR (400 MHz, DMSO-d$_6$) δ ppm 1.69-1.78 (m, 1H) 1.78-1.89 (m, 1H) 2.96 (d, J=11.74 Hz, 1H) 3.13 (br. s, 6H) 3.25-3.31 (m, 2H) 3.38-3.51 (m, 1H) 4.20 (br. s, 1H) 4.86 (d, J=2.57 Hz, 1H) 6.11-6.21 (m, 1H) 6.57-6.66 (m, 1H) 7.33 (d, J=9.17 Hz, 2H) 7.82-7.92 (m, 2H) 8.04 (d, J=2.45 Hz, 1H) 8.71 (d, J=2.45 Hz, 1H) 10.15 (s, 1H) 11.66 (br. s, 1H).

Stage 73.1 6-Chloro-N-(4-(chlorodifluoromethoxy)phenyl)-5-(5-(dimethylcarbamoyl)-1H-pyrrol-2-yl)nicotinamide

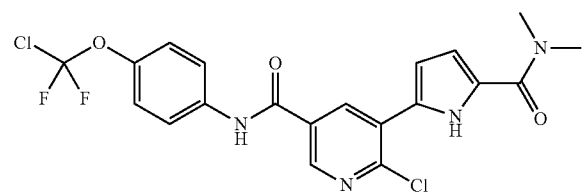 [SMILES: CN(C)C(=O)c1ccc(-c2cc(C(=O)Nc3ccc(OC(F)(F)Cl)cc3)cnc2Cl)[nH]1]

6-Chloro-N-(4-(chlorodifluoromethoxy)phenyl)-5-iodonicotinamide (Stage 48.3, 257 mg, 0.560 mmol), (1-(tert-butoxycarbonyl)-5-(dimethylcarbamoyl)-1H-pyrrol-2-yl)boronic acid (Stage 73.2, 200 mg, 0.709 mmol), Pd(Ph$_3$P)$_4$ (64.7 mg, 0.056 mmol), Na$_2$CO$_3$ (237 mg, 2.240 mmol), water (560 μL) and DME (2.240 mL) were added to a MW vial, which was sealed, evacuated/purged with argon and stirred at 80° C. for 16 h. The RM was diluted with MeOH (1 mL)/DCM (2 mL), treated with Si-Thiol (194 mg, 0.280 mmol), filtered and the filtrate was evaporated off under reduced pressure to give a residue which was purified by flash chromatography (RediSep® Silica gel column, 12 g, cyclohexane-DCM (4:1)/EtOAc, from 5% to 50% EtOAc) to yield the title product as a white solid. UPLC-MS (Condition 3) $t_R$=1.16 min, m/z=469.1 [M+H]$^+$, m/z=513.0 [M+FA+H]$^-$; 1H NMR (400 MHz, DMSO-d$_6$) δ ppm 2.98-3.28 (m, 6H) 6.69-6.75 (m, 1H) 6.76-6.81 (m, 1H) 7.40 (d, J=9.17 Hz, 2H) 7.85-7.93 (m, 2H) 8.62 (d, J=2.32 Hz, 1H) 8.81 (d, J=2.32 Hz, 1H) 10.65 (s, 1H) 11.89 (br. s, 1H).

Stage 73.2 (1-(tert-Butoxycarbonyl)-5-(dimethylcarbamoyl)-1H-pyrrol-2-yl)boronic acid

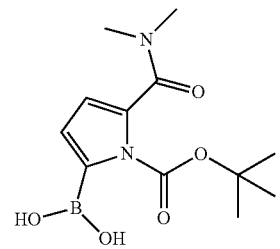 [SMILES: CN(C)C(=O)c1ccc(B(O)O)n1C(=O)OC(C)(C)C]

Oxalyl chloride (2.60 mL, 29.7 mmol) followed by a few drops of DMF were added to a suspension of 1H-pyrrole-2-carboxylic acid (3 g, 27.0 mmol) in DCE (25 mL) and the RM was stirred at RT for 2 h. The solvent was evaporated off under reduced pressure and the residue was dissolved in DCE (25 mL), cooled to 0° C., treated with a solution of dimethylamine 40% in water (25 mL, 197 mmol) and allowed to warm to RT. Water (25 mL) was added and the mixture was extracted with DCM. The combined extracts were washed with 0.5 M HCl (25 mL) and brine, dried over Na$_2$SO$_4$ and the solvent was evaporated off under reduced pressure to give a residue was suspended in cyclohexane, filtered and washed with cyclohexane to give an off-white solid. This solid (2 g, 14.48 mmol) and 4-dimethylaminopyridine (0.177 g, 1.448 mmol) in MeCN (19.30 mL) was added a solution of di-tert-butyl dicarbonate (4.08 g, 18.69 mmol) in MeCN (9.65 mL) and the RM was stirred at RT for 16 h. Trifluoroethanol (1.055 mL, 14.48 mmol) was added to the RM and stirring was continued for 1 h. the solvent was evaporated off under reduced pressure and the residue was treated with DCM (100 mL), washed twice with 0.1 M HCl and brine, dried over Na$_2$SO$_4$ and the solvent was evaporated off under reduced pressure to give an oil. A solution of n-BuLi in 1.6 M n-hexane (2.250 mL, 3.60 mmol) was added to a solution of 2,2,6,6-tetramethylpiperidine (0.532 mL, 3.15 mmol) in THF (10 mL) at −78° C., under an argon atmosphere stirred for 15 min and then allowed to warm to RT. The mixture was cooled to −78° C. and then treated with a solution of the above mentioned oil (715 mg, 3 mmol) in THF (2 mL) and stirred for 30 min. Trimethyl borate (1.672 mL, 15 mmol) was then added and the RM was allowed to warm to RT overnight. Sat. aq. NH$_4$Cl solution was added and the mixture was extracted with Et$_2$O. The combined extracts were washed with 1 M HCl (10 mL) and brine (10 mL), dried over Na$_2$SO$_4$ and the solvent was evaporated off under reduced pressure to give a residue which was suspended in a mixture of Et$_2$O/cyclohexane, filtered, washed with cyclohexane and dried to afford the title compound as an off-white solid. UPLC-MS (Condition 3) $t_R$=0.60 min, m/z=283.0 [M+H]$^+$, m/z=281.0 [M–H]$^-$; 1H NMR (400 MHz, DMSO-d$_6$) δ ppm 1.42-1.58 (m, 10H) 2.88 (s, 3H) 2.93 (s, 3H) 6.25 (d, J=3.18 Hz, 1H) 6.30 (d, J=3.30 Hz, 1H) 8.05-8.09 (m, 2H).

Example 74

6-(trans-3-Fluoro-4-hydroxypyrrolidin-1-yl)-5-(1H-pyrazol-5-yl)-N-(4-(trifluoromethoxy)phenyl)nicotinamide

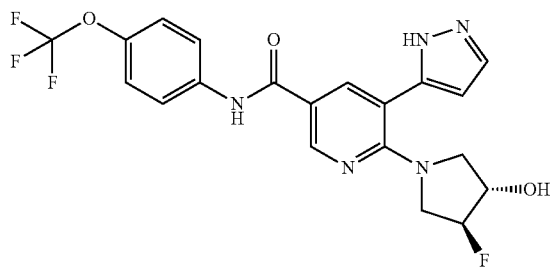 [SMILES: O=C(Nc1ccc(OC(F)(F)F)cc1)c1cnc(N2C[C@H](O)[C@@H](F)C2)c(-c2ccn[nH]2)c1]

The title compound was prepared in an analogous fashion to that described in Example 38 using 6-chloro-5-(1H-pyrazol-5-yl)-N-(4-(trifluoromethoxy)phenyl)nicotinamide (Stage 38.1) and trans-4-fluoropyrrolidin-3-ol (Stage 74.1). The product was purified by chromatography on Silica gel, preparative TLC (eluent EtOAc), followed by preparative SFC (Column 2-EP, from 17-22% in 6 min) to afford the title product as a white solid. UPLC-MS (Condition 8) $t_R$=0.94 min, m/z=452.1 $[M+H]^+$; $^1$H-NMR (600 MHz, DMSO-$d_6$) δ ppm 3.07 (d, J=12.42 Hz, 1H) 3.30-3.51 (m, 2H) 3.56-3.74 (m, 1H) 4.17 (br. s, 1H) 4.86-5.00 (m, 1H) 5.42-5.52 (m, 1H) 6.38-6.46 (m, 1H) 7.35 (d, J=8.66 Hz, 2H) 7.53-7.91 (m, 3H) 8.03-8.13 (m, 1H) 8.71-8.82 (m, 1H) 10.24 (s, 1H).

Stage 74.1 trans-4-Fluoropyrrolidin-3-ol

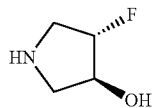

Benzyl trans-3-fluoro-4-hydroxypyrrolidine-1-carboxylate was dissolved in MeOH (20 mL) and hydrogenated (Pd/C 10% 200 mg, 0.1 bar at RT). The mixture was filtered over Celite®, and the solvent was evaporated off under reduced pressure to afford the title product as an oil. HPLC (Condition 4) $t_R$=<1 min, MS: m/z=106.1 $[M+H]^+$.

Example 75

N-(4-(Chlorodifluoromethoxy)phenyl)-6-(trans-3-fluoro-4-hydroxypyrrolidin-1-yl)-5-(1H-pyrazol-5-yl)nicotinamide

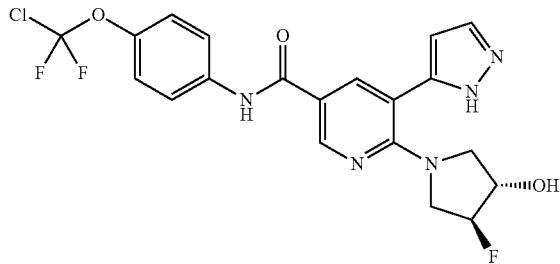 [SMILES: O=C(Nc1ccc(OC(F)(F)Cl)cc1)c1cnc(N2C[C@H](O)[C@@H](F)C2)c(-c2ccn[nH]2)c1]

The title compound was prepared in an analogous fashion to that described in Example 33 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and trans-4-fluoropyrrolidin-3-ol to afford an amorphous white powder. HPLC (Condition 4) $t_R$=5.21 min, UPLC-MS (Condition 3) $t_R$=0.99 min, m/z=468.2 $[M+H]^+$; $^1$H-NMR (400 MHz, DMSO-$d_6$) δ ppm 3.06 (d, J=12.12 Hz, 1H) 3.33-3.49 (m, 2H) 3.53-3.76 (m, 1H) 4.15 (br. s, 1H) 4.77-5.02 (m, 1H) 5.36-5.50 (m, 1H) 6.41 (br. s, 1H) 7.31 (d, J=8.60 Hz, 2H) 7.79-7.91 (m, 3H) 8.06 (d, J=1.96 Hz, 1H) 8.73 (br. s, 1H) 10.21 (s, 1H) 12.90-13.21 (m, 1H).

Example 76

4-((3S,4S)-3-Amino-4-hydroxypyrrolidin-1-yl)-N-(4-(chlorodifluoromethoxy)phenyl)-3-(1H-pyrazol-5-yl)benzamide

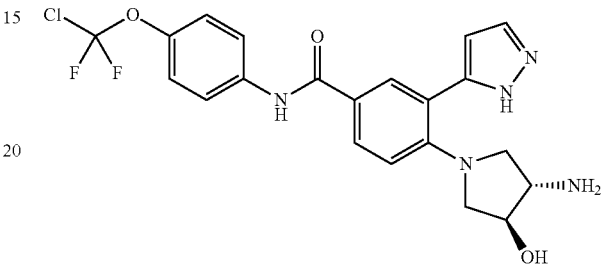

1-(Tetrahydro-2H-pyran-2-yl)-5-(4,4,5,5-tetramethyl-1,3,2-dioxaborolan-2-yl)-1H-pyrazole (82 mg, 0.288 mmol) and PdCl$_2$(dppf)-(CH$_2$Cl$_2$) (10.07 mg, 12 μmol) were added to a mixture of 4-((3S,4S)-3-amino-4-hydroxypyrrolidin-1-yl)-3-bromo-N-(4-(chlorodifluoromethoxy)phenyl)benzamide (Stage 76.1, 100 mg, 0.206 mmol), Na$_2$CO$_3$ (0.308 mL, 0.617 mmol) in DME (2 mL) under argon atmosphere and the RM was heated at 80° C. for 4 h. The RM was filtered through Hyflo® and the solvent was evaporated off under reduced pressure to give a residue which was purified by flash chromatography (Silica gel column, 12 g, DCM/EtOH from 98:2 to 8:2). The resulting intermediate was dissolved in DCM (2 mL), treated with TFA (0.198 mL, 2.57 mmol) and the RM was stirred for RT for 3 h. The solvent was evaporated off under reduced pressure and the residue was treated with sat. aq. Na$_2$CO$_3$, and extracted with EtOAc. The combined extracts were washed with brine (20 mL), dried over Na$_2$SO$_4$ and the solvent was evaporated off under reduced pressure to give the crude product which was purified by flash chromatography (Silica gel column, 12 g, DCM/MeOH from 95:5 to 7:3) and crystallized from n-hexane/DCM to give the title product as a beige solid. HPLC (Condition 7) $t_R$=5.774 min, UPLC-MS (Condition 3) $t_R$=0.77 min, m/z=464.2 $[M+H]^+$; $^1$H-NMR (400 MHz, DMSO-$d_6$) δ ppm 2.73-2.99 (m, 2H) 3.22-3.44 (m, 3H) 3.93-4.04 (m, 1H) 5.33 (br. s, 1H) 6.39 (s, 1H) 6.74-6.94 (m, 1H) 7.31 (d, J=8.60 Hz, 2H) 7.76-8.03 (m, 4H) 10.17 (br. s, 1H).

Stage 76.1 4-((3S,4S)-3-Amino-4-hydroxypyrrolidin-1-yl)-3-bromo-N-(4-(chlorodifluoromethoxy)phenyl)benzamide

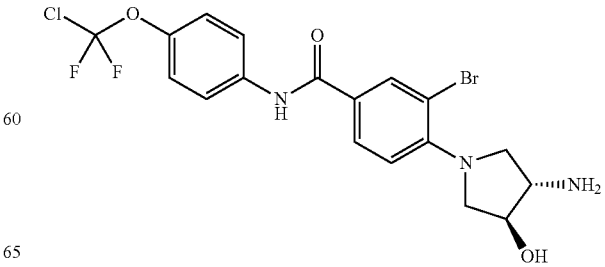

The title compound was prepared in an analogous fashion to that described in Example 1 using 3-bromo-N-(4-(chlorodifluoromethoxy)phenyl)-4-fluorobenzamide (Stage 76.2) and (3S,4S)-4-aminopyrrolidin-3-ol dihydrochloride (Stage 76.3) to give the title product as a beige solid. HPLC (Condition 7) $t_R$=6.08 min, UPLC-MS (Condition 3) $t_R$=0.82 min, m/z=476.1/478.1 [M+H]$^+$.

Stage 76.2 3-Bromo-N-(4-(chlorodifluoromethoxy)phenyl)-4-fluorobenzamide

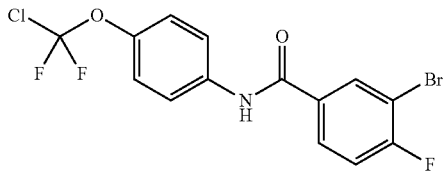 [SMILES: O=C(Nc1ccc(OC(F)(F)Cl)cc1)c1ccc(F)c(Br)c1]

The title compound was prepared in an analogous fashion to that described in Stage 1.2 using 3-bromo-4-fluorobenzoic acid and 4-(chlorodifluoromethoxy)aniline to afford an off-white solid. UPLC-MS (Condition 3) $t_R$=1.25 min, m/z=394.0 [M+H]$^+$, m/z=391.9 [M−H]$^-$; 1H NMR (400 MHz, DMSO-d$_6$) δ ppm 7.37 (d, J=9.17 Hz, 2H) 7.57 (t, J=8.68 Hz, 1H) 7.84-7.91 (m, 2H) 8.03 (ddd, J=8.62, 4.83, 2.32 Hz, 1H) 8.32 (dd, J=6.60, 2.20 Hz, 1H) 10.52 (s, 1H).

Stage 76.3 (3S,4S)-4-Aminopyrrolidin-3-ol dihydrochloride

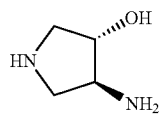

The title compound was prepared in an analogous fashion to that described in Stage 78.1 using (3S,4S)-tert-butyl 3-amino-4-hydroxypyrrolidine-1-carboxylate.

Example 77

N-(4-(Chlorodifluoromethoxy)phenyl)-4-((3S,4S)-3,4-dihydroxypyrrolidin-1-yl)-3-(1H-pyrazol-5-yl)benzamide

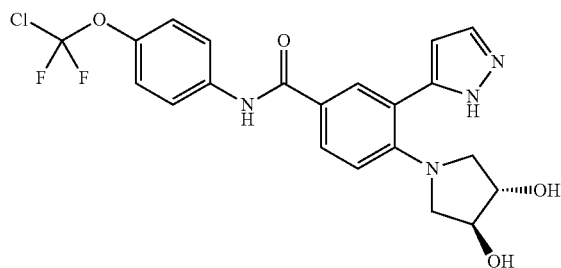 [SMILES: O=C(Nc1ccc(OC(F)(F)Cl)cc1)c1ccc(N2C[C@H](O)[C@@H](O)C2)c(-c2ccn[nH]2)c1]

1-(Tetrahydro-2H-pyran-2-yl)-5-(4,4,5,5-tetramethyl-1,3,2-dioxaborolan-2-yl)-1H-pyrazole (126 mg, 0.451 mmol) and PdCl$_2$(PPh$_3$)$_2$ (15.84 mg, 23 μmol) were added to a mixture of 3-bromo-N-(4-(chlorodifluoromethoxy)phenyl)-4-((3S,4S)-3,4-dihydroxypyrrolidin-1-yl)benzamide (Stage 77.1, 110 mg, 0.226 mmol) and Na$_2$CO$_3$ (0.451 mL, 0.903 mmol) in DME (1.5 mL)/EtOH (0.3 mL) in a vial, which was sealed, purged with argon and the RM was subjected to MW irradiation at 125° C. for 30 min. The RM was filtered through Hyflo® and the solvent was evaporated off under reduced pressure to give a residue which was purified by flash chromatography (Silica gel column, 12 g, n-hexane/EtOAc from 20% to 100% EtOAc). The resulting intermediate was dissolved in DCM (2 mL), treated TFA (0.314 mL, 4.07 mmol) and stirred at RT for 2 h. The solvent was evaporated off under reduced pressure to give a residue which was treated with sat. aq. Na$_2$CO$_3$ and extracted with EtOAc. The combined extracts were washed with brine, dried over Na$_2$SO$_4$ and the solvent was evaporated off under reduced pressure to give the crude product which was purified by preparative HPLC (Condition 10). Fractions containing pure product were combined, treated with sat. aq. Na$_2$CO$_3$ and the MeCN was evaporated off under reduced pressure to give an aq. residue which was extracted with EtOAc. The combined extracts were washed with brine, dried over Na$_2$SO$_4$ and the solvent was evaporated off under reduced pressure to give a residue which was purified by flash chromatography (Silica gel column, 4 g, DCM/EtOH from 98:2 to 92:8) to give the title product as a white solid. HPLC (Condition 7) $t_R$=6.105 min, UPLC-MS (Condition 8) $t_R$=0.91 min, m/z=465.1 [M+H]$^+$; 1H-NMR (400 MHz, DMSO-d$_6$) δ ppm 2.81 (d, J=10.56 Hz, 2H) 3.24-3.38 (m, 2H) 3.81-3.91 (m, 2H) 4.99 (br.s, 1H) 5.04 (br.s, 1H) 6.26-6.36 (m, 1H) 6.72-6.87 (m, 1H) 7.31 (d, J=8.99 Hz, 2H) 7.47-7.94 (m, 5H) 10.10 (s, 1H) 12.75-13.04 (m, 1H).

Stage 77.1 3-Bromo-N-(4-(chlorodifluoromethoxy)phenyl)-4-((3S,4S)-3,4-dihydroxypyrrolidin-1-yl)benzamide

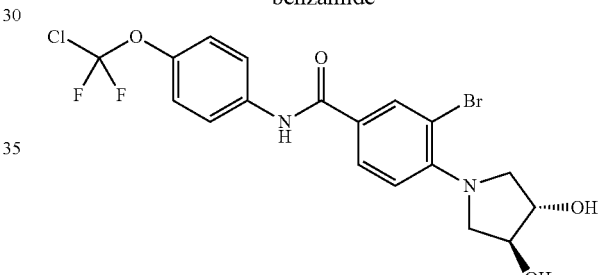

The title compound was prepared in an analogous fashion to that described in Example 1 using 3-bromo-N-(4-(chlorodifluoromethoxy)phenyl)-4-fluorobenzamide (Stage 76.2) and (3S,4S)-pyrrolidine-3,4-diol. The crude product was purified by flash chromatography (Silica gel column, 12 g, n-hexane/EtOAc 10% to 100% EtOAc) to give the title product as a white solid. UPLC-MS (Condition 8) $t_R$=1.02 min, m/z=477.1/478.9 [M+H]$^+$.

Example 78

6-(trans-3-Amino-4-methoxypyrrolidin-1-yl)-5-(1H-pyrazol-5-yl)-N-(4-(trifluoromethoxy)phenyl)nicotinamide

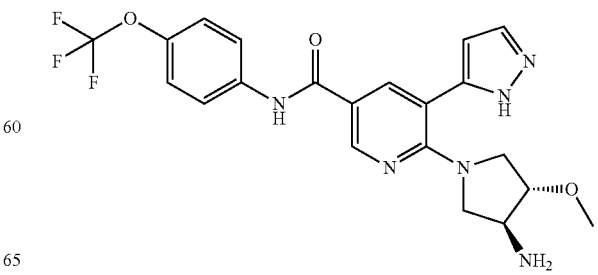

The title compound was prepared in an analogous fashion to that described in Example 38 using 6-chloro-5-(1H-pyrazol-5-yl)-N-(4-(trifluoromethoxy)phenyl)nicotinamide (Stage 38.1) and trans-4-methoxypyrrolidin-3-amine dihydrochloride (Stage 78.1) to afford a white solid. HPLC (Condition 7) $t_R$=5.675 min, UPLC-MS (Condition 3) $t_R$=0.78 min, m/z=463.2 [M+H]$^+$; $^1$H-NMR (400 MHz, DMSO-d$_6$) δ ppm 1.58 (br. s, 2H) 2.83-2.98 (m, 1H) 3.07-3.18 (m, 1H) 3.21 (s, 3H) 3.26-3.43 (m, 2H) 3.45-3.59 (m, 2H) 6.39 (br. s, 1H) 7.33 (d, J=8.99 Hz, 2H) 7.49-7.91 (m, J=8.60 Hz, 3H) 8.03 (br. s, 1H) 8.72 (br. s, 1H) 10.18 (s, 1H) 12.76-13.24 (m, 1H).

Stage 78.1 trans-4-Methoxypyrrolidin-3-amine dihydrochloride

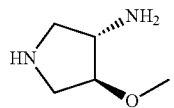

A mixture of (trans)-tert-butyl 3-amino-4-methoxypyrrolidine-1-carboxylate hydrochloride (0.5 g, 1.939 mmol) and HCl in EtOH (15.51 mL, 19.39 mmol) was stirred at RT for 24 h. The solvent was evaporated off under reduced pressure to give the title compound.

Example 79

6-(trans-3-Amino-4-methoxypyrrolidin-1-yl)-N-(4-(chlorodifluoromethoxy)phenyl)-5-(1H-pyrazol-5-yl)nicotinamide

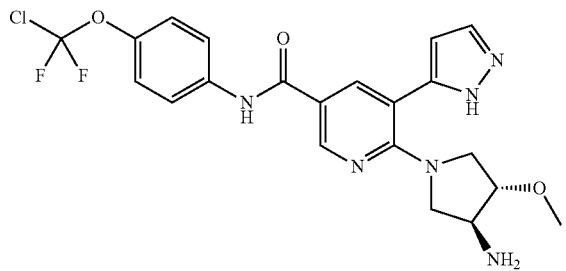 [SMILES: CO[C@H]1CN(c2ncc(C(=O)Nc3ccc(OC(F)(F)Cl)cc3)cc2-c2ccn[nH]2)C[C@@H]1N]

The title compound was prepared in an analogous fashion to that described in Example 48 using 6-chloro-N-(4-(chlorodifluoromethoxy)phenyl)-5-(1H-pyrazol-5-yl)nicotinamide (Stage 48.1) and trans-4-methoxypyrrolidin-3-amine dihydrochloride (Stage 78.1) to afford a beige solid. HPLC (Condition 7) $t_R$=5.797 min, UPLC-MS (Condition 3) $t_R$=0.81 min, m/z=479.1 [M+H]$^+$; $^1$H-NMR (400 MHz, DMSO-d$_6$) δ ppm 2.86-2.98 (m, 1H) 3.06-3.19 (m, 1H) 3.21 (s, 3H) 3.25-3.43 (m, 2H) 3.43-3.59 (m, 2H) 6.32-6.46 (m, 1H) 7.32 (d, J=8.60 Hz, 2H) 7.50-7.92 (m, J=8.99 Hz, 3H) 8.03 (s, 1H) 8.62-8.86 (m, 1H) 10.18 (s, 1H) 12.72-13.25 (m, 1H).

Example 80

6-(cis-3-(Aminomethyl)-4-hydroxypyrrolidin-1-yl)-N-(4-(chlorodifluoromethoxy)phenyl)-5-(1H-pyrazol-5-yl)nicotinamide

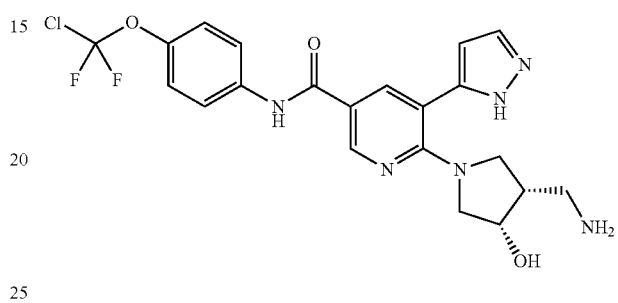

The title compound was prepared in an analogous fashion to that described in Example 48 using 6-chloro-N-(4-(chlorodifluoromethoxy)phenyl)-5-(1H-pyrazol-5-yl)nicotinamide (Stage 48.1) and cis-4-(aminomethyl)pyrrolidin-3-ol dihydrochloride (Stage 80.1). The crude product was purified by preparative HPLC (Condition 10). Fractions containing product were combined, treated with sat. aq. Na$_2$CO$_3$ and the MeCN was evaporated off under reduced pressure to give an aq. residue which was extracted with EtOAc. The combined extracts were washed with brine, dried over Na$_2$SO$_4$ and the solvent was evaporated off under reduced pressure to give a residue was suspended in DCM/n-hexane, filtered and dried to afford the title product as a beige solid. HPLC (Condition 7) $t_R$=5.38 min, UPLC-MS (Condition 3) $t_R$=0.78 min, m/z=479 [M+H]$^+$; $^1$H-NMR (400 MHz, DMSO-d$_6$) δ ppm 1.85-2.05 (m, 1H) 2.38-2.86 (m, 2H) 2.88-3.06 (m, 1H) 3.08-3.23 (m, 1H) 3.24-3.37 (m, 2H) 3.91-4.18 (m, 1H) 6.33-6.42 (m, 1H) 7.32 (d, J=8.60 Hz, 2H) 7.68-7.91 (m, J=9.00 Hz, 3H) 7.97-8.06 (m, 1H) 8.68-8.78 (m, 1H) 10.20 (s, 1H) 12.94 (br. s, 1H).

Stage 80.1 cis-4-(Aminomethyl)pyrrolidin-3-ol dihydrochloride

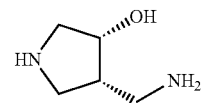

A mixture of 1-N-Boc-cis-(3-(aminomethyl)-4-hydroxy)pyrrolidine (0.3 g, 1.359 mmol) and HCl in EtOH (10.87 mL, 13.59 mmol) were stirred at RT for 24 h. the solvent was evaporated off under reduced pressure and the residue was suspended in n-hexane, filtered, washed with n-hexane and dried to afford the crude title product as a grey solid.

Example 81

(R)—N-(4-(Chlorodifluoromethoxy)phenyl)-6-(3-hydroxy-3-methylpyrrolidin-1-yl)-5-(1H-pyrazol-5-yl)nicotinamide

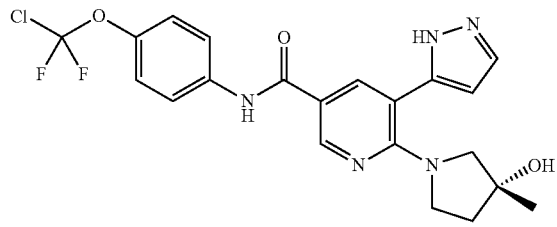 [SMILES: C[C@@]1(O)CCN(c2ncc(C(=O)Nc3ccc(OC(F)(F)Cl)cc3)cc2-c2ccn[nH]2)C1]

A racemic mixture of N-(4-(chlorodifluoromethoxy)phenyl)-6-(3-hydroxy-3-methylpyrrolidin-1-yl)-5-(1H-pyrazol-5-yl)nicotinamide (Example 49, 240 mg, 0.517 mmol) was separated by preparative HPLC (Column Chiralpak AD 20 μm 50×5.0 cm, flow 70 mL/min, mobile phase: EtOH until 25.5 min then MeOH, detection UV 320 nm). The (R)-enantiomer was dissolved in MeOH/DCM and purified by preparative SFC (Column NH$_2$, isocratic 24% in 6 min.) to yield the pure compound as a white solid. UPLC-MS (Condition 3) $t_R$=0.95 min, m/z=464.1 [M+H]$^+$, m/z=462.1 [M−H]$^−$; 1H NMR (400 MHz, DMSO-d$_6$) δ ppm 1.20 (s, 3H) 1.59-1.86 (m, 2H) 2.95-3.12 (m, 2H) 3.24-3.32 (m, 1H) 3.40-3.55 (m, 1H) 4.62-4.73 (m, 1H) 6.33-6.42 (m, 1H) 7.32 (d, J=8.80 Hz, 2H) 7.52-7.84 (m, 1H) 7.87 (d, J=9.05 Hz, 2H) 7.99-8.07 (m, 1H) 8.69-8.80 (m, 1H) 10.18 (s, 1H) 12.82-13.19 (m, 1H).

Example 82

(S)—N-(4-(Chlorodifluoromethoxy)phenyl)-6-(3-hydroxy-3-methylpyrrolidin-1-yl)-5-(1H-pyrazol-5-yl)nicotinamide

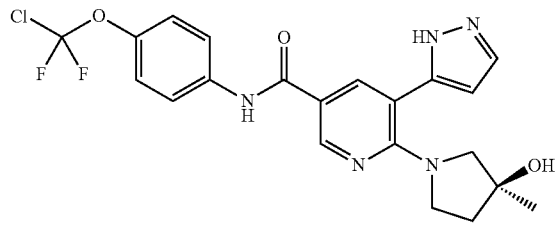 [SMILES: C[C@]1(O)CCN(c2ncc(C(=O)Nc3ccc(OC(F)(F)Cl)cc3)cc2-c2ccn[nH]2)C1]

The title compound was prepared in an analogous fashion to that described in Example 81 using N-(4-(chlorodifluoromethoxy)phenyl)-6-(3-hydroxy-3-methylpyrrolidin-1-yl)-5-(1H-pyrazol-5-yl)nicotinamide (Example 49, 240 mg, 0.517 mmol) to afford a white solid. UPLC-MS (Condition 3) $t_R$=0.95 min, m/z=464.1 [M+H]$^+$, m/z=462.1 [M−H]$^−$; 1H NMR (400 MHz, DMSO-d$_6$) δ ppm 1.20 (s, 3H) 1.57-1.88 (m, 2H) 2.95-3.12 (m, 2H) 3.24-3.31 (m, 1H) 3.41-3.54 (m, 1H) 4.60-4.76 (m, 1H) 6.32-6.43 (m, 1H) 7.32 (d, J=8.80 Hz, 2H) 7.51-7.84 (m, 1H) 7.87 (d, J=9.05 Hz, 2H) 7.99-8.07 (m, 1H) 8.65-8.85 (m, 1H) 10.18 (s, 1H) 12.81-13.16 (m, 1H).

Example 83

6-(3-(Aminomethyl)-3-hydroxypyrrolidin-1-yl)-N-(4-(chlorodifluoromethoxy)phenyl)-5-(1H-pyrazol-5-yl)nicotinamide

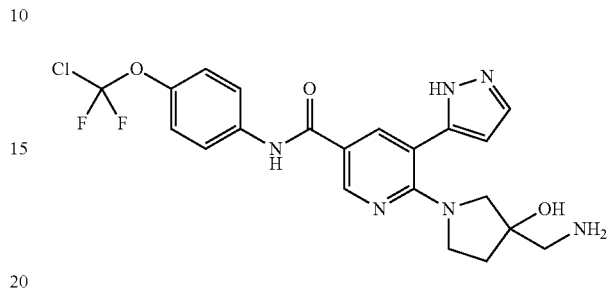

TFA (0.288 mL, 3.74 mmol) was added to a solution of tert-butyl ((1-(5-((4-(chlorodifluoromethoxy)phenyl)carbamoyl)-3-(1-(tetrahydro-2H-pyran-2-yl)-1H-pyrazol-5-yl)pyridin-2-yl)-3-hydroxypyrrolidin-3-yl)methyl)carbamate (Stage 83.1, 74 mg, 0.112 mmol) in DCM (0.6 mL) and the RM was stirred at RT for 4 h. The solvent was evaporated off under reduced pressure and the crude product was purified by preparative HPLC. The fractions containing pure product were combined, the TFA was removed using a PL HCO3-MP cartridge and the solvent was evaporated off under reduced pressure to afford the title compound as a beige solid. UPLC-MS (Condition 8) $t_R$=0.78 min, m/z=479.3 [M+H]$^+$; $^1$H-NMR (400 MHz, DMSO-d$_6$) δ ppm 1.64-1.87 (m, 2H) 2.59 (s, 2H) 3.07 (s, 1H) 3.16-3.48 (m, 3H) 4.74 (br. s, 1H) 6.39 (d, J=1.83 Hz, 1H) 7.34 (d, J=8.93 Hz, 2H) 7.67-7.88 (m, 1H) 7.90 (s, 2H) 8.04 (d, J=2.32 Hz, 1H) 8.74 (s, 1H) 10.20 (s, 1H) 12.93 (br. s, 1H).

Stage 83.1 tert-Butyl ((1-(5-((4-(chlorodifluoromethoxy)phenyl)carbamoyl)-3-(1-(tetrahydro-2H-pyran-2-yl)-1H-pyrazol-5-yl)pyridin-2-yl)-3-hydroxypyrrolidin-3-yl)methyl)carbamate

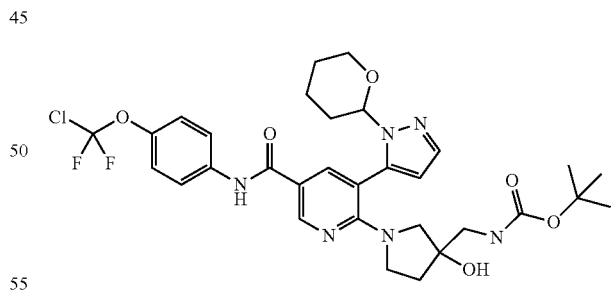

6-Chloro-N-(4-(chlorodifluoromethoxy)phenyl)-5-(1-(tetrahydro-2H-pyran-2-yl)-1H-pyrazol-5-yl)nicotinamide (Stage 48.2, 100 mg, 0.207 mmol), 3-(Boc-aminomethyl)-3-hydroxypyrrolidine (53.7 mg, 0.248 mmol), DIPEA (0.217 mL, 1.241 mmol) and iPrOH (2 mL) were added to a vial, which was sealed, flushed with argon, and stirred at 130° C. for 4 h. More 3-(Boc-aminomethyl)-3-hydroxypyrrolidine (20 mg, 0.092 mmol) and DIPEA (0.08 ml, 0.458 mmol) were added and the RM was stirred for a further 2 h at 130° C. Saturated aq. NH$_4$Cl solution was added and the mixture was extracted with EtOAc. The combined extracts were washed with 1M NaOH and brine, dried over Na$_2$SO$_4$ and the solvent was evaporated off under reduced pressure to give the crude product which was purified by preparative SFC to give the title compound as a white solid. UPLC-MS (Condition 8) t$_R$=1.22 min, m/z=663.5 [M+H]$^+$; $^1$H-NMR (400 MHz, DMSO-d$_6$) δ ppm 1.38 (d, J=3.55 Hz, 9H) 1.42-1.50 (m, 2H) 1.52-1.67 (m, 2H) 1.68-1.83 (m, 1H) 1.84-2.00 (m, 2H) 2.24-2.39 (m, 1H) 2.95-3.14 (m, 4H) 3.15-3.29 (m, 2H) 3.30-3.39 (m, 1H) 3.74-3.93 (m, 1H) 4.75-4.91 (m, 1H) 4.97-5.17 (m, 1H) 6.27-6.50 (m, 0H) 6.71-6.92 (m, 1H) 7.34 (d, J=8.80 Hz, 2H) 7.55-7.65 (m, 1H) 7.87 (d, J=9.05 Hz, 2H) 7.95-8.12 (m, 1H) 8.75-8.88 (m, 1H) 10.21 (br. s, 1H).

Example 84

4-((3S,4S)-3-Amino-4-hydroxypyrrolidin-1-yl)-N-(4-(chlorodifluoromethoxy)phenyl)-3-(3-methyl-1H-pyrazol-5-yl)benzamide

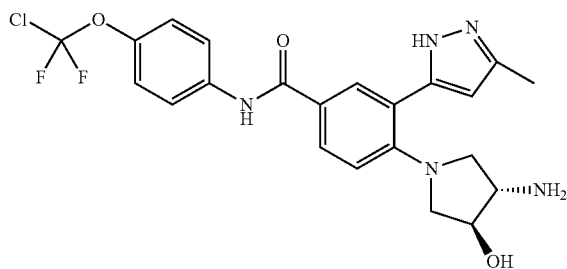 [SMILES: Cc1cc(-c2cc(C(=O)Nc3ccc(OC(F)(F)Cl)cc3)ccc2N2C[C@H](N)[C@@H](O)C2)[nH]n1]

The title compound was prepared in an analogous fashion to that described in Example 76 using 4-((3S,4S)-3-amino-4-hydroxypyrrolidin-1-yl)-3-bromo-N-(4-(chlorodifluoromethoxy)phenyl)benzamide (Stage 76.1) and 3-methyl-1-(tetrahydro-2H-pyran-2-yl)-5-(4,4,5,5-tetramethyl-1,3,2-dioxaborolan-2-yl)-1H-pyrazole to afford the title compound as white solid. HPLC (Condition 7) t$_R$=5.763 min, UPLC-MS (Condition 8) t$_R$=0.82 min, m/z=478.2 [M+H]$^+$; $^1$H-NMR (400 MHz, DMSO-d$_6$) δ ppm 1.52 (br. s, 2H) 2.26 (br. s, 3H) 2.71-2.86 (m, 2H) 3.10 (br. s, 1H) 3.23-3.38 (m, 2H) 3.67-3.79 (m, 1H) 4.95 (br. s, 1H) 6.09 (s, 1H) 6.77 (d, J=8.21 Hz, 1H) 7.31 (d, J=8.99 Hz, 2H) 7.77-7.94 (m, 4H) 10.08 (s, 1H) 12.45 (br. s, 1H).

Example 85

N-(4-(Chlorodifluoromethoxy)phenyl)-6-(4-hydroxypiperidin-1-yl)-5-(1H-pyrazol-5-yl)nicotinamide

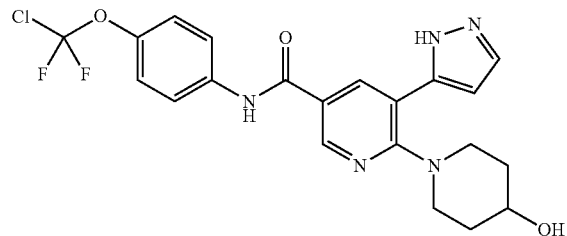 [SMILES: O=C(Nc1ccc(OC(F)(F)Cl)cc1)c1cnc(N2CCC(O)CC2)c(-c2ccn[nH]2)c1]

A mixture of 6-chloro-N-(4-(chlorodifluoromethoxy)phenyl)-5-(1-(tetrahydro-2H-pyran-2-yl)-1H-pyrazol-5-yl)nicotinamide (Stage 48.2, 80 mg, 0.166 mmol), piperidin-4-ol (33.5 mg, 0.331 mmol), DIPEA (0.116 mL, 0.662 mmol) and iPrOH (0.331 mL) was added to a vial, which was sealed and subjected to MW irradiation at 140° C. for 1 h. Aq. 37% HCl (202 μL, 2.46 mmol) and MeOH (1 mL) was added and the mixture was stirred at RT. The RM was treated with sat. aq. NaHCO$_3$ and extracted with EtOAc. The combined extracts were washed with brine, dried over Na$_2$SO$_4$ and the solvent was evaporated off under reduced pressure to give the crude product which was purified by preparative SFC (Column DEAP, from 21% to 26% in 10 min.) to afford the title product as a white solid. UPLC-MS (Condition 3) t$_R$=0.95 min, m/z=464.1 [M+H]$^+$, m/z=508.0 [M+formic acid-H]$^-$; 1H NMR (400 MHz, DMSO-d$_6$) δ ppm 1.33-1.49 (m, 2H) 1.73 (d, J=10.27 Hz, 2H) 2.87 (t, J=10.51 Hz, 2H) 3.50 (d, J=13.08 Hz, 2H) 3.62 (dd, J=8.19, 4.16 Hz, 1H) 4.67 (d, J=4.03 Hz, 1H) 6.54-6.70 (m, 1H) 7.34 (d, J=8.80 Hz, 2H) 7.77 (m, J=1.22 Hz, 2H) 7.88 (d, J=9.05 Hz, 2H) 8.27 (m, J=2.08 Hz, 1H) 8.69-8.78 (m, 1H) 10.31-10.44 (m, 1H) 12.96-13.21 (m, 1H).

Example 86

(S)—N-(4-(Chlorodifluoromethoxy)phenyl)-6-(3-hydroxypiperidin-1-yl)-5-(1H-pyrazol-5-yl)nicotinamide

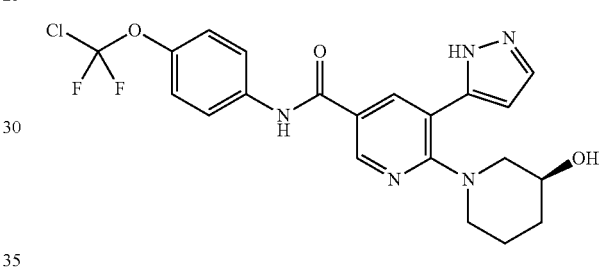

The title compound was prepared in an analogous fashion to that described in Example 85 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and (S)-piperidin-3-ol hydrochloride to afford a white solid. UPLC-MS (Condition 3) t$_R$=0.99 min, m/z=464.1 [M+H]$^+$, m/z=508.1 [M+formic acid-H]$^-$; 1H NMR (400 MHz, DMSO-d$_6$) δ ppm 1.19-1.35 (m, 1H) 1.37-1.52 (m, 1H) 1.56-1.70 (m, 1H) 1.78-1.93 (m, 1H) 2.53-2.64 (m, 1H) 2.65-2.81 (m, 1H) 3.43 (d, J=12.72 Hz, 1H) 3.51-3.61 (m, 1H) 3.65 (d, J=12.23 Hz, 1H) 4.72-4.83 (m, 1H) 6.54-6.69 (m, 1H) 7.34 (d, J=8.93 Hz, 2H) 7.54-7.86 (m, 1H) 7.88 (d, J=9.05 Hz, 2H) 8.15-8.37 (m, 1H) 8.68-8.78 (m, 1H) 10.31-10.46 (m, 1H) 12.96-13.18 (m, 1H).

Example 87

(R)—N-(4-(Chlorodifluoromethoxy)phenyl)-6-(3-hydroxypiperidin-1-yl)-5-(1H-pyrazol-5-yl)nicotinamide

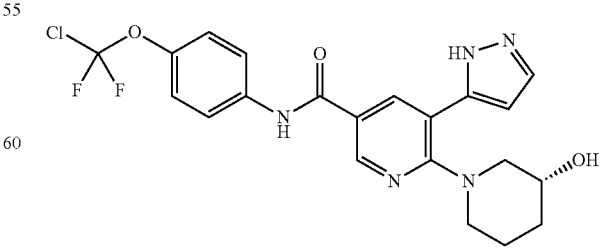

The title compound was prepared in an analogous fashion to that described in Example 85 using 6-chloro-N-(4-(chlorodifluoromethoxy)phenyl)-5-(1-(tetrahydro-2H-pyran-2-yl)-1H-pyrazol-5-yl)nicotinamide (Stage 48.2) and (R)-piperidin-3-ol hydrochloride and was obtained as a white solid. UPLC-MS (Condition 3) $t_R$=0.99 min, m/z=464.1[M+H]$^+$, m/z=508.1[M+formic acid-H]$^-$; 1H NMR (400 MHz, DMSO-d$_6$) δ ppm 1.19-1.35 (m, 1H) 1.37-1.52 (m, 1H) 1.56-1.69 (m, 1H) 1.79-1.93 (m, 1H) 2.52-2.62 (m, 1H) 2.65-2.79 (m, 1H) 3.43 (d, J=12.72 Hz, 1H) 3.50-3.61 (m, 1H) 3.65 (d, J=12.23 Hz, 1H) 4.76 (d, J=4.52 Hz, 1H) 6.55-6.67 (m, 1H) 7.34 (d, J=8.93 Hz, 2H) 7.52-7.86 (m, 1H) 7.88 (d, J=9.17 Hz, 2H) 8.14-8.36 (m, 1H) 8.72 (d, J=2.32 Hz, 1H) 10.32-10.44 (m, 1H) 12.96-13.18 (m, 1H).

Example 88

N-(4-(Chlorodifluoromethoxy)phenyl)-5-(4-fluoro-1H-pyrazol-5-yl)-6-(3-hydroxyazetidin-1-yl)nicotinamide

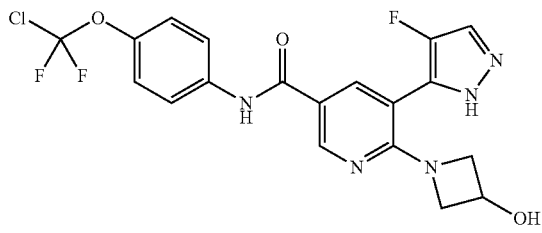 [SMILES: O=C(Nc1ccc(OC(F)(F)Cl)cc1)c1cnc(N2CC(O)C2)c(-c2[nH]ncc2F)c1]

The title compound was prepared in an analogous fashion to that described in Example 92 using N-(4-(chlorodifluoromethoxy)phenyl)-6-(3-hydroxyazetidin-1-yl)-5-iodonicotinamide (Stage 88.1) and 4-fluoro-5-(tributylstannyl)-1H-pyrazole. After purification by flash chromatography on silica gel, the residue was dissolved in MeCN (2 mL), sonicated and then stirred at RT for 90 min. The resulting suspension was filtered, washed with MeCN (3 mL) and dried to afford the title product as a white solid. HPLC (Condition 7) $t_R$=5.72 min, UPLC-MS (Condition 8) $t_R$=0.93 min, m/z=454.1 [M+H]$^+$; $^1$H-NMR (400 MHz, DMSO-d$_6$) δ ppm 3.53-3.61 (m, 2H) 3.91-4.01 (m, 2H) 4.37-4.47 (m, 1H) 5.57 (br. s, 1H) 7.33 (d, J=8.99 Hz, 2H) 7.83-7.97 (m, 3H) 8.04 (d, J=1.96 Hz, 1H) 8.78 (d, J=1.96 Hz, 1H) 10.23 (br. s, 1H) 13.03 (br. s, 1H).

Stage 88.1 N-(4-(Chlorodifluoromethoxy)phenyl)-6-(3-hydroxyazetidin-1-yl)-5-iodonicotinamide

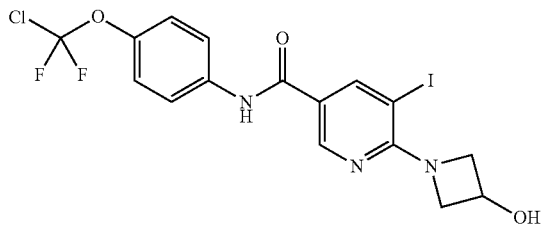 [SMILES: O=C(Nc1ccc(OC(F)(F)Cl)cc1)c1cnc(N2CC(O)C2)c(I)c1]

3-Hydroxyazetidine (164 mg, 2.18 mmol) and DIPEA (0.419 mL, 2.396 mmol) were added to a suspension of 6-chloro-N-(4-(chlorodifluoromethoxy)phenyl)-5-iodonicotinamide (Stage 48.3, 500 mg, 1.089 mmol) in iPrOH (2 mL). and stirred at 140° C. for 16 h. EtOAc (80 mL) was added and the solution was washed with 1 M HCl (30 mL), aq. sat. NaHCO$_3$ solution (30 mL) and water (30 mL), dried over Na$_2$SO$_4$ and the solvent was evaporated off under reduced pressure to give the title product as yellow foam. HPLC (Condition 7) $t_R$=6.64 min, UPLC-MS (Condition 3) $t_R$=1.08 min, m/z=496.0/498.0 [M+H]$^+$.

Example 89

N-(4-(Chlorodifluoromethoxy)phenyl)-6-(3-hydroxyazetidin-1-yl)-5-(3-methyl-1H-pyrazol-5-yl)nicotinamide

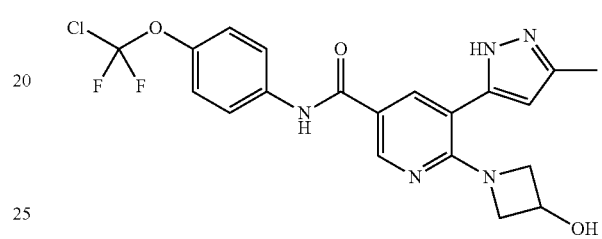

3-Methyl-1-(tetrahydro-2H-pyran-2-yl)-5-(4,4,5,5-tetramethyl-1,3,2-dioxaborolan-2-yl)-1H-pyrazole (252 mg, 0.646 mmol), K$_3$PO$_4$ (206 mg, 0.968 mmol) and Pd(PPh$_3$)$_4$ (18.65 mg, 0.016 mmol) were added to N-(4-(chlorodifluoromethoxy)phenyl)-6-(3-hydroxyazetidin-1-yl)-5-iodonicotinamide (Stage 88.1, 160 mg, 0.323 mmol) was suspended in toluene (2 mL) in a. vial, which was sealed, purged with argon and stirred at 80° C. for 19 h. The RM was treated with EtOAc (60 mL), washed with an aq. sat. NaHCO$_3$ solution (20 mL) and brine (2×20 mL), dried over Na$_2$SO$_4$, and the solvent was evaporated off under reduced pressure. The residue was dissolved in MeOH (3 mL) and filtered through a SPE PL-Thiol cartridge (StratoSphere™, 500 mg, 1.5 mmol), filtered and the filtrate was evaporated off under reduced pressure to give a residue which was purified by flash chromatography (RediSep®Silica gel column, 40 g, DCM/MeOH 95:5), dissolved in DCM (2 mL), treated with TFA (0.554 mL, 7.19 mmol) and stirred at RT for 2 h. The dark yellow RM was treated with EtOAc, washed with aq. sat. NaHCO$_3$ solution and brine, dried over Na$_2$SO$_4$ and the solvent was evaporated off under reduced pressure to give the crude product which was purified by flash chromatography (RediSep® Silica gel column, 24 g, DCM/MeOH 9:1). The fractions containing pure product were combined and the solvent was evaporated off under reduced pressure to give a residue which was dissolved in MeCN (2 mL), sonicated and then stirred at RT for 1 h. The resulting suspension was filtered, washed with MeCN (3 mL) and dried to afford the title product as a white solid. HPLC (Condition 7) $t_R$=5.648 min, UPLC-MS (Condition 8) $t_R$=0.93 min, m/z=450.1 [M+H]$^+$; $^1$H-NMR (400 MHz, DMSO-d$_6$) δ ppm 2.28 (s, 3H) 3.52-3.60 (m, 2H) 3.92-4.01 (m, 2H) 4.34-4.44 (m, 1H) 5.51 (br. s, 1H) 6.16 (s, 1H) 7.33 (d, J=8.60 Hz, 2H) 7.84-7.90 (m, 2H) 8.04 (d, J=2.35 Hz, 1H) 8.71 (d, J=1.96 Hz, 1H) 10.21 (s, 1H) 12.65 (br. s, 1H).

Example 90

N-(4-(Chlorodifluoromethoxy)phenyl)-5-(4-fluoro-1H-pyrazol-5-yl)-6-(3-hydroxy-3-methylazetidin-1-yl)nicotinamide

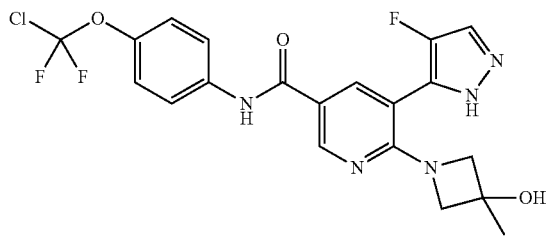 [SMILES: CC1(O)CN(c2ncc(C(=O)Nc3ccc(OC(F)(F)Cl)cc3)cc2-c2[nH]ncc2F)C1]

The title compound was prepared in an analogous fashion to that described in Example 92 using N-(4-(chlorodifluoromethoxy)phenyl)-6-(3-hydroxy-3-methylazetidin-1-yl)-5-iodonicotinamide (Stage 90.1) and 4-fluoro-5-(tributylstannyl)-1H-pyrazole to afford a white solid. HPLC (Condition 7) $t_R$=5.813 min, UPLC-MS (Condition 8) $t_R$=0.98 min, m/z=468.1 [M+H]$^+$; $^1$H-NMR (400 MHz, DMSO-d$_6$) δ ppm 1.34 (s, 3H) 3.54-3.74 (m, 4H) 5.49 (s, 1H) 7.34 (d, J=8.60 Hz, 2H) 7.58-7.71+7.94-8.01 (m, 1H) 7.83-7.92 (m, 2H) 8.05 (br. s, 1H) 8.78 (br. s, 1H) 10.23 (s, 1H) 13.03 (br.s, 1H).

Stage 90.1 N-(4-(Chlorodifluoromethoxy)phenyl)-6-(3-hydroxy-3-methylazetidin-1-yl)-5-iodonicotinamide

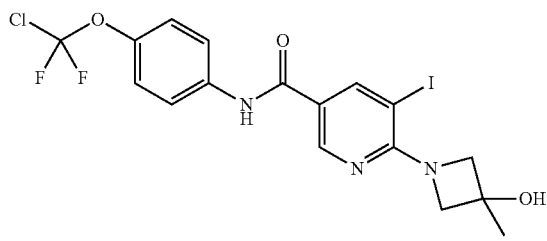 [SMILES: CC1(O)CN(c2ncc(C(=O)Nc3ccc(OC(F)(F)Cl)cc3)cc2I)C1]

The title compound was prepared in an analogous fashion to that described in Stage 88.1 using 6-chloro-N-(4-(chlorodifluoromethoxy)phenyl)-5-iodonicotinamide (Stage 48.3) and 3-methylazetidine-3-ol hydrochloride to afford a beige foam. HPLC (Condition 7) $t_R$=6.84 min, UPLC-MS (Condition 8) $t_R$=1.14 min, m/z=510.0/512.0 [M+H]$^+$.

Example 91

N-(4-(Chlorodifluoromethoxy)phenyl)-6-(3-hydroxy-3-methylazetidin-1-yl)-5-(3-methyl-1H-pyrazol-5-yl)nicotinamide

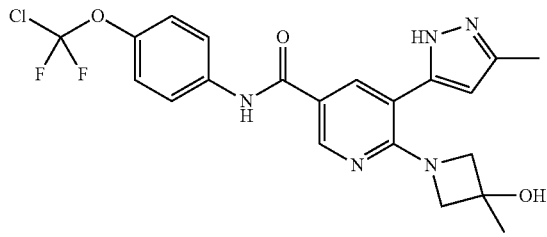 [SMILES: Cc1cc(-c2cc(C(=O)Nc3ccc(OC(F)(F)Cl)cc3)cnc2N2CC(C)(O)C2)[nH]n1]

The title compound was prepared in an analogous fashion to that described in Example 89 using N-(4-(chlorodifluoromethoxy)phenyl)-6-(3-hydroxy-3-methyl azetidin-1-yl)-5-iodonicotinamide (Stage 90.1) and 3-methyl-1-(tetrahydro-2H-pyran-2-yl)-5-(4,4,5,5-tetramethyl-1,3,2-dioxaborolan-2-yl)-1H-pyrazole to give the title product as a white solid. HPLC (Condition 7) $t_R$=5.72 min, UPLC-MS (Condition 8) $t_R$=0.99 min, m/z=464.2 [M+H]$^+$; $^1$H-NMR (400 MHz, DMSO-d$_6$) δ ppm 1.32 (s, 3H) 2.28 (br. s, 3H) 3.66 (s, 4H) 5.42 (br. s, 1H) 6.16 (s, 1H) 7.33 (d, J=8.60 Hz, 2H) 7.84-7.91 (m, 2H) 8.03 (d, J=2.35 Hz, 1H) 8.71 (s, 1H) 10.21 (s, 1H) 12.63 (br. s, 1H).

Example 92

N-(4-(Chlorodifluoromethoxy)phenyl)-5-(4-fluoro-1H-pyrazol-5-yl)-6-(3-(hydroxymethyl)azetidin-1-yl)nicotinamide

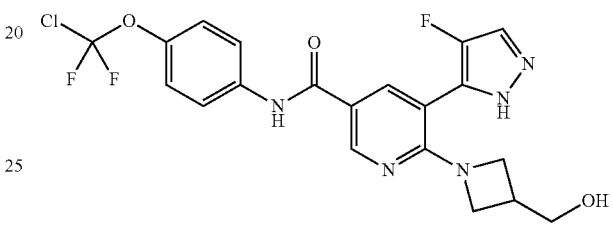

A mixture of N-(4-(chlorodifluoromethoxy)phenyl)-6-(3-(hydroxymethyl)azetidin-1-yl)-5-iodonicotinamide (Stage 92.1, 200 mg, 0.392 mmol), 4-fluoro-5-(tributylstannyl)-1H-pyrazole (147 mg, 0.392 mmol), Pd(PPh$_3$)$_4$ (22.67 mg, 0.02 mmol) in DMSO (2 mL) was stirred at 100° C. under argon atmosphere for 21 h. The RM was treated with EtOAc, washed with sat. aq. NaHCO$_3$ and brine dried over Na$_2$SO$_4$ and the solvent was evaporated off under reduced pressure. The residue was purified by flash chromatography on silica gel, dissolved in MeOH (3 mL), filtered through a SPE PL-Thiol cartridge (StratoSphere™, 500 mg 1.5 mmol), the cartridge was washed with MeOH and the solvent was evaporated off under reduced pressure to give a residue which was further purified by preparative SFC (Column Diol, from 21% to 26% in 6 min) to give the title product as a white solid. HPLC (Condition 7) $t_R$=5.701 min, UPLC-MS (Condition 8) $t_R$=0.95 min, m/z=468.1 [M+H]$^+$; $^1$H-NMR (400 MHz, DMSO-d$_6$) δ ppm 2.58-2.73 (m, 1H) 3.43-3.51 (m, 2H) 3.51-3.60 (m, 2H) 3.75-3.85 (m, 2H) 4.68-4.77 (m, 1H) 7.30-7.38 (m, 3H) 7.83-7.91 (m, 2H) 7.99-8.07 (m, 1H) 8.73-8.83 (m, 1H) 10.21 (s, 1H) 12.92-13.18 (m, 1H).

Stage 92.1 N-(4-(Chlorodifluoromethoxy)phenyl)-6-(3-(hydroxymethyl)azetidin-1-yl)-5-iodonicotinamide

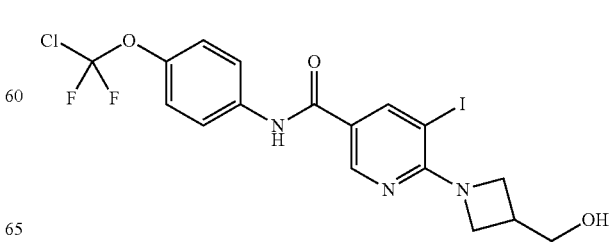

The title compound was prepared in an analogous fashion to that described in Stage 88.1 using 6-chloro-N-(4-(chlorodifluoromethoxy)phenyl)-5-iodonicotinamide (Stage 48.3) and 3-azetidinemethanol hydrochloride to afford a beige solid. HPLC (Condition 7) $t_R$=6.5 min, UPLC-MS (Condition 8) $t_R$=1.1 min, m/z=510.0/512.0 [M+H]$^+$.

Example 93

N-(4-(Chlorodifluoromethoxy)phenyl)-6-(3-(hydroxymethyl)azetidin-1-yl)-5-(3-methyl-1H-pyrazol-5-yl)nicotinamide

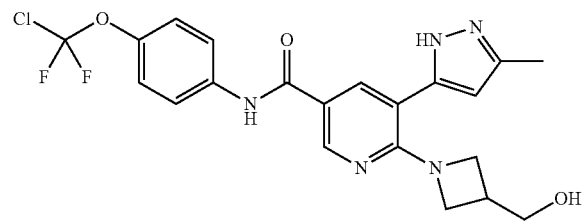 [SMILES: Cc1cc(-c2cc(C(=O)Nc3ccc(OC(F)(F)Cl)cc3)cnc2N2CC(CO)C2)[nH]n1]

A mixture of N-(4-(chlorodifluoromethoxy)phenyl)-6-(3-(hydroxymethyl)azetidin-1-yl)-5-iodonicotinamide (Stage 92.1, 175 mg, 0.343 mmol), 3-methyl-1-(tetrahydro-2H-pyran-2-yl)-5-(4,4,5,5-tetramethyl-1,3,2-dioxaborolan-2-yl)-1H-pyrazole (201 mg, 0.687 mmol), K$_3$PO$_4$ (219 mg, 1.030 mmol) and Pd(PPh$_3$)$_4$ (19.9 mg, 0.017 mmol) and toluene (2 mL) were added to a vial, which was sealed purged with argon stirred at 80° C. for 24 h. EtOAc (60 mL) was added and the solution was washed with aq. sat. NaHCO$_3$ solution (20 mL) and brine (2×20 mL), dried over Na$_2$SO$_4$ and the solvent was evaporated off under reduced pressure to give a residue which was purified by flash chromatography (RediSep® Silica gel column, 40 g, DCM/MeOH 95:5). The resulting intermediate was dissolved in DCM (2 mL), treated with TFA (0.554 mL, 7.19 mmol) and stirred at RT for 18 h. The RM was dissolved in EtOAc, washed with aq. sat. NaHCO$_3$ solution and brine, dried over Na$_2$SO$_4$ and the solvent was evaporated off under reduced pressure to give the crude product which was purified by preparative HPLC (Condition 10). Fractions containing product were combined and the solvent was evaporated off under reduced pressure to give an MeCN aq. residue which was treated with Na$_2$CO$_3$ (1 g) and extracted with EtOAc. The combined organic phases were washed with water, dried over Na$_2$SO$_4$ and the solvent was evaporated off under reduced pressure. The residue was dissolved in MeOH (3 mL), filtered through a SPE PL-Thiol cartridge (StratoSphere™, 500 mg 1.5 mmol), the cartridge was washed with MeOH and the solvent was evaporated off under reduced pressure to give a residue which was purified by preparative SFC (1: Column DEAP, from 20% to 25% in 11 min; 2: Column PFP, from 5% to 10% in 11 min) to give the title product as a white solid. HPLC (Condition 7) $t_R$=5.675 min, UPLC-MS (Condition 8) $t_R$=0.95 min, m/z=464.2 [M+H]$^+$; $^1$H-NMR (600 MHz, DMSO-d$_6$) δ ppm 2.28 (br. s, 3H) 2.57-2.68 (m, 1H) 3.42-3.49 (m, 2H) 3.50-3.57 (m, 2H) 3.72-3.88 (m, 2H) 4.71 (br. s, 1H) 6.16 (s, 1H) 7.33 (d, J=8.53 Hz, 2H) 7.87 (d, J=8.91 Hz, 2H) 8.01 (s, 1H) 8.70 (br. s, 1H) 10.21 (s, 1H).

Example 94

3-((5-((4-(Chlorodifluoromethoxy)phenyl)carbamoyl)-3-(1H-pyrazol-5-yl)pyridin-2-yl)amino)propanoic acid

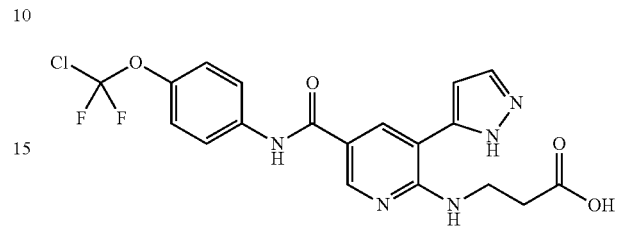

A mixture of 6-chloro-N-(4-(chlorodifluoromethoxy)phenyl)-5-(1H-pyrazol-5-yl)nicotinamide (Stage 48.1, 100 mg, 0.248 mmol), β-Alanine ethyl ester hydrochloride (267 mg, 1.736 mmol), DIPEA (0.433 mL, 2.480 mmol) and iPrOH (3 mL) were added to a vial, which was sealed and the RM was stirred at 110° C. for 44 h. The RM was treated with saturated aq. NH$_4$Cl and extracted with EtOAc. The combined extracts were washed with sat. aq. Na$_2$CO$_3$ (20 mL) and brine (10 mL), dried over Na$_2$SO$_4$ and the solvent was evaporated off under reduced pressure to give a residue which was purified by preparative HPLC (Condition 10). Fractions containing product were combined, treated with sat. aq. Na$_2$CO$_3$ and the MeCN was evaporated off under reduced pressure to give an aq. residue which was extracted with DCM and EtOAc. The combined extracts were dried over Na$_2$SO$_4$ and the solvent was evaporated off under reduced pressure. The resulting ester was dissolved in MeOH (0.5 mL) and THF (1 mL), treated with LiOH.H2O (0.548 mL, 0.548 mmol) and stirred for at RT for 90 min. The RM was acidified with aq. 1 M HCl (4 eq.) and the organic solvents were evaporated off under reduced pressure. The product was filtered off, washed with water and n-hexane and dried to give the title product as a white crystalline solid. HPLC (Condition 7) $t_R$=6.08 min, UPLC-MS (Condition 8) $t_R$=0.98 min, m/z=452 [M+H]$^+$; $^1$H-NMR (400 MHz, DMSO-d$_6$) δ ppm 2.62 (t, J=6.45 Hz, 2H) 3.79 (q, J=6.26 Hz, 2H) 6.95 (s, 1H) 7.35 (d, J=8.99 Hz, 2H) 7.85-7.95 (m, J=9.38 Hz, 3H) 8.41 (d, J=1.95 Hz, 1H) 8.67 (d, J=2.35 Hz, 1H) 8.86-9.06 (m, 1H) 10.22 (s, 1H) 12.23 (br. s, 1H) 13.18 (br. s, 1H).

Example 95

3-((3-(1H-Pyrazol-5-yl)-5-((4-(trifluoromethoxy)phenyl)carbamoyl)pyridin-2-yl)amino)propanoic acid

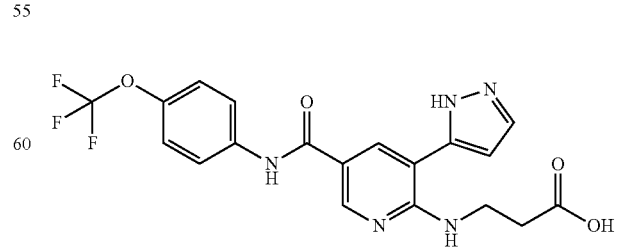

The title compound was prepared in an analogous fashion to that described in Example 94 using (R)-3-bromo-6-chloro- N-(4-(chlorodifluoromethoxy)phenyl)-5-(1H-pyrazol-5-yl) nicotinamide (Stage 48.1) to afford white crystals. UPLC-MS (Condition 8) $t_R$=0.94 min, m/z=436.2 [M+H]$^+$; $^1$H-NMR (400 MHz, DMSO-d$_6$) δ ppm 2.56-2.68 (m, 2H) 3.69-3.92 (m, 2H) 6.97 (br. s, 1H) 7.38 (d, J=8.41 Hz, 2H) 7.89 (d, J=8.66 Hz, 2H) 7.94 (br. s, 1H) 8.43 (br. s, 1H) 8.68 (br. s, 1H) 8.92-9.02 (m, 1H) 10.24 (br. s, 1H).

Example 96

4-((5-((4-(Chlorodifluoromethoxy)phenyl)carbamoyl)-3-(1H-pyrazol-5-yl)pyridin-2-yl)amino)-2-hydroxybutanoic acid

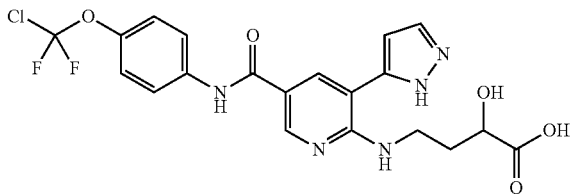 [SMILES: O=C(Nc1ccc(OC(F)(F)Cl)cc1)c1cnc(NCCC(O)C(=O)O)c(-c2ccn[nH]2)c1]

6-Chloro-N-(4-(chlorodifluoromethoxy)phenyl)-5-(1H-pyrazol-5-yl)nicotinamide (Stage 48.1, 20 mg, 0.05 mmol), 4-amino-2-hydroxybutanoic acid (23.4 mg, 0.200 mmol), K$_3$PO$_4$ (106 mg, 0.501 mmol) and NMP (0.4 mL) were added to a MW vial, which was sealed, flushed with argon and stirred at 170° C. for 1 h. The RM was filtered and the residue washed with NMP. The combined organic phases were acidified with TFA, diluted with water and MeCN, filtered and purified by preparative HPLC (Condition 11—gradient to 50% B in 7 min). The MeCN was evaporated off under reduced pressure to give an aqueous solution which was left for 2 days at 4° C. The resulting precipitate was filtered, washed with water and dried to afford the title compound as a white solid. UPLC-MS (Condition 8) $t_R$=0.93 min, m/z=482.2 [M+H]$^+$; $^1$H-NMR (400 MHz, DMSO-d$_6$) δ ppm 1.73-1.91 (m, 1H) 1.99-2.17 (m, 1H) 3.58-3.82 (m, 2H) 4.07 (s, 1H) 5.22-5.50 (m, 1H) 6.97 (s, 1H) 7.36 (d, J=8.44 Hz, 2H) 7.89 (d, J=8.80 Hz, 2H) 7.95 (s, 1H) 8.42 (s, 1H) 8.68 (s, 1H) 8.91 (br. s, 1H) 10.23 (s, 1H) 12.47 (br. s, 1H) 13.19 (br. s, 1H).

Example 97

N-(4-(Chlorodifluoromethoxy)phenyl)-6-((2,4-dihydroxybutyl)amino)-5-(1H-pyrazol-5-yl)nicotinamide

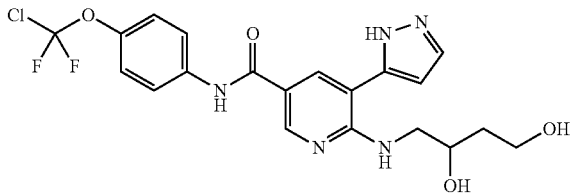 [SMILES: O=C(Nc1ccc(OC(F)(F)Cl)cc1)c1cnc(NCC(O)CCO)c(-c2ccn[nH]2)c1]

6-Chloro-N-(4-(chlorodifluoromethoxy)phenyl)-5-(1H-pyrazol-5-yl)nicotinamide (Stage 48.1, 500 mg, 1.253 mmol), 4-aminobutane-1,3-diol (Stage 97.1, 152 mg, 1.447 mmol), DIPEA (0.667 mL, 3.82 mmol) and iPrOH (2 mL) were added to a MW vial, which was sealed, flushed with argon and stirred at 130° C. for 20 h. The RM was diluted with EtOAc and washed with water and brine, dried over Na$_2$SO$_4$ and the solvent was evaporated off under reduced pressure to give a residue which was treated with iPr$_2$O and the resulting solid was filtered off and purified by flash chromatography (Silica gel column, 40 g, DCM/DCM-MeOH (9:1)) to afford the title compound as a white solid. UPLC-MS (Condition 8) $t_R$=0.94 min, m/z=468 [M+H]$^+$; $^1$H-NMR (400 MHz, DMSO-d$_6$) δ ppm 1H NMR (400 MHz, DMSO-d$_6$) δ ppm 1.46-1.74 (m, 2H) 3.44-3.58 (m, 3H) 3.64-3.72 (m, 1H) 3.77-3.90 (m, 1H) 4.40 (t, J=5.07 Hz, 1H) 4.82 (d, J=5.38 Hz, 1H) 6.96 (t, J=1.96 Hz, 1H) 7.36 (d, J=8.93 Hz, 2H) 7.83-7.99 (m, 3H) 8.41 (d, J=2.32 Hz, 1H) 8.65 (d, J=2.20 Hz, 1H) 9.04 (s, 1H) 10.21 (s, 1H) 13.21 (s, 1H).

Stage 97.1 4-Aminobutane-1,3-diol

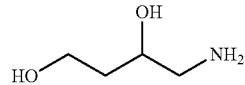

A solution of benzyl (2,4-dihydroxybutyl)carbamate (Stage 97.2, 1 g, 4.18 mmol) in EtOH was hydrogenated over Pd—C 10% (100 mg) at RT. The catalyst was filtered off, and the solvent was evaporated off under reduced pressure to afford the title compounds as a yellow oil.

Stage 97.2 Benzyl (2,4-dihydroxybutyl)carbamate

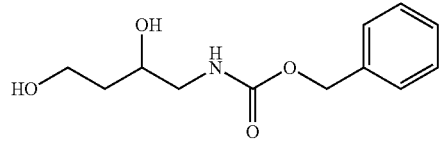 [SMILES: O=C(NCC(O)CCO)OCc1ccccc1]

1 M BH3.THF complex (80 mL, 80 mmol) was added dropwise over 30 min to a solution of 4-(((benzyloxy)carbonyl)amino)-3-hydroxybutanoic acid (prepared as described in Tetrahedron (1994), 50(47), 13347-68, 13.5 g, 53.3 mmol) in THF (53 mL) at 0° C. and the RM was stirred at RT overnight. 10% acetic acid in MeOH (250 mL) was added and the mixture was stirred at RT overnight. The solvent was evaporated off under reduced pressure and the residue was dissolved in EtOAc, washed with aq. sat. NaHCO$_3$ solution and brine, dried over Na$_2$SO$_4$ and the solvent was evaporated off under reduced pressure to give a residue was treated with iPr$_2$O, filtered and dried to afford the title compound as a white solid. UPLC-MS (Condition 8) $t_R$=0.61 min, m/z=240 [M+H]$^+$; $^1$H-NMR (400 MHz, DMSO-d$_6$) δ ppm 1H NMR (400 MHz, DMSO-d$_6$) δ ppm 1.29-1.45 (m, 1H) 1.48-1.61 (m, 1H) 2.98 (t, J=5.56 Hz, 2H) 3.49 (dt, J=11.62, 5.56 Hz, 2H) 3.54-3.65 (m, 1H) 4.35 (t, J=5.01 Hz, 1H) 4.58 (d, J=5.26 Hz, 1H) 5.02 (s, 2H) 7.16 (t, J=5.62 Hz, 1H) 7.26-7.44 (m, 5H).

Example 98

(S)—N-(4-(Chlorodifluoromethoxy)phenyl)-6-((2,4-dihydroxybutyl)amino)-5-(1H-pyrazol-5-yl)nicotinamide

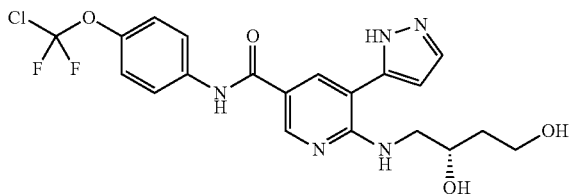 [SMILES: O=C(Nc1ccc(OC(F)(F)Cl)cc1)c1cnc(NC[C@@H](O)CCO)c(-c2ccn[nH]2)c1]

The title compound was prepared by chiral separation (Preparative chiral HPLC, ChiralPak® AS, 20 μm 50×500 mm, mobile phase: n-heptane/EtOH/MeOH (85:10:5)+0.05% DEA, flow rate 68 mL/min, wavelength: 210 nm) of a racemic mixture of N-(4-(chlorodifluoromethoxy)phenyl)-6-((2,4-dihydroxybutyl)amino)-5-(1H-pyrazol-5-yl)nicotinamide (Example 97), slower eluting isomer (Peak 2, $t_R$=12.52 min). Or alternatively, in an analogous fashion to that described in Example 97 using (S)-benzyl(2,4-dihydroxybutyl)carbamate (Stage 98.1) as chiral starting material. HPLC chiral (Chiralpak® AS-H, eluent: n-heptane/EtOH/MeOH (80:12:8)+0.05% DEA, flow rate:1 mL/min, temperature: RT, DAD 300 nm.): $t_R$=9.31 min.

Stage 98.1
(S)-Benzyl(2,4-dihydroxybutyl)carbamate

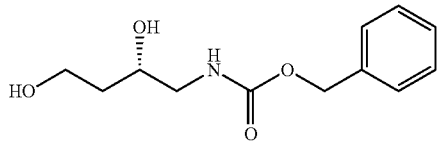

The title compound was prepared by chiral separation (Preparative chiral SFC, ChiralPak® IC-H, 250×30 mm, mobile phase: CO₂/iPrOH (75:35), flow rate: 60 mL/min, back pressure: 100 bar, column temperature: 38° C., wavelength: 210 nm, cycle time: ~3.0 min) of a racemic mixture of benzyl (2,4-dihydroxybutyl)carbamate (Stage 97.2), slower eluting isomer (Peak 2). Analytical chiral SFC (ChiralCel® OD-3, 150×4.6 mm, eluent: CO₂/iPrOH+0.05% DEA (8:2), flow rate: 2.4 mL/min, back pressure: 100 bar, temperature: 33° C., 210 nm): $t_R$=3.77 min.

Example 99

(R)—N-(4-(Chlorodifluoromethoxy)phenyl)-6-((2,4-dihydroxybutyl)amino)-5-(1H-pyrazol-5-yl)nicotinamide

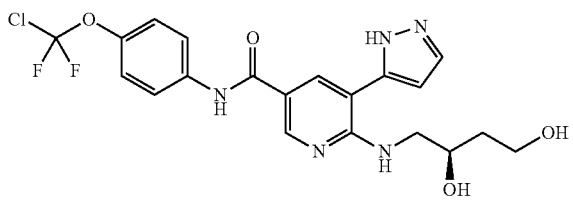 [SMILES: O=C(Nc1ccc(OC(F)(F)Cl)cc1)c1cnc(NC[C@H](O)CCO)c(-c2ccn[nH]2)c1]

The title compound was obtained as faster eluting enantiomer (Peak 1, $t_R$=8.59 min) in the course of the chiral separation for Example 98. Or alternatively, in an analogous fashion to that described in the preparation of Example 97 using (R)-benzyl(2,4-dihydroxybutyl)carbamate (Stage 99.1) as chiral starting material. HPLC chiral (Chiralpak® AS-H, eluent: n-heptane/EtOH/MeOH (80:12:8)+0.05% DEA, flow rate:1 mL/min, temperature: RT, DAD 300 nm.): $t_R$=7.36 min.

Stage 99.1
(R)-Benzyl(2,4-dihydroxybutyl)carbamate

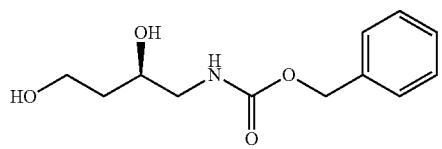 [SMILES: O=C(NC[C@H](O)CCO)OCc1ccccc1]

The title compound was obtained as faster eluting enantiomer (Peak 1) in the course of the chiral separation for Stage 98.1. Analytical chiral SFC (ChiralCel® OD-3, 150×4.6 mm, eluent: CO₂/iPrOH+0.05% DEA (8:2), flow rate: 2.4 mL/min, back pressure: 100 bar, temperature: 33° C., 210 nm): $t_R$=3.09 min.

Example 100

N-(4-(Chlorodifluoromethoxy)phenyl)-6-((3,4-dihydroxybutyl)amino)-5-(1H-pyrazol-5-yl)nicotinamide

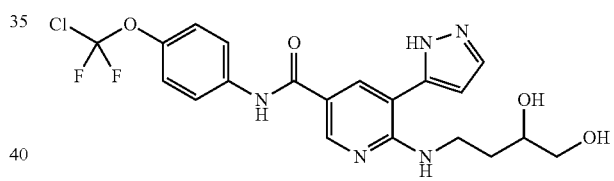

6-chloro-N-(4-(chlorodifluoromethoxy)phenyl)-5-(1-(tetrahydro-2H-pyran-2-yl)-1H-pyrazol-5-yl)nicotinamide (Stage 48.2, 200 mg, 0.414 mmol), 3-buten-1-amine (50.5 μl, 0.497 mmol), DIPEA (145 μL, 0.828 mmol) and iPrOH (414 μL) were added to MW vial, which was sealed, purged with argon, and the RM was stirred at 130° C. for 5 h. iPrOH (1.5 μL) was added and the RM was stirred at 130° C. for 30 min. DIPEA (36.1 μL, 0.207 mmol), 3-buten-1-amine (16.83 μL, 0.166 mmol), and iPrOH (0.1 mL) were added and the RM was stirred at 130° C. for 2 h. The cooled RM was treated with brine and extracted with EtOAc. The combined extracts were dried over Na₂SO₄ and the solvent was evaporated off under reduced pressure to give a residue which was purified by flash chromatography (Silica gel column, 40 g, n-heptane/EtOAc from 20% to 50% EtOAc). N-Methylmorpholin-N-oxide (9.50 mg, 0.081 mmol) and then osmium tetroxide EnCat™ (5.17 mg, 1.545 mmol) were then added to a stirred solution of the aforementioned intermediate (40 mg, 0.077 mmol) in THF (1 mL)/water (0.1 mL) and the RM was stirred at 50° C. for 26 h under an argon atmosphere A 10% aq. solution of KHSO₄ was then added and the mixture was extracted with EtOAc. The combined extracts were washed with water, sat. aq. NH₄Cl and brine, dried over Na₂SO₄ and the solvent was evaporated off under reduced pressure to give a crude product which was suspended in DCM, sonicated, filtered and dried to afford the title product as a white solid. UPLC-MS (Condition 8) $t_R$=0.92 min, m/z=468.2 [M+H]$^+$; $^1$H-NMR (400 MHz, DMSO-d$_6$) δ ppm 1.46-1.65 (m, 1H) 1.78-1.94 (m, 1H) 3.22-3.47 (m, 2H) 3.50-3.67 (m, 2H) 3.67-3.79 (m, 1H) 4.49-4.58 (m, 1H) 4.60-4.68 (m, 1H) 6.91-7.04 (m, 1H) 7.28-7.43 (m, 2H) 7.84-7.99 (m, 3H) 8.37-8.46 (m, 1H) 8.62-8.73 (m, 1H) 8.80-8.96 (m, 1H) 10.16-10.27 (m, 1H) 13.11-13.29 (m, 1H).

Example 101

(S)—N-(4-(Chlorodifluoromethoxy)phenyl)-6-((3,4-dihydroxybutyl)amino)-5-(1H-pyrazol-5-yl)nicotinamide

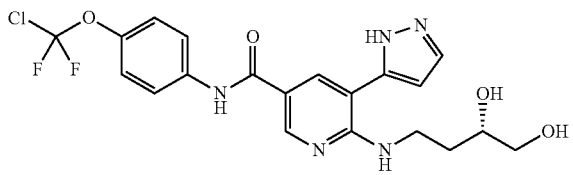 [SMILES: O=C(Nc1ccc(OC(F)(F)Cl)cc1)c1cnc(NCC[C@H](O)CO)c(-c2ccn[nH]2)c1]

The title compound was prepared by chiral separation (Preparative chiral SFC, ChiralPak® AD-H, 250×30 mm, mobile phase: CO$_2$/EtOH (3:2), flow rate: 50 mL/min, back pressure: 100 bar, column temperature: 38° C., wavelength: 220 nm, cycle time: 6.0 min) of a racemic mixture of N-(4-(chlorodifluoromethoxy)phenyl)-6-((3,4-dihydroxybutyl)amino)-5-(1H-pyrazol-5-yl)nicotinamide (Example 100), faster eluting isomer (Peak 1). Or alternatively in an analogous fashion to that described in Example 97 using (S)-benzyl(3,4-dihydroxybutyl)carbamate (Stage 101.1) as chiral starting material. Analytical chiral SFC (ChiralPak® AD-H, 250×4.6 mm, 5 μm, eluent: CO$_2$/EtOH+0.05% DEA (3:2), flow rate: 2.4 mL/min, back pressure: 100 bar, temperature: 35° C., 220 nm): $t_R$=3.18 min.

Stage 101.1
(S)-Benzyl(3,4-dihydroxybutyl)carbamate

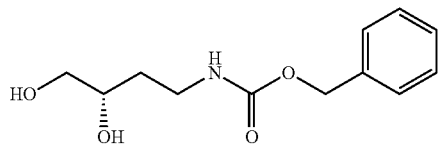 [SMILES: O=C(NCC[C@H](O)CO)OCc1ccccc1]

The title compound was prepared by chiral separation (Preparative chiral SFC, ChiralPak® AD-H, 250×50 mm, mobile phase: CO$_2$/MeOH (3:2), flow rate: 110 mL/min, back pressure: 100 bar, column temperature: 38° C., wavelength: 210 nm, cycletime: ~4.0 min) of a racemic mixture of benzyl (3,4-dihydroxybutyl)carbamate (Prepared accordingly to WO2011107608), faster eluting isomer (Peak 1). Analytical chiral SFC (ChiralPak AD-3, 150×4.6 mm, eluent: CO$_2$/MeOH+0.05% DEA (75:35), flow rate: 2.5 mL/min, back pressure: 100 bar, temperature: 35° C., 210 nm): $t_R$=2.22 min.

Example 102

(R)—N-(4-(Chlorodifluoromethoxy)phenyl)-6-((3,4-dihydroxybutyl)amino)-5-(1H-pyrazol-5-yl)nicotinamide

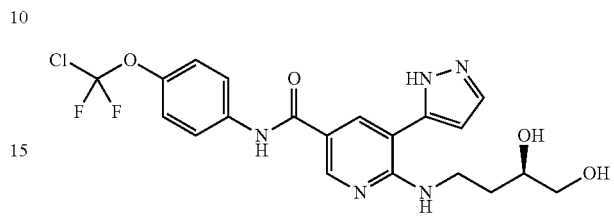

The title compound was obtained as slower eluting enantiomer (Peak 2) in the course of the chiral separation for Example 101. Or alternatively, in an analogous fashion to that described in Example 97 using (R)-benzyl(3,4-dihydroxybutyl)carbamate (Stage 102.1) as chiral starting material. Analytical chiral SFC (ChiralPak® AD-H, 250×4.6 mm, 5 μm, eluent: CO$_2$/EtOH+0.05% DEA (3:2), flow rate: 2.4 mL/min, back pressure: 100 bar, temperature: 35° C., 220 nm): $t_R$=4.51 min.

Stage 102.1
(R)-Benzyl(3,4-dihydroxybutyl)carbamate

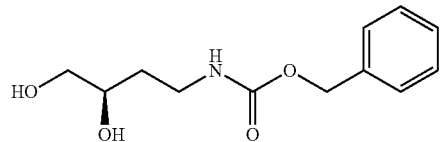 [SMILES: O=C(NCC[C@@H](O)CO)OCc1ccccc1]

The title compound was obtained as slower eluting enantiomer (Peak 2) in the course of the chiral separation for Stage 101.1. Analytical chiral SFC (ChiralPak AD-3, 150×4.6 mm, eluent: CO$_2$/MeOH+0.05% DEA (75:35), flow rate: 2.5 mL/min, back pressure: 100 bar, temperature: 35° C., 210 nm): $t_R$=2.87 min.

Assays

The utility of the compounds of the invention described herein can be evidenced by testing in the following assays. Compounds of the invention were assessed for their ability to inhibit ABL1 activity in biochemical assays and BCR-ABL1 in cellular assays described below.

Biochemical Assays

Expression and Purification of Protein Kinase—

Expression and purification of human ABL was performed using standard expression purification procedures. The ABL64-515 protein was generated and used for in vitro kinase assays. The protein was generated by a co-expression vector carrying the DNA fragments for ABL1 (1a isoform, with an N-terminal His6-tag followed by a PreScission protease cleavage site) and the human protein tyrosine phosphatase-1B (residues 1-283, untagged), using the dual expression vector pCDF Duet-1 (Novagen). The His-ABL was expressed in *E. coli* BL21 (DE3) and the ABL proteins were isolated by Ni-affinity on a Ni-NTA column (Qiagen).

The His-tag was removed by PreScission protease (GE Healthcare) and the non-phosphorylated ABL further purified on a Mono Q HR 10/10 (GE Healthcare, mono-phosphorylated ABL is about 10-20% of total ABL protein) and HiLoad 16/60 Superdex 200 size exclusion column (GE Healthcare). Non-phosphorylated ABL64-515 proteins were analyzed by mass spectroscopic analysis and flash-frozen in aliquots and stored at −80° C. SRC (amino acids 83-535 or Src83-535) was expressed and purified as described (S. W. Cowan-Jacob, G. Fendrich, P. W. Manley, W. Jahnke, D. Fabbro, J. Liebetanz, T. Meyer, c-Src crystal structure provides insights into c-Src activation. Structure 13 (2005) 861-871).

Radio ABL1 (64-515) Assay

For determination of ABL kinase activity, the radiometric filter-binding assay was used. The assay was performed by mixing 10 µL of the compound pre-diluted with 10 µL of ATP (20 µM ATP with 0.1 µCi [γ-33P]-ATP) with the phospho-acceptor peptide poly[Ala6Glu2LysHBr5Tyr1]=polyAEKY) in 20 mM Tris/HCl pH 7.5, 1 mM DTT, 10 mM $MgCl_2$, 0.01 mM $Na_3VO_4$, 50 mM NaCl. 10 µL of enzyme (ranging between 5 nM to 20 nM) was added to initiate the reaction. Pre-incubation of enzyme with compounds (when stated) was performed by exposing the enzyme to compounds prior to addition of the substrate mixture (ATP and/or peptide substrate). After 15 min at room temperature, the reaction was stopped by the addition of 50 µL 125 mM EDTA, and the peptide-bound 33P separated on filter-plates (PVDF or MAIP; Millipore, Volketswil, Switzerland) prepared according to the manufacturer's instructions. Filter-plates were washed 3× with 0.5% $H_3PO_4$, followed by addition of 30 µL scintillation cocktail (Microscint, Perkin Elmer) per well and then analysed in a TopCount NXT scintillation counter (Perkin Elmer). Results were expressed as $IC_{50}$ values. The $K_m$ values for ATP were determined by assaying the ABL kinase with increasing concentrations of ATP and keeping the exogenous acceptor protein substrate (poly-AEKY) at a constant concentration (at about 2-fold its $K_m$) and vice versa. $K_m$ and $V_{max}$ were calculated according to Eadie-Hofstee as described (D. Fabbro, G. Fendrich, V. Guez, T. Meyer, P. Furet, J. Mestan, J. D. Griffin, P. W. Manley, S. W. Cowan-Jacob, Targeted therapy with imatinib: An exception or a rule? Handbook of Experimental Pharmacology 167, Inhibitors of Protein Kinases and Protein Phosphates (2005) 361-389). The data were plotted as V versus V/S, where V is the velocity of the reaction at a given substrate (S) concentration, and fitted to a straight line using linear regression analysis, where the slope of the line corresponds to $-K_m$ and the Y-intercept represents the $V_{max}$.

Caliper ABL1 (64-515) Assay

All assays were performed in 384-well microtiter plates. Each assay plate contained 8-point serial dilutions for 40 test compounds, as well as four 8-point serial dilutions of staurosporine as a reference compound, plus 16 high and 16 low controls. Liquid handling and incubation steps were done on a Thermo CatX workstation equipped with Innovadyne Nanodrop Express. Between pipetting steps, tips were cleaned in wash cycles using wash buffer.

The assay plates were prepared by addition of 50 nL per well of compound solution in 90% DMSO. The kinase reactions were started by stepwise addition of 4.5 µL per well of peptide/ATP-solution (50 mM HEPES, pH 7.5, 1 mM DTT, 0.02% BSA, 0.6% DMSO, 10 mM beta-glycerophosphate, and 10 µM sodium orthovanadate, 20 mM $MgCl_2$, 2 mM $MnCl_2$, 4 µM ATP, 4 µM peptide (FITC-Ahx-EAIYAAP-FAKKK-NH2)) and 4.5 µL per well of enzyme solution (50 mM HEPES, pH 7.5, 1 mM DTT, 0.02% BSA, 0.6% DMSO, 10 mM beta-glycerophosphate, and 10 µM sodium orthovanadate, 20 mM $MgCl_2$, 2 mM $MnCl_2$, 3.5 nM ABL (ABL (64-515), produced in-house from *E. coli*)). Kinase reactions were incubated at 30° C. for 60 minutes and subsequently terminated by addition of 16 µL per well of stop solution (100 mM HEPES pH 7.5, 5% DMSO, 0.1% Caliper coating reagent, 10 mM EDTA, and 0.015% Brij35). Plates with terminated kinase reactions were transferred to the Caliper LC3000 workstations for reading. Phosphorylated and unphosphorylated peptides were separated using the Caliper microfluidic mobility shift technology. Briefly, samples from terminated kinase reactions were applied to the chip. Analytes are transported through the chip by constant buffer flow and the migration of the substrate peptide is monitored by the fluorescence signal of its label. Phosphorylated peptide (product) and unphosphorylated peptide (substrate) are separated in an electric field by their charge/mass ratio. Kinase activities were calculated from the amounts of formed phospho-peptide. IC50 values were determined from percent inhibition values at different compound concentrations by non-linear regression analysis.

Preparation of Compound Dilutions:

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps.

Compound dilutions were made in 96-well plates. This format enabled the assay of maximally 40 individual test compounds at 8 concentrations (single points) including 4 reference compounds. The dilution protocol included the production of "pre-dilution plates", "master plates" and "assay plates".

Pre-Dilution Plates:

Polypropylene 96-well plates were used as pre-dilution plates. A total of 4 pre-dilution plates were prepared including 10 test compounds each on the plate positions A1-A10, one standard compound at A11 and one DMSO control at A12. A11 dilution steps were done on a HamiltonSTAR robot.

Master Plates:

30 µL of individual compound dilutions including standard compound and controls of the 4 "pre-dilution plates" were transferred into a 384 "master plate" including the following concentrations 1, 810, 362, 72.5, 54.6, 14.5, 2.9, 0.58 and 0.120/1, respectively in 90% of DMSO.

Assay Plates:

Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 9.05 µL. This led to a final compound concentration of 10, 2.0, 0.4, 0.08, 0.016, 0.0032, 0.00064 and 0.000128 µM and a final DMSO concentration of 0.5% in the assay.

Cellular Assays

To assess the ability of compounds of the invention to inhibit BCR-ABL1 activity in cellular assays, compounds were evaluated for their ability to selectively inhibit the proliferation of cells dependent on BCR-ABL1 expression relative to cells that do not depend on BCR-ABL1 expression.

The murine bone marrow-derived cell line Ba/F3 was used to generate the appropriate cell line models. Ba/F3 cells were obtained from the German Collection of Microorganisms and Cell Cultures (DSMZ, Braunschweig and DSMZ No. ACC 300). Parental Ba/F3 cells depend on IL3 for growth and survival and were used as the reference cell line that does not depend on BCR-ABL1 activity for growth and survival. These cells are referred to as Ba/F3-WT.

To generate Ba/F3 cells that depend on BCR-ABL1 expression for growth and survival, Ba/F3 cells were engineered to express BCR-ABL1 using retroviral transduction with a MSCV based retroviral vector containing a p210 BCR-ABL1expression cassette. When grown in the absence of IL-3, the proliferation of the cells is dependent on the expression of BCR-ABL1. (Daley, G. Q. and Baltimore, D. Transformation of an interleukin 3-dependent hematopoietic cell line by the chronic myeloid leukemia-specific p210 BCR-ABL1 protein. PNAS 1988; 85:9312-9316). These cells are referred to as Ba/F3-BCR-ABL-WT. A similar approach was used to generate Ba/F3 cells that depend on a BCR-ABL1 variant in which threonine 315 is replaced with isoleucine. These cells are referred to as Ba/F3-BCR-ABL-T315I.

Ba/F3-WT cells were maintained in RPMI1640 media with L-glutamine, HEPES (Lonza), 10% FBS (Gibco) and 5 ng/ml IL-3 (Calbiochem). Ba/F3-BCR-ABL1-WT cells and Ba/F3-BCR-ABL1-T315I cells were maintained in RPMI1640 media with L-glutamine, HEPES (Lonza) and 10% FBS (Gibco).

Proliferation Assay

For each cell line, the cell density was adjusted to 50 000 cells/mL and 50 µL (2500 cells) added per well of a 384-well assay plate.

Test compounds were resuspended in DMSO at a concentration of 10 mM. A serial three-fold dilution of each compound with DMSO was performed in 384-well plates using the Janus Liquid Dispenser (PerkinElmer). Compound was delivered to the assay plates containing 2500 cells in a 50 µL volume via Acoustic delivery from an ATS-100 (EDC). For Ba/F3-BCR-ABL1-WT cell assays, 2 nL of each compound dilution was transferred to the assay plate for final assay concentrations of 0.4 µM, 0.13 µM, 0.044 µM, 0.015 µM, 0.005 µM, 0.001 µM, 0.00033 µM, 0.00011 µM, 0.000037 µM, 0.000012 µM. For Ba/F3-WT and Ba/F3-BCR-ABL1-T315I cell assays, 50 nL of each compound dilution was transferred to the assay plate for final assay concentrations of 10 µM, 3.33 µM, 1.11 µM, 0.37 µM, 0.12 µM, 0.041 µM, 0.014 µM, 0.0046 µM, 0.0015 µM, 0.00051 µM.

Cells were incubated at 37° C. in a humidified environment with 5% carbon dioxide for 48 hours. Britelite plus solution (Perkin Elmer) was prepared according to the manufacturer's instructions and 25 µL added to each well of the assay plate. Plates were incubated for 3-5 minutes and the luminescence detected on an EnVision Multimode plate reader (Perkin Elmer). The degree of luminescence correlates with the number of cells in each well. The effect of each inhibitor concentration can therefore be calculated and $IC_{50}$ values generated.

The compounds of the invention show $IC_{50}$ values in the range of 0.1 nM to 30 nM for inhibition of Abl kinase activity in a radiometric filter binding (Radio). For a microfluidic mobility shift assays (Caliper) assay, $IC_{50}$ values can be found in the range of 0.1 nM to 40 nM. For Ba/F3-BCR-ABL-WT and T315I cellular proliferation assay, $GI_{50}$ values can be found in the range of 0.6 nM to 80 nM and 10 nM to 2000 nM, respectively.

Table of Biochemical Data

| Example | Radio ABL1 (64-515) $IC_{50}$ [µM] | Caliper ABL1 (64-515) $IC_{50}$ [µM] |
|---|---|---|
| 1 | 0.004 | 0.0008 |
| 2 | <0.003 | 0.0035 |
| 3 | 0.003 | 0.0032 |
| 4 | 0.004 | 0.0042 |
| 5 | 0.0011 | 0.0006 |
| 6 | 0.009 | 0.0013 |
| 7 | <0.003 | |
| 8 | 0.009 | |
| 9 | 0.01 | |
| 10 | 0.0053 | 0.0005 |
| 11 | <0.003 | |
| 12 | <0.003 | |
| 13 | 0.001 | 0.0042 |
| 14 | 0.0025 | 0.0028 |
| 15 | <0.003 | 0.0008 |
| 16 | <0.003 | 0.0011 |
| 17 | 0.01 | 0.0014 |
| 18 | 0.005 | 0.0065 |
| 19 | 0.007 | 0.0069 |
| 20 | <0.003 | 0.005 |
| 21 | 0.0009 | 0.0018 |
| 22 | 0.0024 | <0.00013 |
| 23 | 0.0027 | 0.0034 |
| 24 | 0.001 | 0.0013 |
| 25 | 0.0037 | 0.0026 |
| 26 | 0.011 | 0.001 |
| 27 | 0.0045 | 0.001 |
| 28 | 0.003 | 0.0042 |
| 29 | <0.0001 | 0.0005 |
| 30 | 0.006 | 0.0007 |
| 31 | <0.0001 | <0.00013 |
| 32 | | 0.0041 |
| 33 | 0.003 | 0.005 |
| 34 | 0.0015 | 0.0017 |
| 35 | 0.009 | 0.0083 |
| 36 | 0.005 | 0.0081 |
| 37 | 0.002 | 0.0019 |
| 38 | 0.008 | 0.0015 |
| 39 | 0.003 | 0.0045 |
| 40 | 0.004 | 0.0053 |
| 41 | 0.007 | 0.0082 |
| 42 | 0.002 | 0.018 |
| 43 | | 0.0033 |
| 44 | 0.019 | 0.0071 |
| 45 | 0.004 | 0.0007 |
| 46 | 0.001 | 0.0004 |
| 47 | 0.0009 | 0.0016 |
| 48 | 0.0055 | |
| 49 | <0.0001 | 0.0008 |
| 50 | 0.0013 | |
| 51 | 0.0049 | 0.0011 |
| 52 | 0.003 | 0.0034 |
| 53 | <0.0001 | 0.0014 |
| 54 | 0.001 | 0.0004 |
| 55 | 0.001 | 0.0002 |
| 56 | 0.001 | 0.0029 |
| 57 | 0.0058 | 0.0034 |
| 58 | 0.0057 | 0.0024 |
| 59 | 0.026 | 0.0033 |
| 60 | 0.001 | <0.00064 |
| 61 | 0.003 | 0.0045 |
| 62 | 0.0016 | 0.0014 |
| 63 | <0.0001 | 0.0005 |
| 64 | 0.004 | 0.0002 |
| 65 | 0.0056 | 0.0009 |
| 66 | 0.0015 | 0.0008 |
| 67 | 0.0005 | 0.002 |
| 68 | 0.002 | <0.00013 |
| 69 | 0.0002 | 0.0002 |
| 70 | | 0.0064 |
| 71 | | 0.0004 |
| 72 | | 0.0042 |
| 73 | | 0.0011 |
| 74 | | 0.0037 |
| 75 | 0.0030 | 0.0005 |
| 76 | 0.0030 | 0.0014 |
| 77 | | 0.0007 |
| 78 | 0.0040 | 0.0036 |

-continued

Table of Biochemical Data

| Example | Radio ABL1 (64-515) IC$_{50}$ [μM] | Caliper ABL1 (64-515) IC$_{50}$ [μM] |
|---|---|---|
| 79 | 0.0010 | 0.0007 |
| 79 | 0.0010 | 0.0007 |
| 80 | 0.0004 | <0.00013 |
| 81 |  | 0.0004 |
| 82 |  | 0.0010 |
| 83 |  | 0.0004 |
| 84 | 0.0020 | 0.0008 |
| 85 | 0.0020 | 0.0007 |
| 86 | 0.0040 | 0.0015 |
| 87 | 0.0030 | 0.0013 |
| 88 | 0.0010 | 0.0002 |
| 89 | 0.0010 | 0.0002 |
| 90 |  | 0.0007 |
| 91 |  | 0.0014 |
| 92 |  | 0.0008 |
| 93 |  | 0.0012 |
| 94 |  | 0.0230 |
| 95 |  | 0.0470 |
| 96 |  | 0.0053 |
| 97 |  | 0.0057 |
| 98 |  | 0.0057 |
| 99 |  | 0.0051 |
| 100 |  | 0.0066 |
| 101 |  | 0.0078 |
| 102 |  | 0.013 |

Table of Cellular Proliferation Data Ba/F3-BCR-ABL1-WT and T315I

| Example | Ba/F3-BCR-ABL1-WT IC$_{50}$ [μM] | Ba/F3-BCR-ABL1-T315I IC$_{50}$ [μM] |
|---|---|---|
| 1 | 0.0081 | 0.194 |
| 6 | 0.0045 | 0.106 |
| 7 | 0.0059 | 0.674 |
| 10 | 0.0025 | 0.050 |
| 14 | 0.0048 | 0.134 |
| 22 | 0.0008 | 0.027 |
| 30 | 0.0011 | 0.022 |
| 34 | 0.012 | 0.578 |
| 35 | 0.0362 | 1.059 |
| 45 | 0.0006 | 0.013 |
| 61 | 0.0493 | 1.041 |
| 69 | 0.0243 | 0.395 |
| 70 | 0.0058 | 0.106 |
| 71 | 0.0011 | 0.008 |
| 72 | 0.0045 | 0.074 |
| 73 | 0.0004 | 0.007 |
| 75 | 0.0012 | 0.017 |
| 77 | 0.0041 | 0.075 |
| 81 | 0.0004 | 0.007 |
| 93 | 0.0004 | 0.008 |

It is understood that the Examples and embodiments described herein are for illustrative purposes only and that various modifications or changes in light thereof will be suggested to persons skilled in the art and are to be included within the spirit and purview of this application and scope of the appended claims.

We claim:

1. A compound of formula (I):

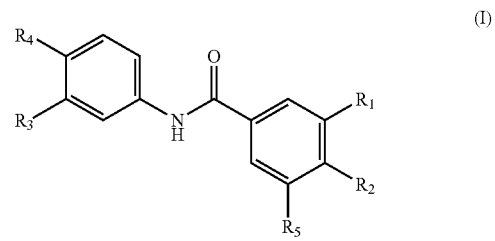

in which:

$R_5$ is selected from hydrogen, methoxy and imidazolyl; wherein said imidazolyl is unsubstituted or substituted with methyl;

$R_1$ is thiazolyl unsubstituted or substituted with 1 to 3 $R_6$ groups;

$R_2$ is selected from pyrrolidinyl unsubstituted or substituted with 2 or 3 $R_7$ groups;

$R_3$ is selected from hydrogen and halo;

$R_4$ is selected from —SF$_5$ and —Y$_2$—CF$_2$—Y$_3$;

$R_6$ at each occurrence is independently selected from hydrogen, hydroxy, methyl, hydroxy, methoxy, cyano, trifluoromethyl, hydroxy-methyl, halo, amino, fluoroethyl, ethyl, cyclopropyl and dimethyl-amino-carbonyl;

$R_7$ at each occurrence is independently selected from hydroxy, methyl, halo, methoxy, hydroxy-methyl, amino, methyl-amino, amino-methyl, trifluoromethyl, 2-hydroxypropan-2-yl, methyl-carbonyl-amino, dimethyl-amino, 2-amino-3-methylbutanoyl)oxy, carboxy, methoxy-carbonyl, phosphonooxy, cyano and amino-carbonyl; or two $R_7$ groups combine with the atom to which they are attached to form a ring selected from cyclopropyl, azetidin-3-yl and 3-azabicyclo[3.1.0]hexan-3-yl;

$Y_2$ is selected from CF$_2$, O and S(O)$_{0-2}$; and $Y_3$ is selected from hydrogen, halo, methyl, difluoromethyl and trifluoromethyl;

or the pharmaceutically acceptable salts thereof.

2. The compound of claim 1 selected from:

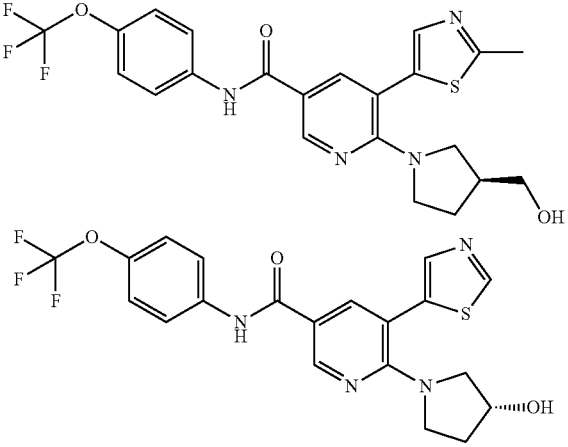

-continued

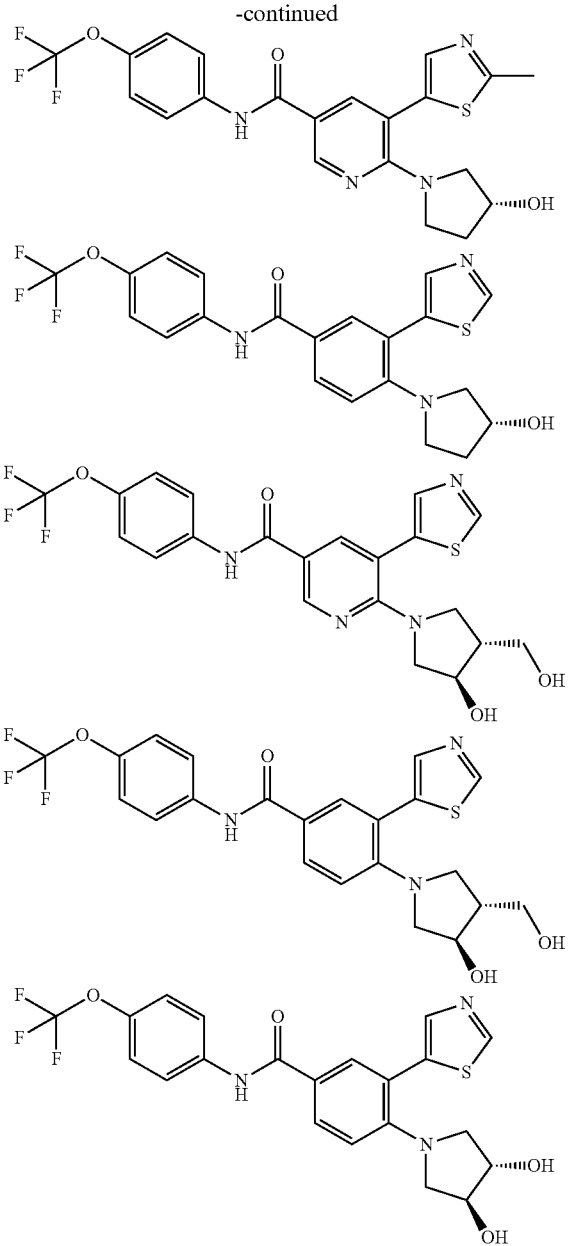

-continued

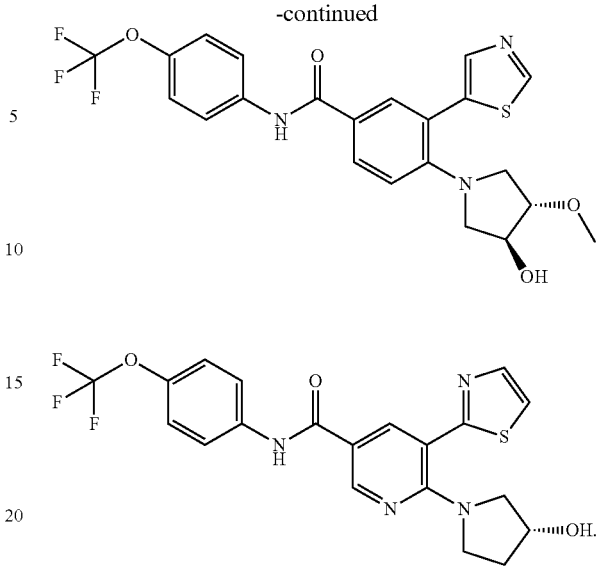

3. A pharmaceutical composition comprising a compound of claim 1, admixed with at least one pharmaceutically acceptable excipient selected from the group consisting of corn starch, potato starch, tapioca starch, starch paste, pregelatinized starch, sugars, gelatin, natural gums, synthetic gums, sodium alginate, alginic acid, tragacanth, guar gum, cellulose, ethyl cellulose, cellulose acetate, carboxymethyl cellulose calcium, sodium carboxymethylcellulose, methyl cellulose, hydroxypropyl methylcellulose, microcrystalline cellulose, magnesium aluminum silicate, polyvinyl pyrrolidone, talc, calcium carbonate, powdered cellulose, dextrates, kaolin, mannitol, silicic acid, sorbitol, agar-agar, sodium carbonate, croscarmellose sodium, crospovidone, polacrilin potassium, sodium starch glycolate, clays, sodium stearate, calcium stearate, magnesium stearate, stearic acid, mineral oil, light mineral oil, glycerin, sorbitol, mannitol, polyethylene glycol, other glycols, sodium lauryl sulfate, hydrogenated vegetable oil, peanut oil, cottonseed oil, sunflower oil, sesame oil, olive oil, corn oil, soybean oil, zinc stearate, sodium oleate, ethyl oleate, ethyl laureate, silica, and combinations thereof.

* * * * *